US008883172B2

(12) United States Patent
Shone et al.

(10) Patent No.: US 8,883,172 B2
(45) Date of Patent: Nov. 11, 2014

(54) CHEMICALLY MODIFIED PEPTIDES WITH IMPROVED IMMUNOGENICITY

(75) Inventors: Clifford Shone, Sallsbury (GB); Xiaomi Tong, Leesburg, VA (US); Joanna Clancy, Wilmington, NC (US); Mili Gu, Gaithersburg, MD (US)

(73) Assignee: The Secretary of State for Health, London (GB)

( * ) Notice: Subject to any disclaimer, the term of this patent is extended or adjusted under 35 U.S.C. 154(b) by 776 days.

(21) Appl. No.: 12/664,218

(22) PCT Filed: Jun. 13, 2008

(86) PCT No.: PCT/GB2008/050449
§ 371 (c)(1),
(2), (4) Date: Aug. 2, 2010

(87) PCT Pub. No.: WO2008/152429
PCT Pub. Date: Dec. 18, 2008

(65) Prior Publication Data
US 2010/0291152 A1    Nov. 18, 2010

Related U.S. Application Data

(60) Provisional application No. 60/929,125, filed on Jun. 14, 2007, provisional application No. 60/960,771, filed on Oct. 12, 2007, provisional application No. 61/060,978, filed on Jun. 12, 2008.

(51) Int. Cl.
*A61K 39/08* (2006.01)
*A61K 39/07* (2006.01)
*A61K 39/00* (2006.01)

(52) U.S. Cl.
CPC .................. *A61K 39/07* (2013.01); *A61K 39/08* (2013.01); *A61K 2039/55505* (2013.01)
USPC ................... 424/247.1; 424/234.1; 424/185.1; 424/190.1; 530/350

(58) Field of Classification Search
None
See application file for complete search history.

(56) References Cited

U.S. PATENT DOCUMENTS 5,919,463 A * 7/1999 Thomas et al. ............ 424/239.1
2003/0009025 A1    1/2003 Smith et al.

FOREIGN PATENT DOCUMENTS

| WO | WO-94/03206 | 2/1994 |
| WO | WO-2004/024909 A2 | 3/2004 |
| WO | WO-2006/017749 A2 | 2/2006 |
| WO | WO-2007/044382 A2 | 4/2007 |

OTHER PUBLICATIONS

Metz et al., "Identification of Formaldehyde-Induced Modifications in Proteins", The Journal of Biological Chemistry, vol. 279, No. 8, pp. 6235-6243, (2004).

Rigoni et al., "Site-Directed Mutagenesis Identifies Active-Site Residues of the Light Chain of Botulinum Neurotoxin Type A", Biochemical and Biophysical Research Communications, vol. 288, pp. 1231-1237, (2001).

Vani et al., "A High Throughput Combinatorial Library Technique for Identifying Formalin-Sensitive Epitopes"; Journal of Immunological Methods, vol. 317, pp. 80-89, (2006).

International Search Report from the European Patent Office for International Application No. PCT/GB2008/050449 (Nov. 5, 2008).

Australian Patent Examination Report No. 2, Australia Patent Application No. 2008263591, mailed Dec. 12, 2012 (4 pages).

Ramirez, D. et al., "Production, Recovery and Immunogenicity of the Protective Antigen from a Recombinant Strain of *Bacillus anthracis*," *Journal of Industrial Microbiology & Biotechnology*, 2002, 28:232-238.

Nencioni, L. et al., "Properties of Pertussis Toxin Mutant PT-9K/129G After Formaldehyde Treatment," *Infection and Immunity*, 1991, 59(2):625-630.

Ibsen, P. "The Effect of Formaldehyde, Hydrogen Peroxide and Genetic Detoxification of Pertussis Toxin on Epitope Recognition by Murine Monoclonal Antibodies," *Vaccine*, 1996, 14(5):359-368.

Cropley, I. et al., "Mucosal and Systemic Immunogenicity of a Recombinant, Non-ADP-Ribosylating Pertussis Toxin: Effects of Formaldehyde Treatment," *Vaccine*, 1995, 13(17):1643-1648.

Petre, J. et al., "The Reaction of Bacterial Toxins with Formaldehyde and Its Use for Antigen Stabilization," *New Approaches to Stabilisation of Vaccines Potency—Developments in Biological Standardization*, 1996, 87:125-134.

Porro, M. et al., "Immunogenic Correlation Between Cross-Reacting Material (CRM197) Produced by a Mutant of *Corynebacterium diphtheriae* and Diphtheria Toxoid," *Journal of Infectious Disease*, 1980, 142(5):716-724.

Gupta, R. et al., "Differences in the Immunogenicity of Native and Formalinized Cross Reacting Material (CRM197) of Diphtheria Toxin in Mice and Guinea Pigs and Their Implications on the Development and Control of Diphtheria Vaccine Based on CRMs," *Vaccine*, 1997, 15(12/13):1341-1343.

Communication Pursuant to Article 94(3) EPC, European Patent Application No. 08 762 559.6-1412, Jan. 29, 2014 (6 pages).

Salnikova, Maya S. et al., "Physical Characterization of *Clostridium difficile* Toxins and Toxoids: Effect of the Formaldehyde Crosslinking on Thermal Stability," J. Pharm. Sciences, vol. 97, No. 9, Sep. 2008, pp. 3735-3751 (18 pages).

(Continued)

*Primary Examiner* — Jennifer Graser
(74) *Attorney, Agent, or Firm* — Finnegan, Henderson, Farabow, Garrett & Dunner LLP

(57) ABSTRACT

The invention provides processes for improving the ability of a peptide to stimulate an immune response, comprising exposing the peptide to a chemical modifying agent. It further provides compositions comprising an antigenic peptide, wherein the peptide has been treated with a chemical modifying agent to improve its ability to stimulate an immune response. It also provides methods of stimulating an immune response in a mammal, comprising administering to the mammal an effective amount of a vaccine.

14 Claims, 3 Drawing Sheets

(56) References Cited

OTHER PUBLICATIONS

Libby, Jeffrey M. et al., "Effects of the Two Toxins of *Clostridium difficile* in Antibiotic-Associated Cecitis in Hamsters," Infect. Immun., vol. 36, No. 2, Jan. 11, 1982, pp. 822-829 (8 pages).

Rappuoli, Rino, "Toxin Inactivation and Antigen Stabilization: Two Different Uses of Formaldehyde," Vaccine, vol. 12, No. 7, 1994, pp. 579-581 (3 pages).

Torres, Javier F. et al., "Evaluation of Formalin-Inactivated *Clostridium difficile* Vaccines Administered by Parenteral and Mucosal Routes of Immunization in Hamsters," Infect. Immun., vol. 63, No. 12, Sep. 21, 1995, pp. 4619-4627 (9 pages).

* cited by examiner

CHEMICALLY MODIFIED PEPTIDES WITH IMPROVED IMMUNOGENICITY

CROSS REFERENCE TO RELATED APPLICATIONS

This application claims the benefit of U.S. Provisional Application Nos. 60/929,125, filed Jun. 14, 2007, 60/960,771, filed Oct. 12, 2007, and 61/060,978, filed Jun. 12, 2008 (USPTO confirmation No. 8650), the entire disclosure of each of which is relied upon and incorporated by reference in its entirety.

SEQUENCE LISTING

The instant application contains a Sequence Listing which has been submitted via EFS-Web and is hereby incorporated by reference in its entirety. The ASCII copy, created on Jul. 22, 2010, is named 09613037.txt, and is 211,203 bytes in size.

FIELD OF THE INVENTION

The present invention relates to methods of preparing compositions and vaccines comprising chemically modified peptides. The invention also includes compositions and vaccines comprising chemically modified peptides.

BACKGROUND

Many viruses and toxins require inactivation before they can be used as vaccines and chemical modifying agents such as formaldehyde have been widely used in vaccine production. Notable examples include, for instance, polio, tetanus, diphtheria, botulinum and anthrax vaccines. Protein modification by formaldehyde is complex and involves the chemical modification of several amino acid residues (such as arginine and lysine) and also the formation of cross-links (methylene bridges) which can lead to extensive protein aggregation (Metz et al. (2004) J. Biol Chem., 279: 6235-6243).

The use of formaldehyde for vaccine production does have its drawbacks, the most common of which is the modification of protein structure which results in a loss of immunogenic epitopes and an over all decrease in the immunogenicity of the protein (Vani et al. (2006) J. Immunol Methods. 317, 80-89). However, for some small proteins, formaldehyde has been reported to enhance the immune response through protein aggregation. For instance, it has been reported that formaldehyde treatment increases the immunogenicity and decreases the toxicity of low molecular weight *Haemophilus ducreyi* cytolethal distending toxins (HdCDT) (Lagergard et al. (2007) Vaccine: 25, 3606-14). Problems associated with formaldehyde treatment, particularly the frequent reduction of immunogenicity and the complexity of the final product through aggregation, have led to a decline in its use, especially with the introduction of recombinant technology which provides a means of rendering harmful proteins inactive through site directed mutagenesis.

The *botulinum* neurotoxins (BoNTs) are a family of seven antigenically different protein toxins (serotypes A-G). These neurotoxins are extremely potent neuroparalytic agents which act primarily at the peripheral nervous system where they inhibit the release of acetylcholine at the neuromuscular junction (Niemann (1991) In Sourcebook of Bacterial Protein Toxins (Alouf, J. E. & Freer, J. H. eds.), pp. 303-348, Academic Press, London). This is mediated via highly specific zinc-dependent endopeptidase activity directed at small proteins involved in the fusion and release of synaptic vesicles.

The *botulinum* neurotoxins are structurally similar; they have 30-40% sequence homology and, as diagrammatically shown immediately below, each neurotoxin consists of a heavy chain (100 kDa) and a light chain (50 kDa) linked by a disulphide bridge (Niemann, 1991, as above). Despite structural similarities, antisera raised against purified neurotoxins show no cross-protection between the neurotoxin serotypes and thus necessitate the development of a separate vaccine for each serotype. In addition, within each serotype, various subtypes exist (Minton (1995) In: Current Topics in Microbiology and Immunology 195 'Clostridial Neurotoxins' (Montecucco, C., ed.) pp. 161-194, Springer, Berlin). Since these subtypes differ in their antigenic properties, the presence of these toxin variants needs to be taken into account in vaccine design to ensure adequate cross protection.

Structure of *Botulinum* Neurotoxins and the $LH_N$ Fragment

The C-terminal 50 kDa fragment ($H_C$ fragment) is responsible for receptor-binding at the presynaptic nerve surface (Halpern & Loftus (1993) J. Biol. Chem. 268, 11188-11192); (Shone et al. (1985) Eur. J. Biochem., 151, 75-82). The N-terminal 50 kDa portion of the heavy chain ($H_N$ fragment) is involved in translocation of the enzymatically active light chain to within the nerve terminal (Shone et al. (1987) Eur. J. Biochem., 167, 175-180). Removal of the $H_C$ domain from the BoNT leaves a fragment ($LH_N$) consisting of the light chain and translocation domain which, although virtually non-toxic, is stable and soluble. Any residual toxicity is eliminated by double mutations in the enzymatic domain yielding a non-toxic $LH_N$ vaccine.

Tetanus and the *botulinum* neurotoxin are extremely potent, bacterial neurotoxins produced by various strains of *Clostridia*. The *botulinum* neurotoxins consist of seven distinct serotypes and a separate vaccine is required for each. First generation tetanus and *botulinum* vaccines consist of purified or partially purified toxins treated with formaldehyde to eliminate the neurotoxic action of these protein toxins. In the case of the *botulinum* toxins, complete detoxification requires incubation of toxin preparations for over three weeks in order to generate the toxoid vaccine derivative. In addition, since the *botulinum* toxins are in the form of high molecular weight (300-900 kDa) protein complexes, the resulting toxoid product is an extremely heterogeneous mixture consisting of very high molecular weight species (Singh et al. (1989) Toxicon 27, 403-410). Another disadvantage of formaldehyde treatment is that in the case of some of the *botulinum* toxoid serotypes (e.g., type A), several epitopes are destroyed in the prolonged toxoiding process (Hallis et al. (1993) Characterization of monoclonal antibodies to BoNT/A. In: *Botulinum* and Tetanus Neurotoxins, (DasGupta, B., Ed.) p 433-436, Plenum Press).

Second generation *botulinum* vaccines are based on non-toxic fragments of the *botulinum* toxins and are designed to eliminate the requirement for a detoxification step with formaldehyde. One such vaccine candidate is the $LH_N$ fragment (light chain domain plus $H_N$ translocation domain), which consists of the N-terminal two-thirds of the *botulinum* neurotoxin moiety. This fragment is a single chain polypeptide which lacks the ability of the parent neurotoxin to bind to nerve endings and in addition may contain one or more amino acid mutations within the light chain domain to render it completely non-toxic. In addition to being non-toxic, the $LH_N$ fragments are easy to characterize being monomeric in solution with none of the complex aggregation associated with the corresponding toxoid which is normally purified as a toxin complex. See, for instance, U.S. patent application Ser. Nos. 11/717,713 and 11/077,550, which are herein incorporated by reference in their entireties.

The diversity within the BoNT family is a major problem for vaccine design and the extent of this problem is only now becoming appreciated. While it is widely recognised that the different BoNT serotypes are antigenically distinct and require separate vaccines, it is less well appreciated that antigenically different sub-types exist within each of the main BoNT serotypes (Smith et al (2005) Infect Immum, 73:5450-5457). BoNT/A, for example, is now known to contain at least 4 sub-types and a similar number of sub-types exists within the BoNT/B family. Differences in the primary structure within the various subtypes are reflected in differences in their antigenic profile, with the result that a vaccine which protects against one toxin subtype may not protect against another. Providing adequate protection against toxin sub-types is an important consideration for vaccine design.

There is therefore a need for improved *botulinum* and tetanus vaccines, such as vaccines having one or more of: an improved protective effect; improved stability; improved cross-serotype protection; and improved cross-subserotype protection.

In addition to the above-mentioned clostridial species, *Clostridium difficile* is now a major problem as a healthcare acquired infection (HCAI). The bacterium causes nosocomial, antibiotic-associated diarrhoea and pseudomembranous colitis in patients treated with broad-spectrum antibiotics. Elderly patients are most at risk from these potentially life-threatening diseases and incidents of hospital infection have increased dramatically over the last 10 years. Strains of *C. difficile* produce a variety of virulence factors, notable among which are several protein toxins: Toxin A, Toxin B and, in some strains, a binary toxin which is similar to *Clostridium perfringens* Iota toxin. Toxin A is a large protein cytotoxin/enterotoxin, which plays a key role in the pathology of infection and which also appears to have some role in the gut colonisation process. Toxin B, which is primarily a cytotoxin, appears to act synergistically with Toxin A.

Antibodies to Toxins A and B have been shown to protect against *Clostridium difficile* associated disease and hence non-toxic fragments of either Toxin A, B, or the binary toxin have potential as vaccines or as antigens for producing therapeutic antibodies. Recombinant fragments of *Clostridium difficile* toxins, however, generally do not produce a strong neutralising response in animals in conjunction with an adjuvant such as aluminium hydroxide (e.g., Alhydrogel).

Again, there is therefore the need for an improved *C. difficile* vaccine such as a vaccine having one or more of: an improved protective effect; and improved stability.

Anthrax is an acute infectious disease in humans and animals that is caused by the bacterium *Bacillus anthracis* and which in some forms is lethal. Protective antigen (PA), lethal factor (LF) and edema factor (EF) are components of anthrax toxin which play a key role in mediating its biological effects and the disease. PA contains domains that bind cell receptors and which can effect the translocation of EF and LF into cells. Once inside the cell, LF and EF have lytic actions via different mechanisms. PA, EF, and LF on their own are non-toxic and are only active in combinations in which one component is PA.

Since PA is the common factor required for both the actions of LF and EF, a recombinant fragment has been assessed as a vaccine for anthrax. Recombinant PA, however, does not elicit a strong protective response against the disease and there have also been issues with its stability.

There is therefore the need for an improved anthrax vaccine, such as a vaccine having one or more of: an improved protective effect; and improved stability.

SUMMARY OF THE INVENTION

The invention provides a method of increasing the protective effect or improving the stability of a peptide or polypeptide by chemically modifying it. In some embodiments, the increased protective effect is an improved ability to stimulate an immune response. In other embodiments, the increased protective effect may be improved cross-serotype protection. In yet other embodiments, the increased protective effect may be improved cross-subtype protection. In still other embodiments, the increased protective effect is a combination of one, two, or three of an improved ability to stimulate an immune response, an improved cross-serotype protection, and an improved cross-subtype protection. Often, although not always, the increased protective effect of the peptide or polypeptide is associated with an increase in stability of the peptide or polypeptide.

In one embodiment, the increase in the protective effect or the improvement of the stability of a peptide is due to the formation of cross-linking or methylene bridges induced by the chemical agent. For instance, the invention includes methods of treating a *Clostridium* neurotoxin fragment with a chemical agent such as formaldehyde that induces the formation of methylene bridges between arginine, lysine and histidine residues.

In one embodiment, the increased protective effect of the methods and vaccine compositions of the invention is not due to polypeptide aggregation. In another embodiment, the increased protective effect is the result of little to no polypeptide aggregation. Specifically, the invention includes methods of treating a bacterial peptide with a chemical agent in such a manner that does not result in peptide aggregation or that does not result in a significant increase in peptide aggregation. For instance, the invention includes treating a *Clostridium* neurotoxin fragment with a chemical agent such as formaldehyde under conditions that do not result in aggregation or a significant amount of aggregation.

In one embodiment, the method involves contacting the peptide or polypeptide with a chemical modification agent for a brief period of time or for a time sufficient to obtain a desired property in the peptide or polypeptide. For instance, in some embodiments, the peptide or polypeptide is contacted with the chemical modification agent such as formaldehyde for a period of less than about 5 days, less than about 4 days, less than about 3 days, less than about 2 days, less than about 1 day, or less than about 12 hours.

In one embodiment of the invention, a chemical modification agent that induces cross-linking increases the immunogenicity and/or stability of a bacterial peptide. In another embodiment, a chemical modification agent that induces methylene bridging increases the immunogenicity and/or stability of a bacterial peptide. In one embodiment of the invention, the chemical modification agent is formaldehyde. However, other agents may also be used. For instance, additional chemical modification agents that induce cross-linking or formation of methylene bridges, include, but are not limited to, C6-succinimidyl 4-hydrazinonicotinate acetone hydrazone, C6-succinimidyl 4-formylbenzoate, BIS-(Sulfosuccinimidyl) suberate, disuccinimidyl suberate, dimethyl suberimidate dihydrochloride, dimethyl pimelimidate 2 HCl, dimethyl adipimidate dihydrochloride, succinimidyl 4-hydrazidoterephthalate hydrochloride, and disuccinimidyl glutarate.

Irrespective of the identity of the chemical modification agent, many embodiments use the agent at a low concentration. In those embodiments, the concentration is less than about 2% (v/v or w/v based on the ratio of the modifying agent to the total reaction mixture). Alternatively, the concentration may be expressed as a molar ratio of agent:polypeptide, in which case the ratio is generally between about 3:1 and about 50:1. In addition, the temperature at which the chemical modification agent and the peptide or polypeptide are contacted may vary. In many embodiments, the contact temperature is between about 3° C. and about 45° C.

Immunogenicity, the protective effect and/or stability of many different peptides or polypeptides can be increased by chemical modification in accordance with the methods of the invention. For example, the methods may be used to increase the protective effect of clostridial neurotoxins. Examples of such clostridial peptides and polypeptides include *C. botulinum* BoNT/A, *C. botulinum* BoNT/B, *C. botulinum* BoNT/E, tetanus toxin, and the different subtypes of each of the BoNT serotypes (e.g., BoNT/A1, BoNT/A2 and BoNT/A3). In various embodiments, the peptide or polypeptide is the native clostridial neurotoxin, a recombinant protein modified to render it non-toxic, or fragments, which may also have been rendered nontoxic via amino acid substitutions or deletions. In other embodiment, the clostridial neurotoxin is a fusion protein comprising a native clostridial neurotoxin, recombinant neurotoxin or neurotoxin fragment and a second polypeptide. The second polypeptide includes, for instance, a toxin (native, recombinant or fragment), a polypeptide useful for the isolation and/or isolation of the fusion protein, and/or a polypeptide useful for increasing the stability of the fusion protein.

Clostridial fragments encompassed by the methods of the present invention include, but are not limited to, the $LH_N$ fragment of BoNT or tetanus toxin. In one embodiment, the Clostridial peptides do not comprise a $H_c$ fragment. Further the Clostridial polypeptides and fragments may be modified so that they are endopeptidase-negative. For instance, in one embodiment, the Clostridial peptide is a formaldehyde-treated $LH_N/E$ fragment modified to be endopeptidase negative. In another embodiment, the Clostridial peptide is a formaldehyde-treated $LH_N/A$ fragment modified to be endopeptidase negative. In yet another embodiment, the Clostridial peptide is a formaldehyde-treated $LH_N/B$ fragment modified to be endopeptidase negative.

In still other embodiments, the methods are useful for increasing the immunogencity and/or stability of *Clostridium difficile* peptides and polypeptides, for instance, *Clostridium difficile* toxins or toxin fragments or toxin fusion proteins. For example, the invention includes, but is not limited to, *Clostridium difficile* Toxin A, Toxin B, binary toxin, or *Clostridium difficile* surface peptides, such as the Cwp 84 peptide.

In yet other embodiments, the methods are useful for increasing the immunogencity and/or stability of *Bacillus anthracis* polypeptides and peptides. Examples include lethal factor and protective antigen. Of course, there are many other peptides and polypeptides for which it is desirable to increase their protective effect, and those peptides and polypeptides are also encompassed by the invention.

The invention also provides compositions comprising chemically modified peptides and polypeptides. In some embodiments, the chemically modified peptides and polypeptides have an increased protective effect that may be measured by their improved ability to stimulate an immune response when compared to an unmodified peptide or polypeptide. In other embodiments, the increased protective effect may be measured by the ability to provide improved cross-serotype protection when compared to an unmodified peptide or polypeptide. In yet other embodiments, the increased protective effect may be measured by the ability to provide improved cross-subtype protection when compared to an unmodified peptide or polypeptide. In still other embodiments, the increased protective effect may be measured by a combination of one, two, or three of the ability to provide an improved immunogenicity, induce a protective immune response, provide an improved cross-serotype protection, and provide an improved cross-subtype protection. Often, although not always, the peptide or polypeptide may display an increase in stability compared to the unmodified peptide or polypeptide. The increased immunogenicity and/or stability is due, at least in some embodiments, to intramolecular cross-links, such as those comprising one or more methylene bonds. Also, in some embodiments, the peptide or polypeptide does not form aggregates.

Vaccines comprising one or more of the chemically modified peptides or polypeptides are also provided. In one embodiment, the vaccine comprises a *Clostridium botulinum* $LH_N$ fragment that has been treated with formaldehyde for less than about 5 days, less than about 4 days, less than about 3 days, less than about 2 days or less than about 1 day. In one embodiment, the formaldehyde-treated $LH_N$ fragment is modified to to be endopeptidase negative and is a $LH_N/A$, $LH_N/B$ or $LH_N/E$ fragment. The invention includes, for instance, a bivalent or trivalent vaccine comprising one or more of formaldehyde-treated, endopeptidase negative $LH_N/A$, $LH_N/B$ or $LH_N/E$ fragments.

The vaccine may further comprise one or more adjuvants. One non-limiting example of an adjuvant is aluminium hydroxide. In one embodiment, the invention includes a monovalent, bivalent or trivalent vaccine comprising one or more of formaldehyde-treated, endopeptidase negative $LH_N/A$, $LH_N/B$ or $LH_N/E$ fragments and an adjuvant.

The invention also provides methods of stimulating an immune response in a mammal, such as a human, by administering to the mammal an amount of a vaccine of the invention sufficient to stimulate an immune response. The invention includes a method of stimulating an immune response in a subject comprising administering to the subject a monovalent, bivalent or trivalent vaccine comprising one or more of formaldehyde-treated, endopeptidase negative $LH_N/A$, $LH_N/B$ or $LH_N/E$ fragments and, optionally, an adjuvant. The invention also includes, for instance, a method of stimulating an immune response in a subject comprising administering to the subject a vaccine comprising a chemically modified bacterial peptide from a BSL-3 pathogen or BSL-4 pathogen, such as *B. anthracis*.

In some embodiments, immune stimulation is measured by an increased protective effect compared to a vaccine comprising the unmodified form of the same peptide or polypeptide. In other embodiments, immune stimulation is measured by an increase in antibody titer that is specific for the antigen in the vaccine. In still other embodiments, immune stimulation is measured by an increased frequency in cytotoxic T lymphocytes specific for the antigen in the vaccine.

The invention also provides methods of preventing or treating an infection in a subject comprising administering a chemically modified bacterial peptide of the invention to a subject. In one embodiment of the invention, the peptide is administered at a dose necessary to induce a protective immune response. In one embodiment, the peptide is administered at a dose necessary to produce neutralizing antibodies. The invention includes, for instance, methods of preventing or treating a Clostridium botulinum invention in a subject comprising administering to the subject a monovalent, bivalent or trivalent vaccine comprising one or more of formaldehyde-treated, endopeptidase negative $LH_N/A$, $LH_N/B$ or $LH_N/E$ fragments and, optionally, an adjuvant.

The invention also provides antisera isolated from animals that have been immunized with a vaccine of the invention. In some embodiments, the antiserum is purified to provide a monoclonal or polyclonal population of antibodies that are specific for the antigen in the vaccine. In one embodiment of the invention, the antisera is isolated from an animal administered one or more peptides of the invention, for instance, one or more of a formaldehyde-treated, endopeptidase negative $LH_N/A$, $LH_N/B$ or $LH_N/E$ fragment. In one embodiment, the isolated and purified population of monoclonal or polyclonal antibodies are from an animal administered one or more peptides of the invention, for instance, one or more of a formaldehyde-treated, endopeptidase negative $LH_N/A$, $LH_N/B$ or $LH_N/E$ fragment.

The purified polyclonal antibodies may provide improved survival when administered to an animal prior to or shortly after exposure to a toxic form of the antigen (such as an agent comprising the toxic form of the antigen) used to prepare the vaccine. The invention includes methods of preventing or treating an infection in a subject comprising administering a population of antibodies to the subject pre- or post-infection, wherein said antibodies are isolated from the antisera from animals administered one or more of the peptides of the invention. In one embodiment, the purified antibodies are specific to one or more of an endopeptidase negative $LH_N/A$, $LH_N/B$ or $LH_N/E$ fragment.

DETAILED DESCRIPTION OF THE INVENTION

Figure 1:
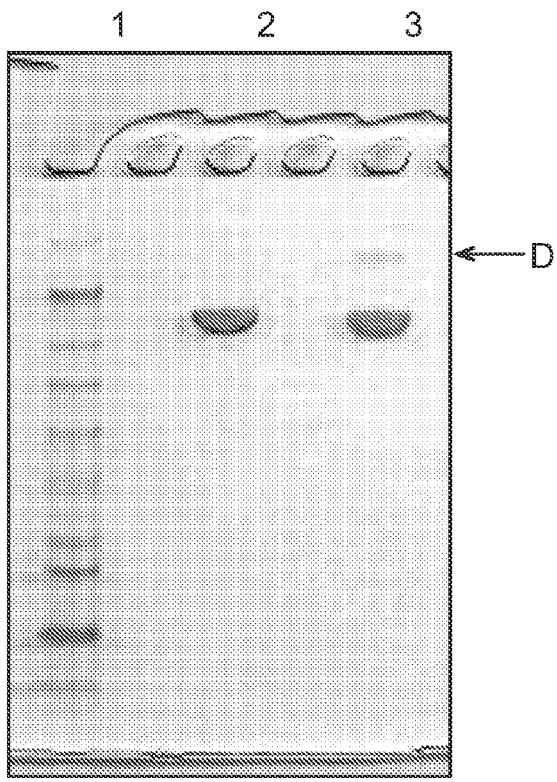
FIG. 1 shows an SDS-PAGE of formaldehyde-treated and control $LH_N/A$ vaccine. Lane 1: mass markers. Lane 2: control $LH_N/A$. Lane 3: formaldehyde-treated $LH_N/A$. 'D' indicates the position of the $LH_N/A$ dimer if it is present.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents defines a term that contradicts that term's definition in the application, the definition in this application controls.

The use of the singular includes the plural unless specifically stated otherwise. The word "a" or "an" means "at least one" unless specifically stated otherwise. The use of "or" means "and/or" unless stated otherwise. The meaning of the phrase "at least one" is equivalent to the meaning of the phrase "one or more." Furthermore, the use of the term "including," as well as other forms, such as "includes" and "included," is not limiting. Also, terms such as "element" or "component" encompass both elements or components comprising one unit and elements or components comprising more than one unit unless specifically stated otherwise.

I. Definitions

In order that the present invention may be more readily understood, certain terms are first defined. Additional definitions are set forth throughout the detailed description.

BoNT: botulinum neurotoxin. When a letter follows this designation, the letter indicates the serotype. For example, BoNT/A is botulinum neurotoxin type A.

$LH_N$: a fragment of a clostridial neurotoxin (botulinum or tetanus) of approximately 100 kDa which may be a single-chain or di-chain molecule comprising the light chain and the $H_N$ domain. The latter domain represents the N-terminal 50 kDa of the neurotoxin heavy chain and is closely associated with the light chain domain in the fragment.

C. difficile Toxins A and B—large peptide toxins (approx 300 kDa) with cytotoxic and enterotoxic activity which are the principal virulence factor of the C. difficile.

C. difficile surface peptide—peptides which are expressed by the bacterium and which are presented on its outer surface. Such peptides play a role in adhesion to the gut wall. More than 29 genes with the prefix cwp (cell wall peptides) have been identified within the C. difficile genome. Examples of C. difficile surface peptides are described in Pechine et al. (2005) J. Clinical Microbiol. 43, 5018-5025, which reference is hereby incorporated by reference in its entirety.

Protective antigen (PA)—the component of anthrax toxin (approx 83 kDa) which contains the receptor-binding and translocation domains. PA binds to cell receptors and is activated by surface proteases. This allows either anthrax lethal factor or edema factor to bind and internalise within the cell. PA peptides may be modified to lack a functional binding site, thereby preventing PA from binding to either Anthrax Toxin Receptor (ATR) - see Bradley, K.A., et al (2001) to which native PA binds, or to native LF. By way of example, a modification made within or near to amino acid residues 315-735, or in some embodiments within or near to residues 596-735 of Domain 4, may render PA incapable of binding to ATR. Alternatively (or in addition), the PA furin cleavage site (i.e., amino acid residues 193-196 of SEQ ID NO: 16) may be inactivated. Furin is an enzyme that activates native PA (i.e., the 83 kDa form) in vivo into the 63 kDa form by proteolytic cleavage, and thus exposes a specific binding site for which LF and EF compete in order to form LT and ET, respectively. One or more amino acid residue changes (i.e., deletion, insertion, or substitution) within or near to the furin cleavage site (RKKR (SEQ ID NO: 29)) may inactivate the furin cleavage site and thereby inactivate PA. By way of example, all of residues 193-196 of native PA (i.e. SEQ ID NO: 16) may be deleted.

Lethal factor (LF)—a component of anthrax toxin containing an endopeptidase activity which can modify proteins in mammalian cells leading to cell death. LF peptides may be modified to lack a functional binding site for PA. By way of example, LF peptides may include a modification within or near to the N-terminal Domain of LF, such as within or near to amino acid residues 1-255. Particular examples include mutagenesis of the VYYEIGK (SEQ ID NOS: 17 and 18) motif of LF (residues 180-186), which renders LF unable to bind to PA. Usually, one or more of the tyrosine, isoleucine, or lysine residues are modified to prevent binding to PA and hence formation of active toxins. Alternatively (or in addition) LF peptides may be modified to lack a functional endopeptidase activity or zinc-binding site. By way of example, LF peptides may include a modification within or near to the C-terminal Domain of LF, such as within or near to the "HEFGHAV" (SEQ ID NOS: 17 and 18) motif found around residues 719-725 of the native LF sequence.

Edema factor (EF)—a component of anthrax toxin containing an enzyme activity which can modify proteins in mammalian cells leading to cell lysis. EF peptides may be modified to lack a functional binding site for PA. By way of example, EF peptides may include a modification within or near to the N-terminal Domain of EF, such as within or near to amino acid residues 1-250 of SEQ ID NO: 21 or 22. Alternatively (or in addition), EF peptides may be modified to lack adenylyl cyclase activity e.g. by mutagenesis of histidine 351 to alanine (SEQ ID NO 22). By way of example, EF peptides may include a modification within or near to the ATP-binding site (e.g., residues 314-321 of SEQ ID NO: 21 or 22) and/or within or near to the calmodium-binding site (e.g., residues 613-767 of SEQ ID NO: 21 or 22). Particular examples include mutagenesis of the VYYEIGK motif, which is found at residues 169-175 of EF (SEQ ID NO: 21 or 22). Mutations in this motif render EF unable to bind to PA. Usually, one or more of the tyrosine, isoleucine, or lysine residues are modified to prevent binding to PA and hence formation of active toxins.

Isolated: a molecule that is substantially free of its original environment. For instance, an isolated peptide is substantially free of material or other proteins from the cell, bacterial, or tissue source from which it was derived.

Purified: a molecule that is substantially free of its original environment and is sufficiently pure for use in pharmaceutical compositions. A substantially pure peptide, as used herein, refers to a peptide at least about 50% (w/w) pure; at least about 60% (w/w) pure; or at least about 70% (w/w) pure; or at least about 80% (w/w) pure; or at least about 85% (w/w/) pure; or at least about 90% (w/w) pure; or at least about 95% (w/w) pure; or at least about 95%, 96%, 97%, 98%, 99%, or 100% (w/w) pure.

Bacterial peptide: refers to proteins, polypeptides, peptides or fragments or variants thereof, wherein the nucleic acid encoding the peptide is derived from a bacterium. The terms peptide, polypeptide and fragment are used interchangeably herein. The term bacterial peptide includes native peptides and recombinant peptides. The bacterial peptide of the invention can be a toxin.

In one embodiment of the invention, the bacterial peptide is a recombinant peptide or toxin fragment. Recombinant bacterial peptides include fusion proteins. For instance, the present invention includes fusion proteins comprising a first bacterial peptide fused to a second peptide, wherein the second peptide is useful for the purification and/or half-life extension of the bacterial peptide.

The peptide may be expressed by the bacterium or may be expressed by a host cell such as a non-pathogenic bacterial host cell, yeast host cell, or mammalian host cell. The bacterial peptide of the invention can be derived from a highly pathogenic bacterium, for instance, *Clostridium difficile, Clostridium botulinum, C. tetani, Bacillus anthracis* or other biosafety level 3 or 4 (BSL-3 or BSL-4) pathogen.

The bacterial peptide may be a fragment of a toxin, for instance, a *Clostridium* $LH_N$ fragment or other non-toxic fragment. Toxin fragments may be prepared by treating native toxins with trypsin. Toxin fragments may comprise a truncated portion of the Hc domain as disclosed in WO 2007/044382, which is herein incorporated by reference in its entirety.

Toxin fragments such as the *Clostridium* $LH_N$ fragment may contain amino acid modifications. For instance, the term bacterial peptide includes $LH_N$ fragments which have been modified to reduce endopeptidase activity and/or have been codon optimized for expression in a host system (e.g., *E. coli*).

In one embodiment of the invention, the bacterial peptide is a therapeutic peptide. In one embodiment of the invention, the peptide elicits a protective immune response when administered to a subject.

The bacterial peptide of the invention can be a moderate to high molecular weight protein in its native state. In one aspect of the invention, the bacterial peptide of the invention is not a low molecular weight peptide. As defined herein, a low molecular weight protein is a protein that less than about 50 kDa. Accordingly, the bacterial peptide of the present invention includes peptides that are at least about 50 kDa, 55 kDa, 60 kDa, 65 kDa, 70 kDa, 75 kDa, 80 kDa, 85 kDa, 90 kDa, 95 kDa, 100 kDa, 105 kDa, 110 kDa, 115 kDa, 120 kDa, 125 kDa, 130 kDa, 135 kDa, 140 kDa, 145 kDa, 150 kDa, 155 kDa, 160 kDa, 165 kDa, 170 kDa, 175 kDa, 180 kDa, 185 kDa, 190 kDa, 195 kDa or 200 kDa or more. Molecular weight can be determined by methods known in the art, for instance, SDS PAGE. Small molecular weight proteins that aggregate to form high molecular weight complexes are not considered to be high molecular weight peptides.

Minimally aggregated: refers to the aggregation or clumping of peptides. The term "minimally aggregated" distinguishes the chemically treated peptide (or population of peptides) of the invention from aggregated peptides that result from prolonged treatment with a chemical-modification agent (such as formaldehyde) as required for detoxification of a toxin.

A minimally aggregated peptide or polypeptide (or population of peptides or polypeptides) can be monomeric or at least predominantly monomeric. A peptide or polypeptide (or population of peptides or polypeptides) is predominantly monomeric if it is, for instance, it is greater than about 70%, 75%, 80%, 85%, 90%, 95%, or even 98% monomeric. In one embodiment, a minimally aggregated population of peptides or polypeptides is at least about 75%, 80%, 85%, 90%, 95%, or even 98% monomeric and dimeric. For instance, included in the definition of minimally aggregated peptides is a population of peptides or polypeptides comprising monomers, dimers and trimers, wherein the population of peptides or polypeptides is at least about 75%,%, 80%, 85%, 90%, 95%, or even 98% monomeric and dimeric.

A population of chemically-modified peptides of the present invention exhibit at least about 1.5 fold, 2 fold, 3 fold, 4 fold, 5 fold, 6 fold, 7 fold, 8 fold, 9 fold, 10 fold, 12 fold or 15 fold less peptide aggregation compared a population of peptides treated with a chemical-modifying agent according to traditional chemical detoxification protocols (e.g., treatment with formaldehyde up to about 25 days). For instance, the chemically-modified peptides of the invention can comprise at least about 2 fold, 3 fold, 4 fold, 5 fold, 6 fold, 7 fold, 8 fold, 9 fold, or 10 fold or fewer trimers or larger complexes than peptides treated with a chemical-modifying agent under conditions required for detoxification (e.g., treatment for a prolonged period of time such as treatment with formaldehyde for up to about 25 days).

The peptides of the invention may be partially purified, substantially purified or purified prior to determination of aggregation.

Endopeptidase negative: displays no endopeptidase activity by conventional assays. In one embodiment, a *Clostridium* neurotoxin or neurotoxin fragment (e.g., $LH_N$) is made endopeptidase negative by modifying one or two or more amino acids by methods known in the art. Amino acid modifications that confer an endopeptidase negative phenotype, include, but are not limited to modifications at residues E224 and/or H227 for *C. botulinum* type A neurotoxin or fragments such as $LH_N$/A (see, for instance, SEQ ID NOs: 1, 2, 3, 8 and 9 which can be modified at one or both of amino acids E224 and H227); residues E231 and/or H234 for *C. botulinum* type B neurotoxin or fragments such as $LH_N$/B (see, for instance, SEQ ID NOs: 6, 23 and 24, which can be modified at one or both of amino acids E231 and H234); and residues E213 and/or H216 for *C. botulinum* type E neurotoxin or fragments such as LHN/E (see, for instance, SEQ ID NOs: 4, 25, 26 and 27, which can be modified at one or both of amino acids E213 and H216. For instance, the invention includes $LH_N$/A comprising E224Q and/or H227Y modifications, $LH_N$/B comprising E231Q and/or H234Y modifications and $LH_N$/E comprising E213Q and/or H216Y modifications.

An example of an assay that can be used to measure the endopeptidase activity of the *botulinum* neurotoxins is described in detail by Hallis et al. (1996) J. Clinical Microbiol. 34:1934-1938, which is incorporated by reference. Thus, absence of detectable endopeptidase activity in the Hallis assay provides a functional definition of "endopeptidase negative."

Protease cleavage site: native proteins may comprise one or more natural protease cleavage sites (e.g., a trypsin cleavage site). For example, the clostridial neurotoxin holotoxin includes a cleavage site located between the L-chain and the H-chain. Cleavage of that site results in the formation of a di-chain molecule, wherein the L-chain and the H-chain are linked together via a disulphide bond. In some embodiments of the invention, a protein, polypeptide, or peptide may include one, some, or all of its native cleavage sites. Examples of native protease cleavage site, and methods of inactivating them, are described elsewhere for the various proteins, polypeptides, and peptides. In some embodiments, however, it is desirable to include a non-native cleavage site, for example, to permit 'controlled' cleavage. For example, in the case of clostridial holotoxin, a non-native cleavage site may be inserted to permit controlled cleavage of the single chain molecule into its di-chain counterpart. Suitable non-native cleavage sites include those for enterokinase (DDDDK↓ (SEQ ID NO: 30)), Factor Xa (IEGR↓ (SEQ ID NO: 31)/IDGR↓ (SEQ ID NO: 32)), TEV(Tobacco Etch virus) (ENLYFQ↓G (SEQ ID NO: 33)), thrombin (LVPR↓GS (SEQ ID NO: 34)), and PreScission (LEVLFQ↓GP (SEQ ID NO: 35)), but other non-native cleavage sites may also be used. Also embraced by the term protease cleavage site is an intein, which is a self-cleaving sequence. The self-splicing reaction is controllable, for example by varying the concentration of reducing agent present.

Intra-molecular cross-linking: chemical bonding introduced within a peptide molecule such that non-contiguous peptide sequences of the same molecule become linked together. Intra-molecular cross-linking does not cross-link different peptide molecules together (this would require inter-molecular cross-linking), and there is little or no aggregation resulting in the generation of higher molecular weight species. The peptides of the present invention include at least one introduced intra-molecular bond. Intra-molecular cross-linking may be demonstrated by SDS-polyacrylamide gel electrophoresis (SDS-PAGE), which displays peptides as bands according to molecular size. A molecule which has been intra-molecularly cross-linked by a chemical agent appears as a peptide band of similar size on SDS-PAGE to the untreated molecule. If, however the molecule is treated with a protease (e.g., trypsin) then the untreated molecule will appear as fragments on SDS-PAGE while the intra-molecularly cross-linked molecule will remain the same size as the original molecule demonstrating a change in peptide tertiary structure of the molecule such that it is no longer susceptible to digestion with the protease (e.g., trypsin) under the conditions of digestion tested. In one embodiment of the present invention, the clostridial intramolecular bond(s) crosslink the L-chain (or fragment thereof) to the H-chain (or fragment thereof).

Antibody: an immunoglobulin or fragment thereof. The term encompasses any polypeptide comprising an antigen-binding fragment or an antigen-binding domain. Examples include, but are not limited to, polyclonal, monoclonal, monospecific, polyspecific, non-specific, humanized, human, single-chain, chimeric, synthetic, recombinant, hybrid, mutated, grafted, and in vitro generated antibodies. An antisera refers to a population of antibodies in serum that possess detectable binding, e.g., by ELISA or flow cytometry, for a particular antigen. Unless preceded by the word "intact", the term "antibody" includes antibody fragments such as Fab, F(ab')$_2$, Fv, scFv, Fd, dAb, and other antibody fragments that retain antigen-binding function. The present invention is not necessarily limited to any particular source, method of production, or other special characteristics of an antibody, unless the context makes clear that such a limitation is intended. Further, particularly when used in the context of diagnostic or therapeutic embodiments, the antibodies may be tagged with a detectable or functional label. These labels include radiolabels (e.g., $^{131}I$ or $^{99}Tc$), enzymatic labels (e.g., horseradish peroxidase or alkaline phosphatase), and other chemical moieties (e.g., biotin).

Specific binding: formation of a complex between two or more molecules that is relatively stable under physiologic conditions. Specific binding is characterized by a high affinity and a low to moderate capacity, as distinguished from nonspecific binding which usually has a low affinity with a moderate to high capacity. Typically, binding is considered specific when the association constant $K_A$ is higher than $10^6 \, M^{-1}$. If necessary, nonspecific binding can be reduced without substantially affecting specific binding by varying the binding conditions. The appropriate binding conditions, such as concentration of antibodies, ionic strength of the solution, temperature, time allowed for binding, concentration of a blocking agent (e.g., serum albumin, milk casein), etc., may be optimized by a skilled artisan using routine techniques.

Effective amount: a dosage or amount that is sufficient to achieve a desired biological outcome. As used herein, a "therapeutically effective amount" refers to an amount which is effective, upon single or multiple dose administration to a subject (such as a human patient) at treating, preventing, curing, delaying, reducing the severity of, ameliorating at least one symptom of a disorder or recurring disorder, or prolonging the survival of the subject beyond that expected in the absence of such treatment.

Treatment: a therapeutic or preventative measure. A treatment may be administered to a subject already having an infection or disease, condition or symptoms associated with an infection. When administered to a subject that already having an infection or disease, condition or symptoms associated with an infection, the therapeutic can cure, delay, reduce the severity of, or ameliorate one or more symptoms, and/or prolong the survival of a subject beyond that expected in the absence of such treatment. Alternatively, it may be administered to one who ultimately may acquire the disorder in order to prevent, cure, delay, reduce the severity of, or ameliorate one or more symptoms of a disorder or recurring disorder, or in order to prolong the survival of a subject beyond that expected in the absence of such treatment. Peptides, vaccines, pharmaceutical compositions, anti-sera and antibodies of the present invention are encompassed, for instance, by the term "treatment."

Vaccine: a composition that, when administered to an animal, stimulates an immune response against an antigen contained within the composition. A vaccine stimulates a protective immune response. The vaccines of the invention can stimulate a humoral and/or cell-mediated immune response when administered to a subject.

A vaccine of the invention can be used, for example, to protect an animal from the lethal effect of a toxin. Vaccine compositions of the invention comprise at least one chemically modified peptide and a pharmaceutically acceptable carrier, excipient, diluent and/or adjuvant. Vaccines include, for instance, monovalent (e.g., a vaccine comprising endopeptidase negative $LH_N/A$ or $LH_N/B$ or $LH_N/E$, bivalent (e.g., a vaccine comprising endopeptidase negative $LH_N/A+LH_N/B$ or endopeptidase negative $LH_N/A+LH_N/E$ or endopeptidase negative $LH_N/B+LH_N/E$) or trivalent (e.g., a vaccine comprising endopeptidase negative $LH_N/A+LH_N/B+LH_N/E$) compositions.

Similarly, multivalent (e.g. bivalent, or trivalent) vaccines of the present invention may include antigens from different sources, for example, a clostridial antigen (such as endopeptidase negative $LH_N/A$ and/or $LH_N/B$ and/or $LH_N/E$) in combination with an anthrax antigen (such as PA and/or LF and/or EF) and/or a *C. difficile* antigen (such as Toxin A peptide and/or Toxin B peptide).

Vaccines of the present invention include passive vaccines, which include corresponding antibodies that bind specifically to peptides of the present invention.

Vaccine efficacy: the ability of a vaccine to protect animals from the lethal effects of toxins. Efficacy can be measured by obtaining an $ED_{50}$ value. The $ED_{50}$ value is the vaccine dose that will protect animals from a pre-defined challenge dose of toxin. In one format of such an assay, animals are injected with varying doses of the vaccine and then at a defined endpoint (e.g., 28 days from the date of immunisation) are challenged with a lethal dose of toxin (e.g., 1000 mouse lethal doses (LD) 50s). The $ED_{50}$ value is then calculated as the vaccine dose that protects 50% of the animals against the challenge dose of toxin. $ED_{50}$ values are commonly expressed as micrograms or nanograms of peptide. The lower the $ED_{50}$ value, the higher the efficacy of the vaccine. The invention includes a chemically modified peptide vaccine with an $ED_{50}$ value at least about 1.5 fold, at least about 2 fold, at least about 2.5 fold, at least about 3 fold, at least about 3.5 fold, at least about 4 fold, at least about 4.5 fold, at least about 5 fold, at least about 10 fold, at least about 15 fold, at least about 20 fold, at least about 25 fold, at least about 30 fold, at least about 35 fold, at least about 40 fold, at least about 45 fold or at least about a 50 fold greater than the $ED_{50}$ value of a vaccine composition comprising an untreated (i.e., not chemically modified) version of the same peptide.

II. Methods of Increasing a Protective Effect

The invention provides methods of increasing the protective effect of a peptide or polypeptide by chemically modifying it. Surprisingly, the inventors of the present invention found that treatment of peptides, including *Clostridium* avirulent neurotoxin fragments, with formaldehyde under conditions that resulted in minimal to no peptide aggregation increased immunogenicity of the peptides.

Protective Effect

In some embodiments, the increased protective effect is due to an improved ability to stimulate an immune response. In other embodiments, the increased protective effect is due to improved cross-serotype protection. In yet other embodiments, the increased protective effect is due to improved cross-subtype protection. In still other embodiments, the increased protective effect is a combination of one, two, or three of an improved ability to stimulate an immune response, an improved cross-serotype protection, and an improved cross-subtype protection. Often, although not always, the increased protective effect of the peptide or polypeptide results from an increase in stability.

Also, in some embodiments, the increased protective effect is not due to aggregation. That is, the peptide or polypeptide is monomeric, or at least predominantly (e.g., greater than about 70, 75, 80, 85, 90, 95, or even 98%) monomeric.

Methods of the invention comprise contacting the peptide or polypeptide with one or more chemical modification agents for a brief period of time or for a period of time sufficient to obtain a desired property in the peptide or polypeptide. In one embodiment of the invention, the peptide is contacted with at least one chemical modification agent for a period of time sufficient to obtain an increase in immunogenicity with minimal to no peptide aggregation.

Treatment with a modifying agent in accordance with the present invention is designed to give minimal aggregation and is carried out over a relatively brief incubation period, for example, when compared with the traditional toxoiding process used in first generation vaccine *botulinum* candidates, which required an incubation period of up to 25 days. Thus, in one embodiment of the invention a vaccine is based on a peptide (e.g. a toxin fragment), which is treated with a modifying agent (e.g. formaldehyde) at a relatively low concentration of modifying agent for a relatively brief incubation period.

Contact Period

The contact period is the time during which the chemical modification agent and the peptide or polypeptide are incubated together in a reaction mixture. The end of the contact period is generally considered the time at which the reaction is stopped, for example, by dialysis of the sample to remove the modification agent or by type of inactivation. As noted, this is generally a brief period of time. For example, the contact period may occur over a period of less than or about 144 hours, less than or about 120 hours, less than or about 96 hours, less than or about 72 hours, less than or about 60 hours, less than or about 48 hours, less than or about 36 hours, less than or about 24 hours, less than or about 18 hours, less than or about 12 hours, less than or about 6 hours, or less than or about 3 hours.

The contact period may also be within a range of time points. For example, in one embodiment, the contact period is from about 3 to about 96 hours, from about 6 to about 96 hours, from about 12 to about 96 hours, from about 18 to about 96 hours, from about 24 to about 96 hours, from about 36 to about 96 hours, from about 48 to about 96 hours, from about 60 to about 96 hours, or from about 72 to about 96 hours. In other embodiments, the contact period is from about 3 to about 72 hours, from about 6 to about 72 hours, from about 12 to about 72 hours, from about 18 to about 72 hours, from about 24 to about 72 hours, from about 36 to about 72 hours, from about 48 to about 72 hours, or from about 60 to about 72 hours. In still other embodiments, the contact period is from about 3 to about 60 hours, from about 6 to about 60 hours, from about 12 to about 60 hours, from about 18 to about 60 hours, from about 24 to about 60 hours, from about 36 to about 60 hours, or from about 48 to about 60 hours. In other embodiments, the contact period is from about 3 to about 48 hours, from about 6 to about 48 hours, from about 12 to about 48 hours, from about 18 to about 48 hours, from about 24 to about 48 hours, or from about 36 to about 48 hours. In still other embodiments, the contact period is from about 3 to about 36 hours, from about 6 to about 36 hours, from about 12 to about 36 hours, from about 18 to about 36 hours, or from about 24 to about 36 hours. In yet other embodiments, the contact period is from about 3 to about 24 hours, from about 6 to about 24 hours, from about 12 to about 24 hours, or from about 18 to about 24 hours. In some embodiments the total period of contact between the chemical modification agent and the peptide or polypeptide is less than a day, for example, the contact period is from about 3 to about 18 hours, from about 6 to about 18 hours, from about 12 to about 18 hours, from about 3 to about 12 hours, from about 6 to about 15 hours, or even from about 3 to about 6 hours.

It is also possible to measure the contact period in days. For example, the contact period can be about 5 days or less, about 4 days or less, about 3 days or less, about 2 days or less, or about a day.

As can be appreciated by a skilled artisan, the contact period may vary based on several factors, including, but not limited to, the type and concentration of the chemical modification agent used, the peptide to be treated and incubation temperature.

The contact period may also be expressed as the time period necessary to attain a particular end result. For example, the contact period may be that period of time that is necessary and sufficient to achieve intra-molecular cross-linking with minimal to no peptide aggregation. In another embodiment, the contact period is the period of time sufficient to achieve production of intra-molecular methylene bridges with minimal to no peptide aggregation.

In another embodiment, the contact period is the period of time sufficient to achieve intra-molecular cross-linking without the modification of key epitopes which can result in loss or reduction of immunogenicity. The invention also includes a contact period that is the period of time sufficient to achieve production of intra-molecular methylene bridges without the modification of key epitopes which can result in loss or reduction of immunogenicity.

In yet another embodiment, the contact period is the period of time necessary and sufficient to achieve at least about a 1.5 fold, at least about a 2 fold, at least about a 3 fold, at least about a 4 fold, at least about a 5 fold, at least about a 10 fold, at least about a 15 fold, at least about a 20 fold, at least about a 30 fold, at least about a 40 fold or at least about a 50 fold enhancement in the efficacy of the polypeptide or peptide when used as a vaccine, compared to untreated peptide or polypeptide, as measured by an $ED_{50}$ value. In yet another embodiment, the contact period is the period of time necessary and sufficient to achieve at least about a 1.5 fold, at least about a 2 fold, at least about a 3 fold, at least about a 4 fold, at least about a 5 fold, at least about a 10 fold, at least about a 20 fold, at least about a 30 fold, at least about a 40 fold or at least about a 50 fold enhancement in the efficacy of the polypeptide or peptide when used as a vaccine, compared to peptide or polypeptide treated with formaldehyde under traditional detoxification protocols (e.g., treatment with formaldehyde up to about 25 days), as measured by an $ED_{50}$ value.

Chemical Modification Agents

The peptides of the present invention are treated with chemical modification agents that are capable of increasing immunogenicity. In one embodiment of the invention, the chemical modification agent induces cross-linking in the bacterial peptide. In another embodiment, the chemical modification agent induces the formation of methylene bridges in a bacterial peptide.

In certain embodiments, the chemical modification agent is formaldehyde or formalin. However, other agents may also be used. Non-limiting examples of other cross-linking agents that may be employed include C6-succinimidyl 4-hydrazinonicotinate acetone hydrazone, C6-succinimidyl 4-formylbenzoate, BIS-(Sulfosuccinimidyl) suberate, disuccinimidyl suberate, dimethyl suberimidate dihydrochloride, dimethyl pimelimidate 2 HCl, dimethyl adipimidate dihydrochloride, succinimidyl 4-hydrazidoterephthalate hydrochloride, and disuccinimidyl glutarate.

Irrespective of the identity of the chemical modification agent, many embodiments use the agent at a low concentration. In most embodiments, the concentration is less than about 2% (v/v or w/v based on the ratio of the modifying agent to the total reaction mixture). In some embodiments, the concentration is less than about 1%, less than about 0.75%, less than about 0.5%, less than about 0.25%, or even less than about 0.1%. Other embodiments employ a concentration range for the modifying agent. Thus, in some embodiments the modifying agent is at a concentration between about 0.05 and about 2.0%, between about 0.1 and 2.0%, between about 0.15 and 2.0%, between about 0.2 and 2.0%, between about 0.25 and 2.0%, between about 0.3 and 2.0%, between about 0.5 and 2.0%, between about 0.75 and 2.0%, or between about 1.0 and 2.0%. In other embodiments, the modifying agent is at a concentration between about 0.05 and about 1.0%, between about 0.1 and 1.0%, between about 0.15 and 1.0%, between about 0.2 and 1.0%, between about 0.25 and 1.0%, between about 0.3 and 1.0%, between about 0.5 and 1.0%, or between about 0.75 and 1.0%. In still other embodiments, the modifying agent is at a concentration between about 0.05 and about 0.75%, between about 0.1 and 0.75%, between about 0.15 and 0.75%, between about 0.2 and 0.75%, between about 0.25 and 0.75%, between about 0.3 and 0.75%, or between about 0.5 and 0.75%. In yet other embodiments, the modifying agent is at a concentration between about 0.05 and about 0.5%, between about 0.1 and 0.5%, between about 0.15 and 0.5%, between about 0.2 and 0.5%, between about 0.25 and 0.5%, or between about 0.3 and 0.5%. In some embodiments, the modifying agent is at a concentration between about 0.05 and about 0.3%, between about 0.1 and 0.3%, between about 0.15 and 0.3%, or between about 0.2 and 0.3%. In still other embodiments, the concentration of the modifying agent is between about 0.05 and about 0.25%, between about 0.1 and 0.25%, between about 0.15 and 0.25%, between about 0.2 and 0.25%, between about 0.05 and about 0.2%, between about 0.1 and 0.2%, between about 0.15 and 0.2%, between about 0.05 and about 0.15%, between about 0.1 and 0.15%, or even between about 0.05 and about 0.1%. In certain embodiments, the concentration is about 1.0%, about 0.2%, or about 0.1%.

Alternatively, the concentration may be expressed as a molar ratio of agent:polypeptide, in which case the ratio is generally between about 3:1 and about 50:1. Thus, in some embodiments, the modifying agent may be employed at a molar ratio of about 50:1, about 25:1, about 20:1, about 15:1, or about 10:1. In other embodiments, the molar ratio may be expressed as a range, for example, between about 3:1 and about 50:1, between about 10:1 and about 50:1, between about 15:1 and about 50:1, between about 20:1 and about 50:1, or between about 25:1 and about 50:1, between about 3:1 and about 25:1, between about 10:1 and about 25:1, between about 15:1 and about 25:1, between about 20:1 and about 25:1, between about 3:1 and about 20:1, between about 10:1 and about 20:1, between about 15:1 and about 20:1, between about 3:1 and about 15:1, between about 10:1 and about 15:1, or between about 3:1 and about 10:1.

As can be appreciated by a skilled artisan, the concentration of the chemical modification agent needed to modify a bacterial peptide without causing damage to the peptide can vary based on several factors, including, but not limited to, the type of chemical modification agent used, the peptide to be treated and other incubation parameters such as incubation time and temperature.

Incubation Temperature

The temperature at which the chemical modification agent and the peptide or polypeptide are contacted may vary. In many embodiments, the contact temperature is between about 3° C. and about 45° C. Thus, the incubation temperature is typically up to about 45° C., about 40° C., or about 35° C. In this regard, the minimum incubation temperature is typically higher than about 15° C., about 20° C., about 25° C., and about 30° C. The incubation temperature may also be expressed as a range, for example, between about 30 to about 37° C., between about 20 to about 24° C., between about 3 to about 7° C., and between about 4 to about 37° C. Thus, some embodiments involve an incubation temperature of between about 15 to about 45° C., between about 20 to about 45° C., between about 25 to about 45° C., between about 30 to about 45° C., between about 35 to about 45° C., between about 37 to about 45° C., or between about 40 to about 45° C.

In other embodiments, the incubation temperature is a range of between about 15 to about 40° C., between about 20 to about 40° C., between about 25 to about 40° C., between about 30 to about 40° C., between about 35 to about 40° C., or between about 37 to about 40° C. In yet other embodiments, the incubation temperature is a range of between about 15 to about 37° C., between about 20 to about 37° C., between about 25 to about 37° C., between about 30 to about 37° C., or between about 35 to about 37° C. For other embodiments, the incubation temperature is a range of between about 15 to about 35° C., between about 20 to about 35° C., between about 25 to about 35° C., or between about 30 to about 35° C., between about 15 to about 30° C., between about 20 to about 30° C., between about 25 to about 30° C., between about 15 to about 25° C., between about 20 to about 25° C., or between about 15 to about 20° C. In some embodiments, the temperature is about 35° C., in other embodiments, it is about 4° C.

III. Peptides and Polypeptides

The protective effect of many different bacterial peptides or polypeptides can be increased by chemical modification in accordance with the invention. For example, the methods may be used to increase the protective effect of clostridial neurotoxins. Non-limiting examples of such peptides and polypeptides include BoNT/A, BoNT/B, BoNT/E, tetanus toxin, and the different subtypes of each of the BoNT serotypes. In various embodiments, the peptide or polypeptide is the native clostridial neurotoxin, a recombinant polypeptide modified to render it nontoxic, or polypeptide fragments, which may also have been rendered nontoxic via amino acid substitutions, deletions, or insertions, such as the $LH_N$ fragment of BoNT or tetanus toxin. The $LH_N$ fragment can be obtained, for instance, by treating native clostridial neurotoxin with trypsin by methods known in the art. In one embodiment of the invention, the peptide or polypeptide is not a native, full length clostridial neurotoxin.

In still other embodiments, the peptides and polypeptides are *Clostridium difficile* toxins, such as Toxin A, Toxin B, and binary toxin, or a *Clostridium difficile* surface peptides, such as the Cwp 84 peptide.

In other embodiments, the polypeptides and peptides are from *Bacillus anthracis*, such as lethal factor, protective antigen, or edema factor.

Of course, there are many other peptides and polypeptides for which it is desirable to increase their protective effect, and those peptides and polypeptides are also encompassed by the invention.

In one embodiment, the peptide or polypeptide to be chemically modified is in a soluble or predominantly soluble form. By predominantly soluble, it is meant that the peptide or polypeptide be at least about 70%, 75%, 80%, 85%, 90%, 95%, 97%, 98%, or even 99% soluble.

In various embodiments, the invention utilizes polypeptides or fragments thereof that are modified. Thus, where noted, the exemplified sequences include one or more amino acid modification, insertion, or deletion relative to the native protein sequence in order to improve the polypeptide's expression characteristics and/or to render the polypeptide less toxic than the corresponding native protein. Details regarding those modifications are described elsewhere in this disclosure.

Amino acid sequences of polypeptides and peptides encompassed by the invention are presented below. The examples should not be construed to in any way limit the invention. They are presented for illustrative purposes only.

Botulinum Proteins, Polypeptides, and Fragments

```
Native Botulinum type A Neurotoxin (SEQ ID NO: 8):
PFVNKQFNYKDPVNGVDIAYIKIPNVGQMQPVKAFKIHNKIWVIPERDTFTNPEEGDLNPPPEAKQVPVSY

YDSTYLSTDNEKDNYLKGVTKLFERIYSTDLGRMLLTSIVRGIPFWGGSTIDTELKVIDTNCINVIQPDGS

YRSEELNLVIIGPSADIIQFECKSFGHEVLNLTRNGYGSTQYIRFSPDFTFGFEESLEVDTNPLLGAGKFA

TDPAVTLAHELIHAGHRLYGIAINPNRVFKVNTNAYYEMSGLEVSFEELRTFGGHDAKFIDSLQENEFRLY

YYNKFKDIASTLNKAKSIVGTTASLQYMKNVFKEKYLLSEDTSGKFSVDKLKFDKLYKMLTEIYTEDNFVK

FFKVLNRKTYLNFDKAVFKINIVPKVNYTIYDGFNLRNTNLAANFNGQNTEINNMNFTKLKNFTGLFEFYK

LLCVRGIITSKTKSLDKGYNKALNDLCIKVNNWDLFFSPSEDNFTNDLNKGEEITSDTNIEAAEENISLDL

IQQYYLTFNFDNEPENISIENLSSDIIGQLELMPNIERFPNGKKYELDKYTMFHYLRAQEFEHGKSRIALT

NSVNEALLNPSRVYTFFSSDYVKKVNKATEAAMFLGWVEQLVYDFTDETSEVSTTDKIADITIIPYIGPA

LNIGNMLYKDDFVGALIFSGAVILLEFIPEIAIPVLGTFALVSYIANKVLTVQTIDNALSKRNEKWDEVYK

YIVTNWLAKVNTQIDLIRKKMKEALENQAEATKAIINYQYNQYTEEEKNNINFNIDDLSSKLNESINKAMI

NINKFLNQCSVSYLMNSMIPYGVKRLEDFDASLKDALLKYIYDNRGTLIGQVDRLKDKVNNTLSTDIPFQL

SKYVDNQRLLSTFTEYIKNIINTSILNLRYESNHLIDLSRYASKINIGSKVNFDPIDKNQIQLFNLESSKI

EVILKNAIVYNSMYENFSTSFWIRIPKYFNSISLNNEYTIINCMENNSGWKVSLNYGEIIWTLQDTQEIKQ

RVVFKYSQMINISDYINRWIFVTITNNRLNNSKIYINGRLIDQKPISNLGNIHASNNIMFKLDGCRDTHRY

IWIKYFNLFDKELNEKEIKDLYDNQSNSGILKDFWGDYLQYDKPYYMLNLYDPNKYVDVNNVGIRGYMYLK

GPRGSVMTTNIYLNSSLYRGTKFIIKKYASGNKDNIVRNNDRVYINVVVKNKEYRLATNASQAGVEKILSA

LEIPDVGNLSQVVVMKSKNDQGITNKCKMNLQDNNGNDIGFIGFHQFNNIAKLVASNWYNRQIERSSRTLG

CSWEFIPVDDGWGERPL
```

This is but one example of a particular BoNT/A protein. Other BoNT/A proteins are known in the art and include GenBank Accession Nos: P10845.4, Q45894.3, A5HZZ9.1, which are incorporated by reference.

In some embodiments, a protein of the invention includes the initiation methionine, whereas in other embodiments, it does not. For example, the native BoNT/A protein shown above lacks the initiation methionine, but the invention nevertheless includes those proteins that retain the initiation methionine. This can also be true for the other proteins of different types, different subtypes, and even the different species described elsewhere in the specification. Peptide variants described herein (for instance, Clostridum neurotoxins and neurotoxin fragments with modifications which confer the endopeptidase negative phenotype) reference peptide sequences with an initiation methionine to more clearly identify the location of an amino acid modification(s).

In addition to presence or absence of the initiation methionine, the various toxin proteins described in the specification can be modified to lack endopeptidase activity and/or a functional $H_C$ binding domain. For instance, the present invention includes C. botulinum $LH_N$ fragments (e.g., $LH_N$/A, $LH_N$/B and $LH_N$/E) modified to lack endopeptidase activity.

An example of a botulinum type A neurotoxin which is both endopeptidase negative and lacks a functional $H_C$ binding domain is SEQ ID NO: 9:

```
PFVNKQFNYKDPVNGVDIAYIKIPNVGQMQPVKAFKIHNKIWVIPERDTFTNPEEGDLNPPPEAKQVPVSY

YDSTYLSTDNEKDNYLKGVTKLFERIYSTDLGRMLLTSIVRGIPFWGGSTIDTELKVIDTNCINVIQPDGS

YRSEELNLVIIGPSADIIQFECKSFGHEVLNLTRNGYGSTQYIRFSPDFTFGFEESLEVDTNPLLGAGKFA

TDPAVTLAHQLIYAGHRLYGIAINPNRVFKVNTNAYYEMSGLEVSFEELRTFGGHDAKFIDSLQENEFRLY

YYNKFKDIASTLNKAKSIVGTTASLQYMKNVFKEKYLLSEDTSGKFSVDKLKFDKLYKMLTEIYTEDNFVK

FFKVLNRKTYLNFDKAVFKINIVPKVNYTIYDGFNLRNTNLAANFNGQNTEINNMNFTKLKNFTGLFEFYK

LLCVRGIITSKTKSLDKGYNKALNDLCIKVNNWDLFFSPSEDNFTNDLNKGEEITSDTNIEAAEENISLDL

IQQYYLTFNFDNEPENISIENLSSDIIGQLELMPNIERFPNGKKYELDKYTMFHYLRAQEFEHGKSRIALT

NSVNEALLNPSRVYTFFSSDYVKKVNKATEAAMFLGWVEQLVYDFTDETSEVSTTDKIADITIIPYIGPA
```

```
LNIGNMLYKDDFVGALIFSGAVILLEFIPEIAIPVLGTFALVSYIANKVLTVQTIDNALSKRNEKWDEVYK

YIVTNWLAKVNTQIDLIRKKMKEALENQAEATKAIINYQYNQYTEEEKNNINFNIDDLSSKLNESINKAMI

NINKFLNQCSVSYLMNSMIPYGVKRLEDFDASLKDALLKYIYDNRGTLIGQVDRLKDKVNNTLSTDIPFQL

SKYVDNQRLLSTFTEYIKNIINTSILNLRYESNHLIDLSRYASKINIGSKVNFDPIDKNQIQLFNLESSKI

EVILKNAIVYNSMYENFSTSFWIRIPKYFNSISLNNEYTIINCMENNSGWKVSLNYGEIIWTLQDTQEIKQ

RVVFKYSQMINISDYINRWIFVTITNNRLNNSKIYINGRLIDQKPISNLGNIHASNNIMFKLDGCRDTHRY

IWIKYFNLFDKELNEKEIKDLYDNQSNSGILKDFWGDYLQYDKPYYMLNLYDPNKYVDVNNVGIRGYMYLK

GPRGSVMTTNIYLNSSLYRGTKFIIKKYASGNKDNIVRNNDRVYINVVVKNKEYRLATNASQAGVEKILSA

LEIPDVGNLSQVVVMKSKNDQGITNKCKMNLQDNNGNDIGFIGFHQFNNIAKLVASNLFNRQIERSSRTLG

CSWEFIPVDDGWGERPL
```

Changes relative to the native *botulinum* type A neurotoxin are shown in bold.

The invention also encompasses fragments, such as the LH$_N$ fragment, of the various *botulinum* neurotoxins, as well as the related tetanus toxin protein. Examples of LH$_N$ fragments of certain subtypes of BoNT and from tetanus toxin follow:

```
LH_N Polypeptide Fragment of Botulinum neurotoxin subtype A_1
(SEQ ID NO: 1):
PFVNKQFNYKDPVNGVDIAYIKIPNVGQMQPVKAFKIHNKIWVIPERDTFTNPEEGDLNPPPEAKQVPVSY

YDSTYLSTDNEKDNYLKGVTKLFERIYSTDLGRMLLTSIVRGIPFWGGSTIDTELKVIDTNCINVIQPDGS

YRSEELNLVIIGPSADIIQFECKSFGHEVLNLTRNGYGSTQYIRFSPDFTFGFEESLEVDTNPLLGAGKFA

TDPAVTLAHQLIYAGHRLYGIAINPNRVFKVNTNAYYEMSGLEVSFEELRTFGGHDAKFIDSLQENEFRLY

YYNKFKDIASTLNKAKSIVGTTASLQYMKNVFKEKYLLSEDTSGKFSVDKLKFDKLYKMLTEIYTEDNFVK

FFKVLNRKTYLNFDKAVFKINIVPKVNYTIYDGFNLRNTNLAANFNGQNTEINNMNFTKLKNFTGLFEFYK

LLCVRGIITSKTKSLDKGYNKALNDLCIKVNNWDLFFSPSEDNFTNDLNKGEEITSDTNIEAAEENISLDL

IQQYYLTFNFDNEPENISIENLSSDIIGQLELMPNIERFPNGKKYELDKYTMFHYLRAQEFEHGKSRIALT

NSVNEALLNPSRVYTFFSSDYVKKVNKATEAAMFLGWVEQLVYDFTDETSEVSTTDKIADITIIIPYIGPA

LNIGNMLYKDDFVGALIFSGAVILLEFIPEIAIPVLGTFALVSYIANKVLTVQTIDNALSKRNEKWDEVYK

YIVTNWLAKVNTQIDLIRKKMKEALENQAEATKAIINYQYNQYTEEEKNNINFNIDDLSSKLNESINKAMI

NINKFLNQCSVSYLMNSMIPYGVKRLEDFDASLKDALLKYIYDNRGTLIGQVDRLKDKVNNTLSTDIPFQL

SKYVDNQRLLSTFTEYIK
```

This is but one example of a polypeptide fragment of one particular BoNT/A$_1$ protein. Other BoNT/A$_1$ proteins are known in the art and include GenBank Accession Nos: ZP_02612822.1, YP_001386738.1, YP_001390123.1, which are incorporated by reference. LH$_N$ fragments from BoNT/A$_1$ proteins include fragments corresponding to the fragment shown above, optionally including, or not, the modifications disclosed elsewhere in this specification, such as those to reduce or eliminate the toxicity of the protein.

LH$_N$ Polypeptide Fragment of Botulinum neurotoxin subtype A$_2$
(SEQ ID NO: 2):
PFVNKQFNYKDPVNGVDIAYIKIPNAGQMQPVKAFKIHNKIWVIPERDTFTNPEEGDLNPPPEAKQVPVSY
YDSTYLSTDNEKDNYLKGVTKLFERIYSTDLGRMLLTSIVRGIPFWGGSTIDTELKVIDTNCINVIQPDGS
YRSEELNLVIIGPSADIIQFECKSFGHDVLNLTRNGYGSTQYIRFSPDFTFGFEESLEVDTNPLLGAGKFA
TDPAVTLAHQLIYAEHRLYGIAINPNRVFKVNTNAYYEMSGLEVSFEELRTFGGHDAKFIDSLQENEFRLY
YYNKFKDVASTLNKAKSIIGTTASLQYMKNVFKEKYLLSEDTSGKFSVDKLKFDKLYKMLTEIYTEDNFVN
FFKVINRKTYLNFDKAVFRINIVPDENYTIKDGFNLKGANLSTNFNGQNTEINSRNFTRLKNFTGLFEFYK
LLCVRGIIPFKTKSLDEGYNKALNDLCIKVNNWDLFFSPSEDNFTNDLDKVEEITADTNIEAAEENISLDL
IQQYYLTFDFDNEPENISIENLSSDIIGQLEPMPNIERFPNGKKYELDKYTMFHYLRAQEFEHGDSRIILT
NSAEEALLKPNVAYTFFSSKYVKKINKAVEAFMFLNWAEELVYDFTDETNEVTTMDKIADITIIVPYIGPA
LNIGNMLSKGEFVEAIIFTGVVAMLEFIPEYALPVFGTFAIVSYIANKVLTVQTINNALSKRNEKWDEVYK
YTVTNWLAKVNTQIDLIREKMKKALENQAEATKAIINYQYNQYTEEEKNNINFNIDDLSSKLNESINSAMI
NINKFLDQCSVSYLMNSMIPYAVKRLKDFDASVRDVLLKYIYDNRGTLVLQVDRLKDEVNNTLSADIPFQL
SKYVDNKKLLSTFTEYIK This is but one example of a polypeptide fragment of one particular BoNT/A$_2$ protein. Other BoNT/A$_2$ proteins are known in the art and include GenBank Accession Nos: AAX53156.1, ABC26002.1, ABY56330.1, which are incorporated by reference. LH$_N$ fragments from BoNT/A$_2$ proteins include fragments corresponding to the fragment shown above, optionally including, or not, the modifications disclosed elsewhere in this specification, such as those to reduce or eliminate the toxicity of the protein.

LH$_N$ Polypeptide Fragment of Botulinum neurotoxin subtype A$_3$
(SEQ ID NO: 3):
PFVNKPFNYRDPGNGVDIAYIKIPNAGQMQPVKAFKIHEGVWVIPERDTFTNPEEGDLNPPPEAKQVPVSY
YDSTYLSTDNEKDNYLKGVIKLFDRIYSTGLGRMLLSFIVKGIPFWGGSTIDTELKVIDTNCINVIEPGGS
YRSEELNLVITGPSADIIQFECKSFGHDVFNLTRNGYGSTQYIRFSPDFTFGFEESLEVDTNPLLGAGTFA
TDPAVTLAHQLIYAAHRLYGIAINPNRVLKVKTNAYYEMSGLEVSFEELRTFGGNDTNFIDSLWQKKFSRD
AYDNLQNIARILNEAKTIVGTTTPLQYMKNIFIRKYFLSEDASGKISVNKAAFKEFYRVLTRGFTELEFVN
PFKVINRKTYLNFDKAVFRINIVPDENYTINEGFNLEGANSNGQNTEINSRNFTRLKNFTGLFEFYKLLCV
RGIIPFKTKSLDEGYNKALNYLCIKVNNWDLFFSPSEDNFTNDLDKVEEITADTNIEAAEENISSDLIQQY
YLTFDFDNEPENISIENLSSDIIGQLEPMPNIERFPNGKKYELDKYTMFHYLRAQEFEHGDSRIILTNSAE
EALLKPNVAYTFFSSKYVKKINKAVEAVIFLSWAEELVYDFTDETNEVTTMDKIADITIIVPYIGPALNIG
NMVSKGEFVEAILFTGVVALLEFIPEYSLPVFGTFAIVSYIANKVLTVQTINNALSKRNEKWDEVYKYTVT
NWLAKVNTQIDLIREKMKKALENQAEATRAIINYQYNQYTEEEKNNINFNIDDLSSKLNRSINRAMININK
FLDQCSVSYLMNSMIPYAVKRLKDFDASVRDVLLKYIYDNRGTLILQVDRLKDEVNNTLSADIPFQLSKYV
NDKKLLSTFTEYIK This is but one example of a polypeptide fragment of one particular BoNT/A$_3$ protein. Other BoNT/A$_3$ proteins are known in the art and include GenBank Accession Nos: YP_001715703.1, ACA57525.1, which are incorporated by reference. LH$_N$ fragments from BoNT/A$_3$ proteins include fragments corresponding to the fragment shown above, optionally including, or not, the modifications disclosed elsewhere in this specification, such as those to reduce or eliminate the toxicity of the protein.

LH$_N$ Polypeptide Fragment of Botulinum neurotoxin type B (SEQ ID NO: 6):

```
PVTINNFNYNDPIDNNNIIMMEPPFARGTGRYYKAFKITDRIWIIPERYTFGYKPEDFNKSSGIFNRDVCE

YYDPDYLNTNDKKNIFLQTMIKLFNRIKSKPLGEKLLEMIINGIPYLGDRRVPLEEFNTNIASVTVNKLIS

NPGEVERKKGIFANLIIFGPGPVLNENETIDIGIQNHFASREGFGGIMQMKFCPEYVSVFNNVQENKGASI

FNRRGYFSDPALILMHQLIYVLHGLYGIKVDDLPIVPNEKKFFMQSTDAIQAEELYTFGGQDPSIITPSTD

KSIYDKVLQNFRGIVDRLNKVLVCISDPNININIYKNKFKDKYKFVEDSEGKYSIDVESFDKLYKSLMFGF

TETNIAENYKIKTRASYFSDSLPPVKIKNLLDNEIYTIEEGFNISDKDMEKEYRGQNKAINKQAYEEISKE

HLAVYKIQMCKSVKAPGICIDVDNEDLFFIADKNSFSDDLSKNERIEYNTQSNYIENDFPINELILDTDLI

SKIELPSENTESLTDFNVDVPVYEKQPAIKKIFTDENTIFQY

LYSQTFPLDIRDISLTSSFDDALLFSNKVYSFFSMDYIKTANKVVEAGLFAGWVKQIVNDFVIEANKSNTM

DKIADISLIVPYIGLALNVGNETAKGNFENAFEIAGASILLEFIPELLIPVVGAFLLESYIDNKNKIIKTI

DNALTKRNEKWSDMYGLIVAQWLSTVNTQFYTIKEGMYKALNYQAQALEEIIKYRYNIYSEKEKSNINIDF

NDINSKLNEGINQAIDNINNFINGCSVSYLMKKMIPLAVEKLLDFDNTLKKNLLNYIDENKLYLIGSAEYE

KSKVNKYLKTIMPFDLSIYTNDTILIEMFNKYNSE
```

This is but one example of a polypeptide fragment of one particular BoNT/B protein. Other BoNT/B proteins are known in the art and include GenBank Accession Nos: YP_001693307.1, ZP_02619070.1, which are incorporated by reference. LH$_N$ fragments from BoNT/B proteins include fragments corresponding to the fragment shown above, optionally including, or not, the modifications disclosed elsewhere in this specification, such as those to reduce or eliminate the toxicity of the protein. By way of example, two BoNT/B sequences of the present invention include:

```
BoNT/B₁ strain NCTC 7273 (SEQ ID NO: 23)
PVTINNFNYNDPIDNNNIIMMEPPFARGTGRYYKAFKITDRIWIIPERYTFGYKPEDFNKSSGIFNRDVCE

YYDPDYLNTNDKKNIFLQTMIKLFNRIKSKPLGEKLLEMIINGIPYLGDRRVPLEEFNTNIASVTVNKLIS

NPGEVERKKGIFANLIIFGPGPVLNENETIDIGIQNHFASREGFGGIMQMKFCPEYVSVFNNVQENKGASI

FNRRGYFSDPALILMHELIHVLHGLYGIKVDDLPIVPNEKKFFMQSTDAIQAEELYTFGGQDPSIITPSTD

KSIYDKVLQNFRGIVDRLNKVLVCISDPNININIYKNKFKDKYKFVEDSEGKYSIDVESFDKLYKSLMFGF

TETNIAENYKIKTRASYFSDSLPPVKIKNLLDNEIYTIEEGFNISDKDMEKEYRGQNKAINKQAYEEISKE

HLAVYKIQMCKSVKAPGICIDVDNEDLFFIADKNSFSDDLSKNERIEYNTQSNYIENDFPINELILDTDLI

SKIELPSENTESLTDFNVDVPVYEKQPAIKKIFTDENTIFQYLYSQTFPLDIRDISLTSSFDDALLFSNKV

YSFFSMDYIKTANKVVEAGLFAGWVKQIVNDFVIEANKSNTMDKIADISLIVPYIGLALNVGNETAKGNFE

NAFEIAGASILLEFIPELLIPVVGAFLLESYIDNKNKIIKTIDNALTKRNEKWSDMYGLIVAQWLSTVNTQ

FYTIKEGMYKALNYQAQALEEIIKYRYNIYSEKEKSNINIDFNDINSKLNEGINQAIDNINNFINGCSVSY

LMKKMIPLAVEKLLDFDNTLKKNLLNYIDENKLYLIGSAEYEKSKVNKYLKTIMPFDLSIYTNDTILIEMF

NKYNSEILNNIILNLRYKDNNLIDLSGYGAKVEVYDGVELNDKNQFKLTSSANSKIRVTQNQNIIFNSVFL

DFSVSFWIRIPKYKNDGIQNYIHNEYTIINCMKNNSGWKISIRGNRIIWTLIDINGKTKSVFFEYNIREDI

SEYINRWFFVTITNNLNNAKIYING

KLESNTDIKDIREVIANGEIIFKLDGDIDRTQFIWMKYFSIFNTELSQSNIEERYKIQSYSEYLKDFWGNP

LMYNKEYYMFNAGNKNSYIKLKKDSPVGEILTRSKYNQNSKYINYRDLYIGEKFIIRRKSNSQSINDDIVR

KEDYIYLDFFNLNQEWRVYTYKYFKKEEEKLFLAPISDSDEFYNTIQIKEYDEQPTYSCQLLFKKDEESTD

EIGLIGIHRFYESGIVFEEYKDYFCISKWYLKEVKRKPYNLKLGCNWQFIPKDEGWTE

BoNT/B₄ strain Eklund (17b) - SEQ ID NO: 24
PVTINNFNYNDPIDNDNIIMMEPPFARGTGRYYKAFKITDRIWIIPERYTFGYKPEDFNKSSGIFNRDVCE

YYDPDYLNTNDKKNIFLQTMIKLFNRIKSKPLGEKLLEMIINGIPYLGDRRVPLEEFNTNIASVTVNKLIS
```

```
-continued
NPGEVEQKKGIFANLIIFGPGPVLNENETIDIGIQNHFASREGFGGIMQMKFCPEYVSVFNNVQENKGASI

FNRRGYFSDPALILMHELIHVLHGLYGIKVDDLPIVPNEKKFFMQSTDTIQAEELY

TFGGQDPSIISPSTDKSIYDKVLQNFRGIVDRLNKVLVCISDPNININIYKNKFKDKYKFVEDSEGKYSID

VESFNKLYKSLMFGFTEINIAENYKIKTRASYFSDSLPPVKIKNLLDNEIYTIEEGFNISDKNMGKEYR

GQNKAINKQA YEEISKEHLA VYKIQMCKSV KVPGICIDVDNENLFFIADK NSFSDDLSKN

ERVEYNTQNNYIGNDFPINELILDTDLISKIELPSENTESLTDFNVDVPVYEKQPAIKKVTDENTIFQYLY

SQTFPLNIRDISLTSSFDDALLVSSKVYSFFSMDYIKTANKVVEAGLFAGWVKQIVDDFVIEANKSSTMDK

IADISLIVPYIGLALNVGDETAKGNFESAFEIAGSSILLEFIPELLIPVVGVFLLESYIDNKNKIIKTIDN

ALTKRVEKWIDMYGLIVAQWLSTVNTQFYTIKEGMYKALNYQAQALEEIIKYKYNIYSEEEKSNININFND

INSKL NDGINQAMDN INDFINECSV SYLMKKMIPL AVKKLLDFDNTLKKNLLNYI DENKLYLIGS

VEDEKSKVDK YLKTIIPFDLSTYTNNEILIKIFNKYNSEILNNIILNLRYRDNNLIDLSG

YGAKVEVYDGVKLNDKNQFKLTSSADSKIRVTQNQNIIFNSMFLDFSVSFWIRIPKYRNDDIQNYIHNEYT

IINCMKNNSGWKISIRGNRIIWTLIDINGKTKSVFFEYNIREDISEYINRWFFVTITNNLDNAKIYINGTL

ESNMDIKDIGEVIVNGEITFKLDGDVDRTQFIWMKYFSIFNTQLNQSNIKEIYKIQSYSEYLKDFWGNPLM

YNKEYYMFNAGNKNSYIKLVKDSSVGEILIRSKYNQNSNYINYRNLYIGEKFIIRRKSNSQSINDDIVRKE

DYIHLDFVNSNEEWRVYAYKNFKEQEQKLFLSIIYDSNEFYKTIQIKEYDEQPTYS CQLLFKKDEE

STDDIGLIGI HRFYESGVLRKKYKDYFCIS KWYLKEVKRK PYKSNLGCNW QFIPKDEGWTE

LH_N Polypeptide Fragment of Botulinum neurotoxin type E
strain E 185 (SEQ ID NO: 4):
PKINSFNYNDPVNDRTILYIKPGGCQEFYKSFNIMKNIWIIPERNVIGTTPQDFHPPTSLKNGDSSYYDPN

YLQSDEEKDRFLKIVTKIFNRINNNLSGGILLEELSKANPYLGNDNTPDNQFHIGDASAVEIKFSNGSQHI

LLPNVIIMGAEPDLFETNSSNISLRNNYMPSNHGFGSIAIVTFSPEYSFRFNDNSINEFIQDPALTLMHQL

IHSLHGLYGAKGITTTCIITQQQNPLITNRKGINIEEFLTFGGNDLNIITVAQYNDIYTNLLNDYRKIASK

LSKVQVSNPQLNPYKDIFQEKYGLDKDASGIYSVNINKFDDILKKLYSFTEFDLATKFQVKCRETYIGQYK

YFKLSNLLNDSIYNISEGYNINNLKVNFRGQNANLNPRIIKPITGRGLVKKIIRFCKNIVSVKGIRKSICI

EINNGELFFVASENSYNDDNINTPKEIDDTVTSNNNYENDLDQVILNFNSESAPGLSDEKLNLTIQNDAYI

PKYDSNGTSDIEQHDVNELNVFFYLDAQKVPEGENNVNLTSSIDTALLEQPKIYTFFSSEFINNVNKPVQA

ALFVSWIQQVLVDFTTEANQKSTVDKIADISIVVPYIGLALNIGNEAQKGNFKDALELLGAGILLEFEPEL

LIPTILVFTIKSFLGSSDNKNKVIKAINNALKERDEKWKEVYSFIVSNWMTKINTQFNKRKEQMYQALQNQ

VNAIKTIIESKYNSYTLEEKNELTNKYDIKQIENELNQKVSIAMNNIDRFLTESSISYLMKLINEVKINKL

REYDENVKTYLLNYIIQHGSILGESQQELNSMVTDTLNNSIPFKLSSYTDDKILISYFNKFFK
```

This is but one example of a polypeptide fragment of one particular BoNT/E protein. Other BoNT/E proteins are known in the art and include GenBank Accession No: ZP_02950249.1 which is incorporated by reference. $LH_N$ fragments from BoNT/E proteins include fragments corresponding to the fragment shown above, optionally including, or not, the modifications disclosed elsewhere in this specification, such as those to reduce or eliminate the toxicity of the protein. By way of example, three BoNT/E sequences of the present invention include:

```
LH_N/E from Beluga strain sequence (SEQ ID NO: 25)
PKINSFNYNDPVNDRTILYIKPGGCQEFYKSFNIMKNIWIIPERNVIGTTPQDFHPPTSLKNGDSSYYDPN

YLQSDEEKDRFLKIVTKIFNRINNNLSGGILLEELSKANPYLGNDNTPDNQFHIGDASAVEIKFSNGSQDI

LLPNVIIMGAEPDLFETNSSNISLRNNYMPSNHRFGSIAIVTFSPEYSFRFNDNCMNEFIQDPALTLMHQL

IHSLHGLYGAKGITTKYTITQKQNPLITNIRGTNIEEFLTFGGTDLNIITSAQSNDIYTNLLADYKKIASK

LSKVQVSNPLLNPYKDVFEAKYGLDKDASGIYSVNINKFNDIFKKLYSFTEFDLRTKFQVKCRQTYIGQYK
```

-continued

YFKLSNLLNDSIYNISEGYNINNLKVNFRGQNANLNPRIITPITGRGLVKKIIRFCKNIVSVKGIRKSICI

EINNGELFFVASENSYNDDNINTPKEIDDTVTSNNNYENDLDQVILNFNSESAPGLSDEKLNLTIQNDAYI

PKYDSNGTSDIEQHDVNELNVFFYLDAQKVPEGENNVNLTSSIDTALLEQPKIYTFFSSEFINNVNKPVQA

ALFVSWIQQVLVDFTTEANQKSTVDKIADISIVVPYIGLALNIGNEAQKGNFKDALELLGAGILLEFEPEL

LIPTILVFTIKSFLGSSDNKNKVIKAINNALKERDEKWKEVYSFIVSNWMTKINTQFNKRKEQMYQALQNQ

VNAIKTIIESKYNSYTLEEKNELTNKYDIKQIENELNQKVSIAMNNIDRFLTESSISYLMKIINEVKINKL

REYDENVKTYLLNYIIQHGSILGESQQELNSMVTDTLNNSIPFKLSSYTDDKILISYFNKFFK

BoNT/E strain E185 (SEQ ID NO: 26)
PKINSFNYNDPVNDRTILYIKPGGCQEFYKSFNIMKNIWIIPERNVIGTTPQDFHPPTSLKNGDSSYYDPN

YLQSDEEKDRFLKIVTKIFNRINNNLSGGILLEELSKANPYLGNDNTPDNQFHIGDASAVEIKFSNGSQHI

LLPNVIIMGAEPDLFETNSSNISLRNNYMPSNHGFGSIAIVTFSPEYSFRFNDNSINEFIQDPALTLMHEL

IHSLHGLYGAKGITTTCIITQQQNPLITNRKGINIEEFLTFGGNDLNIITVAQYNDIYTNLLNDYRKIASK

LSKVQVSNPQLNPYKDIFQEKYGLDKDASGIYSVNINKFDDILKKLYSFTEFDLATKFQVKCRETYIGQYK

YFKLSNLLNDSIYNISEGYNINNLKVNFRGQNANLNPRIIKPITGRGLVKKIIRFCKNIVSVKGIRKSICI

EINNGELFFVASENSYNDDNINTPKEIDDTVTSNNNYENDLDQVILNFNSESAPGLSDEKLNLTIQNDAYI

PKYDSNGTSDIEQHDVNELNVFFYLDAQKVPEGENNVNLTSSIDTALLEQPKIYTFFSSEFINNVNKPVQA

ALFVSWIQQVLVDFTTEANQKSTVDKIADISIVVPYIGLALNIGNEAQKGNFKDALELLGAGILLEFEPEL

LIPTILVFTIKSFLGSSDNKNKVIKAINNALKERDEKWKEVYSFIVSNWMTKINTQFNKRKEQMYQALQNQ

VNAIKTIIESKYNSYTLEEKNELTNKYDIKQIENELNQKVSIAMNNIDRFLTESSISYLMKIINEVKINKL

REYDENVKTYLLNYIIQHGSILGESQQELNSMVTDTLNNSIPFKLSSYTDDKILISYFNKFFKRIKSSSVL

NMRYKNDKYVDTSGYDSNININGDVYKYPTNKNQFGIYNDKLSEVNISQNDYIIYDNKYKNFSISFWVRIP

NYDNKIVNVNNEYTIINCMRDNNSGWKVSLNHNEIIWTLQDNAGINQKLAFNYGNANGISDYINKWIFVTI

TNDRLGDSKLYINGNLIDQKSILNLGNIHVSDNILFKIVNCSYTRYIGIRYFNIFDKELDETEIQTLYSNE

PNTNILKDFWGNYLLYDKEYYLLNVLKPNNFIDRRKDSTLSINNIRSTILLANRLYSGIKVKIQRVNNSST

NDNLVRKNDQVYINFVASKTHLFPLYADTATTNKEKTIKISSSGNRFNQVVVMNSVGNNCTMNFKNNNGNN

IGLLGFKADTVVASTWYYTHMRDHTNSNGCFWNFISEEHGWQEK

BoNT/E Beluga strain (SEQ ID NO: 27)
PKINSFNYNDPVNDRTILYIKPGGCQEFYKSFNIMKNIWIIPERNVIGTTPQDFHPPTSLKNGDSSYYDPN

YLQSDEEKDRFLKIVTKIFNRINNNLSGGILLEELSKANPYLGNDNTPDNQFHIGDASAVEIKFSNGIQDI

LLPNVIIMGAEPDLFETNSSNISLRNNYMPSNHGFGSIAIVTFSPEYSFRFNDNSMNEFIQDPALTLMHEL

IHSLHGLYGAKGITTKYTITQKQNPLITNIRGTNIEEFLTFGGTDLNIITSAQSNDIYTNLLADYKKIASK

LSKVQVSNPLLNPYKDVFEAKYGLDKDASGIYSVNINKFNDIFKKLYSFTEFDLATKFQVKCRQTYIGQYK

YFKLSNLLNDSIYNISEGYNINNLKVNFRGQNANLNPRIITPITGRGLVKKIIRFCKNIVSVKGIRKSICI

EINNGELFFVASENSYNDDNINTPKEIDDTVTSNNNYENDLDQVILNFNSESAPGLSDEKLNLTIQNDAYI

PKYDSNGTSDIEQHDVNELNVFFYLDAQKVPEGENNVNLTSSIDTALLEQPKIYTFFSSEFINNVNKPVQA

ALFVSWIQQVLVDFTTEANQKSTVDKIADISIVVPYIGLALNIGNEAQKGNFKDALELLGAGILLEFEPEL

LIPTILVFTIKSFLGSSDNKNKVIKAINNALKERDEKWKEVYSFIVSNWMTKINTQFNKRKEQMYQALQNQ

VNAIKTIIESKYNSYTLEEKNELTNKYDIKQIENELNQKVSIAMNNIDRFLTESSISYLMKIINEVKINKL

REYDENVKTYLLNYIIQHGSILGESQQELNSMVTDTLNNSIPFKLSSYTDDKILISYFNKFFKRIKSSSVL

NMRYKNDKYVDTSGYDSNININGDVYKYPTNKNQFGIYNDKLSEVNISQNDYIIYDNKYKNFSISFWVRIP

NYDNKIVNVNNEYTIINCMRDNNSGWKVSLNHNEIIWTLQDNAGINQKLAFNYGNANGISDYINKWIFVTI

TNDRLGDSKLYINGNLIDQKSILNLGNIHVSDNILFKIVNCSYTRYIGIRYFNIFDKELDETEIQTLYNNE

LH$_N$ Polypeptide Fragment of Botulinum neurotoxin type F (SEQ ID NO: 7):
PNANILKDFWGNYLLYDKEYYLLNVLKPNNFIDRRTDSTLSINNIRSTILLANRLYSGIKVKIQRVNNSST

NDNLVRKNDQVYINFVASKTHLFPLYADTNTTNKEKTIKSSSSGNRFNQVVVMNSVGNNCTMNFKNNNGNN

IGMLGFKDNTLVASTWYYTHMRDNTNSNGCFWNFISEEHGWQEK

LH$_N$ Polypeptide Fragment of Botulinum neurotoxin type F (SEQ ID NO: 7):
PVAINSFNYNDPVNDDTILYMQIPYEEKSKKYYKAFEIMRNVWIIPERNTIGTNPSDFDPPASLKNGSSAY

YDPNYLTTDAEKDRYLKTTIKLFKRINSNPAGKVLLQEISYAKPYLGNDHTPIDEFSPVTRTTSVNIKLST

NVESSMLLNLLVLGAGPDIFESCCYPVRKLIDPDVVYDPSNYGFGSINIVTFSPEYEYTFNDISGGHNSST

ESFIADPAISLAHQLIYALHGLYGARGVTYEETIEVKQAPLMIAEKPIRLEEFLTFGGQDLNIITSAMKEK

IYNNLLANYEKIATRLSEVNSAPPEYDINEYKDYFQWKYGLDKNADGSYTVNENKFNEIYKKLYSFTESDL

ANKFKVKCRNTYFIKYEFLKVPNLLDDDIYTVSEGFNIGNLAVNNRGQSIKLNPKIIDSIPDKGLVEKIVK

FCKSVIPRKGTKAPPRLCIRVNNSELFFVASESSYNENDINTPKEIDDTTNLNNNYRNNLDEVILDYNSQT

IPQISNRTLNTLVQDNSYVPRYDSNGTSEIEEYDVVDFNVFFYLHAQKVPEGETNISLTSSIDTALLEESK

DIFFSSEFIDTINKPVNAALFIDWISKVIRDFTTEATQKSTVDKIADISLIVPYVGLALNIIIEAEKGNFE

EAFELLGVGILLEFVPELTIPVILVFTIKSYIDSYENKNKAIKAINNSLIEREAKWKEIYSWIVSNWLTRI

NTQFNKRKEQMYQALQNQVDAIKTAIEYKYNNYTSDEKNRLESEYNINNIEEELNKKVSLAMKNIERFMTE

SSISYLMKLINEAKVGKLKKY

This is but one example of a polypeptide fragment of one particular BoNT/F protein. Other BoNT/F proteins are known in the art and include GenBank Accession No: ZP_02619427.1, which is incorporated by reference. LH$_N$ fragments from BoNT/F proteins include fragments corresponding to the fragment shown above, optionally including, or not, the modifications disclosed elsewhere in this specification, such as those to reduce or eliminate the toxicity of the protein.

Tetanus Proteins, Polypeptides, and Fragments

LH$_N$ Polypeptide Fragment of Tetanus Toxin (SEQ ID NO: 5):
PITINNFRYSDPVNNDTIIMMEPPYCKGLDIYYKAFKITDRIWIVPERYEFGTKPEDFNPPSSLIEGASEY

YDPNYLRTDSDKDRFLQTMVKLFNRIKNNVAGEALLDKIINAIPYLGNSYSLLDKFDTNSNSVSFNLLEQD

PSGATTKSAMLTNLIIFGPGPVLKNEVRGIVLRVDNKNYFPCRDGFGSIMQMAFCPEYVPTFDNVIENIT

SLTIGKSKYFQDPALLLMHQLIYVLHGLYGMQVSSHEIIPSKQEIYMQHTYPISAEELFTFGGQDANLISI

DIKNDLYEKTLNDYKAIANKLSQVTSCNDPNIDIDSYKQIYQQKYQFDKDSNGQYIVNEDKFQILYNSIMY

GFTEIELGKKFNIKTRLSYFSMNHDPVKIPNLLDDTIYNDTEGFNIESKDLKSEYKGQNMRVNTNAFRNVD

GSGLVSKLIGLCKKIIPPTNIRENLYNRTASLTDLGGELCIKIKNEDLTFIAEKNSFSEEPFQDEIVSYNT

KNKPLNFNYSLDKIIVDYNLQSKITLPNDRTTPVTKGIPYAPEYKSNAASTIEIHNIDDNTIYQYLYAQKS

PTTLQRITMTNSVDDALINSTKIYSYFPSVISKVNQGAQGILFLQWVRDIIDDFTNESSQKTTIDKISDVS

TIVPYIGPALNIVKQGYEGNFIGALETTGVVLLLEYIPEITLPVIAALSIAESSTQKEKIIKTIDNFLEKR

YEKWIEVYKLVKAKWLGTVNTQFQKRSYQMYRSLEYQVDAIKKIIDYEYKIYSGPDKEQIADEINNLKNKL

EEKANKAMININIFMRESSRSFLVNQMINEAKKQLLEFDTQSKNILMQYIKANSKFIGITELKKLESKINK

VFSTPIPFSYSKNLDCWVDNEEDIDV

This is but one example of a polypeptide fragment of one particular tetanus toxin protein. The amino acid sequences of tetanus toxin proteins, including native proteins, are known in the art and include GenBank Accession No: NP_783831.1, which is incorporated by reference. LH$_N$ fragments from tetanus toxin proteins include fragments corresponding to the fragment shown above, optionally including, or not, the modifications disclosed elsewhere in this specification, such as those to reduce or eliminate the toxicity of the protein.

*C. Difficile* Toxin Proteins, Polypeptides, and Fragments

```
C. difficile Toxin A (C-terminal region) (SEQ ID NO: 10):
QSFNKMSIDFKDIKKLSLGYIMSNFKSFNSENELDRDHLGFKIIDNKTYYYDEDSKLVKGLININNSLFYF

DPIEFNLVTGWQTINGKKYYFDINTGAALTSYKIINGKHFYFNNDGVMQLGVFKGPDGFEYFAPANTQNNN

IEGQAIVYQSKFLTLNGKKYYFDNNSKAVTGWRIINNEKYYFNPNNAIAAVGLQVIDNNKYYFNPDTAIIS

KGWQTVNGSRYYFDTDTAIAFNGYKTIDGKHFYFDSDCVVKIGVFSTSNGFEYFAPANTYNNNIEGQAIVY

QSKFLTLNGKKYYFDNNSKAVTGLQTIDSKKYYFNTNTAEAATGWQTIDGKKYYFNTNTAEAATGWQTIDG

KKYYFNTNTAIASTGYTIINGKHFYFNTDGIMQIGVFKGPNGFEYFAPANTDANNIEGQAILYQNEFLTLN

GKKYYFGSDSKAVTGWRIINNKKYYFNPNNAIAAIHLCTINNDKYYFSYDGILQNGYITIERNNFYFDANN

ESKMVTGVFKGPNGFEYFAPANTHNNNIEGQAIVYQNKFLTLNGKKYYFDNDSKAVTGWQTIDGKKYYFNL

NTAEAATGWQTIDGKKYYFNLNTAEAATGWQTIDGKKYYFNTNTFIASTGYTSINGKHFYFNTDGIMQIGV

FKGPNGFEYFAPANTDANNIEGQAILYQNKFLTLNGKKYYFGSDSKAVTGLRTIDGKKYYFNTNTAVAVTG

WQTINGKKYYFNTNTSIASTGYTIISGKHFYFNTDGIMQIGVFKGPDGFEYFAPANTDANNIEGQAIRYQN

RFLYLHDNIYYFGNNSKAATGWVTIDGNRYYFEPNTAMGANGYKTIDNKNFYFRNGLPQIGVFKGSNGFEY

FAPANTDANNIEGQAIRYQNRFLHLLGKIYYFGNNSKAVTGWQTINGKVYYFMPDTAMAAAGGLFEIDGVI

YFFGVDGVKAPGIYG

C. difficile Toxin A (C-terminal region) (SEQ ID NO: 11):
TGWQTINGKKYYFNTNTSIASTGYTIISGKHFYFNTDGIMQIGVFKGPDGFEYFAPANTDANNIEGQAIRY

QNRFLYLHDNIYYFGNNSKAATGWVTIDGNRYYFEPNTAMGANGYKTIDNKNFYFRNGLPQIGVFKGSNGF

EYFAPANTDANNIEGQAIRYQNRFLHLLGKIYYFGNNSKAVTGWQTINGKVYYFMPDTAMAAAGGLFEIDG

VIYFFGVDGVKAPGIYG

C. difficile Toxin A (N-terminal region) (SEQ ID NO: 13):
MSLISKEELIKLAYSIRPRENEYKTILTNLDEYNKLTTNNNENKYLQLKKLNESIDVFMNKYKTSSRNRAL

SNLKKDILKEVILIKNSNTSPVEKNLHFVWIGGEVSDIALEYIKQWADINAEYNIKLWYDSEAFLVNTLKK

AIVESSTTEALQLLEEEIQNPQFDNMKFYKKRMEFIYDRQKRFINYYKSQINKPTVPTIDDIIKSHLVSEY

NRDETVLESYRTNSLRKINSNHGIDIRANSLFTEQELLNIYSQELLNRGNLAAASDIVRLLALKNFGGVYL

DVDMLPGIHSDLFKTISRPSSIGLDRWEMIKLEAIMKYKKYINNYTSENFDKLDQQLKDNFKLIIESKSEK

SEIFSKLENLNVSDLEIKIAFALGSVINQALISKQGSYLTNLVIEQVKNRYQFLNQHLNPAIESDNNFTDT

TKIFHDSLFNSATAENSMFLTKIAPYLQVGFMPEARSTISLSGPGAYASAYYDFINLQENTIEKTLKASDL

IEFKFPENNLSQLTEQEINSLWSFDQASAKYQFEKYVRDTYGGSLSED
```

These are but three examples of a polypeptide from one particular *C. difficile* toxin protein, toxin A. The amino acid sequences of *C. difficile* toxin A proteins, including native toxin A proteins, are known in the art and include GenBank Accession No: P16154.2, which is incorporated by reference.

Fragments from *C. difficile* toxin proteins include fragments corresponding to the fragments shown above, optionally including, or not, the modifications disclosed elsewhere in this specification, such as those to reduce or eliminate the toxicity of the protein.

```
C. difficile Toxin B (C-terminal region) (SEQ ID NO: 12):
TLANKLSFNFSDKQDVPVSEIILSFTPSYYEDGLIGYDLGLVSLYNEKFYINNFGMMVSGLIYINDSLYYF

KPPVNNLITGFVTVGDDKYYFNPINGGAASIGETIIDDKNYYFNQSGVLQTGVFSTEDGFKYFAPANTLDE

NLEGEAIDFTGKLIIDENIYYFDDNYRGAVEWKELDGEMHYFSPETGKAFKGLNQIGDYKYYFNSDGVMQK

GFVSINDNKHYFDDSGVMKVGYTEIDGKHFYFAENGEMQIGVFNTEDGFKYFAHHNEDLGNEEGEEISYSG

ILNFNNKIYYFDDSFTAVVGWKDLEDGSKYYFDEDTAEAYIGLSLINDGQYYFNDDGIMQVGFVTINDKVF
```

-continued

```
YFSDSGIIESGVQNIDDNYFYIDDNGIVQIGVFDTSDGYKYFAPANTVNDNIYGQAVEYSGLVRVGEDVYY

FGETYTIETGWIYDMENESDKYYFNPETKKACKGINLIDDIKYYFDEKGIMRTGLISFENNNYYFNENGEM

QFGYINIEDKMFYFGEDGVMQIGVFNTPDGFKYFAHQNTLDENFEGESINYTGWLDLDEKRYYFTDEYIAA

TGSVIIDGEEYYFDPDTAQLVISE

C. difficile Toxin B (N-terminal region) (SEQ ID NO: 14):
MSLVNRKQLEKMANVRFRTQEDEYVAILDALEEYHNMSENTVVEKYLKLKDINSLTDIYIDTYKKSGRNKA

LKKFKEYLVTEVLELKNNNLTPVEKNLHFVWIGGQINDTAINYINQWKDVNSDYNVNVFYDSNAFLINTLK

KTVVESAINDTLESFRENLNDPRFDYNKFFRKRMEIIYDKQKNFINYYKAQREENPELIIDDIVKTYLSNE

YSKEIDELNTYIEESLNKITQNSGNDVRNFEEFKNGESFNLYEQELVERWNLAAASDILRISALKEIGGMY

LDVDMLPGIQPDLFESIEKPSSVTVDFWEMTKLEAIMKYKEYIPEYTSEHFDMLDEEVQSSFESVLASKSD

KSEIFSSLGDMEASPLEVKIAFNSKGIINQGLISVKDSYCSNLIVKQIENRYKILNNSLNPAISEDNDFNT

TTNTFIDSIMAEANADNGRFMMELGKYLRVGFFPDVKTTINLSGPEAYAAAYQDLLMFKEGSMNIHLIEAD

LRNFEISKTNISQSTEQEMASLWSFDDARAKAQFEEYKRNYFEGSLGED

C. difficile Toxin B Antigen (C-terminal region, residues
1756 to 2361) (SEQ ID NO: 28)
EENKVSQVKIRFVNVFKDKTLANKLSFNFSDKQDVPVSEIILSFTPSYYEDGLIGYDLGLVSLYNEKFYIN

NFGMMVSGLIYINDSLYYFKPPVNNLITGFVTVGDDKYYFNPINGGAASIGETIIDDKNYYFNQSGVLQTG

VFSTEDGFKYFAPANTLDENLEGEAIDFTGKLIIDENIYYFDDNYRGAVEWKELDGEMHYFSPETGKAFKG

LNQIGDYKYYFNSDGVMQKGFVSINDNKHYFDDSGVMKVGYTEIDGKHFYFAENGEMQIGVFNTEDGFKYF

AHHNEDLGNEEGEEISYSGILNFNNKIYYFDDSFTAVVGWKDLEDGSKYYFDEDTAEAYIGLSLINDGQYY

FNDDGIMQVGFVTINDKVFYFSDSGIIESGVQNIDDNYFYIDDNGIVQIGVFDTSDGYKYFAPANTVNDNI

YGQAVEYSGLVRVGEDVYYFGETYTIETGWIYDMENESDKYYFNPETKKACKGINLIDDIKYYFDEKGIMR

TGLISFENNNYYFNENGEMQFGYINIEDKMFYFGEDGVMQIGVFNTPDGFKYFAHQNTLDENFEGESINYT

GWLDLDEKRYYFTDEYIAATGSVIIDGEEYYFDPDTAQ
```

These are three examples of a polypeptide from another particular *C. difficile* toxin protein, toxin B. The amino acid sequences of *C. difficile* toxin B proteins, including native toxin B proteins, are known in the art and include GenBank Accession No: P16154.2, which is incorporated by reference. Fragments from *C. difficile* toxin proteins include fragments corresponding to the fragments shown above, optionally including, or not, the modifications disclosed elsewhere in this specification, such as those to reduce or eliminate the toxicity of the protein.

Other *C. Difficile* Polypeptides and Polypeptide Fragments Include:

```
C. difficile surface peptide Cwp84 (SEQ ID NO: 15):
MRKYKSKKLSKLLALLTVCFLIVSTIPVSAENHKTLDGVETAEYSESYLQYLEDVKNGDTAKYNGVIPFPH

EMEGTTLRNKGRSSLPSAYKSSVAYNPMDLGLTTPAKNQGSLNTCWSFSGMSTLEAYLKLKGYGTYDLSEE

HLRWWATGGKYGWNLDDMSGSSNVTAIGYLTAWAGPKLEKDIPYNLKSEAQGATKPSNMDTAPTQFNVTDV

VRLNKDKETVKNAIMQYGSVTSGYAHYSTYFNKDETAYNCTNKRAPLNHAVAIVGWDDNYSKDNFASDVKP

ESNGAWLVKSSWGEFNSMKGFFWISYEDKTLLTDTDNYAMKSVSKPDSDKKMYQLEYAGLSKIMSNKVTAA

NVFDFSRDSEKLDSVMFETDSVGAKYEVYYAPVVNGVPQNNSMTKLASGTVSYSGYINVPTNSYSLPKGKG

AIVVVIDNTANPNREKSTLAYETNIDAYYLYEAKANLGESYILQNNKFEDINTYSEFSPCNFVIKAITKTS

SGQATSGESLTGADRYETAVKVSQKGWTSSQNAVLVNGDAIVDALTATPFTAAIDSPILLTGKDNLDSKTK

AELQRLGTKKVYLIGGENSLSKNVQTQLSNMGISVERISGSDRYKTSISLAQKLNSIKSVSQVAVANGVNG

LADAISVGAAAADNNMPIILTNEKSELQGADEFLNSSKITKSYIIGGTATLSSNLESKLSNPTRLAGSNRN

ETNAKIIDKFYPSSDLKYAFVVKDGSKSQGDLIDGLAVGALGAKTDSPVVLVGNKLDESQKNVLKSKKIET

PIRVGGNGNESAFNELNTLLGK
```

*C. difficile* binary toxin fragment A (SEQ ID NO: 19):
KVCNTTYKAPIESFLKDKEKAKEWERKEAERIEQKLERSEKEALESYKKDSVEISKYSQTRNYFYDYQIEA

NSREKEYKELRNAISKNKIDKPMYVYYFESPEKFAFNKVIRTENQNEISLEKFNEFKETIQNKLFKQDGFK

DISLYEPGKGDEKPTPLLMHLKLPRNTGMLPYTNTNNVSTLIEQGYSIKIDKIVRIVIDGKHYIKAEASVV

NSLDFKDDVSKGDSWGKANYNDWSNKLTPNELADVNDYMRGGYTAINNYLISNGPVNNPNPELDSKITNIE

NALKREPIPTNLTVYRRSGPQEFGLTLTSPEYDFNKLENIDAFKSKWEGQALSYPNFISTSIGSVNMSAFA

KRKIVLRITIPKGSPGAYLSAIPGYAGEYEVLLNHGSKFKINKIDSYKDGTITKLIVDATLIP

*C. difficile* binary toxin fragment B (SEQ ID NO: 20):
EIVNEDILPNNGLMGYYFSDEHFKDLKLMAPIKDGNLKFEEKKVDKLLDKDKSDVKSIRWTGRIIPSKDGE

YTLSTDRDDVLMQVNTESTISNTLKVNMKKGKEYKVRIELQDKNLGSIDNLSSPNLYWELDGMKKIIPEEN

LFLRDYSNIEKDDPFIPNNNFFDPKLMSDWEDEDLDTDNDNIPDSYERNGYTIKDLIAVKWEDSFAEQGYK

KYVSNYLESNTAGDPYTDYEKASGSFDKAIKTEARDPLVAAYPIVGVGMEKLIISTNEHASTDQGKTVSRA

TTNSKTESNTAGVSVNVGYQNGFTANVTTNYSHTTDNSTAVQDSNGESWNTGLSINKGESAYINANVRYYN

TGTAPMYKVTPTTNLVLDGDTLSTIKAQENQIGNNLSPGDTYPKKGLSPLALNTMDQFSSRLIPINYDQLK

KLDAGKQIKLETTQVSGNFGTKNSSGQIVTEGNSWSDYISQIDSISASIILDTENESYERRVTAKNLQDPE

DKTPELTIGEAIEKAFGATKKDGLLYFNDIPIDESCVELIFDDNTANKIKDSLKTLSDKKIYNVKLERGMN

ILIKTPTYFTNFDDYNNYPSTWSNVNTTNQDGLQGSANKLNGETKIKIPMSELKPYKRYVFSGYSKDPLTS

NSIIVKIKAKEEKTDYLVPEQGYTKFSYEFETTEKDSSNIEITLIGSGTTYLDNLSITELNSTPEILDEPE

VKIPTDQEIMDAHKIYFADLNFNPSTGNTYINGMYFAPTQTNKEALDYIQKYRVEATLQYSGFKDIGTKDK

EMRNYLGDPNQPKTNYVNLRSYFTGGENIMTYKKLRIYAITPDDRELLVLSVD

Anthrax Proteins, Polypeptides, and Fragments
Anthrax Protective Antigen (PA) (SEQ ID NO: 16):
MKKRKVLIPLMALSTILVSSTGNLEVIQAEVKQENRLLNESESSSQGLLGYYFSDLNFQAPMVVTSSTTGD

LSIPSSELENIPSENQYFQSAIWSGFIKVKKSDEYTFATSADNHVTMWVDDQEVINKASNSNKIRLEKGRL

YQIKIQYQRENPTEKGLDFKLYWTDSQNKKEVISSDNLQLPELKQKSSNSRKKRSTSAGPTVPDRDNDGIP

DSLEVEGYTVDVKNKRTFLSPWISNIHEKKGLTKYKSSPEKWSTASDPYSDFEKVTGRIDKNVSPEARHPL

VAAYPIVHVDMENIILSKNEDQSTQNTDSQTRTISKNTSTSRTHTSEVHGNAEVHASFFDIGGSVSAGFSN

SNSSTVAIDHSLSLAGERTWAETMGLNTADTARLNANIRYVNTGTAPIYNVLPTTSLVLGKNQTLATIKAK

ENQLSQILAPNNYYPSKNLAPIALNAQDDFSSTPITMNYNQFLELEKTKQLRLDTDQVYGNIATYNFENGR

VRVDTGSNWSEVLPQIQETTARIIFNGKDLNLVERRIAAVNPSDPLETTKPDMTLKEALKIAFGFNEPNGN

LQYQGKDITEFDFNFDQQTSQNIKNQLAELNATNIYTVLDKIKLNAKMNILIRDKRFHYDRNNIAVGADES

VVKEAHREVINSSTEGLLLNIDKDIRKILSGYIVEIEDTEGLKEVINDRYDMLNISSLRQDGKTFIDFKKY

NDKLPLYISNPNYKVNVYAVTKENTIINPSENGDTSTNGIKKILIFSKKGYEIG

This is but one example of one particular anthrax protein within the scope of the invention. The amino acid sequences of PA proteins, including native proteins, from various strains of anthrax are known in the art and include, for example, GenBank Accession Nos: NP_652920.1, ZP_02937261.1, ZP_02900013.1, ZP_02880951.1 which are incorporated by reference. Various fragments, mutations, and modifications in PA to reduce its toxicity or to improve its expression characteristics are also known, such as those described elsewhere in the specification.

Anthrax Lethal Factor (LF) (SEQ ID NO: 17):
MNIKKEFIKVISMSCLVTAITLSGPVFIPLVQGAGGHGDVGMHVKEKEKNKDENKRKDEERNKTQEEHLKE

IMKHIVKIEVKGEEAVKKEAAEKLLEKVPSDVLEMYKAIGGKIYIVDGDITKHISLEALSEDKKKIKDIYG

KDALLHEHYVYAKEGYEPVLVIQSSEDYVENTEKALNVYYEIGKILSRDILSKINQPYQKFLDVLNTIKNA

SDSDGQDLLFTNQLKEHPTDFSVEFLEQNSNEVQEVFAKAFAYYIEPQHRDVLQLYAPEAFNYMDKFNEQE

-continued

```
INLSLEELKDQRMLARYEKWEKIKQHYQHWSDSLSEEGRGLLKKLQIPIEPKKDDIIHSLSQEEKELLKRI

QIDSSDFLSTEEKEFLKKLQIDIRDSLSEEEKELLNRIQVDSSNPLSEKEKEFLKKLKLDIQPYDINQRLQ

DTGGLIDSPSINLDVRKQYKRDIQNIDALLHQSIGSTLYNKIYLYENMNINNLTATLGADLVDSTDNTKIN

RGIFNEFKKNFKYSISSNYMIVDINERPALDNERLKWRIQLSPDTRAGYLENGKLILQRNIGLEIKDVQII

KQSEKEYIRIDAKVVPKSKIDTKIQEAQLNINQEWNKALGLPKYTKLITFNVHNRYASNIVESAYLILNEW

KNNIQSDLIKKVTNYLVDGNGRFVFTDITLPNIAEQYTHQDEIYEQVHSKGLYVPESRSILLHGPSKGVEL

RNDSEGFIHEFGHAVDDYAGYLLDKNQSDLVTNSKKFIDIFKEEGSNLTSYGRTNEAEFFAEAFRLMHSTD

HAERLKVQKNAPKTFQFINDQIKFIINS
```

This is but one example of one particular anthrax protein within the scope of the invention. The amino acid sequences of LF proteins, including native proteins, from various strains of anthrax are known in the art and include, for example, GenBank Accession Nos: NP_652928.1 and ZP_02609621.1, which are incorporated by reference. Various fragments, mutations, and modifications in LF to reduce its toxicity or to improve its expression characteristics are also known, such as those described elsewhere in the specification.

An example of a lethal factor protein that has been mutated to ablate its endopeptidase activity is SEQ ID NO: 18:

```
MNIKKEFIKVISMSCLVTAITLSGPVFIPLVQGAGGHGDVGMHVKEKEKNKDENKRKDEERNKTQEEHLKE

IMKHIVKIEVKGEEAVKKEAAEKLLEKVPSDVLEMYKAIGGKIYIVDGDITKHISLEALSEDKKKIKDIYG

KDALLHEHYVYAKEGYEPVLVIQSSEDYVENTEKALNVYYEIGKILSRDILSKINQPYQKFLDVLNTIKNA

SDSDGQDLLFTNQLKEHPTDFSVEFLEQNSNEVQEVFAKAFAYYIEPQHRDVLQLYAPEAFNYMDKFNEQE

INLSLEELKDQRMLARYEKWEKIKQHYQHWSDSLSEEGRGLLKKLQIPIEPKKDDIIHSLSQEEKELLKRI

QIDSSDFLSTEEKEFLKKLQIDIRDSLSEEEKELLNRIQVDSSNPLSEKEKEFLKKLKLDIQPYDINQRLQ

DTGGLIDSPSINLDVRKQYKRDIQNIDALLHQSIGSTLYNKIYLYENMNINNLTATLGADLVDSTDNTKIN

RGIFNEFKKNFKYSISSNYMIVDINERPALDNERLKWRIQLSPDTRAGYLENGKLILQRNIGLEIKDVQII

KQSEKEYIRIDAKVVPKSKIDTKIQEAQLNINQEWNKALGLPKYTKLITFNVHNRYASNIVESAYLILNEW

KNNIQSDLIKKVTNYLVDGNGRFVFTDITLPNIAEQYTHQDEIYEQVHSKGLYVPESRSILLHGPSKGVEL

RNDSEGFIHQFGYAVDDYAGYLLDKNQSDLVTNSKKFIDIFKEEGSNLTSYGRTNEAEFFAEAFRLMHSTD

HAERLKVQKNAPKTFQFINDQIKFIINS
```

Changes relative to the native lethal factor are shown in bold.

```
Anthrax Oedema Factor Antigen (EF) (SEQ ID NO: 21):
MTRNKFIPNKFSIISFSVLLFAISSSQAIEVNAMNEHYTESDIKRNHKTEKNKTEKEKFKDSINNLVKTEF

TNETLDKIQQTQDLLKKIPKDVLEIYSELGGEIYFTDIDLVEHKELQDLSEEEKNSMNSRGEKVPFASRFV

FEKKRETPKLIINIKDYAINSEQSKEVYYEIGKGISLDIISKDKSLDPEFLNLIKSLSDDSDSSDLLFSQK

FKEKLELNNKSIDINFIKENLTEFQHAFSLAFSYYFAPDHRTVLELYAPDMFEYMNKLEKGGFEKISESLK

KEGVEKDRIDVLKGEKALKASGLVPEHADAFKKIARELNTYILFRPVNKLATNLIKSGVATKGLNVHGKSS

DWGPVAGYIPFDQDLSKKHGQQLAVEKGNLENKKSITEHEGEIGKIPLKLDHLRIEELKENGIILKGKKEI

DNGKKYYLLESNNQVYEFRISDENNEVQYKTKEGKITVLGEKFNWRNIEVMAKNVEGVLKPLTADYDLFAL

APSLTEIKKQIPQKEWDKVVNTPNSLEKQKGVTNLLIKYGIERKPDSTKGTLSNWQKQMLDRLNEAVKYTG

YTGGDVVNHGTEQDNEEFPEKDNEIFIINPEGEFILTKNWEMTGRFIEKNITGKDYLYYFNRSYNKIAPGN

KAYIEWTDPITKAKINTIPTSAEFIKNLSSIRRSSNVGVYKDSGDKDEFAKKESVKKIAGYLSDYYNSANH

IFSQEKKRKISIFRGIQAYNEIENVLKSKQIAPEYKNYFQYLKERITNQVQLLLTHQKSNIEFKLLYKQLN

FTENETDNFEVFQKIIDEK
```

This is but one example of one particular anthrax protein within the scope of the invention. The amino acid sequences of EF proteins, including native proteins, from various strains of anthrax are known in the art. Various fragments, mutations, and modifications in EF to reduce its toxicity or to improve its expression characteristics are also known, such as those described elsewhere in the specification. An example of an EF protein that has been mutated to ablate its adenylyl cyclase activity is histidine 351 to alanine SEQ ID NO: 22:

```
Anthrax Oedema Factor Antigen (EF His351Ala) (SEQ ID NO: 22):
MTRNKFIPNKFSIISFSVLLFAISSSQAIEVNAMNEHYTESDIKRNHKTEKNKTEKEKFKDSINNLVKTEF

TNETLDKIQQTQDLLKKIPKDVLEIYSELGGEIYFTDIDLVEHKELQDLSEEEKNSMNSRGEKVPFASRFV

FEKKRETPKLIINIKDYAINSEQSKEVYYEIGKGISLDIISKDKSLDPEFLNLIKSLSDDSDSSDLLFSQK

FKEKLELNNKSIDINFIKENLTEFQHAFSLAFSYYFAPDHRTVLELYAPDMFEYMNKLEKGGFEKISESLK

KEGVEKDRIDVLKGEKALKASGLVPEHADAFKKIARELNTYILFRPVNKLATNLIKSGVATKGLNVAGKSS

DWGPVAGYIPFDQDLSKKHGQQLAVEKGNLENKKSITEHEGEIGKIPLKLDHLRIEELKENGIILKGKKEI

DNGKKYYLLESNNQVYEFRISDENNEVQYKTKEGKITVLGEKFNWRNIEVMAKNVEGVLKPLTADYDLFAL

APSLTEIKKQIPQKEWDKVVNTPNSLEKQKGVTNLLIKYGIERKPDSTKGTLSNWQKQMLDRLNEAVKYTG

YTGGDVVNHGTEQDNEEFPEKDNEIFIINPEGEFILTKNWEMTGRFIEKNITGKDYLYYFNRSYNKIAPGN

KAYIEWTDPITKAKINTIPTSAEFIKNLSSIRRSSNVGVYKDSGDKDEFAKKESVKKIAGYLSDYYNSANH

IFSQEKKRKISIFRGIQAYNEIENVLKSKQIAPEYKNYFQYLKERITNQVQLLLTHQKSNIEFKLLYKQLN

FTENETDNFEVFQKIIDEK
```

In addition to the various mutations and modifications already noted, the present invention also encompasses polypeptides that are substantially homologous to a polypeptide based on any one of the SEQ ID NOS identified in this application (including fragments thereof). The term "substantially homologous" is used to denote polypeptides having at least about 70%, at least about 75%, at least about 80%, in some cases at least about 85%, in other cases at least about 90%, in yet other cases at least about 95%, and in still other cases at least about 98% or even 99% sequence identity to the other polypeptide.

Peptides disclosed in the present application likewise include peptides that are "substantially homologous" thereto, and embrace peptides having at least about 90%, in some cases at least about 95%, and in yet other cases at least about 98% or even 99%, sequence identity thereto. Exemplary peptides are provided in the present application, but unless reference is made to a specific SEQ ID NO or the discussion makes clear that only a specific sequence is intended, then the sequences exemplified in the specification are illustrative only of the various peptides, polypeptides, and proteins described in the application.

Percent sequence identity is determined by conventional methods. See, for example, Altschul et al., *Bull. Math. Bio.* 48: 603-16, 1986 and Henikoff and Henikoff, *Proc. Natl. Acad. Sci. USA* 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in the following chart (amino acids are indicated by the standard one-letter codes):

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as: ([Total number of identical matches]/[length of the longer sequence plus the number of gaps introduced into the longer sequence in order to align the two sequences])×100.

Substantially homologous polypeptides have one or more amino acid substitutions, deletions, or additions. In many embodiments, those changes are of a minor nature, for example, involving only conservative amino acid substitutions. Conservative substitutions are those made by replacing one amino acid with another amino acid within the following groups: Basic: arginine, lysine, histidine; Acidic: glutamic acid, aspartic acid; Polar: glutamine, asparagine; Hydrophobic: leucine, isoleucine, valine; Aromatic: phenylalanine, tryptophan, tyrosine; Small: glycine, alanine, serine, threonine, methionine. Substantially homologous polypeptides also encompass those comprising other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the clostridial polypeptides of the present invention. A limited number of non-conservative amino acids, amino acids that are not encoded by the genetic code, and unnatural amino acids may be substituted for clostridial polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into peptides. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations can be carried out in a cell free system comprising an *E. coli* S30 extract and commercially available enzymes and other reagents. Peptides can be, for instance, purified by chromatography. See, for example, Robertson et al., *J. Am. Chem. Soc.* 113:2722, 1991; Ellman et al., *Methods Enzymol.* 202:301, 1991; Chung et al., *Science* 259: 806-9, 1993; and Chung et al., *Proc. Natl. Acad. Sci. USA* 90:10145-9, 1993). In a second method, translation is carried out in *Xenopus oocytes* by microinjection of mutated mRNA and chemically aminoacylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptdie in place of its natural counterpart. See, Koide et al., *Biochem.* 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

Essential amino acids, such as those in the clostridial polypeptides of the present invention, can be identified according to procedures known in the art, such as site-directed mutagenesis or alanine-scanning mutagenesis (Cunningham and Wells, *Science* 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306-12, 1992; Smith et al., *J. Mol. Biol.* 224:899-904, 1992; Wlodaver et al., *FEBS Lett.* 309:59-64, 1992. The identities of essential amino acids can also be inferred from analysis of homologies with related family members of the polypeptide of interest.

Multiple amino acid substitutions can be made and tested using known methods of mutagenesis and screening, such as those disclosed by Reidhaar-Olson and Sauer (*Science* 241: 53-7, 1988) or Bowie and Sauer (*Proc. Natl. Acad. Sci. USA* 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

It should be noted that reference to proteins, polypeptides, and peptides throughout the present application embraces fragments thereof unless it is clear from the context that a fragment is excluded. In particular, the present invention embraces fragments having at about 100, at least about 150, at least about 200, at least about 250, or at least about 300 contiguous amino acid residues of a peptide (including substantially homologous embodiments thereof) disclosed in the present application. The fragments may embrace at least about 200-300, often at least about 400-500, in many embodiments at least about 600-700, and in certain embodiments at least about 800 contiguous amino acids of a polypeptide (including substantially homologous embodiments thereof) disclosed in the present application.

By way of example, one fragment of the present invention comprises an amino acid sequence having at least about 90% sequence identity, over a sequence of at least about 200 contiguous amino acids. For instance, the invention includes a fragment comprising an amino acid sequence having at least 200 contiguous amino acid residues and having at least 90% sequence identity (e.g., starting at position 350, 400, 440 or 448) with the amino acid sequence as set forth in SEQ ID NO: 8 or 9. In another embodiment, the fragment comprises an amino acid sequence having at least 200 contiguous amino acid residues and having at least 90% sequence identity (e.g., starting at position 449 or 455) with the amino acid sequence as set forth in SEQ ID NO: 8 or 9. Yet other embodiments involve a fragment comprising an amino acid sequence having at least 200 amino acid residues and having at least 90% sequence identity over the contiguous residues 348-548 of the amino acid sequence of SEQ ID NO:8 or 9.

In one embodiment of the invention, a clostridial peptide treated with a chemical modifying agent lacks a $H_c$ region or a functional $H_C$ region. Accordingly, said peptides are not able to bind rat synaptosomal membranes in binding assays as described in Shone et al. (1985) Eur. J. Biochem. 151, 75-82. In one embodiment, the clostridial peptides lack the last about 50 C-terminal amino acids of a clostridial neurotoxin holotoxin. In another embodiment, the clostridial peptides lack the last about 100, the last about 150, the last about 200, the last about 250, or even the last about 300 C-terminal amino acid residues of a clostridial neurotoxin holotoxin. In one embodiment of the invention, the clostridial peptide is not a native peptide.

Alternatively, the Hc binding activity may be negated/reduced by mutagenesis. Often this involves substitution of the amino acid pair WY (tryptophan, tyrosine) with the amino acids LF (leucine, phenylalanine). By way of example, referring to BoNT/A (SEQ ID NOS: 8 and 9), modification of one or two amino acid residue mutations (W1266 to L and Y1267 to F) in the ganglioside binding pocket cause the $H_C$ region to lose its receptor binding function. Analogous mutations may be made to non-serotype A clostridial peptides (e.g., to SEQ ID NOs: 23 and 24 for serotype B; and to SEQ ID NOs: 26 and 27 for serotype E)—by way of example, a construct based on C. botulinum B with mutations (W1262 to L and Y1263 to F) or C. botulinum E (W1224 to L and Y1225 to F). Other mutations to the active site achieve the same ablation of $H_C$ receptor binding activity, e.g. Y1267S in C. botulinum type A toxin (e.g., SEQ ID NO: 8) and the corresponding highly conserved residue in the other clostridial neurotoxins. Details of this and other mutations are described in Rummel et al. (2004) (Molecular Microbiol. 51:631-634), which is hereby incorporated by reference in its entirety.

In one embodiment of the invention, the nucleic acid encoding a bacterial peptide is codon optimized for expression in a host cell. For instance, in one embodiment of the invention, a nucleic acid encoding a $LH_N$ fragment is codon optimized for expression in a E. coli. In another embodiment, the nucleic acid encoding a $LH_N$ fragment is codon optimized for expression in a eukaryotic cell, for instance, a yeast cell, mammalian cell or insect cell. Genes encoding polypeptides such as those described are commercially available with codon bias for any desired expression host (e.g., E. coli, Pichia pastoris).

Polypeptides are expressed from these gene using standard molecular biology methods (e.g., Sambrook et al. 1989, Molecular Cloning a Laboratory Manual, Second Edition, Cold Spring Harbor Laboratory Press, Cold Spring Harbor, N.Y.) and the resulting soluble expressed peptide can be purified by, for instance, a combination of hydrophobic interaction chromatography, ion exchange chromatography and ceramic hydroxyl apatite chromatography. Other chromatographic techniques well known to the art of protein purification, such size exclusion chromatography, may be used.

Methods of manipulating nucleic acids and of expressing the encoded proteins are known in the art, and include those described in Molecular Cloning, A Laboratory Manual (2nd Ed., Sambrook, Fritsch and Maniatis, Cold Spring Harbor) and Current Protocols in Molecular Biology (Eds. Aufubel, Brent, Kingston, More, Feidman, Smith and Stuhl, Greene Publ. Assoc., Wiley-Interscience, NY, N.Y., 1992). Thus, it is possible to express a modified polypeptide by modifying a nucleic acid sequence encoding that polypeptide by replacing the codon for one amino acid with a codon for another amino acid. Techniques for making substitution and deletion mutations at predetermined sites in a nucleic acid having a known sequence are well known and include, but are not limited to, primer mutagenesis and other forms of site-directed mutagenesis.

Similarly, methods of joining two sequence fragments, such as an $LH_N$ and an $H_C$ fragment of a clostridial neurotoxin, and of truncating a sequence, are known in the art. These include, but are not limited to, PCR-based techniques and techniques for ligating together two or more nucleic acid sequences.

Methods of expressing proteins are known to the skilled artisan and can be practiced with no more than routine experimentation. Generally, in order to express a protein, such as a bacterial toxin or fragment thereof, a suitable host cell is transformed with a DNA sequence encoding that protein under the control of known regulatory sequences. The transformed host cells are cultured and the protein recovered and isolated from the culture medium. The isolated expressed proteins are substantially free from other proteins with which they are co-produced as well as from other contaminants.

The peptide or polypeptide to be chemically modified should generally be soluble or predominantly soluble (for instance, at least about 70%, 75%, 80%, 85%, 90%, 95%, 97%, 98%, or even 99% soluble). There are various ways to produce peptides or polypeptides that exhibit increased solubility. The optimal method employed depends upon the particular peptide or polypeptide. Examples of methods that can be used to produce a maximally soluble peptide or polypeptide include the use of particular buffers and/or pH during culture, and the reduction of the temperature during the fermentation process. By way of example, we refer to U.S. 61/060,978 (filed Jun. 12, 2008), which is incorporated by reference in its entirety. Additional examples of methods to increase solubility reduce aggregation are described in WO 2007/044382, which is incorporated by reference in its entirety.

Bacterial cells may be used as suitable hosts for expression of a bacterial toxin or fragment thereof. For example, various strains of E. coli (e.g., HB101, MC1061) are well-known as host cells in the field of biotechnology. Various strains of B. subtilis, Pseudomonas, other bacilli and the like may also be used. For expression of a protein in bacterial cells, DNA encoding the propeptide is generally not necessary. Suitable cells or cell lines may also be mammalian cells, such as Chinese hamster ovary cells (CHO), the monkey kidney COS-1 cell line, or mammalian CV-1 cells. The selection of suitable mammalian host cells and methods for transformation, culturing, amplification, screening, product production and purification are known in the art. (See, e.g., Gething and Sambrook, Nature, 293:620-625 (1981); Kaufman et al., Mol Cell Biol., 5(7):1750-1759 (1985); Howley et al., U.S. Pat. No. 4,419,446.)

In some embodiments, the polypeptide or fragment thereof is expressed using a vector that contains a DNA sequence encoding the polypeptide and appropriate expression control sequences. Expression control sequences for such vectors are known to those skilled in the art and may be selected depending upon the host cells. In other embodiments, the polypeptide or fragment thereof is expressed as a fusion protein comprising the protein sequence of the polypeptide or fragment thereof and, for example, a tag to stabilize the resulting fusion protein or to simplify purification of the bacterial toxin or fragment thereof. Such tags are known in the art. Representative examples include sequences which encode a series of histidine residues, the epitope tag FLAG, the Herpes simplex glycoprotein D, beta-galactosidase, maltose binding protein, streptavidin tag or glutathione S-transferase.

IV. Compositions and Vaccines

The invention also provides compositions comprising chemically modified peptides and polypeptides.

In some embodiments, the chemically modified peptides and polypeptides have an increased protective effect that can be measured by their improved ability to stimulate an immune response when compared to an unmodified peptide or polypeptide. In other embodiments, the increased protective effect can be measured by the ability to provide improved cross-serotype protection when compared to an unmodified peptide or polypeptide. In yet other embodiments, the increased protective effect can be measured by the ability to provide improved cross-subtype protection when compared to an unmodified peptide or polypeptide. In still other embodiments, the increased protective effect can be measured by a combination of one, two, or three of the ability to provide an improved ability to stimulate an immune response, an improved cross-serotype protection, and an improved cross-subtype protection. Often, although not always, the peptide or polypeptide may display an increase in stability compared to the unmodified peptide or polypeptide. The increased stability is due, at least in some embodiments, to the intra-molecular cross-links, such as those comprising one or more methylene bonds.

Also, in some embodiments, the peptide or polypeptide does not form aggregates or forms a minimal amount of aggregates.

The invention includes, for instance, an endopeptidase negative $LH_N$ fragment that has been treated with formaldehyde under conditions which increase the immunogenicity of the toxin fragment as compared to a fragment not treated with formaldehyde. In one embodiment of the invention, the endopeptidase negative LHN fragment is a $LH_N$/E fragment.

The compositions of the invention usually comprise a carrier of some type in addition to the polypeptide or peptide. Generally, the carrier is a pharmaceutically-acceptable carrier. In some embodiments, however, it may be desirable to formulate the composition with a preservative, such as thiomersal or sodium azide, to facilitate long term storage. Non-limiting examples of pharmaceutically acceptable carriers include water, saline, and phosphate-buffered saline. In some embodiments, however, the composition is in lyophilized form, in which case it may include a stabilizer, such as BSA.

Vaccines comprising a composition comprising one or more of the chemically modified peptides or polypeptides are also provided.

The active immunogenic ingredients are often mixed with carriers or excipients which are pharmaceutically acceptable and compatible with the active ingredient. Suitable carriers and excipients include, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

The vaccine may further comprise one or more adjuvants. One non-limiting example of an adjuvant with the scope of the invention is aluminium hydroxide. Other non-limiting examples of adjuvants include but are not limited to: N-acetyl-muramyl-L-threonyl-D-isoglutamine (thr-MDP), N-acetyl-nor-muramyl-L-alanyl-D-isoglutamine (CGP 11637, referred to as nor-MOP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Typically, the vaccines are prepared as injectables, either as liquid solutions or suspensions. Of course, solid forms suitable for solution in, or suspension in, liquid prior to injection may also be prepared. The preparation may also be emulsified, or the peptide encapsulated in liposomes or microcapsules.

Vaccine administration is generally by conventional routes e.g. intravenous, subcutaneous, intraperitoneal, or mucosal routes. The administration may be by parenteral injection, for example, a subcutaneous or intramuscular injection.

The vaccines are administered in a manner compatible with the dosage formulation, and in such amount as will be prophylactically and/or therapeutically effective. The quantity to be administered, which is generally in the range of 5 micrograms to 250 micrograms of antigen per dose, depends on the subject to be treated, capacity of the subject's immune system to synthesize antibodies, and the degree of protection desired. Precise amounts of active ingredient required to be administered may depend on the judgment of the practitioner and may be particular to each subject.

The vaccine may be given in a single dose schedule, or optionally in a multiple dose schedule. A multiple dose schedule is one in which a primary course of vaccination may be with 1-6 separate doses, followed by other doses given at subsequent time intervals required to maintain and or reinforce the immune response, for example, at 1-4 months for a second dose, and if needed, a subsequent dose(s) after several months. The dosage regimen will also, at least in part, be determined by the need of the individual and be dependent upon the judgment of the practitioner.

In addition, the vaccine containing the immunogenic antigen(s) may be administered in conjunction with other immunoregulatory agents, for example, immunoglobulins, antibiotics, interleukins (e.g., IL-2, IL-12), and/or cytokines (e.g., IFNγ).

Additional formulations which are suitable for other modes of administration include microcapsules, suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of about 0.5% to 10%, including for instance, about 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain about 10%-95% of active ingredient, including, for instance, about 25%-70% of active ingredient.

The invention also provides methods of stimulating an immune response in a mammal, such as a human, by administering to the mammal an amount of a vaccine of the invention sufficient to stimulate an immune response. In some embodiments, immune stimulation is measured by an increased protective effect compared to a vaccine comprising the unmodified form of the same peptide or polypeptide. In other embodiments, immune stimulation is measured by increases in antibody titer that is specific for the antigen in the vaccine. In still other embodiments, immune stimulation is measured by an increased frequency in cytotoxic T lymphocytes specific for the antigen in the vaccine.

Thus, one embodiment of the invention is a vaccine comprising peptides in which the peptides are treated with a chemical modifying agent to give a vaccine of much improved efficacy.

In one particular embodiment, the vaccine is based on a peptide (e.g., a *botulinum* toxin fragment, a tetanus toxin fragment, a *C. difficile* toxin or surface peptide fragment, or an anthrax toxin fragment) having intra-molecular cross-linking, which results in a vaccine of much improved efficacy. Treatment with the chemical modifying agent induces the formation of one or more intra-molecular (e.g., methylene) bonds. Since the intra-molecular bond(s) are introduced by a modifying chemical, said bonds are typically absent from the corresponding native (i.e., untreated) peptide. In many embodiments, two, three, or more such bonds are formed. In this regard, the bond(s) typically, originate from arginine and/or lysine amino acid residues, although this is not necessarily the case. As noted, a variety of chemical modifying agents may be employed so long as the agent introduces at least one intramolecular bond (e.g., a methylene bond) into the peptide. In the case of clostridial fragments having two peptide chains (e.g., a L-chain and a H-chain in the case of a clostridial neurotoxin), the intra-molecular bond(s) may form within either chain, and/or across the chains. In some of the embodiments involving clostridial fragments, said bond(s) bridge both chains—e.g., in the case of a clostridial neurotoxin, the L-chain and H-chain are bridged by intra-molecular bond(s).

In one embodiment of the invention, a vaccine is described based on an $LH_N$ fragment of a clostridial neurotoxin (which consists of the light chain and N-terminal 50 kDa of heavy chain) in which this fragment is treated with formaldehyde to give a significantly improved vaccine.

In another embodiment of the invention, a vaccine is described comprising an extended $LH_N$ fragment of a clostridial neurotoxin and lacking a functional $H_C$ domain of a *botulinum* toxin, in which this fragment is treated with a chemical modifying agent to give a significantly improved vaccine. In this embodiment, lack of $H_C$ functionality may be readily conferred by mutation and/or deletion of $H_C$ amino acid residues from a clostridial neurotoxin holotoxin.

In one embodiment of the invention, a vaccine is described based on an $LH_N$ fragment of a clostridial (e.g., *botulinum*) neurotoxin in which the fragment is treated with a chemical modifying agent (e.g., formaldehyde) to give a significantly improved vaccine. In a one embodiment, the clostridial neurotoxin fragment is a *botulinum* type A, B, or E neurotoxin fragment.

In another embodiment of the invention, a vaccine is described based on a peptide consisting of (or corresponding to) amino acid residues 2-871 of *botulinum* neurotoxin serotype A in which this peptide is treated with formaldehyde to give a significantly improved vaccine for *botulinum* type A toxin. One example of a *botulinum* neurotoxin serotype A polypeptide is given in SEQ ID NO: 1. Another example of a *botulinum* neurotoxin serotype A polypeptide is given in SEQ ID NO: 2. Yet another example of a *botulinum* neurotoxin serotype A polypeptide is given in SEQ ID NO: 3.

In one embodiment of the invention, a vaccine is described based on a peptide consisting of (or corresponding to) amino acid residues 2-871 (or a fragment thereof) of *botulinum* neurotoxin serotype A containing 1 or 2 mutations, namely: Glu 224 to Gln and/or His 227 to Tyr. This peptide is then treated with a modifying agent (e.g. formaldehyde) to give a significantly improved vaccine for *botulinum* type A toxin.

In yet another embodiment of the invention, a vaccine is described based on a peptide consisting of (or corresponding to) amino acid residues 2-871 of *botulinum* neurotoxin serotype E in which this peptide is treated with formaldehyde to give a significantly improved vaccine for *botulinum* type E toxin. One example of a *botulinum* neurotoxin serotype E polypeptide is given in SEQ ID NO: 4.

The above-mentioned substitution(s) described in connection with the 2-871 peptide embodiment may be introduced into any of the clostridial peptide embodiments of the present invention. In more detail, said substitution(s) (at least partially) inactivate the metalloprotease activity of the L-chain component. In this regard, simple amino acid sequence alignment of the different clostridial neurotoxin species/serotypes allows identification of the corresponding amino acid residues in clostridial neurotoxin peptides other than serotype A. Another example of a metalloprotease-inactivating mutation comprises substitution/ deletion of Glu262. Again, simple amino acid sequence alignment of the different clostridial toxin species/ serotypes allows identification of the corresponding amino acids in clostridial neurotoxin peptides other than serotype A. A yet further metalloprotease-inactivating mutation comprises modification of the HELIH (SEQ ID NO: 36) active site motif (e.g., serotype A) to an HQLIY (SEQ ID NO: 37) motif. Again, simple amino acid sequence alignment of the different clostridial toxin species/ serotypes allows identification of the corresponding amino acids in clostridial neurotoxin peptides other than serotype A. For botulinum neurotoxin serotypes B, E, F, G and tetanus neurotoxin, an identical change to the HELIH light chain motif (SEQ ID NO: 36) may be made to inactivate the endopeptidase activity of the light chain. For botulinum neurotoxin serotypes C and D, the native motif is HELNH (SEQ ID NO: 38) and HELTH (SEQ ID NO: 39), respectively, which, to inactivate the endopeptidase activity, may be mutated to HQLNY (SEQ ID NO: 40) and HQLTY (SEQ ID NO: 41), respectively.

In another embodiment of the invention, a vaccine for producing protective antibodies against *Clostridium difficile*-associated disease is described, which comprises a surface peptide of *Clostridium difficile* (or a fragment thereof) or a peptide which is substantially homologous thereto. In more detail, at least one intramolecular cross-link is introduced into the surface peptide, and enhances the efficacy of a surface peptide as a vaccine and as an antigen for producing protective antibodies. Said cross-link(s) may be introduced by formaldehyde treatment or using another cross-linking reagents. Introduction of one or more intra-molecular cross-link(s) through treatment with formaldehyde or other cross-linking reagents provides antigen of improved efficacy for inducing a protective immune response compared to the untreated polypeptide.

In one embodiment of the invention, the *C. difficile* vaccine is based on a surface peptide such as Cwp 84 (e.g., SEQ ID NO: 15). In one embodiment, a Cwp 84 fragment treated with an agent comprises either the initial "M" or the last "K" amino acid.

In another embodiment of the invention, a vaccine is described, which comprises modified *C. difficile* toxin peptide. The modified peptide has one or more intramolecular cross-link(s) that have been introduced to enhance its efficacy as a vaccine and as an antigen for producing protective antibodies. Said cross-link(s) may be introduced by formaldehyde treatment or using another cross-linking reagent. In one embodiment, the peptide used as the basis for the *C. difficile* antigen may be a C-terminal region of Toxin A (e.g., SEQ ID NO: 10 or 11) or Toxin B (e.g., SEQ ID NO: 12), or may be based on a peptide sequence that is substantially homologous thereto. Alternatively, the peptide may be derived from (or be substantially homologous to) the N-terminus of Toxin A (e.g., SEQ ID NO: 13) or Toxin B (e.g., SEQ ID NO: 14). Alternatively, for a *C. difficile* antigen based on its binary toxin, a peptide sequence which is substantially homologous to either of the sequences in SEQ ID NO: 19 or SEQ ID NO: 20 may be employed.

In the case of fragments based on the toxin peptide sequences disclosed in SEQ ID NOS: 10, 11 and 13, the fragments include, in one embodiment, the first or last amino acid residue identified. For instance, in the case of a fragment based on the Toxin A sequence illustrated SEQ ID NO: 13, a fragment could include the first "Q" or the last "G" amino acid residue. The same principle applies to fragments based on the other sequences.

Introduction of intra-molecular cross-links through treatment with formaldehyde or other cross-linking reagents provides antigens derived from the *C. difficile* factors which induce a significantly better immune response compared to the equivalent untreated polypeptide.

In another embodiment of the invention, a vaccine for producing protective antibodies against anthrax-associated disease or anthrax toxin poisoning is described. In more detail, one embodiment provides a modified anthrax protective antigen (PA) in which at least one intramolecular cross-link(s) has been introduced to enhance its efficacy as a vaccine. Said cross-link(s) may be introduced by formaldehyde treatment or by another cross-linking reagent. The peptide used as the basis for the anthrax vaccine is PA (or a fragment thereof), for instance, recombinant PA, or a peptide substantially homologous therewith. Introduction of intra-molecular cross-link(s) through treatment with formaldehyde or other cross-linking reagents overcomes the prior art problem of reduced protection or stability and provides an anthrax vaccine having enhanced efficacy or stability.

In yet another embodiment of the invention, a modified (e.g., recombinant) anthrax lethal factor is described in which at least one intramolecular cross-link(s) has been introduced to enhance its efficacy as a vaccine. Said cross-link(s) may be introduced by formaldehyde treatment or another cross-linking reagent. The peptide used as the basis for the anthrax vaccine is LF (e.g., SEQ ID NO: 17 or 18) (or a fragment thereof), or a peptide substantially homologous therewith. In some embodiments, the LF peptide may contain amino acid substitutions to ablate the endopeptidase activity of LF. For LF, the motif sequence HEFGH (residues 719-723 of SEQ ID NO: 17) is mutated to HQFGY (residues 719-723 of SEQ ID NO: 18) to eliminate endopeptidase activity.

In the case of anthrax vaccine based on PA or LF fragments, said fragments often include the first or last amino acid residue. In one embodiment, a PA fragment includes the first "M" or last "G" illustrated in SEQ ID NO: 16. Similarly, an LF fragment may include the first "M" or the last "S" illustrated in SEQ ID NO: 17 or 18.

The above-mentioned anthrax embodiments may further comprise one or more S-layer protein. By way of example, S-layer proteins include Sap (e.g., Sap 1) and/ or EA1 (see Farchaus et al., (1995) J. Bacteriology, 177, pp. 2481-2489; and Mesnage et al. (1997) Molec. Microbiol. 23, pp. 1147-1155).

As discussed in the Examples that follow, studies have established that treatment of peptide preparations treated with 0.2% formaldehyde at 35° C. for 24 hours resulted in intra-molecular cross-linking. In the case of an $LH_N$ peptide preparation of the present invention, SDS-PAGE analysis has confirmed a 97 kDa monomeric fragment as a broad band (as compared to $LH_N/A$ control preparations), and a small amount of dimeric $LH_N/A$ molecules (<5%)—see FIGS. 1 and 2.

It is surprising that, under the above conditions, the modifying agent-treated vaccine displays significantly enhanced efficacy compared to control untreated samples. In the case of a type A vaccine based on formaldehyde-treated $LH_N/A$, the efficacy of the vaccine was increased >15 fold compared to the untreated control sample (see Tables 1-3). The formation of inter-molecular cross-links which would give rise to higher molecular weight aggregates does not appear to occur. This is clearly demonstrated since enhanced efficacy is observed under conditions in which inter-molecular cross-linking and the formation of aggregates does not occur (see FIG. 2). Under such conditions, $ED_{50}$ values obtained were >15 fold (and hence of higher efficacy) than controls (Table 2, Test 3). The enhancement effect is therefore not mediated in the same manner as that reported previously for small peptides in which aggregation appears to be the underlying mechanism. In such cases, formaldehyde would appear to act simply as an agent to increase the overall molecular mass of smaller peptides, by aggregation, thus allowing the immune system to 'see' them more efficiently. In the case of the present invention, the enhancement in efficacy is unexpected since the untreated vaccine is already of sufficient size to be 'seen' by the immune system and does not change in overall size after treatment with formaldehyde.

For the present invention, the finding that aggregation does not have a role in the enhancement of vaccine efficacy suggests that modifying chemical treatment, through the formation of methylene bridges, results in intra-molecular cross-linking leading to the creation of a more rigid molecular structure of functional epitopes which stimulates the more efficient production of high affinity antibodies. It is well established that peptides with a flexible structure may elicit a weaker immune response than proteins which are more highly ordered in tertiary structure (Putz 2003, Hudecz 2001, Novotny 1986).

The $LH_N/A$ vaccine of the invention also protects against various sub-types of BoNT/A (Table 3). Single dose protection was observed for BoNT/A sub-types $A_1$, $A_2$ and $A_3$. For the unmodified $LH_N/A$, no protection against BoNT sub-type $A_2$ was observed in $ED_{50}$ assessments with up to a single dose of 100 μg of native $LH_N/A$.

The above protection studies with clostridial neurotoxin fragments have been repeated with the *C. difficile* and anthrax aspects of the present invention. In this regard, the *C. difficile* and anthrax aspects of the present invention also demonstrate improved efficacy/protection vis-a-vis the corresponding, untreated *C. difficile* and anthrax peptides.

In conventional *botulinum* toxoid vaccines, partially purified toxins are inactivated with formaldehyde over a period up to 25 days which often results in loss of peptide epitopes and a complex, heterogeneous product containing high molecular weight aggregates. In contrast, the present invention describes the production of vaccines, which rely on a comparatively short incubation period with the modifying chemical and one in which the product contains little or no aggregation and is easy to characterise. Such properties offer significant advantages for manufacture, testing and regulatory approval of the vaccine.

The invention also provides antisera isolated from animals that have been immunized with a vaccine of the invention. In some embodiments, the antiserum is purified to provide a monoclonal or polyclonal population of antibodies that are specific for the antigen in the vaccine. Compared to an antisera produced using an unmodified polypeptide vaccine, the antisera may provide improved survival when administered to an animal prior to or shortly after exposure to a toxic form of the antigen (such as an agent comprising the toxic form of the antigen) used to prepare the vaccine. In one embodiment, the antisera is protective against more than one serotype of BoNT. For example, the antisera may protect against BoNT/A and BoNT/B, BoNT/A and BoNT/E, BoNT/B and BoNT/E, or BoNT/A, BoNT/B, and BoNT/A. In other embodiments, the antisera is protective against one or more BoNT subtype. For example, the antisera may protect against all or some of BoNT/$A_1$, BoNT/$A_2$, and BoNT/$A_3$.

Antibodies raised against fragments preferably have the property of recognising the full-length counterpart peptide from which they are derived. For example, an antibody raised against an $LH_N/A$ fragment of the present invention will have common antigenic cross-reactivity with $LH_N/A$. Similarly, a *C. difficile* fragment or an anthrax fragment will have common antigenic cross-reactivity with the corresponding full-length *C. difficile* or anthrax peptide. Antibodies raised against toxin fragments of the invention will also neutralise the toxic activity of the corresponding full-length toxin.

Antisera can be used for the manufacture of a medicament for treating exposure to bacteria and bacterial toxins. Thus, antibody compositions, such as the isolated antisera or antibodies (monoclonal or polyclonal) purified therefrom, can be used as a passive immune serum to prevent or treat patients exposed to the wild-type toxin. For example, antisera raised in by administering a *botulinum* neurotoxin can be used to prevent or treat patients with botulism. In such cases, the patient is a human, including an infant, suspected of having come in contact with the toxin, or is a human, including an infant, who has had known contact with the toxin, but is not yet showing symptoms of exposure. The antibody composition can also be used in a method of treating to ameliorate symptoms in patients that are suffering from the presence of toxin in their body. When the toxin is a clostridial neurotoxin, the symptoms include diarrhea and paralysis.

Methods of preparing immune sera are known in the art. For example, a vaccine composition can be administered to an animal such as a horse or a human until a antibody response (for instance, neutralizing antibody response) to wild type toxin is generated. Neutralizing antibodies can then be harvested, purified, and administered to patients exposed to, or exhibiting symptoms of contact with, the toxin to thereby treat or prevent botulism. In some cases, the antibodies are not purified after harvesting. When the antibodies are from humans, the antibody preparation will generally be free of viruses, such as HIV and hepatitis. Methods of preparing human antisera are known in the art, and include the methods used to prepare IVIg. The neutralizing antibodies can be administered intravenously, intramuscularly, intradermally, or subcutaneously. Antibiotic therapy can be used in conjunction. Dosages for neutralizing antibodies generally vary from about 1 mg to 1000 mg/kg. Often, they are administered at a dosage of about 50-200 mg/kg of body weight.

The invention will be further clarified by the following examples, which are intended to be purely exemplary of the invention and in no way limiting.

EXAMPLES

Example 1

Preparation of a Vaccine for *Botulinum* Type A Neurotoxin

A gene encoding amino acid residues 1-871 of $LH_N/A$ (SEQ ID NO: #) was obtained commercially with codon bias suited to expression in *E. coli*. The gene also coded for the mutations Glu 224 to Gln and His 227 to Tyr. $LH_N/A$ was expressed from this gene using standard molecular biology methods (e.g. Sambrook et al. 1989, Molecular Cloning a Laboratory Manual, Second Edition, Cold Spring Harbor Laboratory Press, Cold Spring Harbor, N.Y.) and the resulting soluble expressed fragment purified by a combination of hydrophobic interaction chromatography, ion exchange chromatography and ceramic hydroxyl apatite chromatography.

The purified $LH_N/A$ fragment was dialysed against buffer (10mm Hepes buffer pH 7.4 containing 100 mM NaCl) and then the $LH_N/A$ at a concentration of 1 mg ml$^{-1}$ was treated with 0.2% formaldehyde (HCHO) for 24 hours at 35° C. After incubation, the formaldehyde was removed from the mixture by dialysis.

Figure 2:
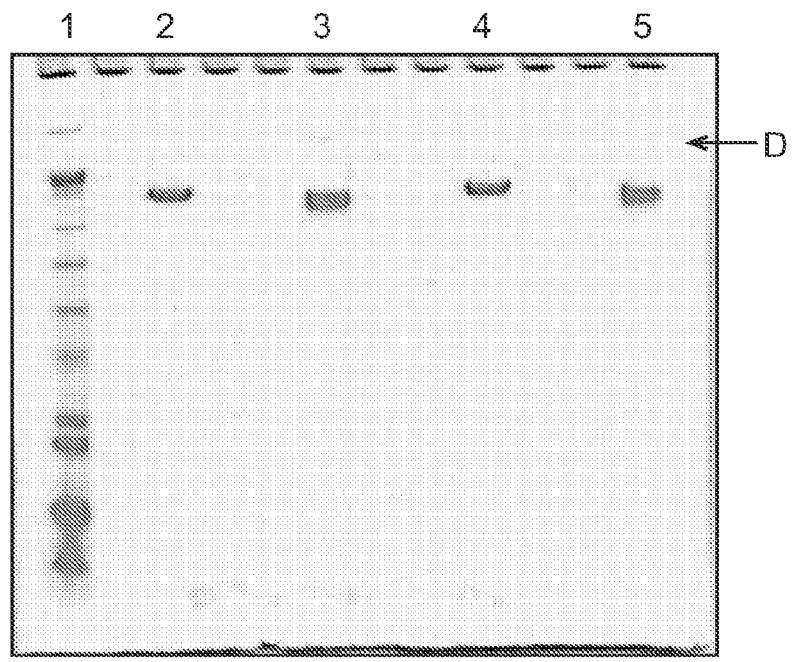
FIG. 2 shows an SDS-PAGE of formaldehyde-treated and control $LH_N/A$ vaccine. Lane 1: mass markers. Lane 2: control $LH_N/A$. Lane 3: formaldehyde-treated $LH_N/A$ (0.1 mg ml$^{-1}$). Lane 4: control $LH_N/A$. Lane 5: formaldehyde-treated $LH_N/A$ (1.0 mg ml$^{-1}$). 'D' indicates the position of the $LH_N/A$ dimer if it is present.

An SDS-PAGE comparison of control $LH_N/A$ and formaldehyde-treated $LH_N/A$ is shown in FIG. 1. Under these conditions, a small % of dimer $LH_N/A$ can be detected (arrow D in FIG. 1).

Example 2

Preparation of Vaccines for Other Clostridial Neurotoxins

Amino acid sequences for other polypeptides that can be used, for instance, to prepare additional vaccine peptides encompassed by the present invention are shown in SEQ ID NOS: 4-7 and 9. The illustrated peptides form the basis of vaccines of the present invention for tetanus toxin and also other botulinum neurotoxin serotypes (e.g., B, E and F). These peptides can contain mutations to the light chain endopeptidase active site. For instance, the motif HELIH (SEQ ID NO: 36) can be changed to HQLIY (SEQ ID NO: 37) to ablate the enzymatic activity. Other mutations to the active site could also be used to achieve the same ablation of light chain activity, e.g. Glu262 in botulinum type A toxin and the corresponding highly conserved residue in the other clostridial neurotoxins. Details of this and other mutations are described in Montecucco et al (2001) (Biochem Biophys Res Comm. 288:1231-7), which is hereby incorporated by reference in its entirety.

Genes encoding peptides such as the above are commercially available with codon bias for any desired expression host (e.g. *E. coli, Pichia pastoris*). Peptides are expressed from these genes using standard molecular biology methods (e.g. Sambrook et al. 1989, Molecular Cloning a Laboratory Manual, Second Edition, Cold Spring Harbor Laboratory Press, Cold Spring Harbor, N.Y.) and the resulting soluble expressed peptide can be purified by a combination of hydrophobic interaction chromatography, ion exchange chromatography and ceramic hydroxyl apatite chromatography. Other chromatographic techniques well known to the art of protein purification, such size exclusion chromatography and/or affinity chromatography, may be used.

The purified peptide can then dialysed against buffer (10 mm Hepes buffer pH 7.4 containing 100 mM NaCl) and then 0.2% formaldehyde is added and incubated for between 24 and 72 hours at 35° C. After incubation, the formaldehyde may be removed from the mixture by dialysis.

Example 3

Preparation of Fragments of the Invention Using Other Cross-Linking Agents

In addition to formaldehyde, other cross-linking agents may be employed to produce vaccines of the invention. Examples of other cross-linking agents that may be employed include C6-succinimidyl 4-hydrazinonicotinate acetone hydrazone, C6-succinimidyl 4-formylbenzoate, BIS-(Sulfo-succinimidyl) suberate, disuccinimidyl suberate, dimethyl suberimidate dihydrochloride, dimethyl pimelimidate 2 HCl, dimethyl adipimidate dihydrochloride, succinimidyl 4-hydrazidoterephthalate hydrochloride, and disuccinimidyl glutarate. The cross linking agent can be dissolved in a suitable solvent (e.g. water, buffer, ethanol or acetone) and then mixed with the vaccine peptide. The cross-linking agent can be added to the peptide in a molar excess which may be between 3-50 fold moles of cross-linker per mole of peptide. The peptide is typically present at a concentration of between 0.1-5 mg/ml, and is typically incubated with the cross-linker from 1-24 hr at temperature between 4-37° C. Exact conditions may be determined as those which provide the optimal immune response in animals (e.g. mice, guinea pigs or rabbits) (see Example 6).

Example 4

Figure 3:
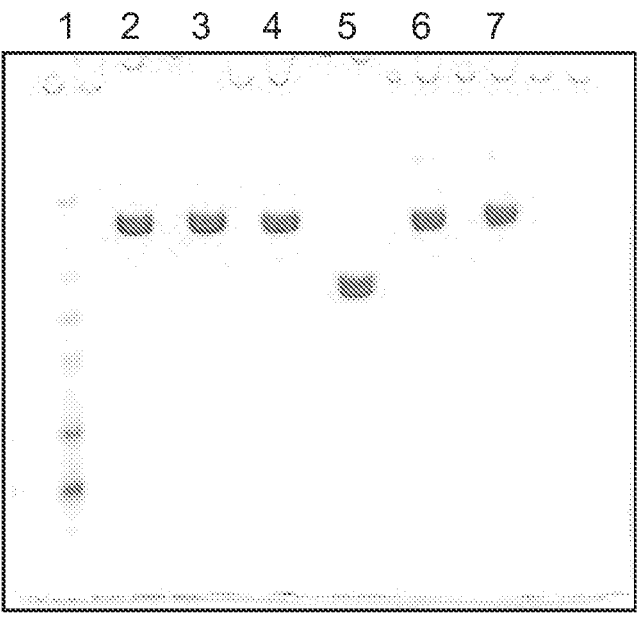
FIG. 3 is an SDS-PAGE gel showing the presence of intramolecular cross-links in formaldehyde-treated $LH_N/A$ vaccine. Lane 1: mass markers. Lane 2: $LH_N/A$ untreated. Lane 3: $LH_N/A$ untreated+DTT. Lane 4: $LH_N/A$ trypsin treated. Lane 5: $LH_N/A$ trypsin treated+DTT. Lane 6: $LH_N/A$ formaldehyde and trypsin treated. Lane 6: $LH_N/A$ formaldehyde and trypsin treated+DTT.

Assessment of Presence or Absence of Intra-Molecular Cross-Linking $LH_N/A$ vaccine ($LH_N$ fragment treated with formaldehyde, e.g. at 0.2% formaldehyde for 24 hours at 35° C.) was assessed for the presence of intra-molecular cross-linking using mild proteolysis with trypsin. $LH_N$ vaccine at a concentration of 1 mg ml$^{-1}$ was treated with trypsin at a final concentration of 10 μg ml$^{-1}$ in 50 mm Hepes buffer containing 100 mM NaCl for 30 min at 37° C. After the incubation period, the tryptic reaction was halted by the heating at 90° C. for 2 minutes. As a control, a sample of $LH_N/A$ which had not been treated with formaldehyde was treated with trypsin under identical conditions. Samples were then analysed by SDS-PAGE under reducing conditions (with 20 mM dithiothreitol added) and non-reducing conditions. Under reducing conditions, the control sample of $LH_N$ runs as two bands of molecular weight approximately 50 kDa indicating the absence of intra-molecular cross-linking to hold the tryptic cleavage products together (FIG. 3, Lane 5). In contrast, the formaldehyde treated $LH_N$ vaccine runs as a band of 100 kDa demonstrating the presence of intra-molecular cross-linking which holds the tryptic cleavage products together (FIG. 3, Lane 7).

Example 6

Assessment of Vaccine Efficacy

Samples of vaccine adsorbed onto an adjuvant such Alhydrogel™ were diluted with buffer containing the same adjuvant to give a range of concentrations of antigen. For example, the following vaccine doses in 0.2 ml could be used: 10, 3.33, 1.11, 0.37, 0.123, 0.041, 0.014, and 0 μg ml$^{-1}$.

Doses of the vaccine were then injected into mice (10 mice per vaccine dose; 0.2 ml into each mouse by the sub-cutaneous route). At 28 days post administration, the mice were challenged with a lethal concentration of toxin (e.g. 1000 $LD_{50}$ administered into the peritoneal cavity) and any deaths were recorded over a 4 day period post-challenge.

The data obtained from such tests were fit to a logistic 4 parameter curve using a statistical analysis package such as SigmaPlot™. From the analysis, the concentration of vaccine that provided protection to 50% of the animals against the challenge dose of toxin was calculated. The $ED_{50}$ value is usually expressed in micrograms of peptide; the lower the value obtained, the more efficacious the vaccine. Tables 1, 2, 3, and 4 summarize the results for $LH_N/A$.

TABLE 1

$LH_N/A$ Vaccine Efficacy Tests (Formaldehyde-Treated & Untreated)

| | Surviving Mice (of 10) Post Challenge (Day 4) | | | |
|---|---|---|---|---|
| Vaccine Dose (μg) | $LH_N/A$ Untreated Test 1 | $LH_N/A$ Untreated Test 2 | $LH_N/A$ Untreated Test 3 | $LH_N/A$ Vaccine Formaldehyde Treated Test 1 |
| 100 | 8 | 3 | n.d. | n.d |
| 50 | 9 | 8 | n.d. | n.d |
| 25 | 8 | 5 | 10 | 10 |
| 12.5 | 6 | 6 | 7 | 10 |
| 6.25 | 7 | 7 | 7 | 10 |
| 3.13 | 6 | 6 | 6 | 10 |
| 1.56 | 2 | 3 | 4 | 10 |
| 0 | 0 | 0 | 0 | 1 |
| $ED_{50}$ Value | 2.4 μg | 3 μg* | 2.6 μg | <1.56 μg |

*Approximate value due to erratic nature of the data

TABLE 2

$LH_N/A$ Vaccine-Efficacy Tests (Formaldehyde (HCHO) - Treated)

| Surviving Mice (of 10) at 4 days Post Challenge | | | | |
|---|---|---|---|---|
| Vaccine Dose (μg) | $LH_N/A$ Vaccine HCHO-Treated Test 2 | $LH_N/A$ Vaccine HCHO-Treated Test 3 | Vaccine Dose (μg) | $LH_N/A$ Vaccine HCHO-Treated Test 4 |
| 5 | 10 | 10 | 5 | 10 |
| 2.5 | 10 | 10 | 1.67 | 9 |
| 1.25 | 9 | 10 | 0.56 | 9 |
| 0.63 | 9 | 10 | 0.185 | 6 |
| 0.31 | 10 | 9 | 0.062 | 1 |
| 0.16 | 8 | 7 | 0.02 | 0 |
| 0.078 | 7 | 8 | 0.007 | 0 |
| 0 | 0 | 0 | 0 | 0 |
| $ED_{50}$ Value | <0.08 μg | <0.08 μg | $ED_{50}$ Value | 0.15 μg |

Test 4 - $LH_N/A$ was treated with formaldehyde at peptide concentration of 0.1 mg/ml to eliminate aggregation of the fragment

TABLE 3

Summary of $ED_{50}$ Determinations on HCHO-Treated and Control $LH_N/A$

| | $ED_{50}$ for $LH_N/A$ Vaccine (μg) | |
|---|---|---|
| Test | Control (Untreated) | Formaldehyde-Treated |
| Test 1 | 2.4 | <1.6 |
| Test 2 | 3.0 | <0.08 |
| Test 3 | 2.6 | <0.08 |
| Test 4 | N.D. | 0.15 ± 0.013 |
| Test 5 | N.D. | 0.049 ± 0.007 |

Example 7

Assessment of Vaccine Efficacy Against Various Sub-Types of BoNT/A $LH_N/A$ was adjusted to 1 mg ml$^{-1}$ with Hepes/NaCl buffer, treated with HCHO (0.2% for 24 h at 35° C.) and adsorbed onto Alhydrogel (3100 μg ml$^{-1}$ final concentration) in 10 mM Hepes pH 7.4/100 mM NaCl buffer (peptide concentration 100 μg ml$^{-1}$).

After mixing and incubation at 4° C. for 4 hours, the mixture was dialysed against the Hepes buffer to remove the formaldehyde and then diluted with buffer containing Alhydrogel to give the following concentrations of antigen of 20, 6.67, 2.22, 0.74, 0.24, 0.08, 0.027, and 0 µg per 0.2 ml dose.

At 28 days post administration, 3 test groups of mice were challenged with either BoNT/$A_1$, BoNT/$A_2$ or BoNT/$A_3$ (1000 $LD_{50}$ i.p. in 0.5 ml). Deaths were recorded over a 4 day period post-challenge. The data, shown in Table 4, show that the vaccine protected against all three BoNT/A sub-types. Calculated $ED_{50}$ values were:

$A_1$ Challenge $ED_{50}$=0.049±0.007 µg $A_2$ Challenge $ED_{50}$=0.28±0.02 µg $A_3$ Challenge $ED_{50}$=2.2±0.6 µg

TABLE 4

Vaccine Efficacy of Formaldehyde-treated $LH_N$/A to BoNT/A Sub-types ($A_1$, $A_2$ and $A_3$)

| Vaccine Dose | Surviving Mice (of 10) at 4 days Post Challenge | | |
|---|---|---|---|
| (µg) | $A_1$ | $A_2$ | $A_3$ |
| 20 | 10 | 10 | 10 |
| 6.67 | 10 | 10 | 9 |
| 2.22 | 9 | 9 | 4 |
| 0.74 | 10 | 9 | 3 |
| 0.24 | 9 | 4 | 2 |
| 0.08 | 7 | 1 | 0 |
| 0.027 | 2 | 0 | 0 |
| 0 | 0 | 0 | 0 |
| Calculated $ED_{50}$ value | 0.049 ± 0.007 µg | 0.28 ± 0.02 µg | 2.2 ± 0.6 µg |

Each challenge dose was 1000 $LD_{50}$ of the BoNT/A subtype

In control experiments assessing the efficacy of sub-types, no protection against BoNT/$A_2$ subtype was observed in efficacy tests in which doses of up to 100 µg of native $LH_N$/A were administered to mouse groups. The protocol was as described in Example 6 and using 1000 $LD_{50}$ of BoNT/$A_2$ as the challenge toxin.

Example 8

Detection of Fragments of the Invention by Immunoassay

Peptide fragments of the invention bear antigenic determinants which are detectable by immunoassays. In the case of the vaccines for the clostridial neurotoxin family, one or more of these antigenic determinants is shared by the $LH_N$ fragments of the homologous neurotoxin fragments and thus antibodies raised against the $LH_N$ fragment also bind fragments of the invention. Immunoassays to detect the presence of fragments of the invention are conducted as follows.

Fragments of the invention are coated onto microtiter plates at concentration of 5 µg/ml in a suitable buffer such 50 mM Hepes pH 7.4 and allowed to bind at 4° C. overnight. After blocking excess protein binding sites with a blocking agent (e.g. 5% foetal bovine serum in PBS), the plate is washed with PBS containing 0.1% tween 20. Antibodies prepared in animals (e.g. rabbits) to the corresponding $LH_N$ fragment are then added to the plate wells. Thus in the case of a test for the presence of fragments of the invention which are designed as a vaccine for BoNT/A, antibodies prepared against $LH_N$/A would be used. The antibody solution is applied at various dilutions, e.g. $1/1000$ to $1/1000,000$ dilution of the neat serum and allowed to bind for 1 hour at 37° C. After washing with PBS/Tween20, a commercially available ant-rabbit IgG peroxidise conjugate solution is added at e.g., a $1/1000$ dilution and allowed to bind for 1 hour at 37° C. The unbound conjugate is then removed by washing with PBS/tween20 and then suitable peroxidise substrates (e.g., 3,3',5,5'-Tetramethylbenzidine and hydrogen peroxide) added. For wells coated with fragments of the invention, colour will develop which is significantly above background levels indicating the presence of a peptide fragment containing epitopes common to the $LH_N$ fragment. The test therefore indicates the presence peptide fragment properties consistent with fragments of the invention.

Example 9

Preparation of Fragments of the Invention Based on Clostridial Neurotoxins which Contain a Mutated, Dysfunctional $H_C$ Domain An example of the amino acid sequence of a *botulinum* vaccine which has a non-functional $H_C$ domain is given in SEQ ID NO: 9. This peptide contains mutations to ganglioside binding site of the $H_C$ domain. In more detail, referring to SEQ ID NO: 9, two amino acid residue mutations (W1266 to L and Y1267 to F) in the ganglioside binding pocket cause the $H_C$ region to lose its receptor binding function. Analogous mutations may be made to non-serotype A clostridial peptides, e.g., a construct based on *botulinum* B with mutations (W1262 to L and Y1263 to F) or *botulinum* E (W1224 to L and Y1225 to F). Other mutations to the active site achieve the same ablation of $H_C$ receptor binding activity, e.g. Y1267S in *botulinum* type A toxin and the corresponding highly conserved residue in the other clostridial neurotoxins. Details of this and other mutations are described in Rummel et al (2004) (Molecular Microbiol. 51:631-634), which is hereby incorporated by reference thereto.

Genes encoding peptides such as the above are commercially available with codon bias for any desired expression host (e.g. *E. coli, Pichia pastoris*). Peptides are expressed from these gene using standard molecular biology methods (e.g., Sambrook et al. 1989, Molecular Cloning a Laboratory Manual, Second Edition, Cold Spring Harbor Laboratory Press, Cold Spring Harbor, N.Y.) and the resulting soluble expressed peptide is purified by a combination of hydrophobic interaction chromatography, ion exchange chromatography and ceramic hydroxyl apatite chromatography. Other chromatographic techniques well known to the art of protein purification, such size exclusion chromatography, may be used.

The peptide is then dialysed against buffer (10 mm Hepes buffer pH 7.4 containing 100 mM NaCl) and then 0.2% formaldehyde added and incubated for between 24 and 72 hours at 35° C. After incubation, the formaldehyde may be removed from the mixture by dialysis.

Example 10

Assays to Demonstrate that Fragments of the Invention do not Possess a Functional $H_C$ Receptor Binding Domain Clostridial neurotoxin is labelled with 125-iodine using chloramine-T and its binding to various cells assessed by standard methods such as described in Evans et al. 1986, Eur J. Biochem., 154, 409 or Wadsworth et al. 1990, Biochem. J. 268, 123). In competitive binding experiments, native clostridial neurotoxins compete for receptors present on neuronal cells or brain synaptosomes with the radiolabelled *botulinum* toxin, thus reducing the binding of the latter. This is measured by a reduction in bound radioactive ligand. All binding experiments are carried out in binding buffers, e.g., 50 mM HEPES pH 7.0, 30 mM NaCl, 0.25% sucrose, 0.25% bovine serum albumin. In a typical binding experiment the radiolabelled clostridial neurotoxin is held at a fixed concentration of between 1-20 nM. Reaction mixtures are prepared by mixing the radiolabelled toxin with various higher concentrations (up to 10 µM) of unlabelled neurotoxin or fragment of the invention. The reaction mixtures are then added to neuronal cells or rat brain synaptosomes and are incubated at 0-3° C. for 2 hr. After this period the neuronal cells of synaptosomes are washed twice with ice-cold binding buffer and the amount of labelled clostridial neurotoxin bound to cells or synaptosomes assessed by γ-counting. In reaction mixtures which contained native neurotoxin, the peptide competes with $^{125}$I-labelled *botulinum* type A neurotoxin for neuronal cell receptors and reduces the binding of the latter. However, when a clostridial peptide of the invention is added to reaction mixture no reduction in binding of the labelled toxin occurs. This demonstrates that clostridial peptides of the invention do not contain a function $H_C$ binding domain.

Example 11

Vaccination by Peptide/Peptide Fragments of the Invention

A vaccine, represented by a peptide/peptide fragment of the invention is prepared by current Good Manufacturing Practice. Using such practices, peptides/peptide fragments of the invention may be bound to an adjuvant of aluminium hydroxide which is commercially available (e.g., Alhydrogel). A typical composition comprises:
  A) A buffer (e.g., Hepes buffer between 5 and 20 mM and pH between 7.0 and 7.5;
  B) A salt component to make the vaccine physiologically isotonic (e.g. between 100 and 150 mM NaCl);
  C) An adjuvant (e.g., aluminium hydroxide at a final aluminium concentration of between 100 and 700 µg per vaccine dose); and
  D) A preservative (e.g., Thiomersal at 0.01% or formaldehyde at 0.01%).

Such vaccine compositions are administered to humans by a variety of different immunisation regimens, e.g.,
  1. A singe dose (e.g., 20 µg adsorbed fragment of the invention) in 0.5 ml administered sub-cutaneously.
  2. Two doses (e.g., of 10 µg adsorbed fragment of the invention) in 0.5 mls administered at 0 and 4 weeks.
  3. Three doses (e.g., of 10 µg adsorbed fragment of the invention) in 0.5 mls administered at 0, 2 and 12 weeks.

These vaccination regimens confer levels of protection against exposure to the homologous serotypes of *botulinum* neurotoxins. An antibody response in humans is measured by standard ELISA assays such as described in Example 8.

During formulation of the fragment of the invention, other antigens may also be included in the formulation. Such antigens may include different *botulinum* serotype vaccines or antigens not related to the *botulinum* toxins.

Example 12

Generation of *Clostridium Difficile* Peptides

Amino acid sequences of a vaccine based on *Clostridium difficile* Toxins A and B are shown in SEQ ID NOS: 10-18 and that for the *Clostridium difficile* binary toxin in SEQ ID NO: 19 and 20. Genes encoding these peptides are made commercially with codon bias for any desired expression host (e.g., *E. coli, Pichia pastoris*). Peptides are expressed from these gene using standard molecular biology methods (e.g. Sambrook et al. 1989, Molecular Cloning a Laboratory Manual, Second Edition, Cold Spring Harbor Laboratory Press, Cold Spring Harbor, N.Y.) and the resulting soluble expressed peptides are purified by a combination of hydrophobic interaction chromatography, ion exchange chromatography and ceramic hydroxyl apatite chromatography. Other chromatographic techniques well known to the art of protein purification, such size exclusion chromatography and/or affinity chromatography, may be used.

If the peptides are produced in an insoluble from then the peptides may be expressed with a histidine-6 purification tag using commercially available expression vector such as pET52b and refolded by on-column refolding techniques as described by the review of Lia et al. and references contained therein (Lia M et al (2004) Protein Expression & Purification 33, 1-10), which is hereby incorporated by reference thereto.

Example 13

Treatment of *C. Difficile* Peptides to Introduce Intramolecular Cross-Links

Purified *C. difficile* peptides at a concentration of between 0.2-2 mg/ml are dialysed against a suitable buffer (e.g. 10 mM Hepes buffer pH 7.4 containing 100 mM NaCl) and then formaldehyde added at a final concentration of between 0.05 and 0.5% and incubated for between 24 and 72 hours at 35° C. After incubation, the formaldehyde is removed from the mixture by dialysis. Conditions for the treatment with formaldehyde may vary between peptides and final conditions may be fine-tuned on the basis of outcome of protective efficacy evaluations.

As an alternative to formaldehyde, purified difficile peptides (at a concentration of between 0.1-5 mg/ml) are dialysed against a suitable buffer, and then reacted with a non-formaldehyde cross-linking agent, such as one of those already described. The cross linking agent is dissolved in a suitable solvent, (e.g., water, buffer, ethanol or acetone) and then mixed with the *C. difficile* peptide, which may be a fragment of a toxin or surface peptide. The cross-linking agent is added to the peptide in a molar excess which includes, for instance, between 3-50 fold moles of cross-linker per mole of peptide. The peptide is normally at a concentration of between 0.1-5 mg/ml and is incubated with the cross-linker from 1-24 hr at temperature between 4-37° C. Exact conditions may be determined by those which provide the optimal immune response in animals (e.g., mice, guinea pigs or rabbits)

Example 14

Demonstration of Protective Efficacy of *C. Difficile* Peptides

After removing formaldehyde or other modification agent from the *C. difficile* peptides, the peptides are adsorbed on to aluminium hydroxide adjuvant (Alhydrogel™) and used to generate antibodies in animals such as guinea pigs, rabbits of goats. The toxin neutralizing activity of the resulting antisera is measured by cellular assays using Vero cells. In these assays, a fixed amount of either purified *C. difficile* Toxin A or Toxin B is mixed with various dilutions of the antibodies, incubated for 1 h at 37° C. and then applied to vero cells growing on 24-well tissue culture plates. Both Toxin A and B possess cytotoxic activity which results in a characteristic rounding of the Vero cells over a period of 24-48 h. In the presence of neutralising antibodies this activity is inhibited and the neutralising strength of an antibody preparation may be assessed by the dilution required to neutralise the effect of a designated quantity of either Toxin A or B.

*C. difficile* toxin peptides into which intramolecular cross-links have been introduced by formaldehyde or another cross-linking reagent produce antisera of higher neutralising titre compared to the corresponding control peptide which has not been treated.

Example 15

Demonstration of Protective Efficacy of *C. Difficile* Peptides in Animals

To demonstrate the protective efficacy of *C. difficile* antigens in vivo, Syrian hamsters are immunised with the *difficile* peptide, which may be combined with an adjuvant (e.g. Alhydrogel™). Immunised animals are then administered with a broad spectrum antibiotic (e.g., clindamycin) and 12-48 h later challenged with *C. difficile* vegetative cells or spores by mouth. Animals are then monitored for up to 15 days for symptoms of *C. difficile*-associated disease. Non-immunised animals develop signs of the disease (e.g., diarrhoea, swollen abdomen, lethargy, ruffled fur) while those immunised with a protecting antigen appear normal. Lower immunising doses of *C. difficile* antigens into which intramolecular cross-links have been introduced by formaldehyde or another cross-linking reagent are required to incur protection compared to the corresponding control peptide which has not been treated.

Example 16

Preparation and Administration of a Vaccine for *C. Difficile*

A vaccine, represented by a peptide of the invention is prepared by current Good Manufacturing Practice. Using such practices, peptides of the invention are bound to an adjuvant of aluminium hydroxide which is commercially available (e.g., Alhydrogel). A typical composition comprises:

A) The antigen which may be an intra-molecularly cross-linked fragment of a *C. difficile* toxin fragment or surface peptide.
B) A buffer (e.g., Hepes buffer between 5 and 20 mM and pH between 7.0 and 7.5) or alternatively if the antigen has a pI greater than 7.5, a buffer containing phosphate ions may be used (e.g., 15 mM sodium phosphate pH 6.0).
C) A salt component to make the vaccine physiologically isotonic (e.g. between 100 and 150 mM NaCl
D) An adjuvant (e.g., aluminium hydroxide at a final aluminium concentration of between 100 and 700 µg per vaccine dose)
E) A preservative (e.g., Thiomersal at 0.01% or formaldehyde at 0.01%)

Such vaccine compositions are administered to humans by a variety of different immunisation regimens, e.g., 1. A singe dose (e.g., 20 µg adsorbed fragment of the invention) in 0.5 ml administered sub-cutaneously
2. Two doses (e.g., of 10 µg adsorbed fragment of the invention) in 0.5 mls administered at 0 and 4 weeks
3. Three doses (e.g., of 10 µg adsorbed fragment of the invention) in 0.5 mls administered at 0, 2 and 12 weeks These vaccination regimens confer levels of protection against exposure to *C. difficile* particularly when broad spectrum antibiotics are in use, e.g. in hospital environment.

During formulation of the fragment of the invention, other antigens may also be included in the formulation, e.g., a combination of difficile surface peptides and toxin fragments.

Example 17

Anthrax Toxin Fragment Production

Amino acid sequences of vaccine peptides are shown in SEQ ID NOS: 16-18. Genes encoding these toxin fragments are commercially with codon bias for any desired expression host (e.g., *E. coli, Pichia pastoris*). Peptides may be expressed from these genes using standard molecular biology methods (e.g. Sambrook et al. 1989, Molecular Cloning a Laboratory Manual, Second Edition, Cold Spring Harbor Laboratory Press, Cold Spring Harbor, N.Y.). An example of an expression vector for use in *E. coli* is pET26b. The resulting soluble expressed peptide is purified by a combination of hydrophobic interaction chromatography, ion exchange chromatography and ceramic hydroxyl apatite chromatography. Other chromatographic techniques well known to the art of protein purification, such size exclusion chromatography and/or affinity chromatography, may be used.

In order to produce an enzymically inactive form of LF, the gene is synthesised with a double mutation within the active site sequence. An inactive form of LF is shown SEQ ID NO: 18.

Example 18

Treatment of Anthrax Toxin Fragments to Introduce Intramolecular Cross-Links

Purified anthrax toxin components (PA or LF) at a concentration of between 0.2-2 mg/ml are dialysed against a suitable buffer (e.g. 10 mM Hepes buffer pH 7.4 containing 100 mM NaCl) and then formaldehyde added at a final concentration of between 0.05 and 0.5% and incubated for between 24 and 72 hours at 35° C. After incubation, the formaldehyde is removed from the mixture by dialysis. Conditions for the treatment with formaldehyde may vary between toxin fragments and final conditions may be fine tuned on the basis of outcome of protective efficacy evaluations.

As an alternative to formaldehyde, purified anthrax toxin fragments at a concentration of between 0.1-5 mg/ml, are dialysed against a suitable buffer and reacted with an alternative cross-linking agent. The cross linking agent is dissolved in a suitable solvent (e.g., water, buffer, ethanol or acetone) and then mixed with the anthrax toxin fragment. The cross-linking agent is added to the peptide in a molar excess which may be between 3-50 fold moles of cross-linker per mole of peptide. The peptide is normally at a concentration of between 0.1-5 mg/ml and is incubated with the cross-linker from 1-24 hr at temperature between 4-37° C. Exact conditions may be determined by those which provide the optimal immune response in animals (e.g., mice, guinea pigs or rabbits)

Example 19

Demonstration of Protective Efficacy of Anthrax Toxin Fragments

After removing formaldehyde from the anthrax toxin or fragments, they are adsorbed on to an adjuvant (e.g. aluminium hydroxide, Alhydrogel™) and used to generate antibodies in animals such as guinea pigs, rabbits of goats. The efficacy of anthrax antigens is determined in toxin neutralising antibody (TNA) assays. In TNA assays, the ability of antiserum to protect macrophages from anthrax toxin is assessed. Macrophages (e.g. J774A cells) are grown in 24 or 96 well plates and maintained in growth medium for 18-24 h under appropriate incubation conditions (37° C., 5% $CO_2$) before testing. Various dilutions of test serum are incubated with anthrax toxin (e.g. 100 ng PA $ml^{-1}$ plus 100 ng LF $ml^{-1}$ final concentration) in buffered growth medium for 1 hr at 37° C. and then added to the macrophages. After 4 h incubation, the cells are treated with 3-[4,5-dimthylthiazol-2-yl]2,5-diphenyltetrazolium bromide (MTT) (e.g. 25 µl of a 5 mg $ml^{-1}$ solution). After further incubation for 2 h, the lysed cell precipitates are dissolved by addition of a solution containing 10% sodium dodecyl sulphate and 50% dimethyl formamide. After incubation to allow solubilisation of the precipitate, the absorbance at 570 nm is measured to provide a measurement of the reduced form of the dye. The MMT reagent assay provides an estimate of the number of viable macrophage cells and hence the ability of a preparation of antiserum to protect the cells from the effects of anthrax toxin.

Anthrax toxin fragments into which intramolecular cross-links have been introduced by formaldehyde or another cross-linking reagent produce antisera of higher neutralising titre compared to the corresponding control fragment which has not been treated.

Example 20

Preparation and Administration of a Vaccine for Anthrax

A vaccine, represented by a peptide of the invention is prepared by current Good Manufacturing Practice. Using such practices, peptides of the invention are bound on to an adjuvant of aluminium hydroxide which is commercially available (e.g. Alhydrogel).

A typical composition comprises:
A) The antigen which may be an intra-molecularly cross-linked fragment derived from PA or LF. Alternatively combinations of antigens may be used, e.g. PA and LF in a 1:1 mixture. In the case of LF, for instance, an enzymatically inactive derivative of the peptide can be employed.
B) A buffer (e.g. Hepes buffer between 5 and 20 mM and pH between 7.0 and 7.5) or alternatively if the antigen has a pI greater than 7.5, a buffer containing phosphate ions may be used (e.g. 15 mM sodium phosphate pH 6.0).
C) A salt component to make the vaccine physiologically isotonic (e.g. between 100 and 150 mM NaCl).
D) An adjuvant (e.g. aluminium hydroxide at a final aluminium concentration of between 100 and 700 µg per vaccine dose).
E) A preservative (e.g. Thiomersal at 0.01% or formaldehyde at 0.01%)

Such vaccine compositions are administered to humans by a variety of different immunisation regimens, e.g.
1. A singe dose (e.g. 20 µg adsorbed fragment of the invention) in 0.5 ml administered sub-cutaneously.
2. Two doses (e.g. of 10 µg adsorbed fragment of the invention) in 0.5 mls administered at 0 and 4 weeks.
3. Three doses (e.g. of 10 µg adsorbed fragment of the invention) in 0.5 mls administered at 0, 2 and 12 weeks.

These vaccination regimens confer levels of protection against exposure to *Bacillus anthracis*.

Example 21

A Bivalent Recombinant Vaccine for *Botulinum* Types A and B Neurotoxins $BoNT/A_1$, $BoNT/A_3$, $BoNT/B_1$ and $BoNT/B_4$ were purified from *C. botulinum* strains ATCC 3502, NCTC 2012, Okra and Eklund 17B strains, respectively using the exchange chromatography methods described in Shone C. C. and H. S Tranter. 1995. Growth of clostridia and preparation of their neurotoxins, pp 143-160. In: C. Montecucco (ed.) Current Topics in Microbiology and Immunology 195 *'Clostridial Neurotoxins'*, Springer, Berlin. $BoNT/A_2$ was obtained from Metabiologics Inc.

Expression and Purification of $LH_N$ Recombinant Fragments

Expression of $LH_N$ fragments. Synthetic genes coding for BoNT/A (amino acid residues 1-871) and BoNT/B (amino acid residues 1-858) were optimised for expression in *E. coli* and synthesised (Geneart AG) with NdeI and XhoI restriction sites at the 5' and 3' ends, respectively to allow insertion into a pET 26b expression vector. Both $LH_N$ sequences contained two amino acid substitutions: for $LH_N/A$, E224Q and H227Y; for $LH_N B$, E231Q, and H234Y. After transformation into *E. coli* ER2566, cells were inoculated into 50 ml growth medium (selected phytone, 24 g $l^{-1}$, bacto yeast extract, 72 g $l^{-1}$; glycerol, 25 g $l^{-1}$; $K_2HPO_4$, 2.3 g $l^{-1}$; $KH_2PO_4$, 12.5 g $l^{-1}$; $MgSO_4$, 2.0 g $l^{-1}$; kanamycin sulphate, 0.03 g $l^{-1}$, antifoam, 0.1 g $l^{-1}$ at pH 7.3) and incubated with agitation for 16-20 h at 37° C. This was then used to inoculate 500 ml growth medium which was similarly incubated and used to inoculate 4.5 l growth medium in a 5 l fermentor. The fermentor was grown at 37° C. until the $OD_{600}$ was between 15-20 after which the temperature was reduced to 16° C. and the culture grown for a further 16-29 h.

Purification of $LH_N/A$. Soluble recombinant $LH_N A$ was extracted from *E. coli* cell paste by resuspension with 20 mM Tris-HCl, pH 8.0, 25 mM EDTA on ice with stirring for 1 h. The suspension was passed twice through an APV1000 homogeniser (9,000 psi), clarified by microfiltration (500 kDa cutoff) and diafiltered into 20 mM Tris-HCl, pH 8.0, 25 mM EDTA. The extract was then made 1M with $(NH_4)_2SO_4$ and applied to a Toyopearl Phenyl-650M column (10 cm [id]×24 cm) equilibrated with 20 mM Tris-HCl, pH 8.0, 5 mM EDTA (Buffer A) and 1 M $(NH_4)_2SO_4$. After washing with Buffer A containing 0.75 M $(NH_4)_2SO_4$ and then the $LH_N A$ eluted from the column with Buffer A containing 0.5 M $(NH_4)_2SO_4$. The eluate was diafiltered against 10 mM Tris-HCl, 0.1 mM EDTA pH 8.0 (Buffer B) and loaded onto a Q Sepharose column (5 cm (id)×11.5 cm) equilibrated with Buffer B. After washing with Buffer B containing 50 mM NaCl, the $LH_N/A$ was eluted with Buffer B containing 130 mM NaCl. and diafiltered against 10 mM sodium phosphate, pH 6.5. This solution was loaded onto a Macro-Prep Ceramic Hydroxyapatite Type I (20 µm; BioRad) column (5 cm (id)× 11.5 cm) equilibrated with 10 mM sodium phosphate, pH 6.5. After washing with 40 mM sodium phosphate, pH 6.5, $LH_N A$ was eluted with 105 mM sodium phosphate, pH 6.5. The eluate from the hydroxyapatite column was concentrated and diafiltered against 10 mM HEPES, pH 7.4, 100 mM NaCl, filtered (0.2 µm) and stored at −70° C.

Purification of $LH_N/B$. The purification process for $LH_N/B$ was very similar to that of $LH_N/A$, except that it was performed at temperatures between 2 to 8° C. After homogenization, the clarified material was loaded onto the Toyopearl phenyl-650M column as above for $LH_N/A$ and eluted with Buffer A containing 0.7 M $(NH_4)_2SO_4$. The remaining chromatography steps were as described for $LH_N/A$ above except that the $LH_N/B$ was eluted from the hydroxyapatite column with 145 mM sodium phosphate, pH 6.5.

Prior to efficacy tests, purified $LH_N/A$ and B proteins were filtered through Mustang E filters to reduce protein-associated endotoxin levels to <1 Endotoxin Unit (EU)/mg or protein as assessed by chromogenic LAL assay.

Formulation and Formaldehyde Treatment $LH_N$ fragments were adsorbed onto Alhydrogel (Biosector 1.3) such that the final formulation contained 10 mM Hepes pH 7.4, 100 mM NaCl, Alhydrogel at 3.2 mg $ml^{-1}$ aluminium and between 0-500 µg $ml^{-1}$ $LH_N$ fragment. Mixtures were incubated by gentle agitation for 6 h at 4° C. and stored at 4° C. until use.

$LH_N$ fragments (1 mg $ml^{-1}$) in 10 mM Hepes pH 7.4 buffer containing 100 mM NaCl were made 0.2% formaldehyde by the slow addition, with stirring, of a 20% stock solution. Mixtures were then incubated at 35° C. for 24 h and absorbed onto Alhydrogel. Formaldehyde was removed by dialysis against 10 mM Hepes pH 7.4, 100 mM NaCl.

Determination of Vaccine Efficacy

The efficacy of vaccine candidates was determined using mice in which groups of 10 animals were immunised with various doses of formulated vaccine (doses in 0.2 ml were administered subcutaneously). For one-dose studies, mice were immunised on Day 0 and then challenged on Day 28 with $10^3$ $MLD_{50}$ of BoNT (in 0.5 ml administered intraperitoneally). Survival of mice was monitored over 4 days post-challenge. For two-dose studies, animals were immunised on Day 0 and Day 14 and challenged on Day 28. $ED_{50}$ values, i.e., the vaccine dose required to protect half the animals in a group from the challenge dose, were calculated using four-parameter logistic curve analysis (SigmaPlot™).

For efficacy studies in guinea pigs, groups of 3 animals were immunised with a single dose of formulated $LH_N$ fragment and bled 28 days post immunisation. Serum pools, combining an equal volume from each of 3 animals, were assessed for toxin neutralisation in mice. For these studies, serum diluted with PBS containing 1 mg $ml^{-1}$ BSA was mixed with $BoNT/A_1$ at a final concentration of 200 $LD_{50}$ $ml^{-1}$. After incubating for 2 h at 22° C., 0.5 ml was injected into groups of 4 mice.

Endopeptidase and ELISA Assays

Endopeptidase assay. Endopeptidase activities of $LH_N$ fragments were measured essentially by the assay procedure described by Hallis et al. (1996) J. Clin. Microbiol. 34: 1934-1938, in which the formation of the BoNT substrate cleavage products were measured using specific antibodies in an ELISA-like assay system.

ELISA assay. For these assays, antibodies raised in goats to toxoids of the purified BoNTs were used. Purified IgG was coated onto microtiter plates a (5 µg $ml^{-1}$; 100 µl/well) and incubated for 1 h at 37° C. After washing with phosphate buffered saline containing 0.1% tween 20 (PBST), the plates were incubated for 1 h at 37° C. (150 µl/well) with blocking buffer (PBST containing 5% foetal bovine serum). After washing with PBST, test samples (BoNTs or $LH_N$ fragments) were diluted in blocking buffer and incubated for 1 hr at 37° C. (100 µl/well). Plates were washed with PBST, incubated with 1 µg $ml^{-1}$ biotinylated goat antibody in blocking buffer for 1 hr at 37° C. (100 µl/well), washed with PBST and then a 1/1000 dilution of a Streptavidin-horseradish peroxidase conjugate (Sigma) was added for 10 min at 37° C. After washing with PBST, substrates 3,3',5,5'-Tetramethylbenzidine and $H_2O_2$ were added for 10-15 min before the reaction stopped with TMB Stop Solution. Plates were read at 450 nm.

Results

Expression and Purification

Figure 4:
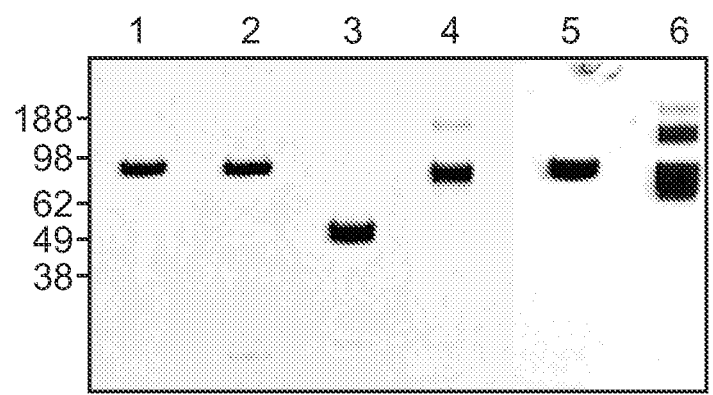
FIG. 4 is an SDS-PAGE gel of $LH_N/A$ and B fragments under various conditions. Lane 1: purified $LH_N/A$ fragment. Lanes 2 and 3: $LH_N/A$ treated with 10 μg ml$^{-1}$ trypsin for 30 minutes at 37° C. under non-reducing and reducing conditions (10 mM DTT), respectively. Lane 4: $LH_N/A$ (1 mg ml−1) treated with 0.2% (v/v) formaldehyde for 24 hours at 35° C. Lane 5: purified $LH_N/B$. Lane 6: $LH_N/B$ treated with 0.2% (v/v) formaldehyde for 24 hours at 35° C.

Both $LH_N/A$ and $LH_N/B$ were expressed as soluble recombinant fragments and purified by a combination of hydrophobic interaction, ion exchange and hydroxyapatite chromatography. Typical yields of purified $LH_N/A$ from three 4.5 l fermentation runs were 1.2, 1.3 and 1.4 g with overall recoveries of 62, 67 and 62%, respectively. Purity was >95% as assessed by SDS-PAGE (FIG. 4). Comparable purity and yields were obtained with $LH_N/B$ at the same scale with an average yield of 1.47 g purified fragment from three fermentation runs.

Figure 5:
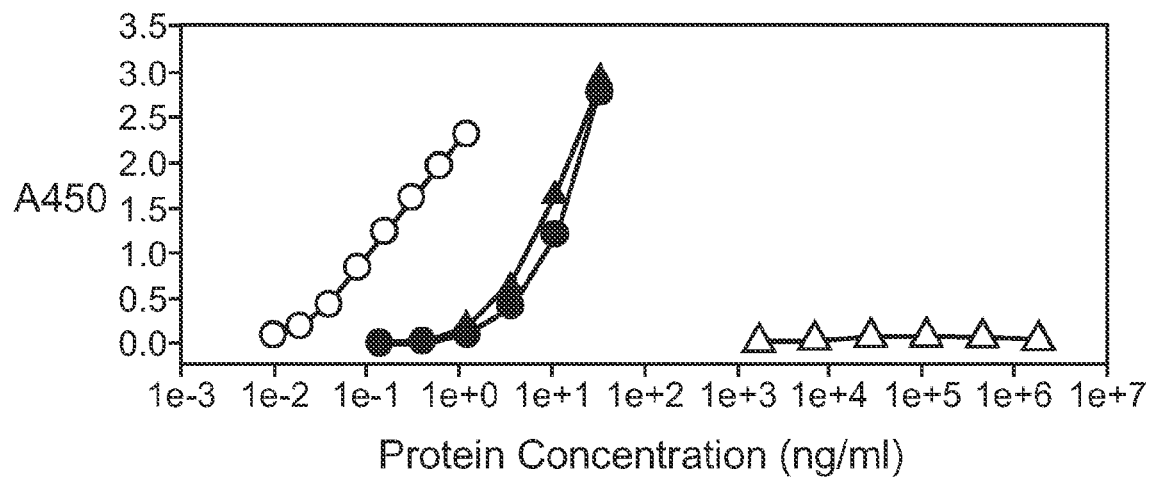
FIG. 5 is a graph showing the results of ELISA and endopeptidase assays on $LH_N/A$ and BoNT/A. Endopeptidase activities of BoNT/A (○) and $LH_N/A$ (Δ) were assessed by the cleavage of SNAP-25 (synaptosomal protein of 25 kDa) bound to microtiter plates followed by detection of cleavage product using specific antibodies. ELISA of BoNT/A (●) and $LH_N/A$ (▲) were performed using goat antibodies raised against BoNT/A toxoid.

The endopeptidase activity of purified $LH_N/A$ was assessed using an antibody-based assay system and compared with that of native, recombinant $LH_N/A$. At the highest concentration of $LH_N/A$ used (1.8 mg $ml^{-1}$), the fragment displayed no measurable endopeptidase activity, and this was >$10^7$ reduced compared to the native fragment. In contrast, $LH_N/A$ showed virtually identical reactivity in an antigen ELISA compared to the holotoxin (FIG. 5). Virtually identical data were obtained for $LH_N/B$ (not shown).

$LH_N/A$ Formulation and Efficacy Evaluation

With a theoretical pI value of 5.25, $LH_N/A$ was predicted to bind strongly to aluminium hydroxide (Alhydrogel™) at physiological pH. In the presence of 10 mM Hepes pH 7.4 and 100 mM NaCl, $LH_N/A$ (500 µg $ml^{-1}$) showed near complete binding (>99%) to Alhydrogel solution (containing 3.1 mg $ml^{-1}$ aluminium) as assessed by protein assay of supernatant solutions after centrifugation of the protein-Alhydrogel mixture. This formulation allowed administration of doses up to 100 µg protein in mouse efficacy studies in which 0.2 ml was injected subcutaneously. Protective efficacy was assessed as an $ED_{50}$, the vaccine dose required to protect 50% of the mice in groups challenged with a BoNT dose of $10^3$ mouse $LD_{50}$. In initial studies, $ED_{50}$ values were estimated after challenge with $BoNT/A_1$ 28 days after administration of a single dose of vaccine (Table 5). Protection against $BoNT/A_1$ challenge provided by the $LH_N/A$ was found to be erratic with complete protection of mouse groups only rarely observed and at relatively high (>20 µg) doses of vaccine. $ED_{50}$ values were difficult to calculate accurately and were between 2-3 µg. No protection was observed against challenge with $BoNT/A_2$ subtype at the highest vaccine dose tested.

With relatively poor protection provided by the recombinant $LH_N/A$ vaccine, several modifications to the protein were assessed. Conversion of the single chain $LH_N/A$ to the di-chain form by trypsin treatment did not significantly improve the vaccine's efficacy and an $ED_{50}$ value of 1.7±0.39 µg was obtained. However, treatment with formaldehyde significantly enhanced the efficacy of $LH_N/A$ as a vaccine. Incubation of $LH_N/A$ (1 mg $ml^{-1}$) with formaldehyde (0.2% at 35° C.) for up to 96 h led to broadening of the protein band on SDS PAGE and also the appearance of a small proportion of a higher molecular weight band consistent in size with that of an dimer of the $LH_N$ fragment (FIG. 4, lane 4). Under the above incubation conditions the appearance of HCHO-treated $LH_N/A$ did not change significantly on SDS-PAGE after 24 h incubation so efficacy assessments were made on $LH_N/A$ treated with 0.2% HCHO for 24 h at 35° C. Initial $ED_{50}$ tests on two different batches of $LH_N/A$ suggested that the $ED_{50}$ value was below 78 ng and a third test gave an $ED_{50}$ of 49±7 ng against challenge with $BoNT/A_1$. As well as providing >30 fold reduction in $ED_{50}$ value, the HCHO-treated $LH_N/A$ also afforded significantly better protection of animals at higher doses (Table 5). An even more marked enhancement in protection against challenge with $BoNT/A_2$ was observed with almost complete protection of animal immunised with vaccines doses >0.5 µg.

TABLE 5

Single Dose Efficacy Studies of Formaldehyde-Treated $LH_N/A$ Vaccine

| | Surviving Mice (of 10) at 4 days post Challenge Untreated $LH_N/A$ | | | | Surviving Mice (of 10) at 4 days Post Challenge | |
|---|---|---|---|---|---|---|
| Vaccine | $A_1$ | $A_1$ | | Vaccine | HCHO-Treated $LH_N/A$ | |
| Dose (μg) | Challenge Test 1 | Challenge Test 2 | $A_2$ Challenge | Dose (μg) | $A_1$ Challenge | $A_2$ Challenge |
| 100 | 3 | 8 | 0 | 20 | 10 | 10 |
| 50 | 8 | 9 | 1 | 6.67 | 10 | 10 |
| 25 | 5 | 8 | 0 | 2.22 | 9 | 9 |
| 12.5 | 6 | 6 | 0 | 0.74 | 10 | 9 |
| 6.25 | 7 | 7 | 0 | 0.24 | 10 | 4 |
| 3.13 | 6 | 6 | 2 | 0.08 | 7 | 1 |
| 1.56 | 3 | 2 | 0 | 0.027 | 2 | 0 |
| 0 | 0 | 0 | 0 | 0 | 0 | 0 |
| $ED_{50}$ | 2.3 μg | 2.17 ± 0.5 μg | >100 μg | $ED_{50}$ | 49 ± 7 ng | 0.28 ± 0.02 |

In guinea-pigs, protective efficacy was also significantly enhanced, although not to the same extent as in mice. For guinea pigs immunised with a single dose (10 μg) of untreated $LH_N/A$, the equivalent of 800 μl pooled serum protected 50% of mice from challenge $10^3 LD_{50}$ of $BoNT/A_1$ in neutralisation tests compared to the equivalent of 200 μl serum from guinea pigs immunised with HCHO-treated $LH_N/A$ which represents a 4-fold enhancement of efficacy.

Figure 6:
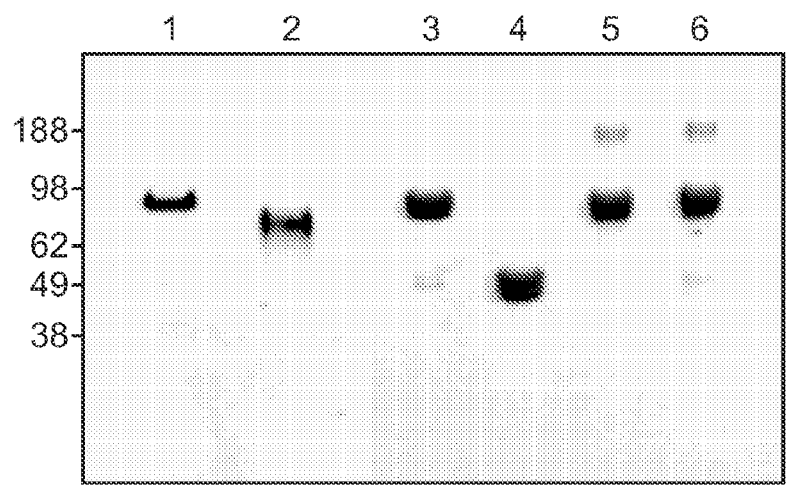
FIG. 6 is an SDS-PAGE gel showing the presence of intramolecular cross-links in formaldehyde-treated $LH_N/A$ vaccine. Lane 1: $LH_N/A$ control. Lane 2: $LH_N/A$ (0.1 mg ml$^{-1}$) treated with 0.2% (v/v) formaldehyde for 24 h at 35° C. Lanes 3 and 4: $LH_N/A$ treated with 10 μg ml$^{-1}$ trypsin for 30 minutes at 37° C., under non-reducing and reducing conditions (10 mM DTT), respectively. Lanes 5 and 6: $LH_N/A$ treated with trypsin and with 0.2% formaldehyde for 24 hours at 35° C., under non-reducing and reducing conditions, respectively.

To investigate possible mechanisms of the HCHO-mediated enhancement of efficacy, $LH_N/A$ was treated with HCHO at lower protein concentrations (0.1 mg ml$^{-1}$) which minimised the production of higher molecular weight forms of the fragment (FIG. 6, Lane 2). Under these conditions, which generated only traces of the dimer $LH_N/A$ form, an $ED_{50}$ of 147±13 ng was obtained which represents a statistically significant enhancement of efficacy compared to untreated controls. The efficacy enhancement would therefore not appear to be mediated by aggregated forms of the $LH_N$ fragment. $LH_N/A$ cleaved by trypsin appeared as two closely running bands of approximately 50 kDa on SDS-PAGE under reducing conditions which represent the light chain and $H_N$ fragments (FIG. 6). Under similar conditions, no such dissociation of the subunits was observed after HCHO treatment which suggests a degree of intra-molecular cross-linking had occurred.

TABLE 6

Summary of $ED_{50}$ Values for $LH_N/A$ Efficacy Studies

| | $ED_{50}$ Value (μg) | | |
|---|---|---|---|
| Efficacy Test | $A_1$ Challenge | $A_2$ Challenge | $A_3$ Challenge |
| One dose | 0.049 ± 0.007 | 0.28 ± 0.02 | 2.2 ± 0.6 |
| One dose (A/B)* | 0.054 ± 0.006 | n.d. | n.d. |
| Two dose | 0.017 ± 0.014 | 0.13 ± 0.034 | 0.65 ± 0.11 |

*Bivalent A/B vaccine formulation containing formaldehyde-treated $LH_N/A$ and untreated $LH_N/B$ $LH_N/A$ Efficacy Against BoNT/A Sub-Types An important consideration in vaccine design for the *botulinum* toxins is that they should offer protection against the principal subtypes of the relevant serotype. Both one and two-dose $ED_{50}$ tests were therefore conducted in which animals were challenged with either $BoNT/A_1$, $A_2$ or $A_3$ toxin subtypes (Table 6). A single dose of formaldehyde-treated $LH_N/A$ provided protection in mice against all three type A subtypes. In terms of $ED_{50}$, protective efficacy against $BoNTA_2$ was reduced approximately 6-fold compared to $BoNT/A_1$ and that against $BoNT/A_3$ approximately 45-fold reduced. In two-dose efficacy studies, sub μM $ED_{50}$ values were obtained for all three type A subtypes (Table 6).

$LH_N/B$ Formulation and Efficacy Studies $LH_N/B$ was formulated under identical conditions as that described for $LH_N/A$ above. Under these conditions, near complete adsorption of $LH_N/B$ was obtained in mixtures containing 500 μg ml$^{-1}$ $LH_N/B$ and Alhydrogel (3.1 mg ml$^{-1}$ Al). Efficacy data for the $LH_N/B$ vaccine are summarised in Table 7. In single dose tests, $LH_N/B$ displayed excellent protective efficacy with $ED_{50}$ values <0.2 μg. In view of the significant enhancing effect of formaldehyde treatment on the efficacy $LH_N/A$, the effect of a similar modification of $LH_N/B$ was assessed. Treatment of $LH_N/B$ with 0.2% HCHO for 24 h at 35° C. was found to induce band broadening and significantly more aggregation than observed with $LH_N/A$ with prominent bands consistent with dimer and trimer formation evident on SDS-PAGE (FIG. 4, lane 6). In single dose efficacy studies, $ED_{50}$ values of were obtained for untreated $LH_N B$ and HCHO-treated $LH_N/B$, respectively which were not significantly different (Table 6). The efficacy of $LH_N/B$ vaccine was also assessed against challenge with $BoNT/B_4$ subtype purified from the non-proteolytic *C. botulinum* strain, Ekland 17B. While protection was 2-3 reduced compared to that against $BoNT/B_1$, $ED_{50}$ values of <1 μg were obtained after a single vaccine dose (Table 6).

Bivalent Efficacy Assessment

Formulations of $LH_N/A$ and B for bivalent efficacy studies, contained final concentrations of 100 μg ml$^{-1}$ of each vaccine candidate. For both $LH_N/A$ and B, single dose $ED_{50}$ values were obtained which were comparable to those obtained from monovalent tests (Table 6 and 7). No evidence of immunosuppression by either fragment was evident.

TABLE 7

Summary of $ED_{50}$ Values for $LH_N/B$ Efficacy Studies

| | $ED_{50}$ Value (μg) | |
|---|---|---|
| Efficacy Test | $B_1$ Challenge | $B_{4\,(np)}$ Challenge |
| One dose (untreated) | 0.14 ± 0.02 | 0.36 ± 0.05 |
| One dose (HCHO-treated) | 0.18 ± 0.03 | n.d. |

TABLE 7-continued

Summary of ED$_{50}$ Values for LH$_N$/B Efficacy Studies

| Efficacy Test | ED$_{50}$ Value (µg) | |
|---|---|---|
| | B$_1$ Challenge | B$_{4\,(np)}$ Challenge |
| One dose (A/B)* | 0.08 ± 0.02 | n.d. |
| Two dose | 0.08 ± 0.001 | n.d |

*Bivalent A/B vaccine formulation containing formaldehyde-treated LH$_N$/A and untreated LH$_N$/B

Example 22

Demonstration of the Enhancing Effect of Intramolecular Cross-Linking on the efficacy of LH$_N$/E Vaccine A synthetic gene encoding *C. botulinum* type E (strain Alaska) endopeptidase negative LH$_N$/E (E213Q modification) was codon-optimized for expression in *E. coli*. The resulting nucleic acid was cloned into a pET26b vector, expressed in *E. coli* ER2566 host cells and isolated as generally provided in Example 21.

LH$_N$/E was adjusted to 1 mg ml$^{-1}$ with Hepes/NaCl buffer, treated with HCHO (0.2% for 24 h at 35° C.) and adsorbed onto Alhydrogel (3100 µg ml$^{-1}$ final concentration) in 10 mM Hepes pH 7.4/100 mM NaCl buffer (peptide concentration 100 µg ml$^{-1}$). A control sample containing unmodified LH$_N$/E at 1 mg ml$^{-1}$ with Hepes/NaCl buffer was also prepared.

After mixing and incubation at 4° C. for 4 hours, the control and HCHO-treated LH$_N$/E preparations were dialysed against the Hepes buffer to remove the formaldehyde (if present) and then diluted with buffer containing Alhydrogel to give the following concentrations of antigen per 0.2 ml:

20 6.67 2.22 0.74 0.24 0.08 0.027 0 µg per 0.2 ml dose

At 28 days post administration, the control and HCHO-treated LH$_N$/E groups of mice were challenged with BoNT/E (1000 LD$_{50}$ i.p. in 0.5 ml). Deaths were recorded over a 4 day period post-challenge.

The data, shown in Table 8, confirm a significant enhancement in protective efficacy (as shown by a lower ED$_{50}$ value) in the case of LH$_N$/E that has been treated with formaldehyde.

Calculated ED$_{50}$ Values Were:

LH$_N$/E untreated control, $ED_{50}$=2.5±0.9 µg

LH$_N$/E HCHO-treated, $ED_{50}$=0.29±0.01 µg

Thus there is a >8-fold enhancement of protective efficacy as a result of formaldehyde treatment.

TABLE 8

LH$_N$/E ED$_{50}$ Values of both HCHO-Treated and Untreated Vaccine

| Vaccine Dose | Surviving Mice (of 10) at 4 days Post Challenge | |
|---|---|---|
| (µg) | Untreated | HCHO |
| 20 | 10 | 10 |
| 6.67 | 7 | 10 |
| 2.22 | 4 | 10 |
| 0.74 | 4 | 9 |
| 0.24 | 1 | 4 |
| 0.08 | 0 | 0 |
| 0.027 | 0 | 1 |
| 0 | 0 | 0 |
| ED$_{50}$ | 2.5 ± 0.9 µg | 0.29 ± 0.01 µg |

Example 23

Demonstration of Enhanced Protective Efficacy After Formaldehyde Treatment of a *C. Difficile* Peptide Derived from the C-Terminal Binding Domain (Residues 1756 to 2361) of *C. Difficile* Toxin B A recombinant fragment of the C-terminal binding domain (residues 1756 to 2361) of *C. difficile* Toxin B (SEQ ID NO: 28) was expressed in *E. coli* and purified by standard chromatography methods. A 1 mg ml$^{-1}$ solution of the peptide was treated with 0.2% formaldehyde for 24 h at 35° C.

After removing formaldehyde from the *C. difficile* Toxin B peptide by dialysis, the peptide was mixed with adjuvant (Titermax™) in a 1:1 ratio and used to immunise guinea pigs using 2 doses of 20 µg given at Day 0 and Day 14. The animals were bled on Day 28 and the serum from 5 animals pooled. Guinea pigs were also immunised in an identical manner with *C. difficile* Toxin B peptide which had not been treated with formaldehyde.

The toxin neutralizing activities of the resulting antiserum pools were measured by cellular assays using Vero cells. In these assays, a fixed amount of purified *C. difficile* Toxin B was mixed with various dilutions of the antibodies, incubated for 1 h at 37° C. and then applied to Vero cells growing on 24-well tissue culture plates. Toxin B possesses cytotoxic activity which results in a characteristic rounding of the Vero cells over a period of 24-48 h. In the presence of neutralising antibodies this activity is inhibited and the neutralising strength of an antibody preparation may be assessed by the dilution required to neutralise the effect of a designated quantity of the Toxin B.

The *C. difficile* toxin peptide which had been treated with formaldehyde produced antiserum of higher neutralising titre compared to the corresponding control peptide which has not been treated. In cytotoxicity assays, the dilution of antiserum required to protect cells from the cytotoxic effects of 0.5 ng/ml of Toxin B were as follows:

Untreated control *C. difficile* Toxin B peptide no protection at ×10 dilution of serum Formaldehyde-treated *C. difficile* Toxin B peptide protection of cells at ×40 dilution of serum The treatment of the C-terminal binding domain (residues 1756 to 2361) of *C. difficile* Toxin B with formaldehyde therefore increased its protective efficacy by at least 4-fold.

We claim:

1. A composition comprising a cross-linked bacterial peptide, wherein the cross-linked bacterial peptide is derived from a non-toxic bacterial peptide treated with formaldehyde over a period of less than 144 hours in a reaction mix at a ratio (formaldehyde: reaction mix) of less than 2% (v/v or w/v) to introduce intra-molecular cross-linking into the non-toxic bacterial peptide,
   wherein the non-toxic bacterial peptide is selected from the group consisting of:
   (i) a non-toxic fragment of clostridial neurotoxin, wherein said non-toxic fragment is $LH_N$,
   (ii) a non-toxic fragment comprising at least 200 contiguous amino acid residues of a *Clostridium difficile* toxin peptide, and
   (iii) a non-toxic *Clostridium difficile* surface peptide; and
   wherein the cross-linked bacterial peptide has enhanced efficacy for inducing a protective immune response as compared to the untreated non-toxic bacterial peptide from which it is derived.

2. The composition of claim 1, wherein said non-toxic fragment of a *Clostridium difficile* toxin peptide is selected from the group consisting of a non-toxic fragment of a *C. difficile* Toxin A peptide, a non-toxic fragment of a *C. difficile* Toxin B peptide, or a non-toxic fragment of a *C. difficile* binary toxin peptide.

3. The composition of claim 1, wherein the non-toxic bacterial peptide is $LH_N$, and wherein the $LH_N$ is from botulinum type A toxin.

4. The composition of claim 3, wherein the $LH_N$ comprises amino acid residues 2-871 of botulinum neurotoxin serotype A.

5. The composition of claim 3 or claim 4, wherein the $LH_N$ comprises a Glu to Gln mutation as residue 224 and a His to Tyr mutation at residue 227.

6. The composition according to claim 1, wherein the non-toxic bacterial peptide is $LH_N$, and wherein the $LH_N$ comprises a protease cleavage site located between the L-chain and the H-chain.

7. The composition of claim 6, wherein the protease cleavage site is located at a position that corresponds to a position between residues 440 and 455 of SEQ ID NO: 1.

8. The composition of claim 6 or claim 7, wherein the protease cleavage site is a non-native clostridial neurotoxin cleavage site.

9. The composition of claim 1, wherein the intra-molecular cross-linking comprises one or more methylene bonds.

10. The composition of claim 1, wherein the cross-linked bacterial peptide is derived from a non-toxic bacterial peptide treated with formaldehyde over a period of less than 3 days, less than 2 days, or over a period of 36 hours or less.

11. The composition of claim 1, wherein the cross-linked bacterial peptide is derived from a non-toxic bacterial peptide treated with formaldehyde in a reaction mix at a ratio (formaldehyde: reaction mix) of between 0.05% and 2% (v/v or w/v), or between 0.1% and 2% (v/v or w/v).

12. A vaccine comprising the composition of claim 1 and an adjuvant.

13. The vaccine of claim 12, wherein the adjuvant is aluminium hydroxide.

14. The composition of claim 1, wherein said non-toxic *Clostridium difficile* surface peptide is a *Clostridium difficile* Cwp 84 peptide.

* * * * *

SEQUENCE LISTING

<160> NUMBER OF SEQ ID NOS: 41

<210> SEQ ID NO 1
<211> LENGTH: 870
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Pro Phe Val Asn Lys Gln Phe Asn Tyr Lys Asp Pro Val Asn Gly Val
1               5                   10                  15

Asp Ile Ala Tyr Ile Lys Ile Pro Asn Val Gly Gln Met Gln Pro Val
            20                  25                  30

Lys Ala Phe Lys Ile His Asn Lys Ile Trp Val Ile Pro Glu Arg Asp
        35                  40                  45

Thr Phe Thr Asn Pro Glu Glu Gly Asp Leu Asn Pro Pro Pro Glu Ala
    50                  55                  60

Lys Gln Val Pro Val Ser Tyr Tyr Asp Ser Thr Tyr Leu Ser Thr Asp
65                  70                  75                  80

Asn Glu Lys Asp Asn Tyr Leu Lys Gly Val Thr Lys Leu Phe Glu Arg
                85                  90                  95

Ile Tyr Ser Thr Asp Leu Gly Arg Met Leu Leu Thr Ser Ile Val Arg
            100                 105                 110

Gly Ile Pro Phe Trp Gly Gly Ser Thr Ile Asp Thr Glu Leu Lys Val
        115                 120                 125

Ile Asp Thr Asn Cys Ile Asn Val Ile Gln Pro Asp Gly Ser Tyr Arg
    130                 135                 140

Ser Glu Glu Leu Asn Leu Val Ile Ile Gly Pro Ser Ala Asp Ile Ile
145                 150                 155                 160

Gln Phe Glu Cys Lys Ser Phe Gly His Glu Val Leu Asn Leu Thr Arg
                165                 170                 175

Asn Gly Tyr Gly Ser Thr Gln Tyr Ile Arg Phe Ser Pro Asp Phe Thr
            180                 185                 190

Phe Gly Phe Glu Glu Ser Leu Glu Val Asp Thr Asn Pro Leu Leu Gly
        195                 200                 205

Ala Gly Lys Phe Ala Thr Asp Pro Ala Val Thr Leu Ala His Gln Leu
    210                 215                 220

Ile Tyr Ala Gly His Arg Leu Tyr Gly Ile Ala Ile Asn Pro Asn Arg
225                 230                 235                 240

Val Phe Lys Val Asn Thr Asn Ala Tyr Tyr Glu Met Ser Gly Leu Glu
                245                 250                 255

Val Ser Phe Glu Glu Leu Arg Thr Phe Gly Gly His Asp Ala Lys Phe
            260                 265                 270

Ile Asp Ser Leu Gln Glu Asn Glu Phe Arg Leu Tyr Tyr Tyr Asn Lys
        275                 280                 285

Phe Lys Asp Ile Ala Ser Thr Leu Asn Lys Ala Lys Ser Ile Val Gly
    290                 295                 300

Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
                325                 330                 335

Phe Asp Lys Leu Tyr Lys Met Leu Thr Glu Ile Tyr Thr Glu Asp Asn
            340                 345                 350

```
Phe Val Lys Phe Phe Lys Val Leu Asn Arg Lys Thr Tyr Leu Asn Phe
            355                 360                 365

Asp Lys Ala Val Phe Lys Ile Asn Ile Val Pro Lys Val Asn Tyr Thr
370                 375                 380

Ile Tyr Asp Gly Phe Asn Leu Arg Asn Thr Asn Leu Ala Ala Asn Phe
385                 390                 395                 400

Asn Gly Gln Asn Thr Glu Ile Asn Asn Met Asn Phe Thr Lys Leu Lys
                405                 410                 415

Asn Phe Thr Gly Leu Phe Glu Phe Tyr Lys Leu Leu Cys Val Arg Gly
            420                 425                 430

Ile Ile Thr Ser Lys Thr Lys Ser Leu Asp Lys Gly Tyr Asn Lys Ala
            435                 440                 445

Leu Asn Asp Leu Cys Ile Lys Val Asn Asn Trp Asp Leu Phe Phe Ser
    450                 455                 460

Pro Ser Glu Asp Asn Phe Thr Asn Asp Leu Asn Lys Gly Glu Glu Ile
465                 470                 475                 480

Thr Ser Asp Thr Asn Ile Glu Ala Ala Glu Asn Ile Ser Leu Asp
                485                 490                 495

Leu Ile Gln Gln Tyr Tyr Leu Thr Phe Asn Phe Asp Asn Glu Pro Glu
            500                 505                 510

Asn Ile Ser Ile Glu Asn Leu Ser Ser Asp Ile Ile Gly Gln Leu Glu
            515                 520                 525

Leu Met Pro Asn Ile Glu Arg Phe Pro Asn Gly Lys Lys Tyr Glu Leu
    530                 535                 540

Asp Lys Tyr Thr Met Phe His Tyr Leu Arg Ala Gln Glu Phe Glu His
545                 550                 555                 560

Gly Lys Ser Arg Ile Ala Leu Thr Asn Ser Val Asn Glu Ala Leu Leu
                565                 570                 575

Asn Pro Ser Arg Val Tyr Thr Phe Phe Ser Ser Asp Tyr Val Lys Lys
            580                 585                 590

Val Asn Lys Ala Thr Glu Ala Ala Met Phe Leu Gly Trp Val Glu Gln
            595                 600                 605

Leu Val Tyr Asp Phe Thr Asp Glu Thr Ser Glu Val Ser Thr Thr Asp
    610                 615                 620

Lys Ile Ala Asp Ile Thr Ile Ile Pro Tyr Ile Gly Pro Ala Leu
625                 630                 635                 640

Asn Ile Gly Asn Met Leu Tyr Lys Asp Asp Phe Val Gly Ala Leu Ile
                645                 650                 655

Phe Ser Gly Ala Val Ile Leu Leu Glu Phe Ile Pro Glu Ile Ala Ile
            660                 665                 670

Pro Val Leu Gly Thr Phe Ala Leu Val Ser Tyr Ile Ala Asn Lys Val
            675                 680                 685

Leu Thr Val Gln Thr Ile Asp Asn Ala Leu Ser Lys Arg Asn Glu Lys
    690                 695                 700

Trp Asp Glu Val Tyr Lys Tyr Ile Val Thr Asn Trp Leu Ala Lys Val
705                 710                 715                 720

Asn Thr Gln Ile Asp Leu Ile Arg Lys Lys Met Lys Glu Ala Leu Glu
                725                 730                 735

Asn Gln Ala Glu Ala Thr Lys Ala Ile Ile Asn Tyr Gln Tyr Asn Gln
            740                 745                 750

Tyr Thr Glu Glu Glu Lys Asn Asn Ile Asn Phe Asn Ile Asp Asp Leu
            755                 760                 765

Ser Ser Lys Leu Asn Glu Ser Ile Asn Lys Ala Met Ile Asn Ile Asn
```

```
            770                 775                 780
Lys Phe Leu Asn Gln Cys Ser Val Ser Tyr Leu Met Asn Ser Met Ile
785                 790                 795                 800

Pro Tyr Gly Val Lys Arg Leu Glu Asp Phe Asp Ala Ser Leu Lys Asp
                805                 810                 815

Ala Leu Leu Lys Tyr Ile Tyr Asp Asn Arg Gly Thr Leu Ile Gly Gln
                820                 825                 830

Val Asp Arg Leu Lys Asp Lys Val Asn Asn Thr Leu Ser Thr Asp Ile
                835                 840                 845

Pro Phe Gln Leu Ser Lys Tyr Val Asp Asn Gln Arg Leu Leu Ser Thr
850                 855                 860

Phe Thr Glu Tyr Ile Lys
865                 870

<210> SEQ ID NO 2
<211> LENGTH: 870
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Pro Phe Val Asn Lys Gln Phe Asn Tyr Lys Asp Pro Val Asn Gly Val
1               5                   10                  15

Asp Ile Ala Tyr Ile Lys Ile Pro Asn Ala Gly Gln Met Gln Pro Val
                20                  25                  30

Lys Ala Phe Lys Ile His Asn Lys Ile Trp Val Ile Pro Glu Arg Asp
                35                  40                  45

Thr Phe Thr Asn Pro Glu Glu Gly Asp Leu Asn Pro Pro Pro Glu Ala
        50                  55                  60

Lys Gln Val Pro Val Ser Tyr Tyr Asp Ser Thr Tyr Leu Ser Thr Asp
65                  70                  75                  80

Asn Glu Lys Asp Asn Tyr Leu Lys Gly Val Thr Lys Leu Phe Glu Arg
                85                  90                  95

Ile Tyr Ser Thr Asp Leu Gly Arg Met Leu Leu Thr Ser Ile Val Arg
                100                 105                 110

Gly Ile Pro Phe Trp Gly Gly Ser Thr Ile Asp Thr Glu Leu Lys Val
            115                 120                 125

Ile Asp Thr Asn Cys Ile Asn Val Ile Gln Pro Asp Gly Ser Tyr Arg
        130                 135                 140

Ser Glu Glu Leu Asn Leu Val Ile Ile Gly Pro Ser Ala Asp Ile Ile
145                 150                 155                 160

Gln Phe Glu Cys Lys Ser Phe Gly His Asp Val Leu Asn Leu Thr Arg
                165                 170                 175

Asn Gly Tyr Gly Ser Thr Gln Tyr Ile Arg Phe Ser Pro Asp Phe Thr
                180                 185                 190

Phe Gly Phe Glu Glu Ser Leu Glu Val Asp Thr Asn Pro Leu Leu Gly
            195                 200                 205

Ala Gly Lys Phe Ala Thr Asp Pro Ala Val Thr Leu Ala His Gln Leu
        210                 215                 220

Ile Tyr Ala Glu His Arg Leu Tyr Gly Ile Ala Ile Asn Pro Asn Arg
225                 230                 235                 240

Val Phe Lys Val Asn Thr Asn Ala Tyr Tyr Glu Met Ser Gly Leu Glu
                245                 250                 255
```

Val Ser Phe Glu Glu Leu Arg Thr Phe Gly Gly His Asp Ala Lys Phe
            260                 265                 270

Ile Asp Ser Leu Gln Glu Asn Glu Phe Arg Leu Tyr Tyr Tyr Asn Lys
            275                 280                 285

Phe Lys Asp Val Ala Ser Thr Leu Asn Lys Ala Lys Ser Ile Ile Gly
            290                 295                 300

Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
            325                 330                 335

Phe Asp Lys Leu Tyr Lys Met Leu Thr Glu Ile Tyr Thr Glu Asp Asn
            340                 345                 350

Phe Val Asn Phe Phe Lys Val Ile Asn Arg Lys Thr Tyr Leu Asn Phe
            355                 360                 365

Asp Lys Ala Val Phe Arg Ile Asn Ile Val Pro Asp Glu Asn Tyr Thr
            370                 375                 380

Ile Lys Asp Gly Phe Asn Leu Lys Gly Ala Asn Leu Ser Thr Asn Phe
385                 390                 395                 400

Asn Gly Gln Asn Thr Glu Ile Asn Ser Arg Asn Phe Thr Arg Leu Lys
            405                 410                 415

Asn Phe Thr Gly Leu Phe Glu Phe Tyr Lys Leu Leu Cys Val Arg Gly
            420                 425                 430

Ile Ile Pro Phe Lys Thr Lys Ser Leu Asp Glu Gly Tyr Asn Lys Ala
            435                 440                 445

Leu Asn Asp Leu Cys Ile Lys Val Asn Asn Trp Asp Leu Phe Phe Ser
450                 455                 460

Pro Ser Glu Asp Asn Phe Thr Asn Asp Leu Asp Lys Val Glu Glu Ile
465                 470                 475                 480

Thr Ala Asp Thr Asn Ile Glu Ala Ala Glu Asn Ile Ser Leu Asp
            485                 490                 495

Leu Ile Gln Gln Tyr Tyr Leu Thr Phe Asp Phe Asp Asn Glu Pro Glu
            500                 505                 510

Asn Ile Ser Ile Glu Asn Leu Ser Ser Asp Ile Ile Gly Gln Leu Glu
            515                 520                 525

Pro Met Pro Asn Ile Glu Arg Phe Pro Asn Gly Lys Lys Tyr Glu Leu
530                 535                 540

Asp Lys Tyr Thr Met Phe His Tyr Leu Arg Ala Gln Glu Phe Glu His
545                 550                 555                 560

Gly Asp Ser Arg Ile Ile Leu Thr Asn Ser Ala Glu Glu Ala Leu Leu
            565                 570                 575

Lys Pro Asn Val Ala Tyr Thr Phe Phe Ser Ser Lys Tyr Val Lys Lys
            580                 585                 590

Ile Asn Lys Ala Val Glu Ala Phe Met Phe Leu Asn Trp Ala Glu Glu
            595                 600                 605

Leu Val Tyr Asp Phe Thr Asp Glu Thr Asn Glu Val Thr Thr Met Asp
            610                 615                 620

Lys Ile Ala Asp Ile Thr Ile Ile Val Pro Tyr Ile Gly Pro Ala Leu
625                 630                 635                 640

Asn Ile Gly Asn Met Leu Ser Lys Gly Glu Phe Val Glu Ala Ile Ile
            645                 650                 655

Phe Thr Gly Val Val Ala Met Leu Glu Phe Ile Pro Glu Tyr Ala Leu
            660                 665                 670

Pro Val Phe Gly Thr Phe Ala Ile Val Ser Tyr Ile Ala Asn Lys Val

```
            675                 680                 685
Leu Thr Val Gln Thr Ile Asn Asn Ala Leu Ser Lys Arg Asn Glu Lys
    690                 695                 700

Trp Asp Glu Val Tyr Lys Tyr Thr Val Thr Asn Trp Leu Ala Lys Val
705                 710                 715                 720

Asn Thr Gln Ile Asp Leu Ile Arg Glu Lys Met Lys Lys Ala Leu Glu
                725                 730                 735

Asn Gln Ala Glu Ala Thr Lys Ala Ile Ile Asn Tyr Gln Tyr Asn Gln
            740                 745                 750

Tyr Thr Glu Glu Glu Lys Asn Asn Ile Asn Phe Asn Ile Asp Asp Leu
        755                 760                 765

Ser Ser Lys Leu Asn Glu Ser Ile Asn Ser Ala Met Ile Asn Ile Asn
    770                 775                 780

Lys Phe Leu Asp Gln Cys Ser Val Ser Tyr Leu Met Asn Ser Met Ile
785                 790                 795                 800

Pro Tyr Ala Val Lys Arg Leu Lys Asp Phe Asp Ala Ser Val Arg Asp
                805                 810                 815

Val Leu Leu Lys Tyr Ile Tyr Asp Asn Arg Gly Thr Leu Val Leu Gln
            820                 825                 830

Val Asp Arg Leu Lys Asp Glu Val Asn Asn Thr Leu Ser Ala Asp Ile
        835                 840                 845

Pro Phe Gln Leu Ser Lys Tyr Val Asp Asn Lys Lys Leu Leu Ser Thr
    850                 855                 860

Phe Thr Glu Tyr Ile Lys
865                 870

<210> SEQ ID NO 3
<211> LENGTH: 866
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Pro Phe Val Asn Lys Pro Phe Asn Tyr Arg Asp Pro Gly Asn Gly Val
1               5                   10                  15

Asp Ile Ala Tyr Ile Lys Ile Pro Asn Ala Gly Gln Met Gln Pro Val
            20                  25                  30

Lys Ala Phe Lys Ile His Glu Gly Val Trp Val Ile Pro Glu Arg Asp
        35                  40                  45

Thr Phe Thr Asn Pro Glu Glu Gly Asp Leu Asn Pro Pro Glu Ala
    50                  55                  60

Lys Gln Val Pro Val Ser Tyr Tyr Asp Ser Thr Tyr Leu Ser Thr Asp
65                  70                  75                  80

Asn Glu Lys Asp Asn Tyr Leu Lys Gly Val Ile Lys Leu Phe Asp Arg
                85                  90                  95

Ile Tyr Ser Thr Gly Leu Gly Arg Met Leu Leu Ser Phe Ile Val Lys
            100                 105                 110

Gly Ile Pro Phe Trp Gly Gly Ser Thr Ile Asp Thr Glu Leu Lys Val
        115                 120                 125

Ile Asp Thr Asn Cys Ile Asn Val Ile Glu Pro Gly Gly Ser Tyr Arg
    130                 135                 140

Ser Glu Glu Leu Asn Leu Val Ile Thr Gly Pro Ser Ala Asp Ile Ile
145                 150                 155                 160
```

-continued

```
Gln Phe Glu Cys Lys Ser Phe Gly His Asp Val Phe Asn Leu Thr Arg
            165                 170                 175

Asn Gly Tyr Gly Ser Thr Gln Tyr Ile Arg Phe Ser Pro Asp Phe Thr
        180                 185                 190

Phe Gly Phe Glu Glu Ser Leu Glu Val Asp Thr Asn Pro Leu Leu Gly
        195                 200                 205

Ala Gly Thr Phe Ala Thr Asp Pro Ala Val Thr Leu Ala His Gln Leu
        210                 215                 220

Ile Tyr Ala Ala His Arg Leu Tyr Gly Ile Ala Ile Asn Pro Asn Arg
225                 230                 235                 240

Val Leu Lys Val Lys Thr Asn Ala Tyr Tyr Glu Met Ser Gly Leu Glu
                245                 250                 255

Val Ser Phe Glu Glu Leu Arg Thr Phe Gly Gly Asn Asp Thr Asn Phe
            260                 265                 270

Ile Asp Ser Leu Trp Gln Lys Lys Phe Ser Arg Asp Ala Tyr Asp Asn
        275                 280                 285

Leu Gln Asn Ile Ala Arg Ile Leu Asn Glu Ala Lys Thr Ile Val Gly
        290                 295                 300

Thr Thr Thr Pro Leu Gln Tyr Met Lys Asn Ile Phe Ile Arg Lys Tyr
305                 310                 315                 320

Phe Leu Ser Glu Asp Ala Ser Gly Lys Ile Ser Val Asn Lys Ala Ala
                325                 330                 335

Phe Lys Glu Phe Tyr Arg Val Leu Thr Arg Gly Phe Thr Glu Leu Glu
            340                 345                 350

Phe Val Asn Pro Phe Lys Val Ile Asn Arg Lys Thr Tyr Leu Asn Phe
        355                 360                 365

Asp Lys Ala Val Phe Arg Ile Asn Ile Val Pro Asp Glu Asn Tyr Thr
        370                 375                 380

Ile Asn Glu Gly Phe Asn Leu Glu Gly Ala Asn Ser Asn Gly Gln Asn
385                 390                 395                 400

Thr Glu Ile Asn Ser Arg Asn Phe Thr Arg Leu Lys Asn Phe Thr Gly
                405                 410                 415

Leu Phe Glu Phe Tyr Lys Leu Leu Cys Val Arg Gly Ile Ile Pro Phe
            420                 425                 430

Lys Thr Lys Ser Leu Asp Glu Gly Tyr Asn Lys Ala Leu Asn Tyr Leu
        435                 440                 445

Cys Ile Lys Val Asn Asn Trp Asp Leu Phe Phe Ser Pro Ser Glu Asp
        450                 455                 460

Asn Phe Thr Asn Asp Leu Asp Lys Val Glu Glu Ile Thr Ala Asp Thr
465                 470                 475                 480

Asn Ile Glu Ala Ala Glu Glu Asn Ile Ser Ser Asp Leu Ile Gln Gln
                485                 490                 495

Tyr Tyr Leu Thr Phe Asp Phe Asp Asn Glu Pro Glu Asn Ile Ser Ile
            500                 505                 510

Glu Asn Leu Ser Ser Asp Ile Ile Gly Gln Leu Glu Pro Met Pro Asn
        515                 520                 525

Ile Glu Arg Phe Pro Asn Gly Lys Lys Tyr Glu Leu Asp Lys Tyr Thr
        530                 535                 540

Met Phe His Tyr Leu Arg Ala Gln Glu Phe Glu His Gly Asp Ser Arg
545                 550                 555                 560

Ile Ile Leu Thr Asn Ser Ala Glu Glu Ala Leu Leu Lys Pro Asn Val
                565                 570                 575

Ala Tyr Thr Phe Phe Ser Ser Lys Tyr Val Lys Lys Ile Asn Lys Ala
```

```
            580                 585                 590
Val Glu Ala Val Ile Phe Leu Ser Trp Ala Glu Glu Leu Val Tyr Asp
            595                 600                 605

Phe Thr Asp Glu Thr Asn Glu Val Thr Thr Met Asp Lys Ile Ala Asp
            610                 615                 620

Ile Thr Ile Ile Val Pro Tyr Ile Gly Pro Ala Leu Asn Ile Gly Asn
625                 630                 635                 640

Met Val Ser Lys Gly Glu Phe Val Glu Ala Ile Leu Phe Thr Gly Val
                645                 650                 655

Val Ala Leu Leu Glu Phe Ile Pro Glu Tyr Ser Leu Pro Val Phe Gly
            660                 665                 670

Thr Phe Ala Ile Val Ser Tyr Ile Ala Asn Lys Val Leu Thr Val Gln
            675                 680                 685

Thr Ile Asn Asn Ala Leu Ser Lys Arg Asn Glu Lys Trp Asp Glu Val
            690                 695                 700

Tyr Lys Tyr Thr Val Thr Asn Trp Leu Ala Lys Val Asn Thr Gln Ile
705                 710                 715                 720

Asp Leu Ile Arg Glu Lys Met Lys Lys Ala Leu Glu Asn Gln Ala Glu
                725                 730                 735

Ala Thr Arg Ala Ile Ile Asn Tyr Gln Tyr Asn Gln Tyr Thr Glu Glu
                740                 745                 750

Glu Lys Asn Asn Ile Asn Phe Asn Ile Asp Asp Leu Ser Ser Lys Leu
            755                 760                 765

Asn Arg Ser Ile Asn Arg Ala Met Ile Asn Ile Asn Lys Phe Leu Asp
            770                 775                 780

Gln Cys Ser Val Ser Tyr Leu Met Asn Ser Met Ile Pro Tyr Ala Val
785                 790                 795                 800

Lys Arg Leu Lys Asp Phe Asp Ala Ser Val Arg Asp Val Leu Leu Lys
                805                 810                 815

Tyr Ile Tyr Asp Asn Arg Gly Thr Leu Ile Leu Gln Val Asp Arg Leu
                820                 825                 830

Lys Asp Glu Val Asn Asn Thr Leu Ser Ala Asp Ile Pro Phe Gln Leu
            835                 840                 845

Ser Lys Tyr Val Asn Asp Lys Lys Leu Leu Ser Thr Phe Thr Glu Tyr
            850                 855                 860

Ile Lys
865

<210> SEQ ID NO 4
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Pro Lys Ile Asn Ser Phe Asn Tyr Asn Asp Pro Val Asn Asp Arg Thr
1               5                   10                  15

Ile Leu Tyr Ile Lys Pro Gly Gly Cys Gln Glu Phe Tyr Lys Ser Phe
            20                  25                  30

Asn Ile Met Lys Asn Ile Trp Ile Ile Pro Glu Arg Asn Val Ile Gly
        35                  40                  45

Thr Thr Pro Gln Asp Phe His Pro Pro Thr Ser Leu Lys Asn Gly Asp
    50                  55                  60
```

```
Ser Ser Tyr Tyr Asp Pro Asn Tyr Leu Gln Ser Asp Glu Glu Lys Asp
 65                  70                  75                  80

Arg Phe Leu Lys Ile Val Thr Lys Ile Phe Asn Arg Ile Asn Asn Asn
                 85                  90                  95

Leu Ser Gly Gly Ile Leu Leu Glu Glu Leu Ser Lys Ala Asn Pro Tyr
            100                 105                 110

Leu Gly Asn Asp Asn Thr Pro Asp Asn Gln Phe His Ile Gly Asp Ala
            115                 120                 125

Ser Ala Val Glu Ile Lys Phe Ser Asn Gly Ser Gln His Ile Leu Leu
130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Gly
                165                 170                 175

Phe Gly Ser Ile Ala Ile Val Thr Phe Ser Pro Glu Tyr Ser Phe Arg
            180                 185                 190

Phe Asn Asp Asn Ser Ile Asn Glu Phe Ile Gln Asp Pro Ala Leu Thr
            195                 200                 205

Leu Met His Gln Leu Ile His Ser Leu His Gly Leu Tyr Gly Ala Lys
        210                 215                 220

Gly Ile Thr Thr Thr Cys Ile Ile Thr Gln Gln Gln Asn Pro Leu Ile
225                 230                 235                 240

Thr Asn Arg Lys Gly Ile Asn Ile Glu Glu Phe Leu Thr Phe Gly Gly
                245                 250                 255

Asn Asp Leu Asn Ile Ile Thr Val Ala Gln Tyr Asn Asp Ile Tyr Thr
            260                 265                 270

Asn Leu Leu Asn Asp Tyr Arg Lys Ile Ala Ser Lys Leu Ser Lys Val
        275                 280                 285

Gln Val Ser Asn Pro Gln Leu Asn Pro Tyr Lys Asp Ile Phe Gln Glu
        290                 295                 300

Lys Tyr Gly Leu Asp Lys Asp Ala Ser Gly Ile Tyr Ser Val Asn Ile
305                 310                 315                 320

Asn Lys Phe Asp Asp Ile Leu Lys Lys Leu Tyr Ser Phe Thr Glu Phe
                325                 330                 335

Asp Leu Ala Thr Lys Phe Gln Val Lys Cys Arg Glu Thr Tyr Ile Gly
            340                 345                 350

Gln Tyr Lys Tyr Phe Lys Leu Ser Asn Leu Leu Asn Asp Ser Ile Tyr
        355                 360                 365

Asn Ile Ser Glu Gly Tyr Asn Ile Asn Asn Leu Lys Val Asn Phe Arg
        370                 375                 380

Gly Gln Asn Ala Asn Leu Asn Pro Arg Ile Ile Lys Pro Ile Thr Gly
385                 390                 395                 400

Arg Gly Leu Val Lys Lys Ile Ile Arg Phe Cys Lys Asn Ile Val Ser
                405                 410                 415

Val Lys Gly Ile Arg Lys Ser Ile Cys Ile Glu Ile Asn Asn Gly Glu
            420                 425                 430

Leu Phe Phe Val Ala Ser Glu Asn Ser Tyr Asn Asp Asp Asn Ile Asn
        435                 440                 445

Thr Pro Lys Glu Ile Asp Asp Thr Val Thr Ser Asn Asn Tyr Glu
        450                 455                 460

Asn Asp Leu Asp Gln Val Ile Leu Asn Phe Asn Ser Glu Ser Ala Pro
465                 470                 475                 480

Gly Leu Ser Asp Glu Lys Leu Asn Leu Thr Ile Gln Asn Asp Ala Tyr
```

```
                485                 490                 495
Ile Pro Lys Tyr Asp Ser Asn Gly Thr Ser Asp Ile Glu Gln His Asp
            500                 505                 510

Val Asn Glu Leu Asn Val Phe Phe Tyr Leu Asp Ala Gln Lys Val Pro
        515                 520                 525

Glu Gly Glu Asn Asn Val Asn Leu Thr Ser Ser Ile Asp Thr Ala Leu
    530                 535                 540

Leu Glu Gln Pro Lys Ile Tyr Thr Phe Phe Ser Ser Glu Phe Ile Asn
545                 550                 555                 560

Asn Val Asn Lys Pro Val Gln Ala Ala Leu Phe Val Ser Trp Ile Gln
                565                 570                 575

Gln Val Leu Val Asp Phe Thr Thr Glu Ala Asn Gln Lys Ser Thr Val
            580                 585                 590

Asp Lys Ile Ala Asp Ile Ser Ile Val Val Pro Tyr Ile Gly Leu Ala
        595                 600                 605

Leu Asn Ile Gly Asn Glu Ala Gln Lys Gly Asn Phe Lys Asp Ala Leu
    610                 615                 620

Glu Leu Leu Gly Ala Gly Ile Leu Leu Glu Phe Glu Pro Glu Leu Leu
625                 630                 635                 640

Ile Pro Thr Ile Leu Val Phe Thr Ile Lys Ser Phe Leu Gly Ser Ser
                645                 650                 655

Asp Asn Lys Asn Lys Val Ile Lys Ala Ile Asn Asn Ala Leu Lys Glu
            660                 665                 670

Arg Asp Glu Lys Trp Lys Glu Val Tyr Ser Phe Ile Val Ser Asn Trp
        675                 680                 685

Met Thr Lys Ile Asn Thr Gln Phe Asn Lys Arg Lys Glu Gln Met Tyr
    690                 695                 700

Gln Ala Leu Gln Asn Gln Val Asn Ala Ile Lys Thr Ile Ile Glu Ser
705                 710                 715                 720

Lys Tyr Asn Ser Tyr Thr Leu Glu Glu Lys Asn Glu Leu Thr Asn Lys
                725                 730                 735

Tyr Asp Ile Lys Gln Ile Glu Asn Glu Leu Asn Gln Lys Val Ser Ile
            740                 745                 750

Ala Met Asn Asn Ile Asp Arg Phe Leu Thr Glu Ser Ser Ile Ser Tyr
        755                 760                 765

Leu Met Lys Leu Ile Asn Glu Val Lys Ile Asn Lys Leu Arg Glu Tyr
    770                 775                 780

Asp Glu Asn Val Lys Thr Tyr Leu Leu Asn Tyr Ile Ile Gln His Gly
785                 790                 795                 800

Ser Ile Leu Gly Glu Ser Gln Gln Glu Leu Asn Ser Met Val Thr Asp
                805                 810                 815

Thr Leu Asn Asn Ser Ile Pro Phe Lys Leu Ser Ser Tyr Thr Asp Asp
            820                 825                 830

Lys Ile Leu Ile Ser Tyr Phe Asn Lys Phe Phe Lys
        835                 840

<210> SEQ ID NO 5
<211> LENGTH: 878
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5
```

```
Pro Ile Thr Ile Asn Phe Arg Tyr Ser Asp Pro Val Asn Asn Asp
1               5                   10                  15

Thr Ile Ile Met Met Glu Pro Pro Tyr Cys Lys Gly Leu Asp Ile Tyr
            20                  25                  30

Tyr Lys Ala Phe Lys Ile Thr Asp Arg Ile Trp Ile Val Pro Glu Arg
            35                  40                  45

Tyr Glu Phe Gly Thr Lys Pro Glu Asp Phe Asn Pro Pro Ser Ser Leu
            50                  55                  60

Ile Glu Gly Ala Ser Glu Tyr Tyr Asp Pro Asn Tyr Leu Arg Thr Asp
65              70                  75                  80

Ser Asp Lys Asp Arg Phe Leu Gln Thr Met Val Lys Leu Phe Asn Arg
            85                  90                  95

Ile Lys Asn Asn Val Ala Gly Glu Ala Leu Leu Asp Lys Ile Ile Asn
            100                 105                 110

Ala Ile Pro Tyr Leu Gly Asn Ser Tyr Ser Leu Leu Asp Lys Phe Asp
            115                 120                 125

Thr Asn Ser Asn Ser Val Ser Phe Asn Leu Leu Glu Gln Asp Pro Ser
            130                 135                 140

Gly Ala Thr Thr Lys Ser Ala Met Leu Thr Asn Leu Ile Ile Phe Gly
145             150                 155                 160

Pro Gly Pro Val Leu Asn Lys Asn Glu Val Arg Gly Ile Val Leu Arg
            165                 170                 175

Val Asp Asn Lys Asn Tyr Phe Pro Cys Arg Asp Gly Phe Gly Ser Ile
            180                 185                 190

Met Gln Met Ala Phe Cys Pro Glu Tyr Val Pro Thr Phe Asp Asn Val
            195                 200                 205

Ile Glu Asn Ile Thr Ser Leu Thr Ile Gly Lys Ser Lys Tyr Phe Gln
            210                 215                 220

Asp Pro Ala Leu Leu Leu Met His Gln Leu Ile Tyr Val Leu His Gly
225             230                 235                 240

Leu Tyr Gly Met Gln Val Ser Ser His Glu Ile Ile Pro Ser Lys Gln
            245                 250                 255

Glu Ile Tyr Met Gln His Thr Tyr Pro Ile Ser Ala Glu Glu Leu Phe
            260                 265                 270

Thr Phe Gly Gly Gln Asp Ala Asn Leu Ile Ser Ile Asp Ile Lys Asn
            275                 280                 285

Asp Leu Tyr Glu Lys Thr Leu Asn Asp Tyr Lys Ala Ile Ala Asn Lys
            290                 295                 300

Leu Ser Gln Val Thr Ser Cys Asn Asp Pro Asn Ile Asp Ile Asp Ser
305             310                 315                 320

Tyr Lys Gln Ile Tyr Gln Gln Lys Tyr Gln Phe Asp Lys Asp Ser Asn
            325                 330                 335

Gly Gln Tyr Ile Val Asn Glu Asp Lys Phe Gln Ile Leu Tyr Asn Ser
            340                 345                 350

Ile Met Tyr Gly Phe Thr Glu Ile Glu Leu Gly Lys Lys Phe Asn Ile
            355                 360                 365

Lys Thr Arg Leu Ser Tyr Phe Ser Met Asn His Asp Pro Val Lys Ile
            370                 375                 380

Pro Asn Leu Leu Asp Asp Thr Ile Tyr Asn Asp Thr Glu Gly Phe Asn
385             390                 395                 400

Ile Glu Ser Lys Asp Leu Lys Ser Glu Tyr Lys Gly Gln Asn Met Arg
            405                 410                 415

Val Asn Thr Asn Ala Phe Arg Asn Val Asp Gly Ser Gly Leu Val Ser
```

-continued

```
                420             425             430
Lys Leu Ile Gly Leu Cys Lys Lys Ile Ile Pro Pro Thr Asn Ile Arg
            435             440             445
Glu Asn Leu Tyr Asn Arg Thr Ala Ser Leu Thr Asp Leu Gly Gly Glu
            450             455             460
Leu Cys Ile Lys Ile Lys Asn Glu Asp Leu Thr Phe Ile Ala Glu Lys
465             470             475             480
Asn Ser Phe Ser Glu Glu Pro Phe Gln Asp Glu Ile Val Ser Tyr Asn
            485             490             495
Thr Lys Asn Lys Pro Leu Asn Phe Asn Tyr Ser Leu Asp Lys Ile Ile
            500             505             510
Val Asp Tyr Asn Leu Gln Ser Lys Ile Thr Leu Pro Asn Asp Arg Thr
            515             520             525
Thr Pro Val Thr Lys Gly Ile Pro Tyr Ala Pro Glu Tyr Lys Ser Asn
            530             535             540
Ala Ala Ser Thr Ile Glu Ile His Asn Ile Asp Asp Asn Thr Ile Tyr
545             550             555             560
Gln Tyr Leu Tyr Ala Gln Lys Ser Pro Thr Thr Leu Gln Arg Ile Thr
            565             570             575
Met Thr Asn Ser Val Asp Asp Ala Leu Ile Asn Ser Thr Lys Ile Tyr
            580             585             590
Ser Tyr Phe Pro Ser Val Ile Ser Lys Val Asn Gln Gly Ala Gln Gly
            595             600             605
Ile Leu Phe Leu Gln Trp Val Arg Asp Ile Ile Asp Asp Phe Thr Asn
            610             615             620
Glu Ser Ser Gln Lys Thr Thr Ile Asp Lys Ile Ser Asp Val Ser Thr
625             630             635             640
Ile Val Pro Tyr Ile Gly Pro Ala Leu Asn Ile Val Lys Gln Gly Tyr
            645             650             655
Glu Gly Asn Phe Ile Gly Ala Leu Glu Thr Thr Gly Val Val Leu Leu
            660             665             670
Leu Glu Tyr Ile Pro Glu Ile Thr Leu Pro Val Ile Ala Ala Leu Ser
            675             680             685
Ile Ala Glu Ser Ser Thr Gln Lys Glu Lys Ile Ile Lys Thr Ile Asp
            690             695             700
Asn Phe Leu Glu Lys Arg Tyr Glu Lys Trp Ile Glu Val Tyr Lys Leu
705             710             715             720
Val Lys Ala Lys Trp Leu Gly Thr Val Asn Thr Gln Phe Gln Lys Arg
            725             730             735
Ser Tyr Gln Met Tyr Arg Ser Leu Glu Tyr Gln Val Asp Ala Ile Lys
            740             745             750
Lys Ile Ile Asp Tyr Glu Tyr Lys Ile Tyr Ser Gly Pro Asp Lys Glu
            755             760             765
Gln Ile Ala Asp Glu Ile Asn Asn Leu Lys Asn Lys Leu Glu Glu Lys
            770             775             780
Ala Asn Lys Ala Met Ile Asn Ile Asn Ile Phe Met Arg Glu Ser Ser
785             790             795             800
Arg Ser Phe Leu Val Asn Gln Met Ile Asn Glu Ala Lys Lys Gln Leu
            805             810             815
Leu Glu Phe Asp Thr Gln Ser Lys Asn Ile Leu Met Gln Tyr Ile Lys
            820             825             830
Ala Asn Ser Lys Phe Ile Gly Ile Thr Glu Leu Lys Lys Leu Glu Ser
            835             840             845
```

Lys Ile Asn Lys Val Phe Ser Thr Pro Ile Pro Phe Ser Tyr Ser Lys
850                 855                 860

Asn Leu Asp Cys Trp Val Asp Asn Glu Glu Asp Ile Asp Val
865                 870                 875

<210> SEQ ID NO 6
<211> LENGTH: 858
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Pro Val Thr Ile Asn Asn Phe Asn Tyr Asn Asp Pro Ile Asp Asn Asn
1               5                   10                  15

Asn Ile Ile Met Met Glu Pro Pro Phe Ala Arg Gly Thr Gly Arg Tyr
            20                  25                  30

Tyr Lys Ala Phe Lys Ile Thr Asp Arg Ile Trp Ile Ile Pro Glu Arg
        35                  40                  45

Tyr Thr Phe Gly Tyr Lys Pro Glu Asp Phe Asn Lys Ser Ser Gly Ile
50                  55                  60

Phe Asn Arg Asp Val Cys Glu Tyr Tyr Asp Pro Asp Tyr Leu Asn Thr
65                  70                  75                  80

Asn Asp Lys Lys Asn Ile Phe Leu Gln Thr Met Ile Lys Leu Phe Asn
                85                  90                  95

Arg Ile Lys Ser Lys Pro Leu Gly Glu Lys Leu Leu Glu Met Ile Ile
            100                 105                 110

Asn Gly Ile Pro Tyr Leu Gly Asp Arg Arg Val Pro Leu Glu Glu Phe
        115                 120                 125

Asn Thr Asn Ile Ala Ser Val Thr Val Asn Lys Leu Ile Ser Asn Pro
130                 135                 140

Gly Glu Val Glu Arg Lys Lys Gly Ile Phe Ala Asn Leu Ile Ile Phe
145                 150                 155                 160

Gly Pro Gly Pro Val Leu Asn Glu Asn Glu Thr Ile Asp Ile Gly Ile
                165                 170                 175

Gln Asn His Phe Ala Ser Arg Glu Gly Phe Gly Gly Ile Met Gln Met
            180                 185                 190

Lys Phe Cys Pro Glu Tyr Val Ser Val Phe Asn Asn Val Gln Glu Asn
        195                 200                 205

Lys Gly Ala Ser Ile Phe Asn Arg Arg Gly Tyr Phe Ser Asp Pro Ala
210                 215                 220

Leu Ile Leu Met His Gln Leu Ile Tyr Val Leu His Gly Leu Tyr Gly
225                 230                 235                 240

Ile Lys Val Asp Asp Leu Pro Ile Val Pro Asn Glu Lys Lys Phe Phe
                245                 250                 255

Met Gln Ser Thr Asp Ala Ile Gln Ala Glu Glu Leu Tyr Thr Phe Gly
            260                 265                 270

Gly Gln Asp Pro Ser Ile Ile Thr Pro Ser Thr Asp Lys Ser Ile Tyr
        275                 280                 285

Asp Lys Val Leu Gln Asn Phe Arg Gly Ile Val Asp Arg Leu Asn Lys
290                 295                 300

Val Leu Val Cys Ile Ser Asp Pro Asn Ile Asn Ile Asn Ile Tyr Lys
305                 310                 315                 320

Asn Lys Phe Lys Asp Lys Tyr Lys Phe Val Glu Asp Ser Glu Gly Lys

-continued

```
                325                 330                 335
Tyr Ser Ile Asp Val Glu Ser Phe Asp Lys Leu Tyr Lys Ser Leu Met
                340                 345                 350
Phe Gly Phe Thr Glu Thr Asn Ile Ala Glu Asn Tyr Lys Ile Lys Thr
                355                 360                 365
Arg Ala Ser Tyr Phe Ser Asp Ser Leu Pro Val Lys Ile Lys Asn
                370                 375                 380
Leu Leu Asp Asn Glu Ile Tyr Thr Ile Glu Glu Gly Phe Asn Ile Ser
385                 390                 395                 400
Asp Lys Asp Met Glu Lys Glu Tyr Arg Gly Gln Asn Lys Ala Ile Asn
                405                 410                 415
Lys Gln Ala Tyr Glu Glu Ile Ser Lys Glu His Leu Ala Val Tyr Lys
                420                 425                 430
Ile Gln Met Cys Lys Ser Val Lys Ala Pro Gly Ile Cys Ile Asp Val
                435                 440                 445
Asp Asn Glu Asp Leu Phe Phe Ile Ala Asp Lys Asn Ser Phe Ser Asp
                450                 455                 460
Asp Leu Ser Lys Asn Glu Arg Ile Glu Tyr Asn Thr Gln Ser Asn Tyr
465                 470                 475                 480
Ile Glu Asn Asp Phe Pro Ile Asn Glu Leu Ile Leu Asp Thr Asp Leu
                485                 490                 495
Ile Ser Lys Ile Glu Leu Pro Ser Glu Asn Thr Glu Ser Leu Thr Asp
                500                 505                 510
Phe Asn Val Asp Val Pro Val Tyr Glu Lys Gln Pro Ala Ile Lys Lys
                515                 520                 525
Ile Phe Thr Asp Glu Asn Thr Ile Phe Gln Tyr Leu Tyr Ser Gln Thr
                530                 535                 540
Phe Pro Leu Asp Ile Arg Asp Ile Ser Leu Thr Ser Ser Phe Asp Asp
545                 550                 555                 560
Ala Leu Leu Phe Ser Asn Lys Val Tyr Ser Phe Phe Ser Met Asp Tyr
                565                 570                 575
Ile Lys Thr Ala Asn Lys Val Val Glu Ala Gly Leu Phe Ala Gly Trp
                580                 585                 590
Val Lys Gln Ile Val Asn Asp Phe Val Ile Glu Ala Asn Lys Ser Asn
                595                 600                 605
Thr Met Asp Lys Ile Ala Asp Ile Ser Leu Ile Val Pro Tyr Ile Gly
                610                 615                 620
Leu Ala Leu Asn Val Gly Asn Glu Thr Ala Lys Gly Asn Phe Glu Asn
625                 630                 635                 640
Ala Phe Glu Ile Ala Gly Ala Ser Ile Leu Leu Glu Phe Ile Pro Glu
                645                 650                 655
Leu Leu Ile Pro Val Val Gly Ala Phe Leu Leu Glu Ser Tyr Ile Asp
                660                 665                 670
Asn Lys Asn Lys Ile Ile Lys Thr Ile Asp Asn Ala Leu Thr Lys Arg
                675                 680                 685
Asn Glu Lys Trp Ser Asp Met Tyr Gly Leu Ile Val Ala Gln Trp Leu
                690                 695                 700
Ser Thr Val Asn Thr Gln Phe Tyr Thr Ile Lys Glu Gly Met Tyr Lys
705                 710                 715                 720
Ala Leu Asn Tyr Gln Ala Gln Ala Leu Glu Glu Ile Ile Lys Tyr Arg
                725                 730                 735
Tyr Asn Ile Tyr Ser Glu Lys Glu Lys Ser Asn Ile Asn Ile Asp Phe
                740                 745                 750
```

```
Asn Asp Ile Asn Ser Lys Leu Asn Glu Gly Ile Asn Gln Ala Ile Asp
        755                 760                 765
Asn Ile Asn Asn Phe Ile Asn Gly Cys Ser Val Ser Tyr Leu Met Lys
770                 775                 780
Lys Met Ile Pro Leu Ala Val Glu Lys Leu Leu Asp Phe Asp Asn Thr
785                 790                 795                 800
Leu Lys Lys Asn Leu Leu Asn Tyr Ile Asp Glu Asn Lys Leu Tyr Leu
            805                 810                 815
Ile Gly Ser Ala Glu Tyr Glu Lys Ser Lys Val Asn Lys Tyr Leu Lys
            820                 825                 830
Thr Ile Met Pro Phe Asp Leu Ser Ile Tyr Thr Asn Asp Thr Ile Leu
            835                 840                 845
Ile Glu Met Phe Asn Lys Tyr Asn Ser Glu
            850                 855

<210> SEQ ID NO 7
<211> LENGTH: 802
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Pro Val Ala Ile Asn Ser Phe Asn Tyr Asn Asp Pro Val Asn Asp Asp
1               5                   10                  15
Thr Ile Leu Tyr Met Gln Ile Pro Tyr Glu Glu Lys Ser Lys Lys Tyr
            20                  25                  30
Tyr Lys Ala Phe Glu Ile Met Arg Asn Val Trp Ile Ile Pro Glu Arg
        35                  40                  45
Asn Thr Ile Gly Thr Asn Pro Ser Asp Phe Asp Pro Pro Ala Ser Leu
50                  55                  60
Lys Asn Gly Ser Ser Ala Tyr Tyr Asp Pro Asn Tyr Leu Thr Thr Asp
65                  70                  75                  80
Ala Glu Lys Asp Arg Tyr Leu Lys Thr Thr Ile Lys Leu Phe Lys Arg
                85                  90                  95
Ile Asn Ser Asn Pro Ala Gly Lys Val Leu Leu Gln Glu Ile Ser Tyr
            100                 105                 110
Ala Lys Pro Tyr Leu Gly Asn Asp His Thr Pro Ile Asp Glu Phe Ser
        115                 120                 125
Pro Val Thr Arg Thr Thr Ser Val Asn Ile Lys Leu Ser Thr Asn Val
    130                 135                 140
Glu Ser Ser Met Leu Leu Asn Leu Leu Val Leu Gly Ala Gly Pro Asp
145                 150                 155                 160
Ile Phe Glu Ser Cys Cys Tyr Pro Val Arg Lys Leu Ile Asp Pro Asp
                165                 170                 175
Val Val Tyr Asp Pro Ser Asn Tyr Gly Phe Gly Ser Ile Asn Ile Val
            180                 185                 190
Thr Phe Ser Pro Glu Tyr Glu Tyr Thr Phe Asn Asp Ile Ser Gly Gly
        195                 200                 205
His Asn Ser Ser Thr Glu Ser Phe Ile Ala Asp Pro Ala Ile Ser Leu
    210                 215                 220
Ala His Gln Leu Ile Tyr Ala Leu His Gly Leu Tyr Gly Ala Arg Gly
225                 230                 235                 240
Val Thr Tyr Glu Glu Thr Ile Glu Val Lys Gln Ala Pro Leu Met Ile
```

```
                245                 250                 255
Ala Glu Lys Pro Ile Arg Leu Glu Glu Phe Leu Thr Phe Gly Gly Gln
                260                 265                 270

Asp Leu Asn Ile Ile Thr Ser Ala Met Lys Glu Lys Ile Tyr Asn Asn
                275                 280                 285

Leu Leu Ala Asn Tyr Glu Lys Ile Ala Thr Arg Leu Ser Glu Val Asn
        290                 295                 300

Ser Ala Pro Pro Glu Tyr Asp Ile Asn Glu Tyr Lys Asp Tyr Phe Gln
305                 310                 315                 320

Trp Lys Tyr Gly Leu Asp Lys Asn Ala Asp Gly Ser Tyr Thr Val Asn
                325                 330                 335

Glu Asn Lys Phe Asn Glu Ile Tyr Lys Lys Leu Tyr Ser Phe Thr Glu
                340                 345                 350

Ser Asp Leu Ala Asn Lys Phe Lys Val Lys Cys Arg Asn Thr Tyr Phe
        355                 360                 365

Ile Lys Tyr Glu Phe Leu Lys Val Pro Asn Leu Leu Asp Asp Asp Ile
    370                 375                 380

Tyr Thr Val Ser Glu Gly Phe Asn Ile Gly Asn Leu Ala Val Asn Asn
385                 390                 395                 400

Arg Gly Gln Ser Ile Lys Leu Asn Pro Lys Ile Ile Asp Ser Ile Pro
                405                 410                 415

Asp Lys Gly Leu Val Glu Lys Ile Val Lys Phe Cys Lys Ser Val Ile
        420                 425                 430

Pro Arg Lys Gly Thr Lys Ala Pro Pro Arg Leu Cys Ile Arg Val Asn
                435                 440                 445

Asn Ser Glu Leu Phe Phe Val Ala Ser Glu Ser Ser Tyr Asn Glu Asn
    450                 455                 460

Asp Ile Asn Thr Pro Lys Glu Ile Asp Asp Thr Thr Asn Leu Asn Asn
465                 470                 475                 480

Asn Tyr Arg Asn Asn Leu Asp Glu Val Ile Leu Asp Tyr Asn Ser Gln
                485                 490                 495

Thr Ile Pro Gln Ile Ser Asn Arg Thr Leu Asn Thr Leu Val Gln Asp
                500                 505                 510

Asn Ser Tyr Val Pro Arg Tyr Asp Ser Asn Gly Thr Ser Glu Ile Glu
        515                 520                 525

Glu Tyr Asp Val Val Asp Phe Asn Val Phe Phe Tyr Leu His Ala Gln
    530                 535                 540

Lys Val Pro Glu Gly Glu Thr Asn Ile Ser Leu Thr Ser Ser Ile Asp
545                 550                 555                 560

Thr Ala Leu Leu Glu Glu Ser Lys Asp Ile Phe Phe Ser Ser Glu Phe
                565                 570                 575

Ile Asp Thr Ile Asn Lys Pro Val Asn Ala Ala Leu Phe Ile Asp Trp
                580                 585                 590

Ile Ser Lys Val Ile Arg Asp Phe Thr Thr Glu Ala Thr Gln Lys Ser
        595                 600                 605

Thr Val Asp Lys Ile Ala Asp Ile Ser Leu Ile Val Pro Tyr Val Gly
    610                 615                 620

Leu Ala Leu Asn Ile Ile Ile Glu Ala Glu Lys Gly Asn Phe Glu Glu
625                 630                 635                 640

Ala Phe Glu Leu Leu Gly Val Gly Ile Leu Leu Glu Phe Val Pro Glu
                645                 650                 655

Leu Thr Ile Pro Val Ile Leu Val Phe Thr Ile Lys Ser Tyr Ile Asp
                660                 665                 670
```

```
Ser Tyr Glu Asn Lys Asn Lys Ala Ile Lys Ala Ile Asn Asn Ser Leu
        675                 680                 685

Ile Glu Arg Glu Ala Lys Trp Lys Glu Ile Tyr Ser Trp Ile Val Ser
690                 695                 700

Asn Trp Leu Thr Arg Ile Asn Thr Gln Phe Asn Lys Arg Lys Glu Gln
705                 710                 715                 720

Met Tyr Gln Ala Leu Gln Asn Gln Val Asp Ala Ile Lys Thr Ala Ile
        725                 730                 735

Glu Tyr Lys Tyr Asn Asn Tyr Thr Ser Asp Glu Lys Asn Arg Leu Glu
                740                 745                 750

Ser Glu Tyr Asn Ile Asn Ile Glu Glu Leu Asn Lys Lys Val
                755                 760                 765

Ser Leu Ala Met Lys Asn Ile Glu Arg Phe Met Thr Glu Ser Ser Ile
770                 775                 780

Ser Tyr Leu Met Lys Leu Ile Asn Glu Ala Lys Val Gly Lys Leu Lys
785                 790                 795                 800

Lys Tyr

<210> SEQ ID NO 8
<211> LENGTH: 1295
<212> TYPE: PRT
<213> ORGANISM: Clostridium botulinum type A

<400> SEQUENCE: 8

Pro Phe Val Asn Lys Gln Phe Asn Tyr Lys Asp Pro Val Asn Gly Val
1               5                   10                  15

Asp Ile Ala Tyr Ile Lys Ile Pro Asn Val Gly Gln Met Gln Pro Val
                20                  25                  30

Lys Ala Phe Lys Ile His Asn Lys Ile Trp Val Ile Pro Glu Arg Asp
            35                  40                  45

Thr Phe Thr Asn Pro Glu Glu Gly Asp Leu Asn Pro Pro Pro Glu Ala
        50                  55                  60

Lys Gln Val Pro Val Ser Tyr Tyr Asp Ser Thr Tyr Leu Ser Thr Asp
65                  70                  75                  80

Asn Glu Lys Asp Asn Tyr Leu Lys Gly Val Thr Lys Leu Phe Glu Arg
                85                  90                  95

Ile Tyr Ser Thr Asp Leu Gly Arg Met Leu Leu Thr Ser Ile Val Arg
            100                 105                 110

Gly Ile Pro Phe Trp Gly Gly Ser Thr Ile Thr Glu Leu Lys Val
        115                 120                 125

Ile Asp Thr Asn Cys Ile Asn Val Ile Gln Pro Asp Gly Ser Tyr Arg
130                 135                 140

Ser Glu Glu Leu Asn Leu Val Ile Ile Gly Pro Ser Ala Asp Ile Ile
145                 150                 155                 160

Gln Phe Glu Cys Lys Ser Phe Gly His Glu Val Leu Asn Leu Thr Arg
                165                 170                 175

Asn Gly Tyr Gly Ser Thr Gln Tyr Ile Arg Phe Ser Pro Asp Phe Thr
            180                 185                 190

Phe Gly Phe Glu Glu Ser Leu Glu Val Asp Thr Asn Pro Leu Leu Gly
        195                 200                 205

Ala Gly Lys Phe Ala Thr Asp Pro Ala Val Thr Leu Ala His Glu Leu
    210                 215                 220

Ile His Ala Gly His Arg Leu Tyr Gly Ile Ala Ile Asn Pro Asn Arg
225                 230                 235                 240
```

```
Val Phe Lys Val Asn Thr Asn Ala Tyr Tyr Glu Met Ser Gly Leu Glu
                245                 250                 255

Val Ser Phe Glu Glu Leu Arg Thr Phe Gly Gly His Asp Ala Lys Phe
                260                 265                 270

Ile Asp Ser Leu Gln Glu Asn Glu Phe Arg Leu Tyr Tyr Tyr Asn Lys
                275                 280                 285

Phe Lys Asp Ile Ala Ser Thr Leu Asn Lys Ala Lys Ser Ile Val Gly
                290                 295                 300

Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
                325                 330                 335

Phe Asp Lys Leu Tyr Lys Met Leu Thr Glu Ile Tyr Thr Glu Asp Asn
                340                 345                 350

Phe Val Lys Phe Phe Lys Val Leu Asn Arg Lys Thr Tyr Leu Asn Phe
                355                 360                 365

Asp Lys Ala Val Phe Lys Ile Asn Ile Val Pro Lys Val Asn Tyr Thr
                370                 375                 380

Ile Tyr Asp Gly Phe Asn Leu Arg Asn Thr Asn Leu Ala Ala Asn Phe
385                 390                 395                 400

Asn Gly Gln Asn Thr Glu Ile Asn Asn Met Asn Phe Thr Lys Leu Lys
                405                 410                 415

Asn Phe Thr Gly Leu Phe Glu Phe Tyr Lys Leu Leu Cys Val Arg Gly
                420                 425                 430

Ile Ile Thr Ser Lys Thr Lys Ser Leu Asp Lys Gly Tyr Asn Lys Ala
                435                 440                 445

Leu Asn Asp Leu Cys Ile Lys Val Asn Asn Trp Asp Leu Phe Phe Ser
                450                 455                 460

Pro Ser Glu Asp Asn Phe Thr Asn Asp Leu Asn Lys Gly Glu Glu Ile
465                 470                 475                 480

Thr Ser Asp Thr Asn Ile Glu Ala Ala Glu Glu Asn Ile Ser Leu Asp
                485                 490                 495

Leu Ile Gln Gln Tyr Tyr Leu Thr Phe Asn Phe Asp Asn Glu Pro Glu
                500                 505                 510

Asn Ile Ser Ile Glu Asn Leu Ser Ser Asp Ile Ile Gly Gln Leu Glu
                515                 520                 525

Leu Met Pro Asn Ile Glu Arg Phe Pro Asn Gly Lys Lys Tyr Glu Leu
                530                 535                 540

Asp Lys Tyr Thr Met Phe His Tyr Leu Arg Ala Gln Glu Phe Glu His
545                 550                 555                 560

Gly Lys Ser Arg Ile Ala Leu Thr Asn Ser Val Asn Glu Ala Leu Leu
                565                 570                 575

Asn Pro Ser Arg Val Tyr Thr Phe Phe Ser Ser Asp Tyr Val Lys Lys
                580                 585                 590

Val Asn Lys Ala Thr Glu Ala Ala Met Phe Leu Gly Trp Val Glu Gln
                595                 600                 605

Leu Val Tyr Asp Phe Thr Asp Glu Thr Ser Glu Val Ser Thr Thr Asp
                610                 615                 620

Lys Ile Ala Asp Ile Thr Ile Ile Ile Pro Tyr Ile Gly Pro Ala Leu
625                 630                 635                 640

Asn Ile Gly Asn Met Leu Tyr Lys Asp Asp Phe Val Gly Ala Leu Ile
                645                 650                 655
```

```
Phe Ser Gly Ala Val Ile Leu Leu Glu Phe Ile Pro Glu Ile Ala Ile
            660                 665                 670

Pro Val Leu Gly Thr Phe Ala Leu Val Ser Tyr Ile Ala Asn Lys Val
        675                 680                 685

Leu Thr Val Gln Thr Ile Asp Asn Ala Leu Ser Lys Arg Asn Glu Lys
    690                 695                 700

Trp Asp Glu Val Tyr Lys Tyr Ile Val Thr Asn Trp Leu Ala Lys Val
705                 710                 715                 720

Asn Thr Gln Ile Asp Leu Ile Arg Lys Lys Met Lys Glu Ala Leu Glu
                725                 730                 735

Asn Gln Ala Glu Ala Thr Lys Ala Ile Ile Asn Tyr Gln Tyr Asn Gln
        740                 745                 750

Tyr Thr Glu Glu Glu Lys Asn Asn Ile Asn Phe Asn Ile Asp Asp Leu
    755                 760                 765

Ser Ser Lys Leu Asn Glu Ser Ile Asn Lys Ala Met Ile Asn Ile Asn
    770                 775                 780

Lys Phe Leu Asn Gln Cys Ser Val Ser Tyr Leu Met Asn Ser Met Ile
785                 790                 795                 800

Pro Tyr Gly Val Lys Arg Leu Glu Asp Phe Asp Ala Ser Leu Lys Asp
                805                 810                 815

Ala Leu Leu Lys Tyr Ile Tyr Asp Asn Arg Gly Thr Leu Ile Gly Gln
        820                 825                 830

Val Asp Arg Leu Lys Asp Lys Val Asn Asn Thr Leu Ser Thr Asp Ile
    835                 840                 845

Pro Phe Gln Leu Ser Lys Tyr Val Asp Asn Gln Arg Leu Leu Ser Thr
    850                 855                 860

Phe Thr Glu Tyr Ile Lys Asn Ile Ile Asn Thr Ser Ile Leu Asn Leu
865                 870                 875                 880

Arg Tyr Glu Ser Asn His Leu Ile Asp Leu Ser Arg Tyr Ala Ser Lys
                885                 890                 895

Ile Asn Ile Gly Ser Lys Val Asn Phe Asp Pro Ile Asp Lys Asn Gln
        900                 905                 910

Ile Gln Leu Phe Asn Leu Glu Ser Ser Lys Ile Glu Val Ile Leu Lys
    915                 920                 925

Asn Ala Ile Val Tyr Asn Ser Met Tyr Glu Asn Phe Ser Thr Ser Phe
    930                 935                 940

Trp Ile Arg Ile Pro Lys Tyr Phe Asn Ser Ile Ser Leu Asn Asn Glu
945                 950                 955                 960

Tyr Thr Ile Ile Asn Cys Met Glu Asn Asn Ser Gly Trp Lys Val Ser
                965                 970                 975

Leu Asn Tyr Gly Glu Ile Ile Trp Thr Leu Gln Asp Thr Gln Glu Ile
        980                 985                 990

Lys Gln Arg Val Val Phe Lys Tyr Ser Gln Met Ile Asn Ile Ser Asp
    995                 1000                1005

Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys
    1025                1030                1035

Pro Ile Ser Asn Leu Gly Asn Ile His Ala Ser Asn Asn Ile Met
    1040                1045                1050

Phe Lys Leu Asp Gly Cys Arg Asp Thr His Arg Tyr Ile Trp Ile
    1055                1060                1065

Lys Tyr Phe Asn Leu Phe Asp Lys Glu Leu Asn Glu Lys Glu Ile
```

-continued

```
                1070                1075                1080
Lys Asp Leu Tyr Asp Asn Gln Ser Asn Ser Gly Ile Leu Lys Asp
        1085                1090                1095

Phe Trp Gly Asp Tyr Leu Gln Tyr Asp Lys Pro Tyr Tyr Met Leu
    1100                1105                1110

Asn Leu Tyr Asp Pro Asn Lys Tyr Val Asp Val Asn Asn Val Gly
        1115                1120                1125

Ile Arg Gly Tyr Met Tyr Leu Lys Gly Pro Arg Gly Ser Val Met
    1130                1135                1140

Thr Thr Asn Ile Tyr Leu Asn Ser Ser Leu Tyr Arg Gly Thr Lys
        1145                1150                1155

Phe Ile Ile Lys Lys Tyr Ala Ser Gly Asn Lys Asp Asn Ile Val
    1160                1165                1170

Arg Asn Asn Asp Arg Val Tyr Ile Asn Val Val Val Lys Asn Lys
        1175                1180                1185

Glu Tyr Arg Leu Ala Thr Asn Ala Ser Gln Ala Gly Val Glu Lys
    1190                1195                1200

Ile Leu Ser Ala Leu Glu Ile Pro Asp Val Gly Asn Leu Ser Gln
        1205                1210                1215

Val Val Met Lys Ser Lys Asn Asp Gln Gly Ile Thr Asn Lys
    1220                1225                1230

Cys Lys Met Asn Leu Gln Asp Asn Asn Gly Asn Asp Ile Gly Phe
        1235                1240                1245

Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly
        1265                1270                1275

Cys Ser Trp Glu Phe Ile Pro Val Asp Asp Gly Trp Gly Glu Arg
    1280                1285                1290

Pro Leu
    1295

<210> SEQ ID NO 9
<211> LENGTH: 1295
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Pro Phe Val Asn Lys Gln Phe Asn Tyr Lys Asp Pro Val Asn Gly Val
1               5                   10                  15

Asp Ile Ala Tyr Ile Lys Ile Pro Asn Val Gly Gln Met Gln Pro Val
            20                  25                  30

Lys Ala Phe Lys Ile His Asn Lys Ile Trp Val Ile Pro Glu Arg Asp
        35                  40                  45

Thr Phe Thr Asn Pro Glu Glu Gly Asp Leu Asn Pro Pro Pro Glu Ala
    50                  55                  60

Lys Gln Val Pro Val Ser Tyr Tyr Asp Ser Thr Tyr Leu Ser Thr Asp
65                  70                  75                  80

Asn Glu Lys Asp Asn Tyr Leu Lys Gly Val Thr Lys Leu Phe Glu Arg
                85                  90                  95

Ile Tyr Ser Thr Asp Leu Gly Arg Met Leu Leu Thr Ser Ile Val Arg
            100                 105                 110
```

-continued

```
Gly Ile Pro Phe Trp Gly Gly Ser Thr Ile Asp Thr Glu Leu Lys Val
            115                 120                 125
Ile Asp Thr Asn Cys Ile Asn Val Ile Gln Pro Asp Gly Ser Tyr Arg
130                 135                 140
Ser Glu Glu Leu Asn Leu Val Ile Ile Gly Pro Ser Ala Asp Ile Ile
145                 150                 155                 160
Gln Phe Glu Cys Lys Ser Phe Gly His Glu Val Leu Asn Leu Thr Arg
                165                 170                 175
Asn Gly Tyr Gly Ser Thr Gln Tyr Ile Arg Phe Ser Pro Asp Phe Thr
            180                 185                 190
Phe Gly Phe Glu Glu Ser Leu Glu Val Asp Thr Asn Pro Leu Leu Gly
        195                 200                 205
Ala Gly Lys Phe Ala Thr Asp Pro Ala Val Thr Leu Ala His Gln Leu
    210                 215                 220
Ile Tyr Ala Gly His Arg Leu Tyr Gly Ile Ala Ile Asn Pro Asn Arg
225                 230                 235                 240
Val Phe Lys Val Asn Thr Asn Ala Tyr Tyr Glu Met Ser Gly Leu Glu
                245                 250                 255
Val Ser Phe Glu Glu Leu Arg Thr Phe Gly Gly His Asp Ala Lys Phe
            260                 265                 270
Ile Asp Ser Leu Gln Glu Asn Glu Phe Arg Leu Tyr Tyr Tyr Asn Lys
        275                 280                 285
Phe Lys Asp Ile Ala Ser Thr Leu Asn Lys Ala Lys Ser Ile Val Gly
    290                 295                 300
Thr Thr Ala Ser Leu Gln Tyr Met Lys Asn Val Phe Lys Glu Lys Tyr
305                 310                 315                 320
Leu Leu Ser Glu Asp Thr Ser Gly Lys Phe Ser Val Asp Lys Leu Lys
                325                 330                 335
Phe Asp Lys Leu Tyr Lys Met Leu Thr Glu Ile Tyr Thr Glu Asp Asn
            340                 345                 350
Phe Val Lys Phe Phe Lys Val Leu Asn Arg Lys Thr Tyr Leu Asn Phe
        355                 360                 365
Asp Lys Ala Val Phe Lys Ile Asn Ile Val Pro Lys Val Asn Tyr Thr
    370                 375                 380
Ile Tyr Asp Gly Phe Asn Leu Arg Asn Thr Asn Leu Ala Ala Asn Phe
385                 390                 395                 400
Asn Gly Gln Asn Thr Glu Ile Asn Asn Met Asn Phe Thr Lys Leu Lys
                405                 410                 415
Asn Phe Thr Gly Leu Phe Glu Phe Tyr Lys Leu Leu Cys Val Arg Gly
            420                 425                 430
Ile Ile Thr Ser Lys Thr Lys Ser Leu Asp Lys Gly Tyr Asn Lys Ala
        435                 440                 445
Leu Asn Asp Leu Cys Ile Lys Val Asn Asn Trp Asp Leu Phe Phe Ser
    450                 455                 460
Pro Ser Glu Asp Asn Phe Thr Asn Asp Leu Asn Lys Gly Glu Glu Ile
465                 470                 475                 480
Thr Ser Asp Thr Asn Ile Glu Ala Ala Glu Glu Asn Ile Ser Leu Asp
                485                 490                 495
Leu Ile Gln Gln Tyr Tyr Leu Thr Phe Asn Phe Asp Asn Glu Pro Glu
            500                 505                 510
Asn Ile Ser Ile Glu Asn Leu Ser Ser Asp Ile Ile Gly Gln Leu Glu
        515                 520                 525
Leu Met Pro Asn Ile Glu Arg Phe Pro Asn Gly Lys Lys Tyr Glu Leu
```

```
              530                 535                 540
Asp Lys Tyr Thr Met Phe His Tyr Leu Arg Ala Gln Glu Phe Glu His
545                 550                 555                 560

Gly Lys Ser Arg Ile Ala Leu Thr Asn Ser Val Asn Glu Ala Leu Leu
                565                 570                 575

Asn Pro Ser Arg Val Tyr Thr Phe Phe Ser Ser Asp Tyr Val Lys Lys
                580                 585                 590

Val Asn Lys Ala Thr Glu Ala Ala Met Phe Leu Gly Trp Val Glu Gln
                595                 600                 605

Leu Val Tyr Asp Phe Thr Asp Glu Thr Ser Glu Val Ser Thr Thr Asp
                610                 615                 620

Lys Ile Ala Asp Ile Thr Ile Ile Ile Pro Tyr Ile Gly Pro Ala Leu
625                 630                 635                 640

Asn Ile Gly Asn Met Leu Tyr Lys Asp Asp Phe Val Gly Ala Leu Ile
                645                 650                 655

Phe Ser Gly Ala Val Ile Leu Leu Glu Phe Ile Pro Glu Ile Ala Ile
                660                 665                 670

Pro Val Leu Gly Thr Phe Ala Leu Val Ser Tyr Ile Ala Asn Lys Val
                675                 680                 685

Leu Thr Val Gln Thr Ile Asp Asn Ala Leu Ser Lys Arg Asn Glu Lys
                690                 695                 700

Trp Asp Glu Val Tyr Lys Tyr Ile Val Thr Asn Trp Leu Ala Lys Val
705                 710                 715                 720

Asn Thr Gln Ile Asp Leu Ile Arg Lys Lys Met Lys Glu Ala Leu Glu
                725                 730                 735

Asn Gln Ala Glu Ala Thr Lys Ala Ile Ile Asn Tyr Gln Tyr Asn Gln
                740                 745                 750

Tyr Thr Glu Glu Glu Lys Asn Asn Ile Asn Phe Asn Ile Asp Asp Leu
                755                 760                 765

Ser Ser Lys Leu Asn Glu Ser Ile Asn Lys Ala Met Ile Asn Ile Asn
                770                 775                 780

Lys Phe Leu Asn Gln Cys Ser Val Ser Tyr Leu Met Asn Ser Met Ile
785                 790                 795                 800

Pro Tyr Gly Val Lys Arg Leu Glu Asp Phe Asp Ala Ser Leu Lys Asp
                805                 810                 815

Ala Leu Leu Lys Tyr Ile Tyr Asp Asn Arg Gly Thr Leu Ile Gly Gln
                820                 825                 830

Val Asp Arg Leu Lys Asp Lys Val Asn Asn Thr Leu Ser Thr Asp Ile
                835                 840                 845

Pro Phe Gln Leu Ser Lys Tyr Val Asp Asn Gln Arg Leu Leu Ser Thr
                850                 855                 860

Phe Thr Glu Tyr Ile Lys Asn Ile Ile Asn Thr Ser Ile Leu Asn Leu
865                 870                 875                 880

Arg Tyr Glu Ser Asn His Leu Ile Asp Leu Ser Arg Tyr Ala Ser Lys
                885                 890                 895

Ile Asn Ile Gly Ser Lys Val Asn Phe Asp Pro Ile Asp Lys Asn Gln
                900                 905                 910

Ile Gln Leu Phe Asn Leu Glu Ser Ser Lys Ile Glu Val Ile Leu Lys
                915                 920                 925

Asn Ala Ile Val Tyr Asn Ser Met Tyr Glu Asn Phe Ser Thr Ser Phe
                930                 935                 940

Trp Ile Arg Ile Pro Lys Tyr Phe Asn Ser Ile Ser Leu Asn Asn Glu
945                 950                 955                 960
```

Tyr Thr Ile Ile Asn Cys Met Glu Asn Asn Ser Gly Trp Lys Val Ser
                965                 970                 975

Leu Asn Tyr Gly Glu Ile Ile Trp Thr Leu Gln Asp Thr Gln Ile
            980                 985                 990

Lys Gln Arg Val Val Phe Lys Tyr Ser Gln Met Ile Asn Ile Ser Asp
        995                 1000                1005

Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys
    1025                1030                1035

Pro Ile Ser Asn Leu Gly Asn Ile His Ala Ser Asn Asn Ile Met
    1040                1045                1050

Phe Lys Leu Asp Gly Cys Arg Asp Thr His Arg Tyr Ile Trp Ile
    1055                1060                1065

Lys Tyr Phe Asn Leu Phe Asp Lys Glu Leu Asn Glu Lys Glu Ile
    1070                1075                1080

Lys Asp Leu Tyr Asp Asn Gln Ser Asn Ser Gly Ile Leu Lys Asp
    1085                1090                1095

Phe Trp Gly Asp Tyr Leu Gln Tyr Asp Lys Pro Tyr Tyr Met Leu
    1100                1105                1110

Asn Leu Tyr Asp Pro Asn Lys Tyr Val Asp Val Asn Asn Val Gly
    1115                1120                1125

Ile Arg Gly Tyr Met Tyr Leu Lys Gly Pro Arg Gly Ser Val Met
    1130                1135                1140

Thr Thr Asn Ile Tyr Leu Asn Ser Ser Leu Tyr Arg Gly Thr Lys
    1145                1150                1155

Phe Ile Ile Lys Lys Tyr Ala Ser Gly Asn Lys Asp Asn Ile Val
    1160                1165                1170

Arg Asn Asn Asp Arg Val Tyr Ile Asn Val Val Lys Asn Lys
    1175                1180                1185

Glu Tyr Arg Leu Ala Thr Asn Ala Ser Gln Ala Gly Val Glu Lys
    1190                1195                1200

Ile Leu Ser Ala Leu Glu Ile Pro Asp Val Gly Asn Leu Ser Gln
    1205                1210                1215

Val Val Val Met Lys Ser Lys Asn Asp Gln Gly Ile Thr Asn Lys
    1220                1225                1230

Cys Lys Met Asn Leu Gln Asp Asn Asn Gly Asn Asp Ile Gly Phe
    1235                1240                1245

Ile Gly Phe His Gln Phe Asn Asn Ile Ala Lys Leu Val Ala Ser
    1250                1255                1260

Asn Leu Phe Asn Arg Gln Ile Glu Arg Ser Ser Arg Thr Leu Gly
    1265                1270                1275

Cys Ser Trp Glu Phe Ile Pro Val Asp Asp Gly Trp Gly Glu Arg
    1280                1285                1290

Pro Leu
    1295

<210> SEQ ID NO 10
<211> LENGTH: 938
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Gln Ser Phe Asn Lys Met Ser Ile Asp Phe Lys Asp Ile Lys Lys Leu
1               5                   10                  15
Ser Leu Gly Tyr Ile Met Ser Asn Phe Lys Ser Phe Asn Ser Glu Asn
            20                  25                  30
Glu Leu Asp Arg Asp His Leu Gly Phe Lys Ile Ile Asp Asn Lys Thr
        35                  40                  45
Tyr Tyr Tyr Asp Glu Asp Ser Lys Leu Val Lys Gly Leu Ile Asn Ile
    50                  55                  60
Asn Asn Ser Leu Phe Tyr Phe Asp Pro Ile Glu Phe Asn Leu Val Thr
65                  70                  75                  80
Gly Trp Gln Thr Ile Asn Gly Lys Lys Tyr Tyr Phe Asp Ile Asn Thr
                85                  90                  95
Gly Ala Ala Leu Thr Ser Tyr Lys Ile Ile Asn Gly Lys His Phe Tyr
            100                 105                 110
Phe Asn Asn Asp Gly Val Met Gln Leu Gly Val Phe Lys Gly Pro Asp
        115                 120                 125
Gly Phe Glu Tyr Phe Ala Pro Ala Asn Thr Gln Asn Asn Asn Ile Glu
    130                 135                 140
Gly Gln Ala Ile Val Tyr Gln Ser Lys Phe Leu Thr Leu Asn Gly Lys
145                 150                 155                 160
Lys Tyr Tyr Phe Asp Asn Asn Ser Lys Ala Val Thr Gly Trp Arg Ile
                165                 170                 175
Ile Asn Asn Glu Lys Tyr Tyr Phe Asn Pro Asn Asn Ala Ile Ala Ala
            180                 185                 190
Val Gly Leu Gln Val Ile Asp Asn Asn Lys Tyr Tyr Phe Asn Pro Asp
        195                 200                 205
Thr Ala Ile Ile Ser Lys Gly Trp Gln Thr Val Asn Gly Ser Arg Tyr
    210                 215                 220
Tyr Phe Asp Thr Asp Thr Ala Ile Ala Phe Asn Gly Tyr Lys Thr Ile
225                 230                 235                 240
Asp Gly Lys His Phe Tyr Phe Asp Ser Asp Cys Val Val Lys Ile Gly
                245                 250                 255
Val Phe Ser Thr Ser Asn Gly Phe Glu Tyr Phe Ala Pro Ala Asn Thr
            260                 265                 270
Tyr Asn Asn Asn Ile Glu Gly Gln Ala Ile Val Tyr Gln Ser Lys Phe
        275                 280                 285
Leu Thr Leu Asn Gly Lys Lys Tyr Tyr Phe Asp Asn Asn Ser Lys Ala
    290                 295                 300
Val Thr Gly Leu Gln Thr Ile Asp Ser Lys Lys Tyr Tyr Phe Asn Thr
305                 310                 315                 320
Asn Thr Ala Glu Ala Ala Thr Gly Trp Gln Thr Ile Asp Gly Lys Lys
                325                 330                 335
Tyr Tyr Phe Asn Thr Asn Thr Ala Glu Ala Thr Gly Trp Gln Thr
            340                 345                 350
Ile Asp Gly Lys Lys Tyr Tyr Phe Asn Thr Asn Thr Ala Ile Ala Ser
        355                 360                 365
Thr Gly Tyr Thr Ile Ile Asn Gly Lys His Phe Tyr Phe Asn Thr Asp
    370                 375                 380
Gly Ile Met Gln Ile Gly Val Phe Lys Gly Pro Asn Gly Phe Glu Tyr
385                 390                 395                 400
Phe Ala Pro Ala Asn Thr Asp Ala Asn Asn Ile Glu Gly Gln Ala Ile
                405                 410                 415
```

```
Leu Tyr Gln Asn Glu Phe Leu Thr Leu Asn Gly Lys Lys Tyr Tyr Phe
            420                 425                 430

Gly Ser Asp Ser Lys Ala Val Thr Gly Trp Arg Ile Ile Asn Asn Lys
            435                 440                 445

Lys Tyr Tyr Phe Asn Pro Asn Ala Ile Ala Ile His Leu Cys
    450                 455                 460

Thr Ile Asn Asn Asp Lys Tyr Tyr Phe Ser Tyr Asp Gly Ile Leu Gln
465                 470                 475                 480

Asn Gly Tyr Ile Thr Ile Glu Arg Asn Asn Phe Tyr Phe Asp Ala Asn
                485                 490                 495

Asn Glu Ser Lys Met Val Thr Gly Val Phe Lys Gly Pro Asn Gly Phe
            500                 505                 510

Glu Tyr Phe Ala Pro Ala Asn Thr His Asn Asn Ile Glu Gly Gln
    515                 520                 525

Ala Ile Val Tyr Gln Asn Lys Phe Leu Thr Leu Asn Gly Lys Lys Tyr
    530                 535                 540

Tyr Phe Asp Asn Asp Ser Lys Ala Val Thr Gly Trp Gln Thr Ile Asp
545                 550                 555                 560

Gly Lys Lys Tyr Tyr Phe Asn Leu Asn Thr Ala Glu Ala Ala Thr Gly
                565                 570                 575

Trp Gln Thr Ile Asp Gly Lys Lys Tyr Tyr Phe Asn Leu Asn Thr Ala
            580                 585                 590

Glu Ala Ala Thr Gly Trp Gln Thr Ile Asp Gly Lys Lys Tyr Tyr Phe
            595                 600                 605

Asn Thr Asn Thr Phe Ile Ala Ser Thr Gly Tyr Thr Ser Ile Asn Gly
    610                 615                 620

Lys His Phe Tyr Phe Asn Thr Asp Gly Ile Met Gln Ile Gly Val Phe
625                 630                 635                 640

Lys Gly Pro Asn Gly Phe Glu Tyr Phe Ala Pro Ala Asn Thr Asp Ala
            645                 650                 655

Asn Asn Ile Glu Gly Gln Ala Ile Leu Tyr Gln Asn Lys Phe Leu Thr
            660                 665                 670

Leu Asn Gly Lys Lys Tyr Tyr Phe Gly Ser Asp Ser Lys Ala Val Thr
            675                 680                 685

Gly Leu Arg Thr Ile Asp Gly Lys Lys Tyr Tyr Phe Asn Thr Asn Thr
            690                 695                 700

Ala Val Ala Val Thr Gly Trp Gln Thr Ile Asn Gly Lys Lys Tyr Tyr
705                 710                 715                 720

Phe Asn Thr Asn Thr Ser Ile Ala Ser Thr Gly Tyr Thr Ile Ile Ser
                725                 730                 735

Gly Lys His Phe Tyr Phe Asn Thr Asp Gly Ile Met Gln Ile Gly Val
            740                 745                 750

Phe Lys Gly Pro Asp Gly Phe Glu Tyr Phe Ala Pro Ala Asn Thr Asp
            755                 760                 765

Ala Asn Asn Ile Glu Gly Gln Ala Ile Arg Tyr Gln Asn Arg Phe Leu
    770                 775                 780

Tyr Leu His Asp Asn Ile Tyr Tyr Phe Gly Asn Asn Ser Lys Ala Ala
785                 790                 795                 800

Thr Gly Trp Val Thr Ile Asp Gly Asn Arg Tyr Tyr Phe Glu Pro Asn
            805                 810                 815

Thr Ala Met Gly Ala Asn Gly Tyr Lys Thr Ile Asp Asn Lys Asn Phe
            820                 825                 830
```

```
Tyr Phe Arg Asn Gly Leu Pro Gln Ile Gly Val Phe Lys Gly Ser Asn
            835                 840                 845

Gly Phe Glu Tyr Phe Ala Pro Ala Asn Thr Asp Ala Asn Asn Ile Glu
850                 855                 860

Gly Gln Ala Ile Arg Tyr Gln Asn Arg Phe Leu His Leu Leu Gly Lys
865                 870                 875                 880

Ile Tyr Tyr Phe Gly Asn Asn Ser Lys Ala Val Thr Gly Trp Gln Thr
                885                 890                 895

Ile Asn Gly Lys Val Tyr Tyr Phe Met Pro Asp Thr Ala Met Ala Ala
            900                 905                 910

Ala Gly Gly Leu Phe Glu Ile Asp Gly Val Ile Tyr Phe Phe Gly Val
            915                 920                 925

Asp Gly Val Lys Ala Pro Gly Ile Tyr Gly
930                 935

<210> SEQ ID NO 11
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Thr Gly Trp Gln Thr Ile Asn Gly Lys Lys Tyr Tyr Phe Asn Thr Asn
1               5                   10                  15

Thr Ser Ile Ala Ser Thr Gly Tyr Thr Ile Ile Ser Gly Lys His Phe
            20                  25                  30

Tyr Phe Asn Thr Asp Gly Ile Met Gln Ile Gly Val Phe Lys Gly Pro
            35                  40                  45

Asp Gly Phe Glu Tyr Phe Ala Pro Ala Asn Thr Asp Ala Asn Asn Ile
50                  55                  60

Glu Gly Gln Ala Ile Arg Tyr Gln Asn Arg Phe Leu Tyr Leu His Asp
65                  70                  75                  80

Asn Ile Tyr Tyr Phe Gly Asn Asn Ser Lys Ala Ala Thr Gly Trp Val
                85                  90                  95

Thr Ile Asp Gly Asn Arg Tyr Tyr Phe Glu Pro Asn Thr Ala Met Gly
            100                 105                 110

Ala Asn Gly Tyr Lys Thr Ile Asp Asn Lys Asn Phe Tyr Phe Arg Asn
            115                 120                 125

Gly Leu Pro Gln Ile Gly Val Phe Lys Gly Ser Asn Gly Phe Glu Tyr
        130                 135                 140

Phe Ala Pro Ala Asn Thr Asp Ala Asn Asn Ile Glu Gly Gln Ala Ile
145                 150                 155                 160

Arg Tyr Gln Asn Arg Phe Leu His Leu Leu Gly Lys Ile Tyr Tyr Phe
                165                 170                 175

Gly Asn Asn Ser Lys Ala Val Thr Gly Trp Gln Thr Ile Asn Gly Lys
            180                 185                 190

Val Tyr Tyr Phe Met Pro Asp Thr Ala Met Ala Ala Ala Gly Gly Leu
        195                 200                 205

Phe Glu Ile Asp Gly Val Ile Tyr Phe Phe Gly Val Asp Gly Val Lys
210                 215                 220

Ala Pro Gly Ile Tyr Gly
225                 230

<210> SEQ ID NO 12
```

<211> LENGTH: 592
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Thr Leu Ala Asn Lys Leu Ser Phe Asn Phe Ser Asp Lys Gln Asp Val
1               5                   10                  15

Pro Val Ser Glu Ile Ile Leu Ser Phe Thr Pro Ser Tyr Tyr Glu Asp
            20                  25                  30

Gly Leu Ile Gly Tyr Asp Leu Gly Leu Val Ser Leu Tyr Asn Glu Lys
        35                  40                  45

Phe Tyr Ile Asn Asn Phe Gly Met Met Val Ser Gly Leu Ile Tyr Ile
    50                  55                  60

Asn Asp Ser Leu Tyr Tyr Phe Lys Pro Pro Val Asn Asn Leu Ile Thr
65                  70                  75                  80

Gly Phe Val Thr Val Gly Asp Asp Lys Tyr Tyr Phe Asn Pro Ile Asn
                85                  90                  95

Gly Gly Ala Ala Ser Ile Gly Glu Thr Ile Ile Asp Asp Lys Asn Tyr
            100                 105                 110

Tyr Phe Asn Gln Ser Gly Val Leu Gln Thr Gly Val Phe Ser Thr Glu
        115                 120                 125

Asp Gly Phe Lys Tyr Phe Ala Pro Ala Asn Thr Leu Asp Glu Asn Leu
    130                 135                 140

Glu Gly Glu Ala Ile Asp Phe Thr Gly Lys Leu Ile Ile Asp Glu Asn
145                 150                 155                 160

Ile Tyr Tyr Phe Asp Asp Asn Tyr Arg Gly Ala Val Glu Trp Lys Glu
                165                 170                 175

Leu Asp Gly Glu Met His Tyr Phe Ser Pro Glu Thr Gly Lys Ala Phe
            180                 185                 190

Lys Gly Leu Asn Gln Ile Gly Asp Tyr Lys Tyr Tyr Phe Asn Ser Asp
        195                 200                 205

Gly Val Met Gln Lys Gly Phe Val Ser Ile Asn Asp Asn Lys His Tyr
    210                 215                 220

Phe Asp Asp Ser Gly Val Met Lys Val Gly Tyr Thr Glu Ile Asp Gly
225                 230                 235                 240

Lys His Phe Tyr Phe Ala Glu Asn Gly Glu Met Gln Ile Gly Val Phe
                245                 250                 255

Asn Thr Glu Asp Gly Phe Lys Tyr Phe Ala His His Asn Glu Asp Leu
            260                 265                 270

Gly Asn Glu Glu Gly Glu Glu Ile Ser Tyr Ser Gly Ile Leu Asn Phe
        275                 280                 285

Asn Asn Lys Ile Tyr Tyr Phe Asp Asp Ser Phe Thr Ala Val Val Gly
    290                 295                 300

Trp Lys Asp Leu Glu Asp Gly Ser Lys Tyr Tyr Phe Asp Glu Asp Thr
305                 310                 315                 320

Ala Glu Ala Tyr Ile Gly Leu Ser Leu Ile Asn Asp Gly Gln Tyr Tyr
                325                 330                 335

Phe Asn Asp Asp Gly Ile Met Gln Val Gly Phe Val Thr Ile Asn Asp
            340                 345                 350

Lys Val Phe Tyr Phe Ser Asp Ser Gly Ile Ile Glu Ser Gly Val Gln
        355                 360                 365

Asn Ile Asp Asp Asn Tyr Phe Tyr Ile Asp Asp Asn Gly Ile Val Gln
```

-continued

```
                370                 375                 380
Ile Gly Val Phe Asp Thr Ser Asp Gly Tyr Lys Tyr Phe Ala Pro Ala
385                 390                 395                 400

Asn Thr Val Asn Asp Asn Ile Tyr Gly Gln Ala Val Glu Tyr Ser Gly
                405                 410                 415

Leu Val Arg Val Gly Glu Asp Val Tyr Tyr Phe Gly Glu Thr Tyr Thr
                420                 425                 430

Ile Glu Thr Gly Trp Ile Tyr Asp Met Glu Asn Glu Ser Asp Lys Tyr
                435                 440                 445

Tyr Phe Asn Pro Glu Thr Lys Lys Ala Cys Lys Gly Ile Asn Leu Ile
                450                 455                 460

Asp Asp Ile Lys Tyr Tyr Phe Asp Glu Lys Gly Ile Met Arg Thr Gly
465                 470                 475                 480

Leu Ile Ser Phe Glu Asn Asn Asn Tyr Tyr Phe Asn Glu Asn Gly Glu
                485                 490                 495

Met Gln Phe Gly Tyr Ile Asn Ile Glu Asp Lys Met Phe Tyr Phe Gly
                500                 505                 510

Glu Asp Gly Val Met Gln Ile Gly Val Phe Asn Thr Pro Asp Gly Phe
                515                 520                 525

Lys Tyr Phe Ala His Gln Asn Thr Leu Asp Glu Asn Phe Glu Gly Glu
                530                 535                 540

Ser Ile Asn Tyr Thr Gly Trp Leu Asp Leu Asp Glu Lys Arg Tyr Tyr
545                 550                 555                 560

Phe Thr Asp Glu Tyr Ile Ala Ala Thr Gly Ser Val Ile Ile Asp Gly
                565                 570                 575

Glu Glu Tyr Tyr Phe Asp Pro Asp Thr Ala Gln Leu Val Ile Ser Glu
                580                 585                 590

<210> SEQ ID NO 13
<211> LENGTH: 545
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
                20                  25                  30

Tyr Asn Lys Leu Thr Thr Asn Asn Glu Asn Lys Tyr Leu Gln Leu
            35                  40                  45

Lys Lys Leu Asn Glu Ser Ile Asp Val Phe Met Asn Lys Tyr Lys Thr
50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
                100                 105                 110

Tyr Ile Lys Gln Trp Ala Asp Ile Asn Ala Glu Tyr Asn Ile Lys Leu
            115                 120                 125

Trp Tyr Asp Ser Glu Ala Phe Leu Val Asn Thr Leu Lys Lys Ala Ile
            130                 135                 140
```

-continued

```
Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
            165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
            195                 200                 205

Leu Val Ser Glu Tyr Asn Arg Asp Glu Thr Val Leu Glu Ser Tyr Arg
210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
            245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
            275                 280                 285

Leu Pro Gly Ile His Ser Asp Leu Phe Lys Thr Ile Ser Arg Pro Ser
290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
            325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
            355                 360                 365

Asp Leu Glu Ile Lys Ile Ala Phe Ala Leu Gly Ser Val Ile Asn Gln
            370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
            405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
            435                 440                 445

Ile Ala Pro Tyr Leu Gln Val Gly Phe Met Pro Glu Ala Arg Ser Thr
450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
            485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
            515                 520                 525

Gln Phe Glu Lys Tyr Val Arg Asp Tyr Thr Gly Gly Ser Leu Ser Glu
            530                 535                 540

Asp
545
```

```
<210> SEQ ID NO 14
<211> LENGTH: 546
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

```
Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
                420                 425                 430

Asp Ser Ile Met Ala Glu Ala Asn Ala Asp Asn Gly Arg Phe Met Met
            435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
                500                 505                 510

Glu Gln Glu Met Ala Ser Leu Trp Ser Phe Asp Ala Arg Ala Lys
    515                 520                 525

Ala Gln Phe Glu Glu Tyr Lys Arg Asn Tyr Phe Glu Gly Ser Leu Gly
    530                 535                 540

Glu Asp
545

<210> SEQ ID NO 15
<211> LENGTH: 803
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Arg Lys Tyr Lys Ser Lys Lys Leu Ser Lys Leu Leu Ala Leu Leu
1               5                   10                  15

Thr Val Cys Phe Leu Ile Val Ser Thr Ile Pro Val Ser Ala Glu Asn
                20                  25                  30

His Lys Thr Leu Asp Gly Val Glu Thr Ala Glu Tyr Ser Glu Ser Tyr
            35                  40                  45

Leu Gln Tyr Leu Glu Asp Val Lys Asn Gly Asp Thr Ala Lys Tyr Asn
    50                  55                  60

Gly Val Ile Pro Phe Pro His Glu Met Glu Gly Thr Thr Leu Arg Asn
65                  70                  75                  80

Lys Gly Arg Ser Ser Leu Pro Ser Ala Tyr Lys Ser Ser Val Ala Tyr
                85                  90                  95

Asn Pro Met Asp Leu Gly Leu Thr Thr Pro Ala Lys Asn Gln Gly Ser
                100                 105                 110

Leu Asn Thr Cys Trp Ser Phe Ser Gly Met Ser Thr Leu Glu Ala Tyr
            115                 120                 125

Leu Lys Leu Lys Gly Tyr Gly Thr Tyr Asp Leu Ser Glu Glu His Leu
    130                 135                 140

Arg Trp Trp Ala Thr Gly Gly Lys Tyr Gly Trp Asn Leu Asp Asp Met
145                 150                 155                 160

Ser Gly Ser Ser Asn Val Thr Ala Ile Gly Tyr Leu Thr Ala Trp Ala
                165                 170                 175
```

```
Gly Pro Lys Leu Glu Lys Asp Ile Pro Tyr Asn Leu Lys Ser Glu Ala
            180                 185                 190

Gln Gly Ala Thr Lys Pro Ser Asn Met Asp Thr Ala Pro Thr Gln Phe
            195                 200                 205

Asn Val Thr Asp Val Val Arg Leu Asn Lys Asp Lys Glu Thr Val Lys
210                 215                 220

Asn Ala Ile Met Gln Tyr Gly Ser Val Thr Ser Gly Tyr Ala His Tyr
225                 230                 235                 240

Ser Thr Tyr Phe Asn Lys Asp Glu Thr Ala Tyr Asn Cys Thr Asn Lys
            245                 250                 255

Arg Ala Pro Leu Asn His Ala Val Ala Ile Val Gly Trp Asp Asp Asn
            260                 265                 270

Tyr Ser Lys Asp Asn Phe Ala Ser Asp Val Lys Pro Glu Ser Asn Gly
            275                 280                 285

Ala Trp Leu Val Lys Ser Ser Trp Gly Glu Phe Asn Ser Met Lys Gly
            290                 295                 300

Phe Phe Trp Ile Ser Tyr Glu Asp Lys Thr Leu Leu Thr Asp Thr Asp
305                 310                 315                 320

Asn Tyr Ala Met Lys Ser Val Ser Lys Pro Asp Ser Asp Lys Lys Met
            325                 330                 335

Tyr Gln Leu Glu Tyr Ala Gly Leu Ser Lys Ile Met Ser Asn Lys Val
            340                 345                 350

Thr Ala Ala Asn Val Phe Asp Phe Ser Arg Asp Ser Glu Lys Leu Asp
            355                 360                 365

Ser Val Met Phe Glu Thr Asp Ser Val Gly Ala Lys Tyr Glu Val Tyr
            370                 375                 380

Tyr Ala Pro Val Val Asn Gly Val Pro Gln Asn Asn Ser Met Thr Lys
385                 390                 395                 400

Leu Ala Ser Gly Thr Val Ser Tyr Ser Gly Tyr Ile Asn Val Pro Thr
            405                 410                 415

Asn Ser Tyr Ser Leu Pro Lys Gly Lys Gly Ala Ile Val Val Val Ile
            420                 425                 430

Asp Asn Thr Ala Asn Pro Asn Arg Glu Lys Ser Thr Leu Ala Tyr Glu
            435                 440                 445

Thr Asn Ile Asp Ala Tyr Tyr Leu Tyr Glu Ala Lys Ala Asn Leu Gly
            450                 455                 460

Glu Ser Tyr Ile Leu Gln Asn Asn Lys Phe Glu Asp Ile Asn Thr Tyr
465                 470                 475                 480

Ser Glu Phe Ser Pro Cys Asn Phe Val Ile Lys Ala Ile Thr Lys Thr
            485                 490                 495

Ser Ser Gly Gln Ala Thr Ser Gly Glu Ser Leu Thr Gly Ala Asp Arg
            500                 505                 510

Tyr Glu Thr Ala Val Lys Val Ser Gln Lys Gly Trp Thr Ser Ser Gln
            515                 520                 525

Asn Ala Val Leu Val Asn Gly Asp Ala Ile Val Asp Ala Leu Thr Ala
            530                 535                 540

Thr Pro Phe Thr Ala Ala Ile Asp Ser Pro Ile Leu Leu Thr Gly Lys
545                 550                 555                 560

Asp Asn Leu Asp Ser Lys Thr Lys Ala Glu Leu Gln Arg Leu Gly Thr
            565                 570                 575

Lys Lys Val Tyr Leu Ile Gly Gly Glu Asn Ser Leu Ser Lys Asn Val
            580                 585                 590
```

```
Gln Thr Gln Leu Ser Asn Met Gly Ile Ser Val Glu Arg Ile Ser Gly
            595                 600                 605
Ser Asp Arg Tyr Lys Thr Ser Ile Ser Leu Ala Gln Lys Leu Asn Ser
610                 615                 620
Ile Lys Ser Val Ser Gln Val Ala Val Ala Asn Gly Val Asn Gly Leu
625                 630                 635                 640
Ala Asp Ala Ile Ser Val Gly Ala Ala Ala Asp Asn Asn Met Pro
                    645                 650                 655
Ile Ile Leu Thr Asn Glu Lys Ser Glu Leu Gln Gly Ala Asp Glu Phe
            660                 665                 670
Leu Asn Ser Ser Lys Ile Thr Lys Ser Tyr Ile Ile Gly Gly Thr Ala
        675                 680                 685
Thr Leu Ser Ser Asn Leu Glu Ser Lys Leu Ser Asn Pro Thr Arg Leu
    690                 695                 700
Ala Gly Ser Asn Arg Asn Glu Thr Asn Ala Lys Ile Ile Asp Lys Phe
705                 710                 715                 720
Tyr Pro Ser Ser Asp Leu Lys Tyr Ala Phe Val Val Lys Asp Gly Ser
                    725                 730                 735
Lys Ser Gln Gly Asp Leu Ile Asp Gly Leu Ala Val Gly Ala Leu Gly
            740                 745                 750
Ala Lys Thr Asp Ser Pro Val Val Leu Val Gly Asn Lys Leu Asp Glu
        755                 760                 765
Ser Gln Lys Asn Val Leu Lys Ser Lys Ile Glu Thr Pro Ile Arg
    770                 775                 780
Val Gly Gly Asn Gly Asn Glu Ser Ala Phe Asn Glu Leu Asn Thr Leu
785                 790                 795                 800
Leu Gly Lys

<210> SEQ ID NO 16
<211> LENGTH: 764
<212> TYPE: PRT
<213> ORGANISM: Bacillus anthracis

<400> SEQUENCE: 16

Met Lys Lys Arg Lys Val Leu Ile Pro Leu Met Ala Leu Ser Thr Ile
1               5                   10                  15
Leu Val Ser Ser Thr Gly Asn Leu Glu Val Ile Gln Ala Glu Val Lys
            20                  25                  30
Gln Glu Asn Arg Leu Leu Asn Glu Ser Glu Ser Ser Gln Gly Leu
        35                  40                  45
Leu Gly Tyr Tyr Phe Ser Asp Leu Asn Phe Gln Ala Pro Met Val Val
    50                  55                  60
Thr Ser Ser Thr Thr Gly Asp Leu Ser Ile Pro Ser Ser Glu Leu Glu
65                  70                  75                  80
Asn Ile Pro Ser Glu Asn Gln Tyr Phe Gln Ser Ala Ile Trp Ser Gly
                85                  90                  95
Phe Ile Lys Val Lys Lys Ser Asp Glu Tyr Thr Phe Ala Thr Ser Ala
            100                 105                 110
Asp Asn His Val Thr Met Trp Val Asp Asp Gln Glu Val Ile Asn Lys
        115                 120                 125
Ala Ser Asn Ser Asn Lys Ile Arg Leu Glu Lys Gly Arg Leu Tyr Gln
    130                 135                 140
Ile Lys Ile Gln Tyr Gln Arg Glu Asn Pro Thr Glu Lys Gly Leu Asp
145                 150                 155                 160
```

```
Phe Lys Leu Tyr Trp Thr Asp Ser Gln Asn Lys Lys Glu Val Ile Ser
            165                 170                 175
Ser Asp Asn Leu Gln Leu Pro Glu Leu Lys Gln Lys Ser Ser Asn Ser
            180                 185                 190
Arg Lys Lys Arg Ser Thr Ser Ala Gly Pro Thr Val Pro Asp Arg Asp
            195                 200                 205
Asn Asp Gly Ile Pro Asp Ser Leu Glu Val Glu Gly Tyr Thr Val Asp
210                 215                 220
Val Lys Asn Lys Arg Thr Phe Leu Ser Pro Trp Ile Ser Asn Ile His
225                 230                 235                 240
Glu Lys Lys Gly Leu Thr Lys Tyr Lys Ser Ser Pro Glu Lys Trp Ser
            245                 250                 255
Thr Ala Ser Asp Pro Tyr Ser Asp Phe Glu Lys Val Thr Gly Arg Ile
            260                 265                 270
Asp Lys Asn Val Ser Pro Glu Ala Arg His Pro Leu Val Ala Ala Tyr
            275                 280                 285
Pro Ile Val His Val Asp Met Glu Asn Ile Ile Leu Ser Lys Asn Glu
            290                 295                 300
Asp Gln Ser Thr Gln Asn Thr Asp Ser Gln Thr Arg Thr Ile Ser Lys
305                 310                 315                 320
Asn Thr Ser Thr Ser Arg Thr His Thr Ser Glu Val His Gly Asn Ala
            325                 330                 335
Glu Val His Ala Ser Phe Phe Asp Ile Gly Gly Ser Val Ser Ala Gly
            340                 345                 350
Phe Ser Asn Ser Asn Ser Ser Thr Val Ala Ile Asp His Ser Leu Ser
            355                 360                 365
Leu Ala Gly Glu Arg Thr Trp Ala Glu Thr Met Gly Leu Asn Thr Ala
370                 375                 380
Asp Thr Ala Arg Leu Asn Ala Asn Ile Arg Tyr Val Asn Thr Gly Thr
385                 390                 395                 400
Ala Pro Ile Tyr Asn Val Leu Pro Thr Thr Ser Leu Val Leu Gly Lys
            405                 410                 415
Asn Gln Thr Leu Ala Thr Ile Lys Ala Lys Glu Asn Gln Leu Ser Gln
            420                 425                 430
Ile Leu Ala Pro Asn Asn Tyr Tyr Pro Ser Lys Asn Leu Ala Pro Ile
            435                 440                 445
Ala Leu Asn Ala Gln Asp Asp Phe Ser Ser Thr Pro Ile Thr Met Asn
450                 455                 460
Tyr Asn Gln Phe Leu Glu Leu Glu Lys Thr Lys Gln Leu Arg Leu Asp
465                 470                 475                 480
Thr Asp Gln Val Tyr Gly Asn Ile Ala Thr Tyr Asn Phe Glu Asn Gly
            485                 490                 495
Arg Val Arg Val Asp Thr Gly Ser Asn Trp Ser Glu Val Leu Pro Gln
            500                 505                 510
Ile Gln Glu Thr Thr Ala Arg Ile Ile Phe Asn Gly Lys Asp Leu Asn
            515                 520                 525
Leu Val Glu Arg Arg Ile Ala Ala Val Asn Pro Ser Asp Pro Leu Glu
530                 535                 540
Thr Thr Lys Pro Asp Met Thr Leu Lys Glu Ala Leu Lys Ile Ala Phe
545                 550                 555                 560
Gly Phe Asn Glu Pro Asn Gly Asn Leu Gln Tyr Gln Gly Lys Asp Ile
            565                 570                 575
Thr Glu Phe Asp Phe Asn Phe Asp Gln Gln Thr Ser Gln Asn Ile Lys
```

```
                580             585             590
Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Gly Leu Lys Glu Val Ile Asn Asp Arg
        675                 680                 685

Tyr Asp Met Leu Asn Ile Ser Ser Leu Arg Gln Asp Gly Lys Thr Phe
        690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
            755                 760

<210> SEQ ID NO 17
<211> LENGTH: 809
<212> TYPE: PRT
<213> ORGANISM: Bacillus anthracis

<400> SEQUENCE: 17

Met Asn Ile Lys Lys Glu Phe Ile Lys Val Ile Ser Met Ser Cys Leu
1               5                   10                  15

Val Thr Ala Ile Thr Leu Ser Gly Pro Val Phe Ile Pro Leu Val Gln
            20                  25                  30

Gly Ala Gly Gly His Gly Asp Val Gly Met His Val Lys Glu Lys Glu
        35                  40                  45

Lys Asn Lys Asp Glu Asn Lys Arg Lys Asp Glu Glu Arg Asn Lys Thr
    50                  55                  60

Gln Glu Glu His Leu Lys Glu Ile Met Lys His Ile Val Lys Ile Glu
65                  70                  75                  80

Val Lys Gly Glu Glu Ala Val Lys Lys Glu Ala Ala Glu Lys Leu Leu
                85                  90                  95

Glu Lys Val Pro Ser Asp Val Leu Glu Met Tyr Lys Ala Ile Gly Gly
            100                 105                 110

Lys Ile Tyr Ile Val Asp Gly Asp Ile Thr Lys His Ile Ser Leu Glu
        115                 120                 125

Ala Leu Ser Glu Asp Lys Lys Lys Ile Lys Asp Ile Tyr Gly Lys Asp
    130                 135                 140

Ala Leu Leu His Glu His Tyr Val Tyr Ala Lys Glu Gly Tyr Glu Pro
145                 150                 155                 160

Val Leu Val Ile Gln Ser Ser Glu Asp Tyr Val Glu Asn Thr Glu Lys
                165                 170                 175

Ala Leu Asn Val Tyr Tyr Glu Ile Gly Lys Ile Leu Ser Arg Asp Ile
            180                 185                 190
```

```
Leu Ser Lys Ile Asn Gln Pro Tyr Gln Lys Phe Leu Asp Val Leu Asn
            195                 200                 205

Thr Ile Lys Asn Ala Ser Asp Ser Asp Gly Gln Asp Leu Leu Phe Thr
    210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
                245                 250                 255

Tyr Ile Glu Pro Gln His Arg Asp Val Leu Gln Leu Tyr Ala Pro Glu
            260                 265                 270

Ala Phe Asn Tyr Met Asp Lys Phe Asn Glu Gln Glu Ile Asn Leu Ser
            275                 280                 285

Leu Glu Glu Leu Lys Asp Gln Arg Met Leu Ala Arg Tyr Glu Lys Trp
    290                 295                 300

Glu Lys Ile Lys Gln His Tyr Gln His Trp Ser Asp Ser Leu Ser Glu
305                 310                 315                 320

Glu Gly Arg Gly Leu Leu Lys Lys Leu Gln Ile Pro Ile Glu Pro Lys
                325                 330                 335

Lys Asp Asp Ile Ile His Ser Leu Ser Gln Glu Glu Lys Glu Leu Leu
            340                 345                 350

Lys Arg Ile Gln Ile Asp Ser Ser Asp Phe Leu Ser Thr Glu Glu Lys
    355                 360                 365

Glu Phe Leu Lys Lys Leu Gln Ile Asp Ile Arg Asp Ser Leu Ser Glu
    370                 375                 380

Glu Glu Lys Glu Leu Leu Asn Arg Ile Gln Val Asp Ser Ser Asn Pro
385                 390                 395                 400

Leu Ser Glu Lys Glu Lys Glu Phe Leu Lys Lys Leu Lys Leu Asp Ile
                405                 410                 415

Gln Pro Tyr Asp Ile Asn Gln Arg Leu Gln Asp Thr Gly Gly Leu Ile
            420                 425                 430

Asp Ser Pro Ser Ile Asn Leu Asp Val Arg Lys Gln Tyr Lys Arg Asp
    435                 440                 445

Ile Gln Asn Ile Asp Ala Leu Leu His Gln Ser Ile Gly Ser Thr Leu
450                 455                 460

Tyr Asn Lys Ile Tyr Leu Tyr Glu Asn Met Asn Ile Asn Asn Leu Thr
465                 470                 475                 480

Ala Thr Leu Gly Ala Asp Leu Val Asp Ser Thr Asp Asn Thr Lys Ile
                485                 490                 495

Asn Arg Gly Ile Phe Asn Glu Phe Lys Lys Asn Phe Lys Tyr Ser Ile
            500                 505                 510

Ser Ser Asn Tyr Met Ile Val Asp Ile Asn Glu Arg Pro Ala Leu Asp
            515                 520                 525

Asn Glu Arg Leu Lys Trp Arg Ile Gln Leu Ser Pro Asp Thr Arg Ala
530                 535                 540

Gly Tyr Leu Glu Asn Gly Lys Leu Ile Leu Gln Arg Asn Ile Gly Leu
545                 550                 555                 560

Glu Ile Lys Asp Val Gln Ile Ile Lys Gln Ser Glu Lys Glu Tyr Ile
                565                 570                 575

Arg Ile Asp Ala Lys Val Pro Lys Ser Lys Ile Asp Thr Lys Ile
            580                 585                 590

Gln Glu Ala Gln Leu Asn Ile Asn Gln Glu Trp Asn Lys Ala Leu Gly
    595                 600                 605

Leu Pro Lys Tyr Thr Lys Leu Ile Thr Phe Asn Val His Asn Arg Tyr
```

-continued

```
                610                 615                 620
Ala Ser Asn Ile Val Glu Ser Ala Tyr Leu Ile Leu Asn Glu Trp Lys
625                 630                 635                 640

Asn Asn Ile Gln Ser Asp Leu Ile Lys Lys Val Thr Asn Tyr Leu Val
                645                 650                 655

Asp Gly Asn Gly Arg Phe Val Phe Thr Asp Ile Thr Leu Pro Asn Ile
            660                 665                 670

Ala Glu Gln Tyr Thr His Gln Asp Glu Ile Tyr Glu Gln Val His Ser
            675                 680                 685

Lys Gly Leu Tyr Val Pro Glu Ser Arg Ser Ile Leu Leu His Gly Pro
        690                 695                 700

Ser Lys Gly Val Glu Leu Arg Asn Asp Ser Glu Gly Phe Ile His Glu
705                 710                 715                 720

Phe Gly His Ala Val Asp Asp Tyr Ala Gly Tyr Leu Leu Asp Lys Asn
                725                 730                 735

Gln Ser Asp Leu Val Thr Asn Ser Lys Lys Phe Ile Asp Ile Phe Lys
                740                 745                 750

Glu Glu Gly Ser Asn Leu Thr Ser Tyr Gly Arg Thr Asn Glu Ala Glu
            755                 760                 765

Phe Phe Ala Glu Ala Phe Arg Leu Met His Ser Thr Asp His Ala Glu
770                 775                 780

Arg Leu Lys Val Gln Lys Asn Ala Pro Lys Thr Phe Gln Phe Ile Asn
785                 790                 795                 800

Asp Gln Ile Lys Phe Ile Ile Asn Ser
                805
```

<210> SEQ ID NO 18
<211> LENGTH: 809
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Asn Ile Lys Lys Glu Phe Ile Lys Val Ile Ser Met Ser Cys Leu
1               5                   10                  15

Val Thr Ala Ile Thr Leu Ser Gly Pro Val Phe Ile Pro Leu Val Gln
                20                  25                  30

Gly Ala Gly Gly His Gly Asp Val Gly Met His Val Lys Glu Lys Glu
            35                  40                  45

Lys Asn Lys Asp Glu Asn Lys Arg Lys Asp Glu Arg Asn Lys Thr
        50                  55                  60

Gln Glu Glu His Leu Lys Glu Ile Met Lys His Ile Val Lys Ile Glu
65                  70                  75                  80

Val Lys Gly Glu Glu Ala Val Lys Lys Glu Ala Glu Lys Leu Leu
                85                  90                  95

Glu Lys Val Pro Ser Asp Val Leu Glu Met Tyr Lys Ala Ile Gly Gly
                100                 105                 110

Lys Ile Tyr Ile Val Asp Gly Asp Ile Thr Lys His Ile Ser Leu Glu
            115                 120                 125

Ala Leu Ser Glu Asp Lys Lys Lys Ile Lys Asp Ile Tyr Gly Lys Asp
        130                 135                 140

Ala Leu Leu His Glu His Tyr Val Tyr Ala Lys Glu Gly Tyr Glu Pro
145                 150                 155                 160
```

```
Val Leu Val Ile Gln Ser Ser Glu Asp Tyr Val Glu Asn Thr Glu Lys
                165                 170                 175

Ala Leu Asn Val Tyr Tyr Glu Ile Gly Lys Ile Leu Ser Arg Asp Ile
            180                 185                 190

Leu Ser Lys Ile Asn Gln Pro Tyr Gln Lys Phe Leu Asp Val Leu Asn
        195                 200                 205

Thr Ile Lys Asn Ala Ser Asp Ser Asp Gly Gln Asp Leu Leu Phe Thr
    210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
                245                 250                 255

Tyr Ile Glu Pro Gln His Arg Asp Val Leu Gln Leu Tyr Ala Pro Glu
            260                 265                 270

Ala Phe Asn Tyr Met Asp Lys Phe Asn Glu Gln Glu Ile Asn Leu Ser
        275                 280                 285

Leu Glu Glu Leu Lys Asp Gln Arg Met Leu Ala Arg Tyr Glu Lys Trp
    290                 295                 300

Glu Lys Ile Lys Gln His Tyr Gln His Trp Ser Asp Ser Leu Ser Glu
305                 310                 315                 320

Glu Gly Arg Gly Leu Leu Lys Lys Leu Gln Ile Pro Ile Glu Pro Lys
                325                 330                 335

Lys Asp Asp Ile Ile His Ser Leu Ser Gln Glu Lys Glu Leu Leu
            340                 345                 350

Lys Arg Ile Gln Ile Asp Ser Ser Asp Phe Leu Ser Thr Glu Glu Lys
        355                 360                 365

Glu Phe Leu Lys Lys Leu Gln Ile Asp Ile Arg Asp Ser Leu Ser Glu
    370                 375                 380

Glu Glu Lys Glu Leu Leu Asn Arg Ile Gln Val Asp Ser Ser Asn Pro
385                 390                 395                 400

Leu Ser Glu Lys Glu Lys Glu Phe Leu Lys Lys Leu Lys Leu Asp Ile
                405                 410                 415

Gln Pro Tyr Asp Ile Asn Gln Arg Leu Gln Asp Thr Gly Gly Leu Ile
            420                 425                 430

Asp Ser Pro Ser Ile Asn Leu Asp Val Arg Lys Gln Tyr Lys Arg Asp
        435                 440                 445

Ile Gln Asn Ile Asp Ala Leu Leu His Gln Ser Ile Gly Ser Thr Leu
    450                 455                 460

Tyr Asn Lys Ile Tyr Leu Tyr Glu Asn Met Asn Ile Asn Asn Leu Thr
465                 470                 475                 480

Ala Thr Leu Gly Ala Asp Leu Val Asp Ser Thr Asp Asn Thr Lys Ile
                485                 490                 495

Asn Arg Gly Ile Phe Asn Glu Phe Lys Lys Asn Phe Lys Tyr Ser Ile
            500                 505                 510

Ser Ser Asn Tyr Met Ile Val Asp Ile Asn Glu Arg Pro Ala Leu Asp
        515                 520                 525

Asn Glu Arg Leu Lys Trp Arg Ile Gln Leu Ser Pro Asp Thr Arg Ala
    530                 535                 540

Gly Tyr Leu Glu Asn Gly Lys Leu Ile Leu Gln Arg Asn Ile Gly Leu
545                 550                 555                 560

Glu Ile Lys Asp Val Gln Ile Ile Lys Gln Ser Glu Lys Glu Tyr Ile
                565                 570                 575

Arg Ile Asp Ala Lys Val Val Pro Lys Ser Lys Ile Asp Thr Lys Ile
```

```
            580                 585                 590
Gln Glu Ala Gln Leu Asn Ile Asn Gln Glu Trp Asn Lys Ala Leu Gly
                595                 600                 605

Leu Pro Lys Tyr Thr Lys Leu Ile Thr Phe Asn Val His Asn Arg Tyr
    610                 615                 620

Ala Ser Asn Ile Val Glu Ser Ala Tyr Leu Ile Leu Asn Glu Trp Lys
625                 630                 635                 640

Asn Asn Ile Gln Ser Asp Leu Ile Lys Lys Val Thr Asn Tyr Leu Val
                645                 650                 655

Asp Gly Asn Gly Arg Phe Val Phe Thr Asp Ile Thr Leu Pro Asn Ile
            660                 665                 670

Ala Glu Gln Tyr Thr His Gln Asp Glu Ile Tyr Gln Val His Ser
        675                 680                 685

Lys Gly Leu Tyr Val Pro Glu Ser Arg Ser Ile Leu Leu His Gly Pro
    690                 695                 700

Ser Lys Gly Val Glu Leu Arg Asn Asp Ser Glu Gly Phe Ile His Gln
705                 710                 715                 720

Phe Gly Tyr Ala Val Asp Asp Tyr Ala Gly Tyr Leu Leu Asp Lys Asn
                725                 730                 735

Gln Ser Asp Leu Val Thr Asn Ser Lys Lys Phe Ile Asp Ile Phe Lys
            740                 745                 750

Glu Glu Gly Ser Asn Leu Thr Ser Tyr Gly Arg Thr Asn Glu Ala Glu
        755                 760                 765

Phe Phe Ala Glu Ala Phe Arg Leu Met His Ser Thr Asp His Ala Glu
    770                 775                 780

Arg Leu Lys Val Gln Lys Asn Ala Pro Lys Thr Phe Gln Phe Ile Asn
785                 790                 795                 800

Asp Gln Ile Lys Phe Ile Ile Asn Ser
                805

<210> SEQ ID NO 19
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Lys Val Cys Asn Thr Thr Tyr Lys Ala Pro Ile Glu Ser Phe Leu Lys
1               5                   10                  15

Asp Lys Glu Lys Ala Lys Glu Trp Glu Arg Lys Glu Ala Glu Arg Ile
            20                  25                  30

Glu Gln Lys Leu Glu Arg Ser Glu Lys Glu Ala Leu Glu Ser Tyr Lys
        35                  40                  45

Lys Asp Ser Val Glu Ile Ser Lys Tyr Ser Gln Thr Arg Asn Tyr Phe
    50                  55                  60

Tyr Asp Tyr Gln Ile Glu Ala Asn Ser Arg Glu Lys Glu Tyr Lys Glu
65                  70                  75                  80

Leu Arg Asn Ala Ile Ser Lys Asn Lys Ile Asp Lys Pro Met Tyr Val
                85                  90                  95

Tyr Tyr Phe Glu Ser Pro Glu Lys Phe Ala Phe Asn Lys Val Ile Arg
            100                 105                 110

Thr Glu Asn Gln Asn Glu Ile Ser Leu Glu Lys Phe Asn Glu Phe Lys
        115                 120                 125
```

-continued

```
Glu Thr Ile Gln Asn Lys Leu Phe Lys Gln Asp Gly Phe Lys Asp Ile
            130                 135                 140

Ser Leu Tyr Glu Pro Gly Lys Gly Asp Glu Lys Pro Thr Pro Leu Leu
145                 150                 155                 160

Met His Leu Lys Leu Pro Arg Asn Thr Gly Met Leu Pro Tyr Thr Asn
                165                 170                 175

Thr Asn Asn Val Ser Thr Leu Ile Glu Gln Gly Tyr Ser Ile Lys Ile
            180                 185                 190

Asp Lys Ile Val Arg Ile Val Asp Gly Lys His Tyr Ile Lys Ala
            195                 200                 205

Glu Ala Ser Val Val Asn Ser Leu Asp Phe Lys Asp Val Ser Lys
210                 215                 220

Gly Asp Ser Trp Gly Lys Ala Asn Tyr Asn Asp Trp Ser Asn Lys Leu
225                 230                 235                 240

Thr Pro Asn Glu Leu Ala Asp Val Asn Asp Tyr Met Arg Gly Gly Tyr
                245                 250                 255

Thr Ala Ile Asn Asn Tyr Leu Ile Ser Asn Gly Pro Val Asn Asn Pro
            260                 265                 270

Asn Pro Glu Leu Asp Ser Lys Ile Thr Asn Ile Glu Asn Ala Leu Lys
        275                 280                 285

Arg Glu Pro Ile Pro Thr Asn Leu Thr Val Tyr Arg Arg Ser Gly Pro
    290                 295                 300

Gln Glu Phe Gly Leu Thr Leu Thr Ser Pro Glu Tyr Asp Phe Asn Lys
305                 310                 315                 320

Leu Glu Asn Ile Asp Ala Phe Lys Ser Lys Trp Glu Gly Gln Ala Leu
                325                 330                 335

Ser Tyr Pro Asn Phe Ile Ser Thr Ser Ile Gly Ser Val Asn Met Ser
            340                 345                 350

Ala Phe Ala Lys Arg Lys Ile Val Leu Arg Ile Thr Ile Pro Lys Gly
        355                 360                 365

Ser Pro Gly Ala Tyr Leu Ser Ala Ile Pro Gly Tyr Ala Gly Glu Tyr
    370                 375                 380

Glu Val Leu Leu Asn His Gly Ser Lys Phe Lys Ile Asn Lys Ile Asp
385                 390                 395                 400

Ser Tyr Lys Asp Gly Thr Ile Thr Lys Leu Ile Val Asp Ala Thr Leu
                405                 410                 415

Ile Pro

<210> SEQ ID NO 20
<211> LENGTH: 834
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Ile Val Asn Glu Asp Ile Leu Pro Asn Asn Gly Leu Met Gly Tyr
1               5                   10                  15

Tyr Phe Ser Asp Glu His Phe Lys Asp Leu Lys Leu Met Ala Pro Ile
            20                  25                  30

Lys Asp Gly Asn Leu Lys Phe Glu Glu Lys Val Asp Lys Leu Leu
        35                  40                  45

Asp Lys Asp Lys Ser Asp Val Lys Ser Ile Arg Trp Thr Gly Arg Ile
    50                  55                  60
```

Ile Pro Ser Lys Asp Gly Glu Tyr Thr Leu Ser Thr Asp Arg Asp Asp
65                  70                  75                  80

Val Leu Met Gln Val Asn Thr Glu Ser Thr Ile Ser Asn Thr Leu Lys
            85                  90                  95

Val Asn Met Lys Lys Gly Lys Glu Tyr Lys Val Arg Ile Glu Leu Gln
            100                 105                 110

Asp Lys Asn Leu Gly Ser Ile Asp Asn Leu Ser Ser Pro Asn Leu Tyr
            115                 120                 125

Trp Glu Leu Asp Gly Met Lys Lys Ile Ile Pro Glu Asn Leu Phe
130                 135                 140

Leu Arg Asp Tyr Ser Asn Ile Glu Lys Asp Asp Pro Phe Ile Pro Asn
145             150                 155                 160

Asn Asn Phe Phe Asp Pro Lys Leu Met Ser Asp Trp Glu Asp Glu Asp
            165                 170                 175

Leu Asp Thr Asp Asn Asp Asn Ile Pro Asp Ser Tyr Glu Arg Asn Gly
            180                 185                 190

Tyr Thr Ile Lys Asp Leu Ile Ala Val Lys Trp Glu Asp Ser Phe Ala
            195                 200                 205

Glu Gln Gly Tyr Lys Lys Tyr Val Ser Asn Tyr Leu Glu Ser Asn Thr
210                 215                 220

Ala Gly Asp Pro Tyr Thr Asp Tyr Glu Lys Ala Ser Gly Ser Phe Asp
225                 230                 235                 240

Lys Ala Ile Lys Thr Glu Ala Arg Asp Pro Leu Val Ala Ala Tyr Pro
            245                 250                 255

Ile Val Gly Val Gly Met Glu Lys Leu Ile Ile Ser Thr Asn Glu His
            260                 265                 270

Ala Ser Thr Asp Gln Gly Lys Thr Val Ser Arg Ala Thr Thr Asn Ser
    275                 280                 285

Lys Thr Glu Ser Asn Thr Ala Gly Val Ser Val Asn Val Gly Tyr Gln
    290                 295                 300

Asn Gly Phe Thr Ala Asn Val Thr Thr Asn Tyr Ser His Thr Thr Asp
305                 310                 315                 320

Asn Ser Thr Ala Val Gln Asp Ser Asn Gly Glu Ser Trp Asn Thr Gly
            325                 330                 335

Leu Ser Ile Asn Lys Gly Glu Ser Ala Tyr Ile Asn Ala Asn Val Arg
            340                 345                 350

Tyr Tyr Asn Thr Gly Thr Ala Pro Met Tyr Lys Val Thr Pro Thr Thr
        355                 360                 365

Asn Leu Val Leu Asp Gly Asp Thr Leu Ser Thr Ile Lys Ala Gln Glu
    370                 375                 380

Asn Gln Ile Gly Asn Asn Leu Ser Pro Gly Asp Thr Tyr Pro Lys Lys
385                 390                 395                 400

Gly Leu Ser Pro Leu Ala Leu Asn Thr Met Asp Gln Phe Ser Ser Arg
            405                 410                 415

Leu Ile Pro Ile Asn Tyr Asp Gln Leu Lys Lys Leu Asp Ala Gly Lys
            420                 425                 430

Gln Ile Lys Leu Glu Thr Thr Gln Val Ser Gly Asn Phe Gly Thr Lys
        435                 440                 445

Asn Ser Ser Gly Gln Ile Val Thr Glu Gly Asn Ser Trp Ser Asp Tyr
            450                 455                 460

Ile Ser Gln Ile Asp Ser Ile Ser Ala Ser Ile Ile Leu Asp Thr Glu
465                 470                 475                 480

Asn Glu Ser Tyr Glu Arg Arg Val Thr Ala Lys Asn Leu Gln Asp Pro

-continued

```
                485                 490                 495
Glu Asp Lys Thr Pro Glu Leu Thr Ile Gly Glu Ala Ile Glu Lys Ala
            500                 505                 510
Phe Gly Ala Thr Lys Lys Asp Gly Leu Leu Tyr Phe Asn Asp Ile Pro
        515                 520                 525
Ile Asp Glu Ser Cys Val Glu Leu Ile Phe Asp Asp Asn Thr Ala Asn
    530                 535                 540
Lys Ile Lys Asp Ser Leu Lys Thr Leu Ser Asp Lys Lys Ile Tyr Asn
545                 550                 555                 560
Val Lys Leu Glu Arg Gly Met Asn Ile Leu Ile Lys Thr Pro Thr Tyr
                565                 570                 575
Phe Thr Asn Phe Asp Asp Tyr Asn Asn Tyr Pro Ser Thr Trp Ser Asn
            580                 585                 590
Val Asn Thr Thr Asn Gln Asp Gly Leu Gln Gly Ser Ala Asn Lys Leu
        595                 600                 605
Asn Gly Glu Thr Lys Ile Lys Ile Pro Met Ser Glu Leu Lys Pro Tyr
    610                 615                 620
Lys Arg Tyr Val Phe Ser Gly Tyr Ser Lys Asp Pro Leu Thr Ser Asn
625                 630                 635                 640
Ser Ile Ile Val Lys Ile Lys Ala Lys Glu Lys Thr Asp Tyr Leu
                645                 650                 655
Val Pro Glu Gln Gly Tyr Thr Lys Phe Ser Tyr Glu Phe Glu Thr Thr
            660                 665                 670
Glu Lys Asp Ser Ser Asn Ile Glu Ile Thr Leu Ile Gly Ser Gly Thr
        675                 680                 685
Thr Tyr Leu Asp Asn Leu Ser Ile Thr Glu Leu Asn Ser Thr Pro Glu
    690                 695                 700
Ile Leu Asp Glu Pro Glu Val Lys Ile Pro Thr Asp Gln Glu Ile Met
705                 710                 715                 720
Asp Ala His Lys Ile Tyr Phe Ala Asp Leu Asn Phe Asn Pro Ser Thr
                725                 730                 735
Gly Asn Thr Tyr Ile Asn Gly Met Tyr Phe Ala Pro Thr Gln Thr Asn
            740                 745                 750
Lys Glu Ala Leu Asp Tyr Ile Gln Lys Tyr Arg Val Glu Ala Thr Leu
        755                 760                 765
Gln Tyr Ser Gly Phe Lys Asp Ile Gly Thr Lys Asp Lys Glu Met Arg
    770                 775                 780
Asn Tyr Leu Gly Asp Pro Asn Gln Pro Lys Thr Asn Tyr Val Asn Leu
785                 790                 795                 800
Arg Ser Tyr Phe Thr Gly Gly Glu Asn Ile Met Thr Tyr Lys Lys Leu
                805                 810                 815
Arg Ile Tyr Ala Ile Thr Pro Asp Asp Arg Glu Leu Leu Val Leu Ser
            820                 825                 830
Val Asp

<210> SEQ ID NO 21
<211> LENGTH: 800
<212> TYPE: PRT
<213> ORGANISM: Bacillus anthracis

<400> SEQUENCE: 21

Met Thr Arg Asn Lys Phe Ile Pro Asn Lys Phe Ser Ile Ile Ser Phe
1               5                   10                  15

Ser Val Leu Leu Phe Ala Ile Ser Ser Ser Gln Ala Ile Glu Val Asn
```

-continued

```
                20                  25                  30
Ala Met Asn Glu His Tyr Thr Glu Ser Asp Ile Lys Arg Asn His Lys
            35                  40                  45
Thr Glu Lys Asn Lys Thr Glu Lys Glu Lys Phe Lys Asp Ser Ile Asn
 50                  55                  60
Asn Leu Val Lys Thr Glu Phe Thr Asn Glu Thr Leu Asp Lys Ile Gln
 65                  70                  75                  80
Gln Thr Gln Asp Leu Leu Lys Lys Ile Pro Lys Asp Val Leu Glu Ile
                85                  90                  95
Tyr Ser Glu Leu Gly Gly Glu Ile Tyr Phe Thr Asp Ile Asp Leu Val
                100                 105                 110
Glu His Lys Glu Leu Gln Asp Leu Ser Glu Glu Lys Asn Ser Met
                115                 120                 125
Asn Ser Arg Gly Glu Lys Val Pro Phe Ala Ser Arg Phe Val Phe Glu
                130                 135                 140
Lys Lys Arg Glu Thr Pro Lys Leu Ile Ile Asn Ile Lys Asp Tyr Ala
145                 150                 155                 160
Ile Asn Ser Glu Gln Ser Lys Glu Val Tyr Tyr Glu Ile Gly Lys Gly
                165                 170                 175
Ile Ser Leu Asp Ile Ile Ser Lys Asp Lys Ser Leu Asp Pro Glu Phe
                180                 185                 190
Leu Asn Leu Ile Lys Ser Leu Ser Asp Ser Asp Ser Ser Asp Leu
                195                 200                 205
Leu Phe Ser Gln Lys Phe Lys Glu Lys Leu Glu Leu Asn Asn Lys Ser
                210                 215                 220
Ile Asp Ile Asn Phe Ile Lys Glu Asn Leu Thr Glu Phe Gln His Ala
225                 230                 235                 240
Phe Ser Leu Ala Phe Ser Tyr Tyr Phe Ala Pro Asp His Arg Thr Val
                245                 250                 255
Leu Glu Leu Tyr Ala Pro Asp Met Phe Glu Tyr Met Asn Lys Leu Glu
                260                 265                 270
Lys Gly Gly Phe Glu Lys Ile Ser Glu Ser Leu Lys Lys Glu Gly Val
                275                 280                 285
Glu Lys Asp Arg Ile Asp Val Leu Lys Gly Glu Lys Ala Leu Lys Ala
                290                 295                 300
Ser Gly Leu Val Pro Glu His Ala Asp Ala Phe Lys Lys Ile Ala Arg
305                 310                 315                 320
Glu Leu Asn Thr Tyr Ile Leu Phe Arg Pro Val Asn Lys Leu Ala Thr
                325                 330                 335
Asn Leu Ile Lys Ser Gly Val Ala Thr Lys Gly Leu Asn Val His Gly
                340                 345                 350
Lys Ser Ser Asp Trp Gly Pro Val Ala Gly Tyr Ile Pro Phe Asp Gln
                355                 360                 365
Asp Leu Ser Lys His Gly Gln Gln Leu Ala Val Glu Lys Gly Asn
                370                 375                 380
Leu Glu Asn Lys Lys Ser Ile Thr Glu His Glu Gly Glu Ile Gly Lys
385                 390                 395                 400
Ile Pro Leu Lys Leu Asp His Leu Arg Ile Glu Glu Leu Lys Glu Asn
                405                 410                 415
Gly Ile Ile Leu Lys Gly Lys Lys Glu Ile Asp Asn Gly Lys Lys Tyr
                420                 425                 430
Tyr Leu Leu Glu Ser Asn Asn Gln Val Tyr Glu Phe Arg Ile Ser Asp
                435                 440                 445
```

Glu Asn Asn Glu Val Gln Tyr Lys Thr Lys Glu Gly Lys Ile Thr Val
    450                 455                 460

Leu Gly Glu Lys Phe Asn Trp Arg Asn Ile Glu Val Met Ala Lys Asn
465                 470                 475                 480

Val Glu Gly Val Leu Lys Pro Leu Thr Ala Asp Tyr Asp Leu Phe Ala
            485                 490                 495

Leu Ala Pro Ser Leu Thr Glu Ile Lys Lys Gln Ile Pro Gln Lys Glu
                500                 505                 510

Trp Asp Lys Val Val Asn Thr Pro Asn Ser Leu Glu Lys Gln Lys Gly
            515                 520                 525

Val Thr Asn Leu Leu Ile Lys Tyr Gly Ile Glu Arg Lys Pro Asp Ser
    530                 535                 540

Thr Lys Gly Thr Leu Ser Asn Trp Gln Lys Gln Met Leu Asp Arg Leu
545                 550                 555                 560

Asn Glu Ala Val Lys Tyr Thr Gly Tyr Thr Gly Gly Asp Val Val Asn
            565                 570                 575

His Gly Thr Glu Gln Asp Asn Glu Glu Phe Pro Lys Asp Asn Glu
                580                 585                 590

Ile Phe Ile Ile Asn Pro Glu Gly Glu Phe Ile Leu Thr Lys Asn Trp
    595                 600                 605

Glu Met Thr Gly Arg Phe Ile Glu Lys Asn Ile Thr Gly Lys Asp Tyr
610                 615                 620

Leu Tyr Tyr Phe Asn Arg Ser Tyr Asn Lys Ile Ala Pro Gly Asn Lys
625                 630                 635                 640

Ala Tyr Ile Glu Trp Thr Asp Pro Ile Thr Lys Ala Lys Ile Asn Thr
            645                 650                 655

Ile Pro Thr Ser Ala Glu Phe Ile Lys Asn Leu Ser Ser Ile Arg Arg
                660                 665                 670

Ser Ser Asn Val Gly Val Tyr Lys Asp Ser Gly Asp Lys Asp Glu Phe
            675                 680                 685

Ala Lys Lys Glu Ser Val Lys Lys Ile Ala Gly Tyr Leu Ser Asp Tyr
    690                 695                 700

Tyr Asn Ser Ala Asn His Ile Phe Ser Gln Glu Lys Lys Arg Lys Ile
705                 710                 715                 720

Ser Ile Phe Arg Gly Ile Gln Ala Tyr Asn Glu Ile Glu Asn Val Leu
            725                 730                 735

Lys Ser Lys Gln Ile Ala Pro Glu Tyr Lys Asn Tyr Phe Gln Tyr Leu
                740                 745                 750

Lys Glu Arg Ile Thr Asn Gln Val Gln Leu Leu Thr His Gln Lys
    755                 760                 765

Ser Asn Ile Glu Phe Lys Leu Leu Tyr Lys Gln Leu Asn Phe Thr Glu
    770                 775                 780

Asn Glu Thr Asp Asn Phe Glu Val Phe Gln Lys Ile Ile Asp Glu Lys
785                 790                 795                 800

<210> SEQ ID NO 22
<211> LENGTH: 800
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Thr Arg Asn Lys Phe Ile Pro Asn Lys Phe Ser Ile Ile Ser Phe

-continued

```
  1               5                   10                  15
Ser Val Leu Leu Phe Ala Ile Ser Ser Gln Ala Ile Glu Val Asn
          20                  25                  30

Ala Met Asn Glu His Tyr Thr Glu Ser Asp Ile Lys Arg Asn His Lys
              35                  40                  45

Thr Glu Lys Asn Lys Thr Glu Lys Glu Lys Phe Lys Asp Ser Ile Asn
 50                  55                  60

Asn Leu Val Lys Thr Glu Phe Thr Asn Glu Thr Leu Asp Lys Ile Gln
 65                  70                  75                  80

Gln Thr Gln Asp Leu Leu Lys Lys Ile Pro Lys Asp Val Leu Glu Ile
              85                  90                  95

Tyr Ser Glu Leu Gly Gly Glu Ile Tyr Phe Thr Asp Ile Asp Leu Val
              100                 105                 110

Glu His Lys Glu Leu Gln Asp Leu Ser Glu Glu Lys Asn Ser Met
              115                 120                 125

Asn Ser Arg Gly Glu Lys Val Pro Phe Ala Ser Arg Phe Val Phe Glu
 130                 135                 140

Lys Lys Arg Glu Thr Pro Lys Leu Ile Ile Asn Ile Lys Asp Tyr Ala
145                 150                 155                 160

Ile Asn Ser Glu Gln Ser Lys Glu Val Tyr Tyr Glu Ile Gly Lys Gly
              165                 170                 175

Ile Ser Leu Asp Ile Ile Ser Lys Asp Lys Ser Leu Asp Pro Glu Phe
              180                 185                 190

Leu Asn Leu Ile Lys Ser Leu Ser Asp Asp Ser Asp Ser Ser Asp Leu
              195                 200                 205

Leu Phe Ser Gln Lys Phe Lys Glu Lys Leu Glu Leu Asn Asn Lys Ser
 210                 215                 220

Ile Asp Ile Asn Phe Ile Lys Glu Asn Leu Thr Glu Phe Gln His Ala
225                 230                 235                 240

Phe Ser Leu Ala Phe Ser Tyr Tyr Phe Ala Pro Asp His Arg Thr Val
              245                 250                 255

Leu Glu Leu Tyr Ala Pro Asp Met Phe Glu Tyr Met Asn Lys Leu Glu
              260                 265                 270

Lys Gly Gly Phe Glu Lys Ile Ser Glu Ser Leu Lys Lys Glu Gly Val
 275                 280                 285

Glu Lys Asp Arg Ile Asp Val Leu Lys Gly Glu Lys Ala Leu Lys Ala
 290                 295                 300

Ser Gly Leu Val Pro Glu His Ala Asp Ala Phe Lys Lys Ile Ala Arg
305                 310                 315                 320

Glu Leu Asn Thr Tyr Ile Leu Phe Arg Pro Val Asn Lys Leu Ala Thr
              325                 330                 335

Asn Leu Ile Lys Ser Gly Val Ala Thr Lys Gly Leu Asn Val Ala Gly
              340                 345                 350

Lys Ser Ser Asp Trp Gly Pro Val Ala Gly Tyr Ile Pro Phe Asp Gln
              355                 360                 365

Asp Leu Ser Lys Lys His Gly Gln Gln Leu Ala Val Glu Lys Gly Asn
              370                 375                 380

Leu Glu Asn Lys Lys Ser Ile Thr Glu His Glu Gly Glu Ile Gly Lys
385                 390                 395                 400

Ile Pro Leu Lys Leu Asp His Leu Arg Ile Glu Glu Leu Lys Glu Asn
              405                 410                 415

Gly Ile Ile Leu Lys Gly Lys Lys Glu Ile Asp Asn Gly Lys Lys Tyr
              420                 425                 430
```

Tyr Leu Leu Glu Ser Asn Asn Gln Val Tyr Glu Phe Arg Ile Ser Asp
        435                 440                 445

Glu Asn Asn Glu Val Gln Tyr Lys Thr Lys Glu Gly Lys Ile Thr Val
    450                 455                 460

Leu Gly Glu Lys Phe Asn Trp Arg Asn Ile Glu Val Met Ala Lys Asn
465                 470                 475                 480

Val Glu Gly Val Leu Lys Pro Leu Thr Ala Asp Tyr Asp Leu Phe Ala
                485                 490                 495

Leu Ala Pro Ser Leu Thr Glu Ile Lys Lys Gln Ile Pro Gln Lys Glu
            500                 505                 510

Trp Asp Lys Val Val Asn Thr Pro Asn Ser Leu Glu Lys Gln Lys Gly
            515                 520                 525

Val Thr Asn Leu Leu Ile Lys Tyr Gly Ile Glu Arg Lys Pro Asp Ser
    530                 535                 540

Thr Lys Gly Thr Leu Ser Asn Trp Gln Lys Gln Met Leu Asp Arg Leu
545                 550                 555                 560

Asn Glu Ala Val Lys Tyr Thr Gly Tyr Thr Gly Gly Asp Val Val Asn
                565                 570                 575

His Gly Thr Glu Gln Asp Asn Glu Glu Phe Pro Glu Lys Asp Asn Glu
            580                 585                 590

Ile Phe Ile Ile Asn Pro Glu Gly Glu Phe Ile Leu Thr Lys Asn Trp
        595                 600                 605

Glu Met Thr Gly Arg Phe Ile Glu Lys Asn Ile Thr Gly Lys Asp Tyr
    610                 615                 620

Leu Tyr Tyr Phe Asn Arg Ser Tyr Asn Lys Ile Ala Pro Gly Asn Lys
625                 630                 635                 640

Ala Tyr Ile Glu Trp Thr Asp Pro Ile Thr Lys Ala Lys Ile Asn Thr
                645                 650                 655

Ile Pro Thr Ser Ala Glu Phe Ile Lys Asn Leu Ser Ser Ile Arg Arg
            660                 665                 670

Ser Ser Asn Val Gly Val Tyr Lys Asp Ser Gly Asp Lys Asp Glu Phe
        675                 680                 685

Ala Lys Lys Glu Ser Val Lys Lys Ile Ala Gly Tyr Leu Ser Asp Tyr
    690                 695                 700

Tyr Asn Ser Ala Asn His Ile Phe Ser Gln Glu Lys Lys Arg Lys Ile
705                 710                 715                 720

Ser Ile Phe Arg Gly Ile Gln Ala Tyr Asn Glu Ile Glu Asn Val Leu
                725                 730                 735

Lys Ser Lys Gln Ile Ala Pro Glu Tyr Lys Asn Tyr Phe Gln Tyr Leu
            740                 745                 750

Lys Glu Arg Ile Thr Asn Gln Val Gln Leu Leu Leu Thr His Gln Lys
        755                 760                 765

Ser Asn Ile Glu Phe Lys Leu Leu Tyr Lys Gln Leu Asn Phe Thr Glu
    770                 775                 780

Asn Glu Thr Asp Asn Phe Glu Val Phe Gln Lys Ile Ile Asp Glu Lys
785                 790                 795                 800

<210> SEQ ID NO 23
<211> LENGTH: 1290
<212> TYPE: PRT
<213> ORGANISM: Clostridium botulinum type B1
<220> FEATURE:
<223> OTHER INFORMATION: Strain NCTC 7273

<400> SEQUENCE: 23

```
Pro Val Thr Ile Asn Asn Phe Asn Tyr Asn Asp Pro Ile Asp Asn Asn
 1               5                  10                 15

Asn Ile Ile Met Met Glu Pro Pro Phe Ala Arg Gly Thr Gly Arg Tyr
                20                  25                  30

Tyr Lys Ala Phe Lys Ile Thr Asp Arg Ile Trp Ile Ile Pro Glu Arg
            35                  40                  45

Tyr Thr Phe Gly Tyr Lys Pro Glu Asp Phe Asn Lys Ser Ser Gly Ile
 50                  55                  60

Phe Asn Arg Asp Val Cys Glu Tyr Tyr Asp Pro Asp Tyr Leu Asn Thr
 65               70                  75                  80

Asn Asp Lys Lys Asn Ile Phe Leu Gln Thr Met Ile Lys Leu Phe Asn
                85                  90                  95

Arg Ile Lys Ser Lys Pro Leu Gly Glu Lys Leu Leu Glu Met Ile Ile
                100                 105                 110

Asn Gly Ile Pro Tyr Leu Gly Asp Arg Arg Val Pro Leu Glu Glu Phe
            115                 120                 125

Asn Thr Asn Ile Ala Ser Val Thr Val Asn Lys Leu Ile Ser Asn Pro
 130                 135                 140

Gly Glu Val Glu Arg Lys Lys Gly Ile Phe Ala Asn Leu Ile Ile Phe
 145                 150                 155                 160

Gly Pro Gly Pro Val Leu Asn Glu Asn Glu Thr Ile Asp Ile Gly Ile
                165                 170                 175

Gln Asn His Phe Ala Ser Arg Glu Gly Phe Gly Gly Ile Met Gln Met
            180                 185                 190

Lys Phe Cys Pro Glu Tyr Val Ser Val Phe Asn Asn Val Gln Glu Asn
            195                 200                 205

Lys Gly Ala Ser Ile Phe Asn Arg Arg Gly Tyr Phe Ser Asp Pro Ala
 210                 215                 220

Leu Ile Leu Met His Glu Leu Ile His Val Leu His Gly Leu Tyr Gly
 225                 230                 235                 240

Ile Lys Val Asp Asp Leu Pro Ile Val Pro Asn Glu Lys Lys Phe Phe
                245                 250                 255

Met Gln Ser Thr Asp Ala Ile Gln Ala Glu Glu Leu Tyr Thr Phe Gly
            260                 265                 270

Gly Gln Asp Pro Ser Ile Ile Thr Pro Ser Thr Asp Lys Ser Ile Tyr
            275                 280                 285

Asp Lys Val Leu Gln Asn Phe Arg Gly Ile Val Asp Arg Leu Asn Lys
 290                 295                 300

Val Leu Val Cys Ile Ser Asp Pro Asn Ile Asn Ile Asn Ile Tyr Lys
 305                 310                 315                 320

Asn Lys Phe Lys Asp Lys Tyr Lys Phe Val Glu Asp Ser Glu Gly Lys
                325                 330                 335

Tyr Ser Ile Asp Val Glu Ser Phe Asp Lys Leu Tyr Lys Ser Leu Met
            340                 345                 350

Phe Gly Phe Thr Glu Thr Asn Ile Ala Glu Asn Tyr Lys Ile Lys Thr
            355                 360                 365

Arg Ala Ser Tyr Phe Ser Asp Ser Leu Pro Pro Val Lys Ile Lys Asn
 370                 375                 380

Leu Leu Asp Asn Glu Ile Tyr Thr Ile Glu Glu Gly Phe Asn Ile Ser
 385                 390                 395                 400

Asp Lys Asp Met Glu Lys Glu Tyr Arg Gly Gln Asn Lys Ala Ile Asn
                405                 410                 415
```

```
Lys Gln Ala Tyr Glu Glu Ile Ser Lys Glu His Leu Ala Val Tyr Lys
            420                 425                 430

Ile Gln Met Cys Lys Ser Val Lys Ala Pro Gly Ile Cys Ile Asp Val
            435                 440                 445

Asp Asn Glu Asp Leu Phe Phe Ile Ala Asp Lys Asn Ser Phe Ser Asp
450                 455                 460

Asp Leu Ser Lys Asn Glu Arg Ile Glu Tyr Asn Thr Gln Ser Asn Tyr
465                 470                 475                 480

Ile Glu Asn Asp Phe Pro Ile Asn Glu Leu Ile Leu Asp Thr Asp Leu
                485                 490                 495

Ile Ser Lys Ile Glu Leu Pro Ser Glu Asn Thr Glu Ser Leu Thr Asp
            500                 505                 510

Phe Asn Val Asp Val Pro Val Tyr Glu Lys Gln Pro Ala Ile Lys Lys
            515                 520                 525

Ile Phe Thr Asp Glu Asn Thr Ile Phe Gln Tyr Leu Tyr Ser Gln Thr
            530                 535                 540

Phe Pro Leu Asp Ile Arg Asp Ile Ser Leu Thr Ser Ser Phe Asp Asp
545                 550                 555                 560

Ala Leu Leu Phe Ser Asn Lys Val Tyr Ser Phe Phe Ser Met Asp Tyr
                565                 570                 575

Ile Lys Thr Ala Asn Lys Val Val Glu Ala Gly Leu Phe Ala Gly Trp
            580                 585                 590

Val Lys Gln Ile Val Asn Asp Phe Val Ile Glu Ala Asn Lys Ser Asn
            595                 600                 605

Thr Met Asp Lys Ile Ala Asp Ile Ser Leu Ile Val Pro Tyr Ile Gly
            610                 615                 620

Leu Ala Leu Asn Val Gly Asn Glu Thr Ala Lys Gly Asn Phe Glu Asn
625                 630                 635                 640

Ala Phe Glu Ile Ala Gly Ala Ser Ile Leu Leu Glu Phe Ile Pro Glu
                645                 650                 655

Leu Leu Ile Pro Val Val Gly Ala Phe Leu Leu Glu Ser Tyr Ile Asp
            660                 665                 670

Asn Lys Asn Lys Ile Ile Lys Thr Ile Asp Asn Ala Leu Thr Lys Arg
            675                 680                 685

Asn Glu Lys Trp Ser Asp Met Tyr Gly Leu Ile Val Ala Gln Trp Leu
690                 695                 700

Ser Thr Val Asn Thr Gln Phe Tyr Thr Ile Lys Glu Gly Met Tyr Lys
705                 710                 715                 720

Ala Leu Asn Tyr Gln Ala Gln Ala Leu Glu Glu Ile Ile Lys Tyr Arg
                725                 730                 735

Tyr Asn Ile Tyr Ser Glu Lys Glu Lys Ser Asn Ile Asn Ile Asp Phe
            740                 745                 750

Asn Asp Ile Asn Ser Lys Leu Asn Glu Gly Ile Asn Gln Ala Ile Asp
            755                 760                 765

Asn Ile Asn Asn Phe Ile Asn Gly Cys Ser Val Ser Tyr Leu Met Lys
            770                 775                 780

Lys Met Ile Pro Leu Ala Val Glu Lys Leu Leu Asp Phe Asp Asn Thr
785                 790                 795                 800

Leu Lys Lys Asn Leu Leu Asn Tyr Ile Asp Glu Asn Lys Leu Tyr Leu
                805                 810                 815

Ile Gly Ser Ala Glu Tyr Glu Lys Ser Lys Val Asn Lys Tyr Leu Lys
            820                 825                 830

Thr Ile Met Pro Phe Asp Leu Ser Ile Tyr Thr Asn Asp Thr Ile Leu
```

-continued

```
                835                 840                 845
Ile Glu Met Phe Asn Lys Tyr Asn Ser Glu Ile Leu Asn Asn Ile Ile
    850                 855                 860
Leu Asn Leu Arg Tyr Lys Asp Asn Asn Leu Ile Asp Leu Ser Gly Tyr
865                 870                 875                 880
Gly Ala Lys Val Glu Val Tyr Asp Gly Val Glu Leu Asn Asp Lys Asn
                885                 890                 895
Gln Phe Lys Leu Thr Ser Ser Ala Asn Ser Lys Ile Arg Val Thr Gln
            900                 905                 910
Asn Gln Asn Ile Ile Phe Asn Ser Val Phe Leu Asp Phe Ser Val Ser
            915                 920                 925
Phe Trp Ile Arg Ile Pro Lys Tyr Lys Asn Asp Gly Ile Gln Asn Tyr
    930                 935                 940
Ile His Asn Glu Tyr Thr Ile Ile Asn Cys Met Lys Asn Asn Ser Gly
945                 950                 955                 960
Trp Lys Ile Ser Ile Arg Gly Asn Arg Ile Ile Trp Thr Leu Ile Asp
                965                 970                 975
Ile Asn Gly Lys Thr Lys Ser Val Phe Phe Glu Tyr Asn Ile Arg Glu
            980                 985                 990
Asp Ile Ser Glu Tyr Ile Asn Arg Trp Phe Phe Val Thr Ile Thr Asn
            995                 1000                1005
Asn Leu Asn Asn Ala Lys Ile Tyr Ile Asn Gly Lys Leu Glu Ser
        1010                1015                1020
Asn Thr Asp Ile Lys Asp Ile Arg Glu Val Ile Ala Asn Gly Glu
        1025                1030                1035
Ile Ile Phe Lys Leu Asp Gly Asp Ile Asp Arg Thr Gln Phe Ile
        1040                1045                1050
Trp Met Lys Tyr Phe Ser Ile Phe Asn Thr Glu Leu Ser Gln Ser
        1055                1060                1065
Asn Ile Glu Glu Arg Tyr Lys Ile Gln Ser Tyr Ser Glu Tyr Leu
        1070                1075                1080
Lys Asp Phe Trp Gly Asn Pro Leu Met Tyr Asn Lys Glu Tyr Tyr
        1085                1090                1095
Met Phe Asn Ala Gly Asn Lys Asn Ser Tyr Ile Lys Leu Lys Lys
        1100                1105                1110
Asp Ser Pro Val Gly Glu Ile Leu Thr Arg Ser Lys Tyr Asn Gln
        1115                1120                1125
Asn Ser Lys Tyr Ile Asn Tyr Arg Asp Leu Tyr Ile Gly Glu Lys
        1130                1135                1140
Phe Ile Ile Arg Arg Lys Ser Asn Ser Gln Ser Ile Asn Asp Asp
        1145                1150                1155
Ile Val Arg Lys Glu Asp Tyr Ile Tyr Leu Asp Phe Phe Asn Leu
        1160                1165                1170
Asn Gln Glu Trp Arg Val Tyr Thr Tyr Lys Tyr Phe Lys Lys Glu
        1175                1180                1185
Glu Glu Lys Leu Phe Leu Ala Pro Ile Ser Asp Ser Asp Glu Phe
        1190                1195                1200
Tyr Asn Thr Ile Gln Ile Lys Glu Tyr Asp Glu Gln Pro Thr Tyr
        1205                1210                1215
Ser Cys Gln Leu Leu Phe Lys Lys Asp Glu Glu Ser Thr Asp Glu
        1220                1225                1230
Ile Gly Leu Ile Gly Ile His Arg Phe Tyr Glu Ser Gly Ile Val
        1235                1240                1245
```

Phe Glu Glu Tyr Lys Asp Tyr Phe Cys Ile Ser Lys Trp Tyr Leu
   1250                1255                1260

Lys Glu Val Lys Arg Lys Pro Tyr Asn Leu Lys Leu Gly Cys Asn
   1265                1270                1275

Trp Gln Phe Ile Pro Lys Asp Glu Gly Trp Thr Glu
   1280                1285                1290

<210> SEQ ID NO 24
<211> LENGTH: 1289
<212> TYPE: PRT
<213> ORGANISM: Clostridium botulinum

<400> SEQUENCE: 24

Pro Val Thr Ile Asn Asn Phe Asn Tyr Asn Asp Pro Ile Asp Asn
1               5                   10                  15

Asn Ile Ile Met Met Glu Pro Pro Phe Ala Arg Gly Thr Gly Arg
              20                  25                  30

Tyr Tyr Lys Ala Phe Lys Ile Thr Asp Arg Ile Trp Ile Ile Pro Glu Arg
              35                  40                  45

Tyr Thr Phe Gly Tyr Lys Pro Glu Asp Phe Asn Lys Ser Ser Gly Ile
              50                  55                  60

Phe Asn Arg Asp Val Cys Glu Tyr Tyr Asp Pro Asp Tyr Leu Asn Thr
65                  70                  75                  80

Asn Asp Lys Lys Asn Ile Phe Leu Gln Thr Met Ile Lys Leu Phe Asn
                    85                  90                  95

Arg Ile Lys Ser Lys Pro Leu Gly Glu Lys Leu Leu Glu Met Ile Ile
                   100                 105                 110

Asn Gly Ile Pro Tyr Leu Gly Asp Arg Arg Val Pro Leu Glu Glu Phe
               115                 120                 125

Asn Thr Asn Ile Ala Ser Val Thr Val Asn Lys Leu Ile Ser Asn Pro
   130                 135                 140

Gly Glu Val Glu Gln Lys Lys Gly Ile Phe Ala Asn Leu Ile Ile Phe
145                 150                 155                 160

Gly Pro Gly Pro Val Leu Asn Glu Asn Glu Thr Ile Asp Ile Gly Ile
                   165                 170                 175

Gln Asn His Phe Ala Ser Arg Glu Gly Phe Gly Gly Ile Met Gln Met
               180                 185                 190

Lys Phe Cys Pro Glu Tyr Val Ser Val Phe Asn Asn Val Gln Glu Asn
               195                 200                 205

Lys Gly Ala Ser Ile Phe Asn Arg Arg Gly Tyr Phe Ser Asp Pro Ala
   210                 215                 220

Leu Ile Leu Met His Glu Leu Ile His Val Leu His Gly Leu Tyr Gly
225                 230                 235                 240

Ile Lys Val Asp Asp Leu Pro Ile Val Pro Asn Glu Lys Lys Phe Phe
                   245                 250                 255

Met Gln Ser Thr Asp Thr Ile Gln Ala Glu Glu Leu Tyr Thr Phe Gly
               260                 265                 270

Gly Gln Asp Pro Ser Ile Ile Ser Pro Ser Thr Asp Lys Ser Ile Tyr
               275                 280                 285

Asp Lys Val Leu Gln Asn Phe Arg Gly Ile Val Asp Arg Leu Asn Lys
   290                 295                 300

Val Leu Val Cys Ile Ser Asp Pro Asn Ile Asn Ile Asn Ile Tyr Lys
305                 310                 315                 320

Asn Lys Phe Lys Asp Lys Tyr Lys Phe Val Glu Asp Ser Glu Gly Lys

```
            325                 330                 335
Tyr Ser Ile Asp Val Glu Ser Phe Asn Lys Leu Tyr Lys Ser Leu Met
            340                 345                 350
Phe Gly Phe Thr Glu Ile Asn Ile Ala Glu Asn Tyr Lys Ile Lys Thr
            355                 360                 365
Arg Ala Ser Tyr Phe Ser Asp Ser Leu Pro Pro Val Lys Ile Lys Asn
            370                 375                 380
Leu Leu Asp Asn Glu Ile Tyr Thr Ile Glu Glu Gly Phe Asn Ile Ser
385                 390                 395                 400
Asp Lys Asn Met Gly Lys Glu Tyr Arg Gly Gln Asn Lys Ala Ile Asn
            405                 410                 415
Lys Gln Ala Tyr Glu Glu Ile Ser Lys Glu His Leu Ala Val Tyr Lys
            420                 425                 430
Ile Gln Met Cys Lys Ser Val Lys Val Pro Gly Ile Cys Ile Asp Val
            435                 440                 445
Asp Asn Glu Asn Leu Phe Phe Ile Ala Asp Lys Asn Ser Phe Ser Asp
            450                 455                 460
Asp Leu Ser Lys Asn Glu Arg Val Glu Tyr Asn Thr Gln Asn Asn Tyr
465                 470                 475                 480
Ile Gly Asn Asp Phe Pro Ile Asn Glu Leu Ile Leu Asp Thr Asp Leu
            485                 490                 495
Ile Ser Lys Ile Glu Leu Pro Ser Glu Asn Thr Glu Ser Leu Thr Asp
            500                 505                 510
Phe Asn Val Asp Val Pro Val Tyr Glu Lys Gln Pro Ala Ile Lys Lys
            515                 520                 525
Val Thr Asp Glu Asn Thr Ile Phe Gln Tyr Leu Tyr Ser Gln Thr Phe
            530                 535                 540
Pro Leu Asn Ile Arg Asp Ile Ser Leu Thr Ser Ser Phe Asp Asp Ala
545                 550                 555                 560
Leu Leu Val Ser Ser Lys Val Tyr Ser Phe Phe Ser Met Asp Tyr Ile
            565                 570                 575
Lys Thr Ala Asn Lys Val Val Glu Ala Gly Leu Phe Ala Gly Trp Val
            580                 585                 590
Lys Gln Ile Val Asp Asp Phe Val Ile Glu Ala Asn Lys Ser Ser Thr
            595                 600                 605
Met Asp Lys Ile Ala Asp Ile Ser Leu Ile Val Pro Tyr Ile Gly Leu
            610                 615                 620
Ala Leu Asn Val Gly Asp Glu Thr Ala Lys Gly Asn Phe Glu Ser Ala
625                 630                 635                 640
Phe Glu Ile Ala Gly Ser Ser Ile Leu Leu Glu Phe Ile Pro Glu Leu
            645                 650                 655
Leu Ile Pro Val Val Gly Val Phe Leu Leu Glu Ser Tyr Ile Asp Asn
            660                 665                 670
Lys Asn Lys Ile Ile Lys Thr Ile Asp Asn Ala Leu Thr Lys Arg Val
            675                 680                 685
Glu Lys Trp Ile Asp Met Tyr Gly Leu Ile Val Ala Gln Trp Leu Ser
            690                 695                 700
Thr Val Asn Thr Gln Phe Tyr Thr Ile Lys Glu Gly Met Tyr Lys Ala
705                 710                 715                 720
Leu Asn Tyr Gln Ala Gln Ala Leu Glu Glu Ile Ile Lys Tyr Lys Tyr
            725                 730                 735
Asn Ile Tyr Ser Glu Glu Glu Lys Ser Asn Ile Asn Ile Asn Phe Asn
            740                 745                 750
```

-continued

```
Asp Ile Asn Ser Lys Leu Asn Asp Gly Ile Asn Gln Ala Met Asp Asn
    755                 760                 765
Ile Asn Asp Phe Ile Asn Glu Cys Ser Val Ser Tyr Leu Met Lys Lys
770                 775                 780
Met Ile Pro Leu Ala Val Lys Lys Leu Leu Asp Phe Asp Asn Thr Leu
785                 790                 795                 800
Lys Lys Asn Leu Leu Asn Tyr Ile Asp Glu Asn Lys Leu Tyr Leu Ile
                    805                 810                 815
Gly Ser Val Glu Asp Glu Lys Ser Lys Val Asp Lys Tyr Leu Lys Thr
                820                 825                 830
Ile Ile Pro Phe Asp Leu Ser Thr Tyr Thr Asn Asn Glu Ile Leu Ile
                835                 840                 845
Lys Ile Phe Asn Lys Tyr Asn Ser Glu Ile Leu Asn Asn Ile Ile Leu
            850                 855                 860
Asn Leu Arg Tyr Arg Asp Asn Asn Leu Ile Asp Leu Ser Gly Tyr Gly
865                 870                 875                 880
Ala Lys Val Glu Val Tyr Asp Gly Val Lys Leu Asn Asp Lys Asn Gln
                    885                 890                 895
Phe Lys Leu Thr Ser Ser Ala Asp Ser Lys Ile Arg Val Thr Gln Asn
                900                 905                 910
Gln Asn Ile Ile Phe Asn Ser Met Phe Leu Asp Phe Ser Val Ser Phe
                915                 920                 925
Trp Ile Arg Ile Pro Lys Tyr Arg Asn Asp Asp Ile Gln Asn Tyr Ile
930                 935                 940
His Asn Glu Tyr Thr Ile Ile Asn Cys Met Lys Asn Asn Ser Gly Trp
945                 950                 955                 960
Lys Ile Ser Ile Arg Gly Asn Arg Ile Ile Trp Thr Leu Ile Asp Ile
                    965                 970                 975
Asn Gly Lys Thr Lys Ser Val Phe Phe Glu Tyr Asn Ile Arg Glu Asp
                980                 985                 990
Ile Ser Glu Tyr Ile Asn Arg Trp Phe Phe Val Thr Ile Thr Asn Asn
            995                 1000                1005
Leu Asp Asn Ala Lys Ile Tyr Ile Asn Gly Thr Leu Glu Ser Asn
    1010                1015                1020
Met Asp Ile Lys Asp Ile Gly Glu Val Ile Val Asn Gly Glu Ile
    1025                1030                1035
Thr Phe Lys Leu Asp Gly Asp Val Asp Arg Thr Gln Phe Ile Trp
    1040                1045                1050
Met Lys Tyr Phe Ser Ile Phe Asn Thr Gln Leu Asn Gln Ser Asn
    1055                1060                1065
Ile Lys Glu Ile Tyr Lys Ile Gln Ser Tyr Ser Glu Tyr Leu Lys
    1070                1075                1080
Asp Phe Trp Gly Asn Pro Leu Met Tyr Asn Lys Glu Tyr Tyr Met
    1085                1090                1095
Phe Asn Ala Gly Asn Lys Asn Ser Tyr Ile Lys Leu Val Lys Asp
    1100                1105                1110
Ser Ser Val Gly Glu Ile Leu Ile Arg Ser Lys Tyr Asn Gln Asn
    1115                1120                1125
Ser Asn Tyr Ile Asn Tyr Arg Asn Leu Tyr Ile Gly Glu Lys Phe
    1130                1135                1140
Ile Ile Arg Arg Lys Ser Asn Ser Gln Ser Ile Asn Asp Asp Ile
    1145                1150                1155
```

```
Val Arg Lys Glu Asp Tyr Ile His Leu Asp Phe Val Asn Ser Asn
    1160                1165                1170

Glu Glu Trp Arg Val Tyr Ala Tyr Lys Asn Phe Lys Glu Gln Glu
    1175                1180                1185

Gln Lys Leu Phe Leu Ser Ile Ile Tyr Asp Ser Asn Glu Phe Tyr
    1190                1195                1200

Lys Thr Ile Gln Ile Lys Glu Tyr Asp Glu Gln Pro Thr Tyr Ser
    1205                1210                1215

Cys Gln Leu Leu Phe Lys Lys Asp Glu Gly Ser Thr Asp Asp Ile
    1220                1225                1230

Gly Leu Ile Gly Ile His Arg Phe Tyr Glu Ser Gly Val Leu Arg
    1235                1240                1245

Lys Lys Tyr Lys Asp Tyr Phe Cys Ile Ser Lys Trp Tyr Leu Lys
    1250                1255                1260

Glu Val Lys Arg Lys Pro Tyr Lys Ser Asn Leu Gly Cys Asn Trp
    1265                1270                1275

Gln Phe Ile Pro Lys Asp Glu Gly Trp Thr Glu
    1280                1285

<210> SEQ ID NO 25
<211> LENGTH: 844
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Pro Lys Ile Asn Ser Phe Asn Tyr Asn Asp Pro Val Asn Asp Arg Thr
1               5                   10                  15

Ile Leu Tyr Ile Lys Pro Gly Gly Cys Gln Glu Phe Tyr Lys Ser Phe
                20                  25                  30

Asn Ile Met Lys Asn Ile Trp Ile Ile Pro Glu Arg Asn Val Ile Gly
            35                  40                  45

Thr Thr Pro Gln Asp Phe His Pro Pro Thr Ser Leu Lys Asn Gly Asp
        50                  55                  60

Ser Ser Tyr Tyr Asp Pro Asn Tyr Leu Gln Ser Asp Glu Glu Lys Asp
65                  70                  75                  80

Arg Phe Leu Lys Ile Val Thr Lys Ile Phe Asn Arg Ile Asn Asn Asn
                85                  90                  95

Leu Ser Gly Gly Ile Leu Leu Glu Glu Leu Ser Lys Ala Asn Pro Tyr
            100                 105                 110

Leu Gly Asn Asp Asn Thr Pro Asp Asn Gln Phe His Ile Gly Asp Ala
        115                 120                 125

Ser Ala Val Glu Ile Lys Phe Ser Asn Gly Ser Gln Asp Ile Leu Leu
    130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Arg
                165                 170                 175

Phe Gly Ser Ile Ala Ile Val Thr Phe Ser Pro Glu Tyr Ser Phe Arg
            180                 185                 190

Phe Asn Asp Asn Cys Met Asn Glu Phe Ile Gln Asp Pro Ala Leu Thr
        195                 200                 205

Leu Met His Gln Leu Ile His Ser Leu His Gly Leu Tyr Gly Ala Lys
    210                 215                 220
```

```
Gly Ile Thr Thr Lys Tyr Thr Ile Thr Gln Lys Gln Asn Pro Leu Ile
225                 230                 235                 240

Thr Asn Ile Arg Gly Thr Asn Ile Glu Glu Phe Leu Thr Phe Gly Gly
            245                 250                 255

Thr Asp Leu Asn Ile Ile Thr Ser Ala Gln Ser Asn Asp Ile Tyr Thr
        260                 265                 270

Asn Leu Leu Ala Asp Tyr Lys Lys Ile Ala Ser Lys Leu Ser Lys Val
    275                 280                 285

Gln Val Ser Asn Pro Leu Leu Asn Pro Tyr Lys Asp Val Phe Glu Ala
290                 295                 300

Lys Tyr Gly Leu Asp Lys Asp Ala Ser Gly Ile Tyr Ser Val Asn Ile
305                 310                 315                 320

Asn Lys Phe Asn Asp Ile Phe Lys Lys Leu Tyr Ser Phe Thr Glu Phe
            325                 330                 335

Asp Leu Arg Thr Lys Phe Gln Val Lys Cys Arg Gln Thr Tyr Ile Gly
        340                 345                 350

Gln Tyr Lys Tyr Phe Lys Leu Ser Asn Leu Leu Asn Asp Ser Ile Tyr
    355                 360                 365

Asn Ile Ser Glu Gly Tyr Asn Ile Asn Asn Leu Lys Val Asn Phe Arg
370                 375                 380

Gly Gln Asn Ala Asn Leu Asn Pro Arg Ile Ile Thr Pro Ile Thr Gly
385                 390                 395                 400

Arg Gly Leu Val Lys Lys Ile Ile Arg Phe Cys Lys Asn Ile Val Ser
            405                 410                 415

Val Lys Gly Ile Arg Lys Ser Ile Cys Ile Glu Ile Asn Asn Gly Glu
        420                 425                 430

Leu Phe Phe Val Ala Ser Glu Asn Ser Tyr Asn Asp Asp Asn Ile Asn
    435                 440                 445

Thr Pro Lys Glu Ile Asp Asp Thr Val Thr Ser Asn Asn Asn Tyr Glu
450                 455                 460

Asn Asp Leu Asp Gln Val Ile Leu Asn Phe Asn Ser Glu Ser Ala Pro
465                 470                 475                 480

Gly Leu Ser Asp Glu Lys Leu Asn Leu Thr Ile Gln Asn Asp Ala Tyr
            485                 490                 495

Ile Pro Lys Tyr Asp Ser Asn Gly Thr Ser Asp Ile Glu Gln His Asp
        500                 505                 510

Val Asn Glu Leu Asn Val Phe Phe Tyr Leu Asp Ala Gln Lys Val Pro
    515                 520                 525

Glu Gly Glu Asn Asn Val Asn Leu Thr Ser Ser Ile Asp Thr Ala Leu
530                 535                 540

Leu Glu Gln Pro Lys Ile Tyr Thr Phe Phe Ser Ser Glu Phe Ile Asn
545                 550                 555                 560

Asn Val Asn Lys Pro Val Gln Ala Ala Leu Phe Val Ser Trp Ile Gln
            565                 570                 575

Gln Val Leu Val Asp Phe Thr Thr Glu Ala Asn Gln Lys Ser Thr Val
        580                 585                 590

Asp Lys Ile Ala Asp Ile Ser Ile Val Val Pro Tyr Ile Gly Leu Ala
    595                 600                 605

Leu Asn Ile Gly Asn Glu Ala Gln Lys Gly Asn Phe Lys Asp Ala Leu
610                 615                 620

Glu Leu Leu Gly Ala Gly Ile Leu Leu Glu Phe Glu Pro Glu Leu Leu
625                 630                 635                 640
```

```
Ile Pro Thr Ile Leu Val Phe Thr Ile Lys Ser Phe Leu Gly Ser Ser
                645                 650                 655

Asp Asn Lys Asn Lys Val Ile Lys Ala Ile Asn Asn Ala Leu Lys Glu
    660                 665                 670

Arg Asp Glu Lys Trp Lys Glu Val Tyr Ser Phe Ile Val Ser Asn Trp
        675                 680                 685

Met Thr Lys Ile Asn Thr Gln Phe Asn Lys Arg Lys Glu Gln Met Tyr
    690                 695                 700

Gln Ala Leu Gln Asn Gln Val Asn Ala Ile Lys Thr Ile Ile Glu Ser
705                 710                 715                 720

Lys Tyr Asn Ser Tyr Thr Leu Glu Glu Lys Asn Glu Leu Thr Asn Lys
                725                 730                 735

Tyr Asp Ile Lys Gln Ile Glu Asn Glu Leu Asn Gln Lys Val Ser Ile
            740                 745                 750

Ala Met Asn Asn Ile Asp Arg Phe Leu Thr Glu Ser Ser Ile Ser Tyr
        755                 760                 765

Leu Met Lys Ile Ile Asn Glu Val Lys Ile Asn Lys Leu Arg Glu Tyr
    770                 775                 780

Asp Glu Asn Val Lys Thr Tyr Leu Leu Asn Tyr Ile Ile Gln His Gly
785                 790                 795                 800

Ser Ile Leu Gly Glu Ser Gln Gln Glu Leu Asn Ser Met Val Thr Asp
                805                 810                 815

Thr Leu Asn Asn Ser Ile Pro Phe Lys Leu Ser Ser Tyr Thr Asp Asp
            820                 825                 830

Lys Ile Leu Ile Ser Tyr Phe Asn Lys Phe Phe Lys
        835                 840

<210> SEQ ID NO 26
<211> LENGTH: 1251
<212> TYPE: PRT
<213> ORGANISM: Clostridium botulinum

<400> SEQUENCE: 26

Pro Lys Ile Asn Ser Phe Asn Tyr Asn Asp Pro Val Asn Asp Arg Thr
1               5                   10                  15

Ile Leu Tyr Ile Lys Pro Gly Gly Cys Gln Glu Phe Tyr Lys Ser Phe
            20                  25                  30

Asn Ile Met Lys Asn Ile Trp Ile Ile Pro Glu Arg Asn Val Ile Gly
        35                  40                  45

Thr Thr Pro Gln Asp Phe His Pro Pro Thr Ser Leu Lys Asn Gly Asp
    50                  55                  60

Ser Ser Tyr Tyr Asp Pro Asn Tyr Leu Gln Ser Asp Glu Glu Lys Asp
65                  70                  75                  80

Arg Phe Leu Lys Ile Val Thr Lys Ile Phe Asn Arg Ile Asn Asn Asn
                85                  90                  95

Leu Ser Gly Gly Ile Leu Leu Glu Glu Leu Ser Lys Ala Asn Pro Tyr
            100                 105                 110

Leu Gly Asn Asp Asn Thr Pro Asp Asn Gln Phe His Ile Gly Asp Ala
        115                 120                 125

Ser Ala Val Glu Ile Lys Phe Ser Asn Gly Ser Gln His Ile Leu Leu
    130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Gly
                165                 170                 175
```

```
Phe Gly Ser Ile Ala Ile Val Thr Phe Ser Pro Glu Tyr Ser Phe Arg
            180                 185                 190

Phe Asn Asp Asn Ser Ile Asn Glu Phe Ile Gln Asp Pro Ala Leu Thr
            195                 200                 205

Leu Met His Glu Leu Ile His Ser Leu His Gly Leu Tyr Gly Ala Lys
210                 215                 220

Gly Ile Thr Thr Thr Cys Ile Ile Thr Gln Gln Asn Pro Leu Ile
225                 230                 235                 240

Thr Asn Arg Lys Gly Ile Asn Ile Glu Glu Phe Leu Thr Phe Gly Gly
            245                 250                 255

Asn Asp Leu Asn Ile Ile Thr Val Ala Gln Tyr Asn Asp Ile Tyr Thr
            260                 265                 270

Asn Leu Leu Asn Asp Tyr Arg Lys Ile Ala Ser Lys Leu Ser Lys Val
            275                 280                 285

Gln Val Ser Asn Pro Gln Leu Asn Pro Tyr Lys Asp Ile Phe Gln Glu
            290                 295                 300

Lys Tyr Gly Leu Asp Lys Asp Ala Ser Gly Ile Tyr Ser Val Asn Ile
305                 310                 315                 320

Asn Lys Phe Asp Asp Ile Leu Lys Lys Leu Tyr Ser Phe Thr Glu Phe
            325                 330                 335

Asp Leu Ala Thr Lys Phe Gln Val Lys Cys Arg Glu Thr Tyr Ile Gly
            340                 345                 350

Gln Tyr Lys Tyr Phe Lys Leu Ser Asn Leu Leu Asn Asp Ser Ile Tyr
            355                 360                 365

Asn Ile Ser Glu Gly Tyr Asn Ile Asn Asn Leu Lys Val Asn Phe Arg
            370                 375                 380

Gly Gln Asn Ala Asn Leu Asn Pro Arg Ile Ile Lys Pro Ile Thr Gly
385                 390                 395                 400

Arg Gly Leu Val Lys Lys Ile Arg Phe Cys Lys Asn Ile Val Ser
            405                 410                 415

Val Lys Gly Ile Arg Lys Ser Ile Cys Ile Glu Ile Asn Asn Gly Glu
            420                 425                 430

Leu Phe Phe Val Ala Ser Glu Asn Ser Tyr Asn Asp Asp Asn Ile Asn
            435                 440                 445

Thr Pro Lys Glu Ile Asp Asp Thr Val Thr Ser Asn Asn Asn Tyr Glu
450                 455                 460

Asn Asp Leu Asp Gln Val Ile Leu Asn Phe Asn Ser Glu Ser Ala Pro
465                 470                 475                 480

Gly Leu Ser Asp Glu Lys Leu Asn Leu Thr Ile Gln Asn Asp Ala Tyr
            485                 490                 495

Ile Pro Lys Tyr Asp Ser Asn Gly Thr Ser Asp Ile Glu Gln His Asp
            500                 505                 510

Val Asn Glu Leu Asn Val Phe Phe Tyr Leu Asp Ala Gln Lys Val Pro
            515                 520                 525

Glu Gly Glu Asn Asn Val Asn Leu Thr Ser Ser Ile Asp Thr Ala Leu
            530                 535                 540

Leu Glu Gln Pro Lys Ile Tyr Thr Phe Phe Ser Ser Glu Phe Ile Asn
545                 550                 555                 560

Asn Val Asn Lys Pro Val Gln Ala Ala Leu Phe Val Ser Trp Ile Gln
            565                 570                 575

Gln Val Leu Val Asp Phe Thr Thr Glu Ala Asn Gln Lys Ser Thr Val
            580                 585                 590
```

```
Asp Lys Ile Ala Asp Ile Ser Ile Val Val Pro Tyr Ile Gly Leu Ala
            595                 600                 605
Leu Asn Ile Gly Asn Glu Ala Gln Lys Gly Asn Phe Lys Asp Ala Leu
        610                 615                 620
Glu Leu Leu Gly Ala Gly Ile Leu Leu Glu Phe Glu Pro Glu Leu Leu
625                 630                 635                 640
Ile Pro Thr Ile Leu Val Phe Thr Ile Lys Ser Phe Leu Gly Ser Ser
                645                 650                 655
Asp Asn Lys Asn Lys Val Ile Lys Ala Ile Asn Asn Ala Leu Lys Glu
            660                 665                 670
Arg Asp Glu Lys Trp Lys Glu Val Tyr Ser Phe Ile Val Ser Asn Trp
        675                 680                 685
Met Thr Lys Ile Asn Thr Gln Phe Asn Lys Arg Lys Glu Gln Met Tyr
    690                 695                 700
Gln Ala Leu Gln Asn Gln Val Asn Ala Ile Lys Thr Ile Ile Glu Ser
705                 710                 715                 720
Lys Tyr Asn Ser Tyr Thr Leu Glu Glu Lys Asn Glu Leu Thr Asn Lys
                725                 730                 735
Tyr Asp Ile Lys Gln Ile Glu Asn Glu Leu Asn Gln Lys Val Ser Ile
            740                 745                 750
Ala Met Asn Asn Ile Asp Arg Phe Leu Thr Glu Ser Ser Ile Ser Tyr
        755                 760                 765
Leu Met Lys Leu Ile Asn Glu Val Lys Ile Asn Lys Leu Arg Glu Tyr
    770                 775                 780
Asp Glu Asn Val Lys Thr Tyr Leu Leu Asn Tyr Ile Ile Gln His Gly
785                 790                 795                 800
Ser Ile Leu Gly Glu Ser Gln Gln Glu Leu Asn Ser Met Val Thr Asp
                805                 810                 815
Thr Leu Asn Asn Ser Ile Pro Phe Lys Leu Ser Ser Tyr Thr Asp Asp
            820                 825                 830
Lys Ile Leu Ile Ser Tyr Phe Asn Lys Phe Phe Lys Arg Ile Lys Ser
        835                 840                 845
Ser Ser Val Leu Asn Met Arg Tyr Lys Asn Asp Lys Tyr Val Asp Thr
    850                 855                 860
Ser Gly Tyr Asp Ser Asn Ile Asn Ile Asn Gly Asp Val Tyr Lys Tyr
865                 870                 875                 880
Pro Thr Asn Lys Asn Gln Phe Gly Ile Tyr Asn Asp Lys Leu Ser Glu
                885                 890                 895
Val Asn Ile Ser Gln Asn Asp Tyr Ile Ile Tyr Asp Asn Lys Tyr Lys
            900                 905                 910
Asn Phe Ser Ile Ser Phe Trp Val Arg Ile Pro Asn Tyr Asp Asn Lys
        915                 920                 925
Ile Val Asn Val Asn Asn Glu Tyr Thr Ile Ile Asn Cys Met Arg Asp
    930                 935                 940
Asn Asn Ser Gly Trp Lys Val Ser Leu Asn His Asn Glu Ile Ile Trp
945                 950                 955                 960
Thr Leu Gln Asp Asn Ala Gly Ile Asn Gln Lys Leu Ala Phe Asn Tyr
                965                 970                 975
Gly Asn Ala Asn Gly Ile Ser Asp Tyr Ile Asn Lys Trp Ile Phe Val
            980                 985                 990
Thr Ile Thr Asn Asp Arg Leu Gly Asp Ser Lys Leu Tyr Ile Asn Gly
        995                 1000                1005
Asn Leu Ile Asp Gln Lys Ser Ile Leu Asn Leu Gly Asn Ile His
```

-continued

Val Ser Asp Asn Ile Leu Phe Lys Ile Val Asn Cys Ser Tyr Thr
1025                1030                1035

Arg Tyr Ile Gly Ile Arg Tyr Phe Asn Ile Phe Asp Lys Glu Leu
1040                1045                1050

Asp Glu Thr Glu Ile Gln Thr Leu Tyr Ser Asn Glu Pro Asn Thr
1055                1060                1065

Asn Ile Leu Lys Asp Phe Trp Gly Asn Tyr Leu Leu Tyr Asp Lys
1070                1075                1080

Glu Tyr Tyr Leu Leu Asn Val Leu Lys Pro Asn Asn Phe Ile Asp
1085                1090                1095

Arg Arg Lys Asp Ser Thr Leu Ser Ile Asn Asn Ile Arg Ser Thr
1100                1105                1110

Ile Leu Leu Ala Asn Arg Leu Tyr Ser Gly Ile Lys Val Lys Ile
1115                1120                1125

Gln Arg Val Asn Asn Ser Ser Thr Asn Asp Asn Leu Val Arg Lys
1130                1135                1140

Asn Asp Gln Val Tyr Ile Asn Phe Val Ala Ser Lys Thr His Leu
1145                1150                1155

Phe Pro Leu Tyr Ala Asp Thr Ala Thr Thr Asn Lys Glu Lys Thr
1160                1165                1170

Ile Lys Ile Ser Ser Ser Gly Asn Arg Phe Asn Gln Val Val Val
1175                1180                1185

Met Asn Ser Val Gly Asn Asn Cys Thr Met Asn Phe Lys Asn Asn
1190                1195                1200

Asn Gly Asn Asn Ile Gly Leu Leu Gly Phe Lys Ala Asp Thr Val
1205                1210                1215

Val Ala Ser Thr Trp Tyr Tyr Thr His Met Arg Asp His Thr Asn
1220                1225                1230

Ser Asn Gly Cys Phe Trp Asn Phe Ile Ser Glu Glu His Gly Trp
1235                1240                1245

Gln Glu Lys
1250

<210> SEQ ID NO 27
<211> LENGTH: 1251
<212> TYPE: PRT
<213> ORGANISM: Clostridium botulinum type E
<220> FEATURE:
<223> OTHER INFORMATION: Beluga strain

<400> SEQUENCE: 27

Pro Lys Ile Asn Ser Phe Asn Tyr Asn Asp Pro Val Asn Asp Arg Thr
1               5                   10                  15

Ile Leu Tyr Ile Lys Pro Gly Gly Cys Gln Glu Phe Tyr Lys Ser Phe
                20                  25                  30

Asn Ile Met Lys Asn Ile Trp Ile Ile Pro Glu Arg Asn Val Ile Gly
            35                  40                  45

Thr Thr Pro Gln Asp Phe His Pro Pro Thr Ser Leu Lys Asn Gly Asp
        50                  55                  60

Ser Ser Tyr Tyr Asp Pro Asn Tyr Leu Gln Ser Asp Glu Glu Lys Asp
65                  70                  75                  80

Arg Phe Leu Lys Ile Val Thr Lys Ile Phe Asn Arg Ile Asn Asn Asn
                85                  90                  95

Leu Ser Gly Gly Ile Leu Leu Glu Glu Leu Ser Lys Ala Asn Pro Tyr

```
              100                 105                 110
Leu Gly Asn Asp Asn Thr Pro Asp Asn Gln Phe His Ile Gly Asp Ala
            115                 120                 125

Ser Ala Val Glu Ile Lys Phe Ser Asn Gly Ile Gln Asp Ile Leu Leu
        130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Gly
                165                 170                 175

Phe Gly Ser Ile Ala Ile Val Thr Phe Ser Pro Glu Tyr Ser Phe Arg
            180                 185                 190

Phe Asn Asp Asn Ser Met Asn Glu Phe Ile Gln Asp Pro Ala Leu Thr
        195                 200                 205

Leu Met His Glu Leu Ile His Ser Leu His Gly Leu Tyr Gly Ala Lys
    210                 215                 220

Gly Ile Thr Thr Lys Tyr Thr Ile Thr Gln Lys Gln Asn Pro Leu Ile
225                 230                 235                 240

Thr Asn Ile Arg Gly Thr Asn Ile Glu Glu Phe Leu Thr Phe Gly Gly
                245                 250                 255

Thr Asp Leu Asn Ile Ile Thr Ser Ala Gln Ser Asn Asp Ile Tyr Thr
            260                 265                 270

Asn Leu Leu Ala Asp Tyr Lys Lys Ile Ala Ser Lys Leu Ser Lys Val
        275                 280                 285

Gln Val Ser Asn Pro Leu Leu Asn Pro Tyr Lys Asp Val Phe Glu Ala
    290                 295                 300

Lys Tyr Gly Leu Asp Lys Asp Ala Ser Gly Ile Tyr Ser Val Asn Ile
305                 310                 315                 320

Asn Lys Phe Asn Asp Ile Phe Lys Lys Leu Tyr Ser Phe Thr Glu Phe
                325                 330                 335

Asp Leu Ala Thr Lys Phe Gln Val Lys Cys Arg Gln Thr Tyr Ile Gly
            340                 345                 350

Gln Tyr Lys Tyr Phe Lys Leu Ser Asn Leu Leu Asn Asp Ser Ile Tyr
        355                 360                 365

Asn Ile Ser Glu Gly Tyr Asn Ile Asn Asn Leu Lys Val Asn Phe Arg
    370                 375                 380

Gly Gln Asn Ala Asn Leu Asn Pro Arg Ile Ile Thr Pro Ile Thr Gly
385                 390                 395                 400

Arg Gly Leu Val Lys Lys Ile Ile Arg Phe Cys Lys Asn Ile Val Ser
                405                 410                 415

Val Lys Gly Ile Arg Lys Ser Ile Cys Ile Glu Ile Asn Asn Gly Glu
            420                 425                 430

Leu Phe Phe Val Ala Ser Glu Asn Ser Tyr Asn Asp Asp Asn Ile Asn
        435                 440                 445

Thr Pro Lys Glu Ile Asp Asp Thr Val Thr Ser Asn Asn Asn Tyr Glu
    450                 455                 460

Asn Asp Leu Asp Gln Val Ile Leu Asn Phe Asn Ser Glu Ser Ala Pro
465                 470                 475                 480

Gly Leu Ser Asp Glu Lys Leu Asn Leu Thr Ile Gln Asn Asp Ala Tyr
                485                 490                 495

Ile Pro Lys Tyr Asp Ser Asn Gly Thr Ser Asp Ile Glu Gln His Asp
            500                 505                 510

Val Asn Glu Leu Asn Val Phe Phe Tyr Leu Asp Ala Gln Lys Val Pro
        515                 520                 525
```

```
Glu Gly Glu Asn Asn Val Asn Leu Thr Ser Ser Ile Asp Thr Ala Leu
        530                 535                 540

Leu Glu Gln Pro Lys Ile Tyr Thr Phe Phe Ser Ser Glu Phe Ile Asn
545                 550                 555                 560

Asn Val Asn Lys Pro Val Gln Ala Ala Leu Phe Val Ser Trp Ile Gln
                565                 570                 575

Gln Val Leu Val Asp Phe Thr Thr Glu Ala Asn Gln Lys Ser Thr Val
            580                 585                 590

Asp Lys Ile Ala Asp Ile Ser Ile Val Val Pro Tyr Ile Gly Leu Ala
        595                 600                 605

Leu Asn Ile Gly Asn Glu Ala Gln Lys Gly Asn Phe Lys Asp Ala Leu
610                 615                 620

Glu Leu Leu Gly Ala Gly Ile Leu Leu Glu Phe Glu Pro Glu Leu Leu
625                 630                 635                 640

Ile Pro Thr Ile Leu Val Phe Thr Ile Lys Ser Phe Leu Gly Ser Ser
                645                 650                 655

Asp Asn Lys Asn Lys Val Ile Lys Ala Ile Asn Asn Ala Leu Lys Glu
            660                 665                 670

Arg Asp Glu Lys Trp Lys Glu Val Tyr Ser Phe Ile Val Ser Asn Trp
        675                 680                 685

Met Thr Lys Ile Asn Thr Gln Phe Asn Lys Arg Lys Glu Gln Met Tyr
690                 695                 700

Gln Ala Leu Gln Asn Gln Val Asn Ala Ile Lys Thr Ile Ile Glu Ser
705                 710                 715                 720

Lys Tyr Asn Ser Tyr Thr Leu Glu Glu Lys Asn Glu Leu Thr Asn Lys
                725                 730                 735

Tyr Asp Ile Lys Gln Ile Glu Asn Glu Leu Asn Gln Lys Val Ser Ile
            740                 745                 750

Ala Met Asn Asn Ile Asp Arg Phe Leu Thr Glu Ser Ser Ile Ser Tyr
        755                 760                 765

Leu Met Lys Leu Ile Asn Glu Val Lys Ile Asn Lys Leu Arg Glu Tyr
770                 775                 780

Asp Glu Asn Val Lys Thr Tyr Leu Leu Asn Tyr Ile Ile Gln His Gly
785                 790                 795                 800

Ser Ile Leu Gly Glu Ser Gln Gln Glu Leu Asn Ser Met Val Thr Asp
                805                 810                 815

Thr Leu Asn Asn Ser Ile Pro Phe Lys Leu Ser Ser Tyr Thr Asp Asp
            820                 825                 830

Lys Ile Leu Ile Ser Tyr Phe Asn Lys Phe Phe Lys Arg Ile Lys Ser
        835                 840                 845

Ser Ser Val Leu Asn Met Arg Tyr Lys Asn Asp Lys Tyr Val Asp Thr
850                 855                 860

Ser Gly Tyr Asp Ser Asn Ile Asn Ile Asn Gly Asp Val Tyr Lys Tyr
865                 870                 875                 880

Pro Thr Asn Lys Asn Gln Phe Gly Ile Tyr Asn Asp Lys Leu Ser Glu
                885                 890                 895

Val Asn Ile Ser Gln Asn Asp Tyr Ile Ile Tyr Asp Asn Lys Tyr Lys
            900                 905                 910

Asn Phe Ser Ile Ser Phe Trp Val Arg Ile Pro Asn Tyr Asp Asn Lys
        915                 920                 925

Ile Val Asn Val Asn Asn Glu Tyr Thr Ile Ile Asn Cys Met Arg Asp
930                 935                 940
```

```
Asn Asn Ser Gly Trp Lys Val Ser Leu Asn His Asn Glu Ile Ile Trp
945                 950                 955                 960

Thr Leu Gln Asp Asn Ala Gly Ile Asn Gln Lys Leu Ala Phe Asn Tyr
            965                 970                 975

Gly Asn Ala Asn Gly Ile Ser Asp Tyr Ile Asn Lys Trp Ile Phe Val
            980                 985                 990

Thr Ile Thr Asn Asp Arg Leu Gly Asp Ser Lys Leu Tyr Ile Asn Gly
        995                 1000                1005

Asn Leu Ile Asp Gln Lys Ser Ile Leu Asn Leu Gly Asn Ile His
    1010                1015                1020

Val Ser Asp Asn Ile Leu Phe Lys Ile Val Asn Cys Ser Tyr Thr
    1025                1030                1035

Arg Tyr Ile Gly Ile Arg Tyr Phe Asn Ile Phe Asp Lys Glu Leu
    1040                1045                1050

Asp Glu Thr Glu Ile Gln Thr Leu Tyr Asn Asn Glu Pro Asn Ala
    1055                1060                1065

Asn Ile Leu Lys Asp Phe Trp Gly Asn Tyr Leu Leu Tyr Asp Lys
    1070                1075                1080

Glu Tyr Tyr Leu Leu Asn Val Leu Lys Pro Asn Asn Phe Ile Asp
    1085                1090                1095

Arg Arg Thr Asp Ser Thr Leu Ser Ile Asn Asn Ile Arg Ser Thr
    1100                1105                1110

Ile Leu Leu Ala Asn Arg Leu Tyr Ser Gly Ile Lys Val Lys Ile
    1115                1120                1125

Gln Arg Val Asn Asn Ser Ser Thr Asn Asp Asn Leu Val Arg Lys
    1130                1135                1140

Asn Asp Gln Val Tyr Ile Asn Phe Val Ala Ser Lys Thr His Leu
    1145                1150                1155

Phe Pro Leu Tyr Ala Asp Thr Asn Thr Thr Asn Lys Glu Lys Thr
    1160                1165                1170

Ile Lys Ser Ser Ser Ser Gly Asn Arg Phe Asn Gln Val Val Val
    1175                1180                1185

Met Asn Ser Val Gly Asn Asn Cys Thr Met Asn Phe Lys Asn Asn
    1190                1195                1200

Asn Gly Asn Asn Ile Gly Met Leu Gly Phe Lys Asp Asn Thr Leu
    1205                1210                1215

Val Ala Ser Thr Trp Tyr Tyr Thr His Met Arg Asp Asn Thr Asn
    1220                1225                1230

Ser Asn Gly Cys Phe Trp Asn Phe Ile Ser Glu Glu His Gly Trp
    1235                1240                1245

Gln Glu Lys
    1250

<210> SEQ ID NO 28
<211> LENGTH: 606
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Glu Asn Lys Val Ser Gln Val Lys Ile Arg Phe Val Asn Val Phe
1               5                   10                  15

Lys Asp Lys Thr Leu Ala Asn Lys Leu Ser Phe Asn Phe Ser Asp Lys
            20                  25                  30
```

```
Gln Asp Val Pro Val Ser Glu Ile Ile Leu Ser Phe Thr Pro Ser Tyr
         35                  40                  45

Tyr Glu Asp Gly Leu Ile Gly Tyr Asp Leu Gly Leu Val Ser Leu Tyr
 50                  55                  60

Asn Glu Lys Phe Tyr Ile Asn Asn Phe Gly Met Met Val Ser Gly Leu
 65                  70                  75                  80

Ile Tyr Ile Asn Asp Ser Leu Tyr Tyr Phe Lys Pro Pro Val Asn Asn
                 85                  90                  95

Leu Ile Thr Gly Phe Val Thr Val Gly Asp Asp Lys Tyr Tyr Phe Asn
            100                 105                 110

Pro Ile Asn Gly Gly Ala Ala Ser Ile Gly Glu Thr Ile Ile Asp Asp
            115                 120                 125

Lys Asn Tyr Tyr Phe Asn Gln Ser Gly Val Leu Gln Thr Gly Val Phe
            130                 135                 140

Ser Thr Glu Asp Gly Phe Lys Tyr Phe Ala Pro Ala Asn Thr Leu Asp
145                 150                 155                 160

Glu Asn Leu Glu Gly Glu Ala Ile Asp Phe Thr Gly Lys Leu Ile Ile
                165                 170                 175

Asp Glu Asn Ile Tyr Tyr Phe Asp Asn Tyr Arg Gly Ala Val Glu
                180                 185                 190

Trp Lys Glu Leu Asp Gly Glu Met His Tyr Phe Ser Pro Glu Thr Gly
            195                 200                 205

Lys Ala Phe Lys Gly Leu Asn Gln Ile Gly Asp Tyr Lys Tyr Tyr Phe
            210                 215                 220

Asn Ser Asp Gly Val Met Gln Lys Gly Phe Val Ser Ile Asn Asp Asn
225                 230                 235                 240

Lys His Tyr Phe Asp Asp Ser Gly Val Met Lys Val Gly Tyr Thr Glu
                245                 250                 255

Ile Asp Gly Lys His Phe Tyr Phe Ala Glu Asn Gly Glu Met Gln Ile
            260                 265                 270

Gly Val Phe Asn Thr Glu Asp Gly Phe Lys Tyr Phe Ala His His Asn
            275                 280                 285

Glu Asp Leu Gly Asn Glu Gly Glu Glu Ile Ser Tyr Ser Gly Ile
            290                 295                 300

Leu Asn Phe Asn Asn Lys Ile Tyr Tyr Phe Asp Asp Ser Phe Thr Ala
305                 310                 315                 320

Val Val Gly Trp Lys Asp Leu Glu Asp Gly Ser Lys Tyr Tyr Phe Asp
            325                 330                 335

Glu Asp Thr Ala Glu Ala Tyr Ile Gly Leu Ser Leu Ile Asn Asp Gly
            340                 345                 350

Gln Tyr Tyr Phe Asn Asp Asp Gly Ile Met Gln Val Gly Phe Val Thr
            355                 360                 365

Ile Asn Asp Lys Val Phe Tyr Phe Ser Asp Ser Gly Ile Ile Glu Ser
            370                 375                 380

Gly Val Gln Asn Ile Asp Asp Asn Tyr Phe Tyr Ile Asp Asp Asn Gly
385                 390                 395                 400

Ile Val Gln Ile Gly Val Phe Asp Thr Ser Asp Gly Tyr Lys Tyr Phe
            405                 410                 415

Ala Pro Ala Asn Thr Val Asn Asp Asn Ile Tyr Gly Gln Ala Val Glu
            420                 425                 430

Tyr Ser Gly Leu Val Arg Val Gly Glu Asp Val Tyr Tyr Phe Gly Glu
            435                 440                 445
```

```
Thr Tyr Thr Ile Glu Thr Gly Trp Ile Tyr Asp Met Glu Asn Glu Ser
    450                 455                 460
Asp Lys Tyr Tyr Phe Asn Pro Glu Thr Lys Lys Ala Cys Lys Gly Ile
465                 470                 475                 480
Asn Leu Ile Asp Asp Ile Lys Tyr Tyr Phe Asp Glu Lys Gly Ile Met
                485                 490                 495
Arg Thr Gly Leu Ile Ser Phe Glu Asn Asn Asn Tyr Tyr Phe Asn Glu
            500                 505                 510
Asn Gly Glu Met Gln Phe Gly Tyr Ile Asn Ile Glu Asp Lys Met Phe
        515                 520                 525
Tyr Phe Gly Glu Asp Gly Val Met Gln Ile Gly Val Phe Asn Thr Pro
    530                 535                 540
Asp Gly Phe Lys Tyr Phe Ala His Gln Asn Thr Leu Asp Glu Asn Phe
545                 550                 555                 560
Glu Gly Glu Ser Ile Asn Tyr Thr Gly Trp Leu Asp Leu Asp Glu Lys
                565                 570                 575
Arg Tyr Tyr Phe Thr Asp Glu Tyr Ile Ala Ala Thr Gly Ser Val Ile
            580                 585                 590
Ile Asp Gly Glu Glu Tyr Tyr Phe Asp Pro Asp Thr Ala Gln
        595                 600                 605

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Lys Lys Arg
1

<210> SEQ ID NO 30
<211> LENGTH: 5
<212> TYPE: PRT
<213> ORGANISM: Unknown
<220> FEATURE:
<223> OTHER INFORMATION: Description of Unknown: Enterokinase cleavage
      site peptide

<400> SEQUENCE: 30

Asp Asp Asp Asp Lys
1               5

<210> SEQ ID NO 31
<211> LENGTH: 4
<212> TYPE: PRT
<213> ORGANISM: Unknown
<220> FEATURE:
<223> OTHER INFORMATION: Description of Unknown: Factor Xa cleavage site
      peptide

<400> SEQUENCE: 31

Ile Glu Gly Arg
1

<210> SEQ ID NO 32
<211> LENGTH: 4
<212> TYPE: PRT
<213> ORGANISM: Unknown
<220> FEATURE:
<223> OTHER INFORMATION: Description of Unknown: Factor Xa cleavage site
```

```
                              peptide

<400> SEQUENCE: 32

Ile Asp Gly Arg
1

<210> SEQ ID NO 33
<211> LENGTH: 7
<212> TYPE: PRT
<213> ORGANISM: Tobacco etch virus

<400> SEQUENCE: 33

Glu Asn Leu Tyr Phe Gln Gly
1               5

<210> SEQ ID NO 34
<211> LENGTH: 6
<212> TYPE: PRT
<213> ORGANISM: Unknown
<220> FEATURE:
<223> OTHER INFORMATION: Description of Unknown: Thrombin cleavage site
      peptide

<400> SEQUENCE: 34

Leu Val Pro Arg Gly Ser
1               5

<210> SEQ ID NO 35
<211> LENGTH: 8
<212> TYPE: PRT
<213> ORGANISM: Unknown
<220> FEATURE:
<223> OTHER INFORMATION: Description of Unknown: PreScission cleavage
      site peptide

<400> SEQUENCE: 35

Leu Glu Val Leu Phe Gln Gly Pro
1               5

<210> SEQ ID NO 36
<211> LENGTH: 5
<212> TYPE: PRT
<213> ORGANISM: Clostridium botulinum type A

<400> SEQUENCE: 36

His Glu Leu Ile His
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

His Gln Leu Ile Tyr
1               5

<210> SEQ ID NO 38
<211> LENGTH: 5
<212> TYPE: PRT
<213> ORGANISM: Clostridium botulinum type A

<400> SEQUENCE: 38
```

```
His Glu Leu Asn His
1               5

<210> SEQ ID NO 39
<211> LENGTH: 5
<212> TYPE: PRT
<213> ORGANISM: Clostridium botulinum type A

<400> SEQUENCE: 39

His Glu Leu Thr His
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

His Gln Leu Asn Tyr
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

His Gln Leu Thr Tyr
1               5
```